United States Patent
Yoshida et al.

(10) Patent No.: US 9,321,757 B2
(45) Date of Patent: Apr. 26, 2016

(54) HETEROCYCLIC COMPOUND

(71) Applicant: Takeda Pharmaceutical Company Limited, Chuo-ku, Osaka-shi, Osaka (JP)

(72) Inventors: Masato Yoshida, Kanagawa (JP); Kazuaki Takami, Kanagawa (JP); Yusuke Tominari, Kanagawa (JP); Zenyu Shiokawa, Kanagawa (JP); Akito Shibuya, Kanagawa (JP); Yusuke Sasaki, Kanagawa (JP); Tony Gibson, San Diego, CA (US); Terufumi Takagi, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 14/533,326

(22) Filed: Nov. 5, 2014

(65) Prior Publication Data
US 2015/0133451 A1    May 14, 2015

(30) Foreign Application Priority Data

Nov. 8, 2013  (JP) ................. 2013-232571
Jun. 23, 2014  (JP) ................. 2014-128562

(51) Int. Cl.
| | |
|---|---|
| *C07D 401/14* | (2006.01) |
| *C07D 487/04* | (2006.01) |
| *C07D 417/14* | (2006.01) |
| *C07D 487/10* | (2006.01) |
| *A61P 37/00* | (2006.01) |
| *C07D 403/14* | (2006.01) |
| *A61K 31/4155* | (2006.01) |
| *C07D 413/14* | (2006.01) |
| *C07D 409/14* | (2006.01) |
| *C07D 405/14* | (2006.01) |
| *C07D 401/04* | (2006.01) |
| *A61K 9/06* | (2006.01) |
| *A61K 9/20* | (2006.01) |
| *A61K 9/48* | (2006.01) |

(52) U.S. Cl.
CPC ............ *C07D 413/14* (2013.01); *A61K 9/06* (2013.01); *A61K 9/2018* (2013.01); *A61K 9/2054* (2013.01); *A61K 9/4858* (2013.01); *C07D 401/04* (2013.01); *C07D 401/14* (2013.01); *C07D 403/14* (2013.01); *C07D 405/14* (2013.01); *C07D 409/14* (2013.01); *C07D 417/14* (2013.01); *C07D 487/04* (2013.01); *C07D 487/10* (2013.01)

(58) Field of Classification Search
CPC .. C07D 413/14; C07D 487/04; C07D 401/14; C07D 401/04; C07D 409/14; C07D 487/10; C07D 403/14; C07D 417/14; A61K 31/4155; A61P 37/00
USPC ..................... 514/236.5; 546/268.1
See application file for complete search history.

(56) References Cited

U.S. PATENT DOCUMENTS

| | | |
|---|---|---|
| 2009/0203715 A1 | 8/2009 | Bothe et al. |
| 2010/0160324 A1 | 6/2010 | Berdini et al. |

FOREIGN PATENT DOCUMENTS

| | | |
|---|---|---|
| EP | 2070924 A1 | 6/2009 |
| WO | WO 2006/070198 A1 | 7/2006 |
| WO | WO 2011/043371 A1 | 4/2011 |

OTHER PUBLICATIONS

Dorwald; "Side Reactions in Organic Synthesis: A Guide to Successful Synthesis Design" 2005 Wiley-VCH Verlag GmbH & Co. KGaA, Wienheim.*
Chaudhary; J. Med. Chem. 2015, 58, 96-110.*
Hynes; Annual Reports in Medicinal Chemistry, 2014, 49, 117-133.*
English translation of WO 2011/043371 A1, Apr. 14, 2011, of Astellas Pharma Inc.

\* cited by examiner

*Primary Examiner* — Janet L Andres
*Assistant Examiner* — Daniel Carcanague
(74) *Attorney, Agent, or Firm* — Foley & Lardner LLP

(57) ABSTRACT

The present invention provides a heterocyclic compound having an IRAK-4 inhibitory action, which is useful for the prophylaxis or treatment of inflammatory disease, autoimmune disease, osteoarticular degenerative disease, neoplastic disease and the like, and a medicament containing thereof. The present invention relates to a compound represented by the formula (I):

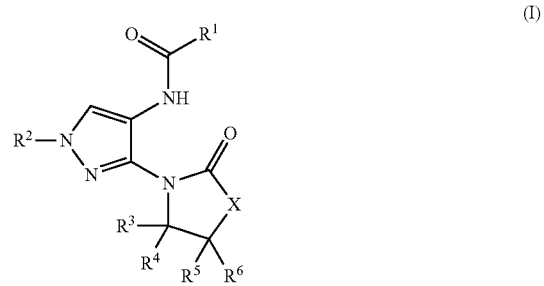

(I)

wherein each symbol is as defined in the specification, or a salt thereof.

13 Claims, No Drawings

HETEROCYCLIC COMPOUND

TECHNICAL FIELD

The present invention relates to a heterocyclic compound having an interleukin 1 receptor-associated kinase 4 (IRAK-4) inhibitory action, which is useful for the prophylaxis or treatment of inflammatory disease, autoimmune disease, osteoarticular degenerative disease, neoplastic disease and the like, and a medicament containing thereof.

BACKGROUND OF THE INVENTION

IRAK-4 is a member of the IRAK family which is a protein kinase, and lies downstream of all Toll-like receptors (TLRs) excluding TLR3 and interleukin-1, -18 and -33 receptors (IL-1R, IL-18R, IL-33R) (Non-Patent Document 1). IRAK-4 is activated via an adapter molecule which is called myeloid differentiation factor 88 (MyD88), and transmits signals in downstream. The signaling via MyD88 activates downstream molecule including NF-κB and MAPK, and produces cytokine, chemokine and the like which are involved in inflammatory response (Non-Patent Document 2).

Accordingly, IRAK-4 and MyD88 are considered to contribute to physiological reactions such as protection against pathogen, inflammation, control of natural immunity and/or acquired immunity, and cell survival and/or growth, by controlling the production of an inflammatory mediator. In addition, they are involved in acute and chronic inflammatory diseases, and autoimmune diseases such as rheumatoid arthritis (Non-Patent Document 3), systemic lupus erythematosus (Non-Patent Document 4), multiple sclerosis (Non-Patent Document 5) and the like (Non-Patent Document 6).

In addition, since the signaling via IRAK-4 and MyD88 is involved in NF-κB and MAPK, it is also be intimately related to cell growth. For example, it is evident that therapeutic effect of vinblastine on malignant melanoma is increased due to inhibition of IRAK-4 and IRAK-1 (Non-Patent Document 7).

From the foregoing, IRAK-4 inhibitor has the potential to show high efficacy of the treatment of acute and chronic inflammatory disease, autoimmune disease and cancer.

Examples of the compound having a structure similar to the compound described in the present specification include the following compounds.
(1) A compound represented by the following formula:

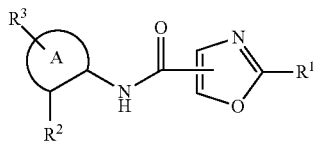

wherein
Ring A is monocyclic heteroaryl;
$R^1$ is optionally substituted monocyclic or bicyclic heteroaryl;
$R^2$ is —$CONH_2$, —CONH—$R^0$, —CONH—$R^{00}$—OH, phenyl, oxadiazolyl, tetrazolyl or the like;
$R^3$ is H, hetero cycloalkyl (optionally substituted by $R^0$, halogen and the like) or the like;
$R^0$ is lower alkyl; and
$R^{00}$ is lower alkylene, which is IRAK-4 inhibitor and useful for the prophylaxis or treatment of inflammatory disease, autoimmune disease and the like (Patent Document 1).

DOCUMENT LIST

Patent Document

[Patent Document 1] WO 2011/043371

Non-Patent Document

[Non-Patent Document 1] Biochemical Pharmacology, 2010, 80, 1981-1991
[Non-Patent Document 2] Nature Medicine, 2007, 13, 552-559
[Non-Patent Document 3] Arthritis & Rheumatism, 2009, 60(6), 1661-1671
[Non-Patent Document 4] Joint Bone Spine, 2011, 78, 124-130
[Non-Patent Document 5] Journal of Neuroimmunology, 2011, 239, 1-12
[Non-Patent Document 6] The International Journal of Biochemistry & Cell Biology, 2010, 42, 506-518
[Non-Patent Document 7] Cancer Research, 2012, 72(23), 6209-6216

SUMMARY OF THE INVENTION

Problems to be Solved by the Invention

An object of the present invention is to provide a heterocyclic compound having an IRAK-4 inhibitory action, which is useful for the prophylaxis or treatment of inflammatory disease, autoimmune disease, osteoarticular degenerative disease, neoplastic disease and the like, and a medicament containing thereof.

Means of Solving the Problems

The present inventors have conducted intensive studies in an attempt to solve the above-mentioned problem and found that compound represented by the following formula (I) has a superior IRAK-4 inhibitory action, which resulted in the completion of the present invention.

Accordingly, the present invention provides the following.
[1] A compound represented by the formula (I):

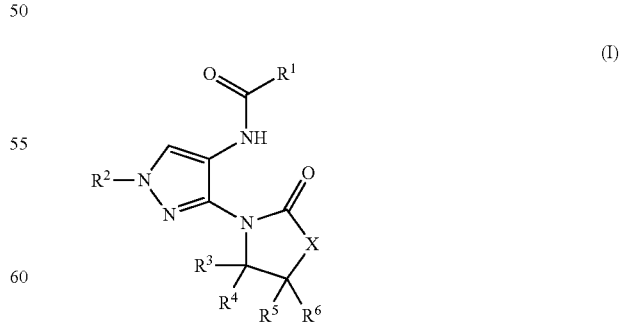

wherein
$R^1$ is an optionally substituted aromatic heterocyclic group or an optionally substituted $C_{6-14}$ aryl group;
$R^2$ is a hydrogen atom or a substituent;

$R^3$ and $R^4$ are independently a hydrogen atom or a substituent, or $R^3$ and $R^4$ in combination optionally form an optionally substituted ring;

$R^5$ and $R^6$ are independently a hydrogen atom or a substituent, or $R^5$ and $R^6$ in combination optionally form an optionally substituted ring;

X is $CR^7R^8$, $NR^9$, O or S;

$R^7$ and $R^8$ are independently a hydrogen atom or a substituent, or $R^7$ and $R^8$ in combination optionally form an optionally substituted ring; and $R^9$ is a hydrogen atom or a substituent, or a salt thereof (hereinafter sometime to be referred to as "compound (I)").

[2] The compound or salt of [1], wherein $R^1$ is an aromatic, heterocyclic group or a $C_{6-14}$ aryl group, each of which is optionally substituted by 1 to 3 substituents selected from a halogen atom, an optionally substituted $C_{1-6}$ alkyl group, an optionally substituted $C_{6-14}$ aryl group, an optionally substituted heterocyclic group, a $C_{3-10}$ cycloalkylsulfonyl group, a $C_{1-6}$ alkyl-carbonyl group, an aromatic heterocyclylsulfonyl group and a halogenated sulfanyl group;

$R^2$ is an optionally substituted $C_{1-6}$ alkyl group, an optionally substituted $C_{3-10}$ cycloalkyl group or an optionally substituted non-aromatic heterocyclic group;

$R^3$ and $R^4$ are independently a hydrogen atom or an optionally substituted $C_{1-6}$ alkyl group;

$R^5$ and $R^6$ are independently (1) a hydrogen atom, (2) a hydroxy group, (3) an optionally substituted $C_{1-6}$ alkyl group, (4) an optionally substituted $C_{1-6}$ alkoxy group, (5) an amino group optionally mono- or di-substituted by substituent(s) selected from (i) an optionally substituted $C_{1-6}$ alkyl group, (ii) an optionally substituted $C_{1-6}$ alkyl-carbonyl group, and (iii) an optionally substituted $C_{1-6}$ alkylsulfonyl group, (6) an optionally substituted non-aromatic heterocyclic group, (7) a carboxy group, or (8) a carbamoyl group optionally mono- or di-substituted by $C_{1-6}$ alkyl group(s), or $R^5$ and $R^6$ in combination optionally form an optionally substituted non-aromatic heterocycle or an optionally substituted $C_{3-10}$ cycloalkane;

X is $CR^7R^8$, $NR^9$, O or S;

$R^7$ and $R^8$ are independently a hydrogen atom, a cyano group, an optionally substituted $C_{1-6}$ alkyl group or a hydroxy group, or $R^7$ and $R^8$ in combination optionally form an optionally substituted $C_{3-10}$ cycloalkane or an optionally substituted non-aromatic heterocycle; and $R^9$ is a hydrogen atom, an optionally substituted $C_{1-6}$ alkyl group, an optionally substituted $C_{2-6}$ alkenyl group or an optionally substituted $C_{7-16}$ aralkyl group.

[3] The compound or salt of [1] or [2], wherein

X is $CR^7R^8$ or $NR^9$; and $R^3$ and $R^4$ are both hydrogen atoms.

[4] N-(3-(3-(2-Hydroxyethyl)-2-oxoimidazolidin-1-yl)-1-methyl-1H-pyrazol-4-yl)-2-(2-((2,2,2-trifluoroethyl)amino)pyridin-4-yl)-1,3-oxazole-4-carboxamide or a salt thereof.

[5] N-(1-Methyl-3-(2-oxoimidazolidin-1-yl)-1H-pyrazol-4-yl)-2-(2-((2,2,2-trifluoroethyl)amino)pyridin-4-yl)-1,3-oxazole-4-carboxamide or a salt thereof.

[6] N-(1-Methyl-3-((3S)-3-methyl-2-oxopyrrolidin-1-yl)-1H-pyrazol-4-yl)-2-(2-((2,2,2-trifluoroethyl)amino)pyridin-4-yl)-1,3-oxazole-4-carboxamide or a salt thereof.

[7] A medicament comprising the compound or salt of any of [1]-[6].

[8] The medicament of [7], which is an interleukin 1 receptor-associated kinase 4 inhibitor.

[9] The medicament of [7], which is an agent for the prophylaxis or treatment of autoimmune disease and/or inflammatory disease.

[10] The medicament of [7], which is an agent for the prophylaxis or treatment of multiple sclerosis, systemic lupus erythematosus, gout or hay fever.

[11] The compound or salt of any of [1]-[6] for use in the prophylaxis or treatment of autoimmune disease and/or inflammatory disease.

[12] The compound or salt of any of [1]-[6] for use in the prophylaxis or treatment of multiple sclerosis, systemic lupus erythematosus, gout or hay fever.

[13] A method of inhibiting interleukin 1 receptor-associated kinase 4 in a mammal, which comprises administering an effective amount of the compound or salt of any of [1]-[6] to the mammal.

[14] A method for the prophylaxis or treatment of autoimmune disease and/or inflammatory disease in a mammal, which comprises administering an effective amount of the compound or salt of any of [1]-[6] to the mammal.

[15] A method for the prophylaxis or treatment of multiple sclerosis, systemic lupus erythematosus, gout or hay fever in a mammal, which comprises administering an effective amount of the compound or salt of any of [1]-[6] to the mammal.

[16] Use of the compound or salt of any of [1]-[6] for the production of an agent for the prophylaxis or treatment of autoimmune disease and/or inflammatory disease.

[17] Use of the compound or salt of any of [1]-[6] for the production of an agent for the prophylaxis or treatment of multiple sclerosis, systemic lupus erythematosus, gout or hay fever.

Effect of the Invention

Compound (I) has a superior IRAK-4 inhibitory action, which is useful as an agent for the prophylaxis or treatment of inflammatory disease, autoimmune disease, osteoarticular degenerative disease, neoplastic disease and the like.

DETAILED DESCRIPTION OF THE INVENTION

The present invention is explained in detail below.

The definition of each substituent used in the present specification is described in detail in the following. Unless otherwise specified, each substituent has the following definition.

In the present specification, examples of the "halogen atom" include fluorine, chlorine, bromine and iodine.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "optionally halogenated $C_{1-6}$ alkyl group" include a $C_{1-6}$ alkyl group optionally having 1 to 7, preferably 1 to 5 halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5 halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-14}$ aryl group" include phenyl, 1-naphthyl, 2-naphthyl, 1-anthryl, 2-anthryl and 9-anthryl.

In the present specification, examples of the "$C_{7-16}$ aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy, group" include a $C_{1-6}$ alkoxy group optionally having 1 to 7, preferably 1 to 5 halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio and hexylthio.

In the present specification, examples of the "optionally halogenated $C_{1-6}$ alkylthio group" include a $C_{1-6}$ alkylthio group optionally having 1 to 7, preferably 1 to 5 halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1-6}$ alkyl-carbonyl group" include a $C_{1-6}$ alkyl-carbonyl group optionally having 1 to 7, preferably 1 to 5 halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-14}$ arylcarbonyl group" include benzoyl, 1-naphthoyl and 2-naphthoyl.

In the present specification, examples of the "$C_{7-16}$ aralkylcarbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-$C_{1-6}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{7-16}$ aralkyl-carbamoyl group" include benzylcarbamoyl and phenethylcarbamoyl.

In the present specification, examples of the "$C_{1-6}$ alkylsulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated $C_{1-6}$ alkylsulfonyl group" include a $C_{1-6}$ alkylsulfonyl group optionally having 1 to 7, preferably 1 to 5 halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "$C_{6-14}$ arylsulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including "hydrocarbon group" of "optionally substituted hydrocarbon group") include a $C_{1-6}$ alkyl group, a $C_{2-6}$ alkenyl group, a $C_{2-6}$ alkynyl group, a $C_{3-10}$ cycloalkyl group, a $C_{3-40}$ cycloalkenyl group, a $C_{6-14}$ aryl group and a $C_{7-16}$ aralkyl group.

In the present specification, examples of the "optionally substituted hydrocarbon group" include a hydrocarbon group optionally having substituent(s) selected from the following Substituent Group A.

[Substituent Group A]
(1) a halogen atom,
(2) a nitro group,
(3) a cyano group,
(4) an oxo group,
(5) a hydroxy group,
(6) an optionally halogenated $C_{1-6}$ alkoxy group,
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),

(11) a $C_{1-6}$ alkyl-carbonyloxy group (e.g., acetoxy, propanoyloxy),
(12) a $C_{6-14}$ aryl-carbonyloxy group (e.g., benzoyloxy, naphthoyloxy, 2-naphthoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(19) a $C_{6-14}$ arylsulfonyloxy group optionally substituted by a $C_{1-6}$ alkyl group (e.g., phenylsulfonyloxy, toluenesulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(39) a $C_{6-14}$ arylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(42) a $C_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),
(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),
(51) a ($C_{1-6}$ alkyl) ($C_{1-6}$ alkyl-carbonyl)amino group (e.g., N-acetyl-N-methylamino),
(52) a $C_{6-14}$ aryl-carbonylamino group (e.g., phenylcarbonylamino, naphthylcarbonylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$ alkylsulfonylamino group (e.g., methylsulfonylamino, ethylsulfonylamino),
(56) a $C_{6-14}$ arylsulfonylamino group optionally substituted by a $C_{1-6}$ alkyl group (e.g., phenylsulfonylamino, toluenesulfonylamino),
(57) an optionally halogenated $C_{1-6}$ alkyl group,
(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group and
(62) a $C_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "heterocyclic group" (including "heterocyclic group" of "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 hetero atoms selected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5- to 10-membered) aromatic heterocyclic group containing, as a ring-constituting atom besides carbon atom, 1 to 4 hetero atoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and
8- to 14-membered fused polycyclic (preferably bi or tricyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 hetero atoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered fused polycyclic (preferably bi or tricyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacrydinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include a "heterocyclic group" containing at least one nitrogen atom as a ring-constituting atom.

In the present specification, examples of the "optionally substituted heterocyclic group" include a heterocyclic group optionally having substituent(s) selected from the above-mentioned Substituent Group A.

The number of the substituents in the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbon-sulfonyl group, a heterocyclylsulfonyl group, a hydrocarbon-sulfinyl group and a heterocyclylsulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group and the heterocyclylsulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxy-carbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{7-16}$ aralkyl-carbamoyl group, a 5- to 14-membered aromatic heterocyclylcarbamoyl group (e.g., pyridylcarbamoyl), a thiocarbamoyl group, a mono- or di-$C_{1-6}$ alkyl-thiocarbamoyl group (e.g., methylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a $C_{1-6}$ alkylsulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{1-6}$ alkylphosphono group (e.g., dimethylphosphono, diethylphosphono, diisopropylphosphono, dibutylphosphono).

In the present specification, examples of the "optionally substituted amino group" include an amino group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from Substituent Group A".

Preferable examples of the optionally substituted amino group include an amino group, a mono- or di-(optionally halogenated $C_{1-6}$ alkyl)amino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di-(optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$ alkyl-carbamoyl)amino group (e.g., methylcarbamoylamino), a (mono- or di-$C_{7-16}$ aralkyl-carbamoyl)amino group (e.g., benzylcarbamoylamino), a $C_{1-6}$ alkylsulfonylamino group (e.g., methylsulfonylamino, ethylsulfonylamino), a $C_{6-14}$ arylsulfonylamino group (e.g., phenylsulfonylamino), a ($C_{1-6}$ alkyl) ($C_{1-6}$ alkyl-carbonyl) amino group (e.g., N-acetyl-N-methylamino) and a ($C_{1-6}$ alkyl) ($C_{6-14}$ aryl-carbonyl)amino group (e.g., N-benzoyl-N-methylamino).

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent Group A".

Preferable examples of the optionally substituted carbamoyl group include a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ carbonyl-carbamoyl group (e.g., benzoylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent Group A".

Preferable examples of the optionally substituted thiocarbamoyl group include a thiocarbamoyl group, a mono- or alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_{1-6}$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent Group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., diallylsulfamoyl), a mono- or di-$C_{3-10}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from Substituent Group A".

Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$ alkoxy-carbonyloxy group (e.g., tert-butoxycarbonyloxy), a 5- to 14-membered aromatic heterocyclyloxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkylsulfonyloxy group (e.g., methylsulfonyloxy, ethylsulfonyloxy) and a $C_{6-14}$ arylsulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group and a 5- to 14-membered aromatic heterocyclic group, each of which optionally has 1 to 3 substituents selected from Substituent Group A" and a halogenated sulfanyl group.

Preferable examples of the optionally substituted sulfanyl group include a sulfanyl (—SH) group, a $C_{1-6}$ alkylthio group, a $C_{2-6}$ alkenylthio group (e.g., allylthio, 2-butenylthio, 2-pentenylthio, 3-hexenylthio), a $C_{3-10}$ cycloalkylthio group (e.g., cyclohexylthio), a $C_{6-14}$ arylthio group (e.g., phenylthio, naphthylthio), a $C_{7-16}$ aralkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-16}$ aralkyl group, each of which optionally has 1 to 3 substituents selected from Substituent Group A".

Preferable examples of the optionally substituted silyl group include a tri-$C_{1-6}$ alkylsilyl group (e.g., trimethylsilyl, tert-butyl(dimethyl)silyl).

In the present specification, examples of the "$C_{1-6}$ alkylene group" include —CH$_2$—, —(CH$_2$)$_2$—, —(CH$_2$)$_3$—, —(CH$_2$)$_4$—, —(CH$_2$)$_5$—, —(CH$_2$)$_6$—, —CH(CH$_3$)—, —C(CH$_3$)$_2$—, —CH(C$_2$H$_5$)—, —CH(C$_3$H$_7$)—, —CH(CH(CH$_3$)$_2$)—, —(CH(CH$_3$))$_2$—, —CH$_2$—CH(CH$_3$)—, —CH(CH$_3$)—CH$_2$—, —CH$_2$—CH$_2$—C(CH$_3$)$_2$—, —C(CH$_3$)$_2$—CH$_2$—CH$_2$—, —CH$_2$—CH$_2$—CH$_2$—C(CH$_3$)$_2$— and —C(CH$_3$)$_2$—CH$_2$—CH$_2$—CH$_2$—.

In the present specification, examples of the "$C_{2-6}$ alkenylene group" include —CH═CH—, —CH$_2$—CH═CH—, —CH═CH—CH$_2$—, —C(CH$_3$)$_2$—CH═CH—, —CH═CH—C(CH$_3$)$_2$—, —CH$_2$—CH═CH—CH$_2$—, —CH$_2$—CH$_2$—CH═CH—, —CH═CH—CH$_2$—CH$_2$—, —CH═CH—CH═CH—, —CH═CH—CH$_2$—CH$_2$—CH$_2$— and —CH$_2$—CH$_2$—CH$_2$—CH═CH—.

In the present specification, examples of the "$C_{2-6}$ alkynylene group" include —C≡C—, —CH$_2$—C≡C—, —C≡C—CH$_2$—, —C(CH$_3$)$_2$—C≡C—, —C≡C—C(CH$_3$)$_2$—, —CH$_2$—C≡C—CH$_2$—, —CH$_2$—CH$_2$—C≡C—, —C≡C—CH$_2$—CH$_2$—, —C≡C—C≡C—, —C≡C—CH$_2$—CH$_2$—CH$_2$— and —CH$_2$—CH$_2$—CH$_2$—C≡C—.

In the present specification, examples of the "hydrocarbon ring" include a $C_{6-14}$ aromatic hydrocarbon ring, $C_{3-10}$ cycloalkane and $C_{3-10}$ cycloalkene.

In the present specification, examples of the "$C_{6-14}$ aromatic hydrocarbon ring" include benzene and naphthalene.

In the present specification, examples of the "$C_{3-10}$ cycloalkane" include cyclopropane, cyclobutane, cyclopentane, cyclohexane, cycloheptane and cyclooctane.

In the present specification, examples of the "$C_{3-10}$ cycloalkene" include cyclopropene, cyclobutene, cyclopentene, cyclohexene, cycloheptene and cyclooctene.

In the present specification, examples of the "heterocycle" include an aromatic heterocycle and a non-aromatic heterocycle, each containing, as a ring-constituting atom besides carbon atom, 1 to 4 hetero atoms selected from a nitrogen atom, a sulfur atom and an oxygen atom.

In the present specification, examples of the "aromatic heterocycle" include a 5- to 14-membered (preferably 5- to 10-membered) aromatic heterocycle containing, as a ring-constituting atom besides carbon atom, 1 to 4 hetero atoms selected from a nitrogen atom, a sulfur atom and an oxygen atom. Preferable examples of the "aromatic heterocycle" include 5- or 6-membered monocyclic aromatic heterocycles such as thiophene, furan, pyrrole, imidazole, pyrazole, thiazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, triazole, tetrazole, triazine and the like; and 8- to 14-membered fused polycyclic (preferably bi or tricyclic) aromatic heterocycles such as benzothiophene, benzofuran, benzimidazole, benzoxazole, benzisoxazole, benzothiazole, benzisothiazole, benzotriazole, imidazopyridine, thienopyridine, furopyridine, pyrrolopyridine, pyrazolopyridine, oxazolopyridine, thiazolopyridine, imidazopyrazine, imidazopyrimidine, thienopyrimidine, furopyrimidine, pyrrolopyrimidine, pyrazolopyrimidine, oxazolopyrimidine, thiazolopyrimidine, pyrazolopyrimidine, pyrazolotriazine, naphtho[2,3-b]thiophene, phenoxathiine, indole, isoindole, 1H-indazole, purine, isoquinoline, quinoline, phthalazine, naphthyridine, quinoxaline, quinazoline, cinnoline, carbazole, β-carboline, phenanthridine, acridine, phenazine, phenothiazine, phenoxathiine and the like.

In the present specification, examples of the "non-aromatic heterocycle" include a 3- to 14-membered (preferably 4- to 10-membered) non-aromatic heterocycle containing, as a ring-constituting atom besides carbon atom, 1 to 4 hetero atoms selected from a nitrogen atom, a sulfur atom and an oxygen atom. Preferable examples of the "non-aromatic heterocycle" include 3- to 8-membered monocyclic non-aromatic heterocycles such as aziridine, oxirane, thiirane, azetidine, oxetane, thietane, tetrahydrothiophene, tetrahydrofuran, pyrroline, pyrrolidine, imidazoline, imidazolidine, oxazoline, oxazolidine, pyrazoline, pyrazolidine, thiazoline, thiazolidine, tetrahydroisothiazole, tetrahydrooxazole, tetrahydroisoxazole, piperidine, piperazine, tetrahydropyridine, dihydropyridine, dihydrothiopyran, tetrahydropyrimidine, tetrahydropyridazine, dihydropyran, tetrahydropyran, tetrahydrothiopyran, morpholine, thiomorpholine, azepanine, diazepane, azepine, azocane, diazocane, oxepane and the like; and 9- to 14-membered fused polycyclic (preferably bi or tricyclic) non-aromatic heterocycles such as dihydrobenzofuran, dihydrobenzimidazole, dihydrobenzoxazole, dihydrobenzothiazole, dihydrobenzisothiazole, dihydronaphtho[2,3-b]thiophene, tetrahydroisoquinoline, tetrahydroquinoline, 4H-quinolizine, indoline, isoindoline, tetrahydrothieno[2,3-c]pyridine, tetrahydrobenzazepine, tetrahydroquinoxaline, tetrahydrophenanthridine, hexahydrophenothiazine, hexahydrophenoxazine, tetrahydrophthalazine, tetrahydronaphthyridine, tetrahydroquinazoline, tetrahydrocinnoline, tetrahydrocarbazole, tetrahydro-β-carboline, tetrahydroacridine, tetrahydrophenazine, tetrahydrothioxanthene, octahydroisoquinoline and the like.

In the present specification, examples of the "nitrogen-containing heterocycle" include a "heterocycle" containing at least one nitrogen atom as a ring-constituting atom.

In one embodiment, preferable examples of the "non-aromatic heterocyclic group" include a 7- to 14-membered spiro heterocyclic group such as triazaspirononyl (e.g., 1,3,7-triazaspiro[4.4]nonyl), thiadiazaspirononyl (e.g., 7-thia-1,3-diazaspiro[4.4]nonyl), dioxidothiadiazaspirononyl (e.g., 7,7-dioxido-7-thia-1,3-diazaspiro[4.4]nonyl) and the like, in addition to the above-mentioned "3- to 8-membered monocyclic non-aromatic heterocyclic group" and "9- to 14-membered fused polycyclic (preferably bi- or tri-cyclic) non-aromatic heterocyclic group".

Each symbol in formula (I) is explained below.

$R^1$ is an optionally substituted aromatic heterocyclic group or an optionally substituted $C_{6-14}$ aryl group.

The "aromatic heterocyclic group" of the "optionally substituted aromatic heterocyclic group" and the "$C_{6-14}$ aryl group" of the "optionally substituted $C_{6-14}$ aryl group" for $R^1$ each optionally has 1 to 3 substituents at substitutable position(s). When the number of the substituents is plural, the respective substituents may be the same or different.

In one embodiment, examples of the "substituent" for the "aromatic heterocyclic group" of the "optionally substituted aromatic heterocyclic group" and the "$C_{6-14}$ aryl group" of the "optionally substituted $C_{6-14}$ aryl group" for $R^1$ include a halogen atom, a cyano group, a nitro group, an optionally substituted hydrocarbon group, an optionally substituted heterocyclic group (the "heterocyclic group" optionally has substituent(s) selected from Substituent Group A (the substituent is optionally further substituted by substituent(s) selected from Substituent Group A)), an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group, and an optionally substituted silyl group.

Preferable examples of the "substituent" for the "aromatic heterocyclic group" of the "optionally substituted aromatic heterocyclic group" and the "$C_{6-14}$ aryl group" of the "optionally substituted $C_{6-14}$ aryl group" for $R^1$ include
(1) an optionally substituted hydrocarbon group (e.g., a hydrocarbon group optionally having substituent(s) selected from Substituent Group A),
(2) an optionally substituted heterocyclic group (e.g., a heterocyclic group optionally having substituent(s) selected from Substituent Group A (the substituent is optionally further substituted by substituent(s) selected from Substituent Group A)), and
(3) an acyl group.

In another embodiment, examples of the "substituent" for the "aromatic heterocyclic group" of the "optionally substituted aromatic heterocyclic group" and the "$C_{6-14}$ aryl group" of the "optionally substituted $C_{6-14}$ aryl group" for $R^1$ include a halogen atom, a cyano group, a nitro group, an optionally substituted hydrocarbon group, an optionally substituted heterocyclic group (the "heterocyclic group" optionally has substituent(s) selected from Substituent Group A and a thioxo group (the substituent is optionally further substituted by substituent(s) selected from Substituent Group A, an azido group and a mono- or di-$C_{1-6}$ alkylamino group (the alkyl is substituted by substituent(s) selected from a $C_{3-10}$ cycloalkyl group and a halogen atom))), an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group, and an optionally substituted silyl group.

Preferable examples of the "substituent" for the "aromatic heterocyclic group" of the "optionally substituted aromatic heterocyclic group" and the "$C_{6-14}$ aryl group" of the "optionally substituted $C_{6-14}$ aryl group" for $R^1$ include
(1) a halogen atom,
(2) an optionally substituted hydrocarbon group (e.g., a hydrocarbon group optionally having substituent(s) selected from Substituent Group A),
(3) an optionally substituted heterocyclic group (e.g., a heterocyclic group optionally having substituent(s) selected from Substituent Group A and a thioxo group (the substituent is optionally further substituted by substituent(s) selected from Substituent Group A, an azido group and a mono- or di-$C_{1-6}$ alkylamino group (the alkyl is substituted by substituent(s) selected from a $C_{3-10}$ cycloalkyl group and a halogen atom))),
(4) an acyl group, and
(5) an optionally substituted sulfanyl (SH) group.

In one embodiment, $R^1$ is preferably an aromatic heterocyclic group (preferably a 5- to 14-membered aromatic heterocyclic group) or a $C_{6-14}$ aryl group, each of which is optionally substituted by 1 to 3 substituents selected from
(1) an optionally substituted $C_{1-6}$ alkyl group (e.g., a $C_{1-6}$ alkyl group optionally having substituent(s) selected from Substituent Group A),
(2) an optionally substituted $C_{6-14}$ aryl group (e.g., a $C_{6-14}$ aryl group optionally having substituent(s) selected from Substituent Group A),
(3) an optionally substituted heterocyclic group (e.g., a heterocyclic group optionally having substituent(s) selected from Substituent Group A (the substituent is optionally further substituted by substituent(s) selected from Substituent Group A)),
(4) a $C_{3-10}$ cycloalkylsulfonyl group,
(5) a $C_{1-6}$ alkyl-carbonyl group, and
(6) an aromatic heterocyclylsulfonyl group (preferably a 5- to 14-membered aromatic heterocyclylsulfonyl group).

$R^1$ is more preferably an aromatic heterocyclic group (preferably a 5- to 14-membered aromatic heterocyclic group, more preferably a 5- to 6-membered monocyclic aromatic heterocyclic group, a 8- to 14-membered fused polycyclic aromatic heterocyclic group) (e.g., oxazolyl, thiazolyl, thienyl, pyrazolyl, pyridyl, imidazopyridyl (e.g., imidazo[1,5-a]pyridyl), imidazopyridazinyl (e.g., imidazo[1,2-b]pyridazinyl), pyrazolopyrimidinyl (e.g., pyrazolo[1,5-a]pyrimidinyl)), or a $C_{6-14}$ aryl group (e.g., phenyl), each of which is optionally substituted by 1 to 3 substituents selected from
(1) a $C_{1-6}$ alkyl group (e.g., methyl, ethyl, isopropyl) optionally substituted by 1 to 3 substituents selected from
(i) a halogen atom (e.g., a fluorine atom), and
(ii) a hydroxy group,
(2) a $C_{5-14}$ aryl group (e.g., phenyl) optionally substituted by 1 to 3 halogen atoms (e.g., a fluorine atom),
(3) an aromatic heterocyclic group (preferably a 5- to 14-membered aromatic heterocyclic group, more preferably a 5- to 6-membered monocyclic aromatic heterocyclic group) (e.g., pyridyl, thienyl) optionally substituted by amino group(s) optionally mono- or di-substituted by $C_{1-6}$ alkyl group(s) (e.g., ethyl) optionally substituted by 1 to 3 halogen atoms (e.g., a fluorine atom),
(4) a non-aromatic heterocyclic group (preferably a 3- to 14-membered non-aromatic heterocyclic group, more preferably a 3- to 8-membered monocyclic non-aromatic heterocyclic group) (e.g., morpholinyl) optionally substituted by 1 to 3 $C_{1-6}$ alkyl groups (e.g., methyl),
(5) a $C_{3-10}$ cycloalkylsulfonyl group (e.g., cyclopentylsulfonyl),
(6) a $C_{1-6}$ alkyl-carbonyl group (e.g., acetyl), and
(7) an aromatic heterocyclylsulfonyl group (preferably a 5- to 14-membered aromatic heterocyclylsulfonyl group, more preferably a 5- to 6-membered monocyclic aromatic heterocyclylsulfonyl group) (e.g., thiazolylsulfonyl).

$R^1$ is further more preferably (1) an aromatic heterocyclic group (preferably a 5- to 14-membered aromatic heterocyclic group, more preferably a 5- to 6-membered monocyclic aromatic heterocyclic group, a 8- to 14-membered fused polycyclic aromatic heterocyclic group) (e.g., oxazolyl, thiazolyl, thienyl, pyrazolyl, pyridyl, imidazopyridyl (e.g., imidazo[1,5-a]pyridyl), imidazopyridazinyl (e.g., imidazo[1,2-b]pyridazinyl), pyrazolopyrimidinyl (e.g., pyrazolo[1,5-a]pyrimidinyl)) optionally substituted by 1 to 3 substituents selected from
- (i) a $C_{1-6}$ alkyl group (e.g., methyl, ethyl, isopropyl) optionally substituted by 1 to 3 substituents selected from
  - (a) a halogen atom (e.g., a fluorine atom), and
  - (b) a hydroxy group,
- (ii) a $C_{6-14}$ aryl group (e.g., phenyl) optionally substituted by 1 to 3 halogen atoms (e.g., a fluorine atom),
- (iii) an aromatic heterocyclic group (preferably a 5- to 14-membered aromatic heterocyclic group, more preferably a 5- to 6-membered monocyclic aromatic heterocyclic group) (e.g., pyridyl, thienyl) optionally substituted by amino group(s) optionally mono- or di-substituted by $C_{1-6}$ alkyl group(s) (e.g., ethyl) optionally substituted by 1 to 3 halogen atoms (e.g., a fluorine atom),
- (iv) a non-aromatic heterocyclic group (preferably a 3- to 14-membered non-aromatic heterocyclic group, more preferably a 3- to 8-membered monocyclic non-aromatic heterocyclic group) (e.g., morpholinyl) optionally substituted by 1 to 3 $C_{1-6}$ alkyl groups (e.g., methyl),
- (v) a $C_{3-10}$ cycloalkylsulfonyl group (e.g., cyclopentylsulfonyl), and
- (vi) a $C_{1-6}$ alkyl-carbonyl group (e.g., acetyl), or (2) a $C_{6-14}$ aryl group (e.g., phenyl) optionally substituted by 1 to 3 substituents selected from
- (i) a $C_{1-6}$ alkyl group (e.g., methyl),
- (ii) a $C_{3-10}$ cycloalkylsulfonyl group (e.g., cyclopentylsulfonyl), and
- (iii) an aromatic heterocyclylsulfonyl group (preferably a 5- to 14-membered aromatic heterocyclylsulfonyl group, more preferably a 5- to 6-membered monocyclic aromatic heterocyclylsulfonyl group) (e.g., thiazolylsulfonyl).

$R^1$ is particularly preferably an aromatic heterocyclic group (preferably a 5- to 14-membered aromatic heterocyclic group, more preferably a 5- to 6-membered monocyclic aromatic heterocyclic group) (e.g., oxazolyl) optionally substituted by aromatic heterocyclic group(s) (preferably a 5- to 14-membered aromatic heterocyclic group, more preferably a 5- to 6-membered monocyclic aromatic heterocyclic group) (e.g., pyridyl) optionally substituted by amino group(s) optionally mono- or di-substituted by $C_{1-6}$ alkyl group(s) (e.g., methyl, ethyl) optionally substituted by 1 to 3 halogen atoms (e.g., a fluorine atom).

In another embodiment, $R^1$ is more preferably an aromatic heterocyclic group (preferably a 5- to 14-membered aromatic heterocyclic group, more preferably a 5- to 6-membered monocyclic aromatic heterocyclic group, a 8- to 14-membered fused polycyclic aromatic heterocyclic group) (e.g., oxazolyl, thiazolyl, thienyl, pyrazolyl, pyridyl, imidazopyridyl (e.g., imidazo[1,5-a]pyridyl), imidazopyridazinyl (e.g., imidazo[1,2-b]pyridazinyl), pyrazolopyrimidinyl (e.g., pyrazolo[1,5-a]pyrimidinyl)), or a $C_{6-14}$ aryl group (e.g., phenyl), each of which is optionally substituted by 1 to 3 substituents selected from
- (1) a $C_{1-6}$ alkyl group (e.g., methyl, ethyl, isopropyl) optionally substituted by 1 to 3 substituents selected from
  - (i) a halogen atom (e.g., a fluorine atom), and
  - (ii) a hydroxy group,
- (2) a $C_{6-14}$ aryl group (e.g., phenyl) optionally substituted by 1 to 3 halogen atoms (e.g., a fluorine atom),
- (3) an aromatic heterocyclic group (preferably a 5- to 14-membered aromatic heterocyclic group, more preferably a 5- to 6-membered monocyclic aromatic heterocyclic group) (e.g., pyridyl, thienyl) optionally substituted by amino group(s) optionally mono- or di-substituted by $C_{1-6}$ alkyl group(s) (e.g., methyl, ethyl) optionally substituted by 1 to 3 substituents selected from
  - (i) a halogen atom (e.g., a fluorine atom), and
  - (ii) a $C_{3-10}$ cycloalkyl group (e.g., cyclopropyl),
- (4) a non-aromatic heterocyclic group (preferably a 3- to 14-membered non-aromatic heterocyclic group, more preferably a 3- to 8-membered monocyclic non-aromatic heterocyclic group) (e.g., morpholinyl) optionally substituted by 1 to 3 $C_{1-6}$ alkyl groups (e.g., methyl),
- (5) a $C_{3-10}$ cycloalkylsulfonyl group (e.g., cyclopentylsulfonyl),
- (6) a $C_{1-6}$ alkyl-carbonyl group (e.g., acetyl), and
- (7) an aromatic heterocyclylsulfonyl group (preferably a 5- to 14-membered aromatic heterocyclylsulfonyl group, more preferably a 5- to 6-membered monocyclic aromatic heterocyclylsulfonyl group) (e.g., thiazolylsulfonyl).

$R^1$ is further more preferably
(1) an aromatic heterocyclic group (preferably a 5- to 14-membered aromatic heterocyclic group, more preferably a 5- to 6-membered monocyclic aromatic heterocyclic group, a 8- to 14-membered fused polycyclic aromatic heterocyclic group) (e.g., oxazolyl, thiazolyl, thienyl, pyrazolyl, pyridyl, imidazopyridyl (e.g., imidazo[1,5-a]pyridyl), imidazopyridazinyl (e.g., imidazo[1,2-b]pyridazinyl), pyrazolopyrimidinyl (e.g., pyrazolo[1,5-a]pyrimidinyl)) optionally substituted by 1 to 3 substituents selected from
- (i) a $C_{1-6}$ alkyl group (e.g., methyl, ethyl, isopropyl) optionally substituted by 1 to 3 substituents selected from
  - (a) a halogen atom (e.g., a fluorine atom), and
  - (b) a hydroxy group,
- (ii) a $C_{6-14}$ aryl group (e.g., phenyl) optionally substituted by 1 to 3 halogen atoms (e.g., a fluorine atom),
- (iii) an aromatic heterocyclic group (preferably a 5- to 14-membered aromatic heterocyclic group, more preferably a 5- to 6-membered monocyclic aromatic heterocyclic group) (e.g., pyridyl, thienyl) optionally substituted by amino group(s) optionally mono- or di-substituted by $C_{1-6}$ alkyl group(s) (e.g., methyl, ethyl) optionally substituted by 1 to 3 substituents selected from
  - (a) a halogen atom (e.g., a fluorine atom), and
  - (b) a $C_{3-10}$ cycloalkyl group (e.g., cyclopropyl),
- (iv) a non-aromatic heterocyclic group (preferably a 3- to 14-membered non-aromatic heterocyclic group, more preferably a 3- to 8-membered monocyclic non-aromatic heterocyclic group) (e.g., morpholinyl) optionally substituted by 1 to 3 $C_{1-6}$ alkyl groups (e.g., methyl),
- (v) a $C_{3-10}$ cycloalkylsulfonyl group (e.g., cyclopentylsulfonyl), and
- (vi) a $C_{1-5}$ alkyl-carbonyl group (e.g., acetyl), or (2) a $C_{6-14}$ aryl group (e.g., phenyl) optionally substituted by 1 to 3 substituents selected from
- (i) a $C_{1-6}$ alkyl group (e.g., methyl),
- (ii) a $C_{3-10}$ cycloalkylsulfonyl group (e.g., cyclopentylsulfonyl), and
- (iii) an aromatic heterocyclylsulfonyl group (preferably a 5- to 14-membered aromatic heterocyclylsulfonyl group, more preferably a 5- to 6-membered monocyclic aromatic heterocyclylsulfonyl group) (e.g., thiazolylsulfonyl).

In yet another embodiment, $R^1$ is preferably an aromatic heterocyclic group (preferably a 5- to 14-membered aromatic heterocyclic group) or a $C_{6-14}$ aryl group, each of which is optionally substituted by 1 to 3 substituents selected from
- (1) a halogen atom,
- (2) an optionally substituted $C_{1-6}$ alkyl group (e.g., a $C_{1-6}$ alkyl group optionally having substituent(s) selected from Substituent Group A),
- (3) an optionally substituted $C_{6-14}$ aryl group (e.g., a $C_{6-14}$ aryl group optionally having substituent(s) selected from Substituent Group A),
- (4) an optionally substituted heterocyclic group (e.g., a heterocyclic group optionally having substituent(s) selected from Substituent Group A and a thioxo group (the substituent is optionally further substituted by substituent(s) selected from Substituent Group A, an azido group and a mono- or di-$C_{1-6}$ alkylamino group (the alkyl is substituted by substituent(s) selected from a $C_{3-10}$ cycloalkyl group and a halogen atom))),
- (5) a $C_{3-10}$ cycloalkylsulfonyl group,
- (6) a $C_{1-6}$ alkyl-carbonyl group,
- (7) an aromatic heterocyclylsulfonyl group (preferably a 5- to 14-membered aromatic heterocyclylsulfonyl group), and
- (8) a halogenated sulfanyl group.

$R^1$ is more preferably an aromatic heterocyclic group (preferably a 5- to 14-membered aromatic heterocyclic group, more preferably a 5- to 6-membered monocyclic aromatic heterocyclic group, a 8- to 14-membered fused polycyclic aromatic heterocyclic group) (e.g., oxazolyl, thiazolyl, thienyl, pyrazolyl, pyridyl, imidazopyridyl (e.g., imidazo[1,5-a]pyridyl), imidazopyridazinyl (e.g., imidazo[1,2-b]pyridazinyl), pyrazolopyrimidinyl (e.g., pyrazolo[1,5-a]pyrimidinyl)), or a $C_{6-14}$ aryl group (e.g., phenyl), each of which is optionally substituted by 1 to 3 substituents selected from
- (1) a halogen atom (e.g., a fluorine atom),
- (2) a $C_{1-6}$ alkyl group (e.g., methyl, ethyl, isopropyl) optionally substituted by 1 to 3 substituents selected from
  - (i) a halogen atom (e.g., a fluorine atom), and
  - (ii) a hydroxy group,
- (3) a $C_{6-14}$ aryl group (e.g., phenyl) optionally substituted by 1 to 3 halogen atoms (e.g., a fluorine atom),
- (4) an aromatic heterocyclic group (preferably a 5- to 14-membered aromatic heterocyclic group, more preferably a 5- to 6-membered monocyclic aromatic heterocyclic group, a 8- to 14-membered fused polycyclic aromatic heterocyclic group) (e.g., pyridyl, thienyl, pyrimidinyl, imidazolyl, pyrazolyl, tetrazolyl, benzimidazolyl (e.g., 1H-benzimidazolyl), thiazolyl) optionally substituted by 1 to 3 substituents selected from
  - (i) an amino group optionally mono- or di-substituted by $C_{1-6}$ alkyl group(s) (e.g., methyl, ethyl) optionally substituted by 1 to 3 substituents selected from
    - (a) a halogen atom (e.g., a fluorine atom), and
    - (b) a $C_{3-10}$ cycloalkyl group (e.g., cyclopropyl),
  - (ii) a halogen atom (e.g., a chlorine atom),
  - (iii) a $C_{1-6}$ alkoxy group (e.g., methoxy),
  - (iv) a cyano group,
  - (v) a $C_{1-6}$ alkyl group (e.g., methyl, ethyl) optionally substituted by 1 to 3 substituents selected from
    - (a) an azido group,
    - (b) an amino group optionally mono- or di-substituted by $C_{1-6}$ alkyl group(s) (e.g., methyl, ethyl) optionally substituted by 1 to 3 substituents selected from a halogen atom (e.g., a fluorine atom) and a $C_{3-10}$ cycloalkyl group (e.g., cyclopropyl),
    - (c) a hydroxy group, and
    - (d) a halogen atom (e.g., a fluorine atom),
  - (vi) a formyl group,
  - (vii) a carboxy group,
  - (viii) a carbamoyl group,
  - (ix) a $C_{3-10}$ cycloalkyl group (e.g., cyclopropyl), and
  - (x) a non-aromatic heterocyclic group (preferably a 3- to 14-membered non-aromatic heterocyclic group, more preferably a 3- to 8-membered monocyclic non-aromatic heterocyclic group) (e.g., dioxolanyl (e.g., 1,3-dioxolanyl)),
- (5) a non-aromatic heterocyclic group (preferably a 3- to 14-membered non-aromatic heterocyclic group, more preferably a 3- to 8-membered monocyclic non-aromatic heterocyclic group, a 9- to 14-membered fused polycyclic non-aromatic heterocyclic group, a 7- to 14-membered spiro heterocyclic group) (e.g., morpholinyl, dihydropyranyl (e.g., 3,6-dihydro-2H-pyranyl), tetrahydropyranyl, dihydropyridyl (e.g., 1,2-dihydropyridyl), dihydrobenzofuranyl (e.g., 2,3-dihydrobenzofuranyl), imidazolidinyl, pyrrolidinyl, dihydroisoxazolyl (e.g., 4,5-dihydroisoxazolyl), dihydropyrrolopyrazolyl (e.g., 5,6-dihydropyrrolo[3,4-c]pyrazolyl), piperazinyl, triazaspirononyl (e.g., 1,3,7-triazaspiro[4.4]nonyl), thiadiazaspirononyl (e.g., 7-thia-1,3-diazaspiro[4.4]nonyl), dioxidothiadiazaspirononyl (e.g., 7,7-dioxido-7-thia-1,3-diazaspiro[4.4]nonyl)) optionally substituted by 1 to 3 substituents selected from
  - (i) a $C_{1-6}$ alkyl group (e.g., methyl, ethyl) optionally substituted by 1 to 3 substituents selected from
    - (a) a hydroxy group,
    - (b) an amino group optionally mono- or di-substituted by $C_{1-6}$ alkyl group(s) (e.g., methyl),
    - (c) a cyano group, and
    - (d) a $C_{6-14}$ aryl group (e.g., phenyl),
  - (ii) an oxo group,
  - (iii) a hydroxy group,
  - (iv) a carbamoyl group, and
  - (v) a thioxo group,
- (6) a $C_{3-10}$ cycloalkylsulfonyl group (e.g., cyclopentylsulfonyl),
- (7) a $C_{1-6}$ alkyl-carbonyl group (e.g., acetyl),
- (8) an aromatic heterocyclylsulfonyl group (preferably a 5- to 14-membered aromatic heterocyclylsulfonyl group, more preferably a 5- to 6-membered monocyclic aromatic heterocyclylsulfonyl group) (e.g., thiazolylsulfonyl), and
- (9) a halogenated thio group (e.g., pentafluorothio).

$R^1$ is further more preferably
(1) an aromatic heterocyclic group (preferably a 5- to 14-membered aromatic heterocyclic group, more preferably a 5- to 6-membered monocyclic aromatic heterocyclic group, a 8- to 14-membered fused polycyclic aromatic heterocyclic group) (e.g., oxazolyl, thiazolyl, thienyl, pyrazolyl, pyridyl, imidazopyridyl (e.g., imidazo[1,5-a]pyridyl), imidazopyridazinyl (e.g., imidazo[1,2-b]pyridazinyl), pyrazolopyrimidinyl (e.g., pyrazolo[1,5-a]pyrimidinyl)) optionally substituted by 1 to 3 substituents selected from
  - (i) a $C_{1-6}$ alkyl group (e.g., methyl, ethyl, isopropyl) optionally substituted by 1 to 3 substituents selected from
    - (a) a halogen atom (e.g., a fluorine atom), and
    - (b) a hydroxy group, (ii) a $C_{6-14}$ aryl group (e.g., phenyl) optionally substituted by 1 to 3 halogen atoms (e.g., a fluorine atom),
(iii) an aromatic heterocyclic group (preferably a 5- to 14-membered aromatic heterocyclic group, more preferably a 5- to 6-membered monocyclic aromatic heterocyclic group) (e.g., pyridyl, thienyl, pyrimidinyl, pyrazolyl, thiazolyl, imidazolyl) optionally substituted by 1 to 3 substituents selected from
  (a) an amino group optionally mono- or di-substituted by $C_{1-6}$ alkyl group(s) (e.g., methyl, ethyl) optionally substituted by 1 to 3 substituents selected from
    (I) a halogen atom (e.g., a fluorine atom), and
    (II) a $C_{3-10}$ cycloalkyl group (e.g., cyclopropyl),
  (b) a halogen atom (e.g., a chlorine atom),
  (c) a $C_{1-6}$ alkoxy group (e.g., methoxy),
  (d) a cyano group,
  (e) a $C_{1-6}$ alkyl group (e.g., methyl, ethyl) optionally substituted by 1 to 3 substituents selected from
    (I) an azido group,
    (II) an amino group optionally mono- or di-substituted by $C_{1-6}$ alkyl group(s) (e.g., methyl, ethyl) optionally substituted by 1 to 3 substituents selected from a halogen atom (e.g., a fluorine atom) and a $C_{3-10}$ cycloalkyl group (e.g., cyclopropyl),
    (III) a hydroxy group, and
    (IV) a halogen atom (e.g., a fluorine atom),
  (f) a formyl group,
  (g) a carboxy group,
  (h) a carbamoyl group,
  (i) a $C_{3-10}$ cycloalkyl group (e.g., cyclopropyl), and
  (j) a non-aromatic heterocyclic group (preferably a 3- to 14-membered non-aromatic heterocyclic group, more preferably a 3- to 8-membered monocyclic non-aromatic heterocyclic group) (e.g., dioxolanyl (e.g., 1,3-dioxolanyl)),
(iv) a non-aromatic heterocyclic group (preferably a 3- to 14-membered non-aromatic heterocyclic group, more preferably a 3- to 8-membered monocyclic non-aromatic heterocyclic group, a 9- to 14-membered fused polycyclic non-aromatic heterocyclic group, a 7- to 14-membered spiro heterocyclic group) (e.g., morpholinyl, dihydropyranyl (e.g., 3,6-dihydro-2H-pyranyl), tetrahydropyranyl, dihydropyridyl (e.g., 1,2-dihydropyridyl), dihydrobenzofuranyl (e.g., 2,3-dihydrobenzofuranyl), imidazolidinyl, pyrrolidinyl, dihydroisoxazolyl (e.g., 4,5-dihydroisoxazolyl), dihydropyrrolopyrazolyl (e.g., 5,6-dihydropyrrolo[3,4-c]pyrazolyl), piperazinyl, triazaspirononyl (e.g., 1,3,7-triazaspiro[4.4]nonyl), thiadiazaspirononyl (e.g., 7-thia-1,3-diazaspiro[4.4]nonyl), dioxidothiadiazaspirononyl (e.g., 7,7-dioxido-7-thia-1,3-diazaspiro[4.4]nonyl)) optionally substituted by 1 to 3 substituents selected from
  (a) a $C_{1-6}$ alkyl group (e.g., methyl, ethyl) optionally substituted by 1 to 3 substituents selected from
    (I) a hydroxy group,
    (II) an amino group optionally mono- or di-substituted by $C_{1-6}$ alkyl group(s) (e.g., methyl),
    (III) a cyano group, and
    (IV) a $C_{6-14}$ aryl group (e.g., phenyl),
  (b) an oxo group,
  (c) a hydroxy group,
  (d) a carbamoyl group, and
  (e) a thioxo group,
(v) a $C_{3-10}$ cycloalkylsulfonyl group (e.g., cyclopentylsulfonyl), and
(vi) a $C_{1-6}$ alkyl-carbonyl group (e.g., acetyl), or (2) a $C_{6-14}$ aryl group (e.g., phenyl) optionally substituted by 1 to 3 substituents selected from
  (i) a halogen atom (e.g., a fluorine atom),
  (ii) a $C_{1-6}$ alkyl group (e.g., methyl),
  (iii) an aromatic heterocyclic group (preferably a 5- to 14-membered aromatic heterocyclic group, more preferably a 5- to 6-membered monocyclic aromatic heterocyclic group, a 8- to 14-membered fused polycyclic aromatic heterocyclic group) (e.g., imidazolyl, pyrazolyl, tetrazolyl, benzimidazolyl (e.g., 1H-benzimidazolyl)),
  (iv) a $C_{3-10}$ cycloalkylsulfonyl group (e.g., cyclopentylsulfonyl),
  (v) an aromatic heterocyclylsulfonyl group (preferably a 5- to 14-membered aromatic heterocyclylsulfonyl group, more preferably a 5- to 6-membered monocyclic aromatic heterocyclylsulfonyl group) (e.g., thiazolylsulfonyl),
  (vi) a halogenated thio group (e.g., pentafluorothio), and
  (vii) a non-aromatic heterocyclic group (preferably a 3- to 14-membered non-aromatic heterocyclic group, more preferably a 3- to 8-membered monocyclic non-aromatic heterocyclic group, a 7- to 14-membered spiro heterocyclic group) (e.g., imidazolidinyl, triazaspirononyl (e.g., 1,3,7-triazaspiro[4.4]nonyl)) optionally substituted by 1 to 3 substituents selected from
    (a) a $C_{1-6}$ alkyl group (e.g., methyl) optionally substituted by 1 to 3 amino groups, and
    (b) an oxo group.

$R^1$ is still more preferably
(1) an aromatic heterocyclic group (preferably a 5- to 14-membered aromatic heterocyclic group, more preferably a 5- to 6-membered monocyclic aromatic heterocyclic group) (e.g., oxazolyl, pyridyl; pyrazolyl) optionally substituted by 1 to 3 substituents selected from
  (i) a $C_{1-6}$ alkyl group (e.g., methyl) optionally substituted by 1 to 3 halogen atoms (e.g., a fluorine atom),
  (ii) an aromatic heterocyclic group (preferably a 5- to 14-membered aromatic heterocyclic group, more preferably a 5- to 6-membered monocyclic aromatic heterocyclic group) (e.g., pyridyl, pyrazolyl) optionally substituted by 1 to 3 substituents selected from
    (a) an amino group optionally mono- or di-substituted by $C_{1-6}$ alkyl group(s) (e.g., methyl, ethyl) optionally substituted by 1 to 3 substituents selected from
      (I) a halogen atom (e.g., a fluorine atom), and
      (II) a $C_{3-10}$ cycloalkyl group (e.g., cyclopropyl), and
    (b) a $C_{1-6}$ alkyl group (e.g., methyl) optionally substituted by 1 to 3 amino groups, and
  (iii) a non-aromatic heterocyclic group (preferably a 3- to 14-membered non-aromatic heterocyclic group, more preferably a 3- to 8-membered monocyclic non-aromatic heterocyclic group, a 7- to 14-membered spiro heterocyclic group) (e.g., imidazolidinyl, triazaspirononyl (e.g., 1,3,7-triazaspiro[4.4]nonyl)) optionally substituted by 1 to 3 substituents selected from
    (a) a $C_{1-6}$ alkyl group (e.g., methyl) optionally substituted by 1 to 3 amino groups, and
    (b) an oxo group, or
(2) a $C_{6-14}$ aryl group (e.g., phenyl) optionally substituted by 1 to 3 $C_{1-6}$ alkyl groups (e.g., methyl).

$R^1$ is particularly preferably an aromatic heterocyclic group (preferably a 5- to 14-membered aromatic heterocyclic group, more preferably a 5- to 6-membered monocyclic aromatic heterocyclic group) (e.g., oxazolyl) optionally substituted by aromatic heterocyclic group(s) (preferably a 5- to 14-membered aromatic heterocyclic group, more preferably a 5- to 6-membered monocyclic aromatic heterocyclic group) (e.g., pyridyl) optionally substituted by amino group(s) optionally mono- or di-substituted by $C_{1-6}$ alkyl group(s) (e.g., methyl, ethyl) optionally substituted by 1 to 3 substituents selected from (1) a halogen atom (e.g., a fluorine atom), and
(2) a $C_{3-10}$ cycloalkyl group (e.g., cyclopropyl).

$R^2$ is a hydrogen atom or a substituent.

In one embodiment, examples of the "substituent" for $R^2$ include those similar to the "substituent" exemplified in the present specification.

The "substituent" for $R^2$ is preferably an optionally substituted hydrocarbon group (e.g., a hydrocarbon group optionally having substituent(s) selected from Substituent Group A), more preferably an optionally substituted $C_{1-6}$ alkyl group (e.g., a $C_{1-6}$ alkyl group optionally having substituent(s) selected from Substituent Group A).

In another embodiment, examples of the "substituent" for $R^2$ include a halogen atom, a cyano group, a nitro group, an optionally substituted hydrocarbon group (the "hydrocarbon group" optionally has substituent(s) selected from Substituent Group A, and a non-aromatic heterocyclic group having oxo group(s)), an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group, and an optionally substituted silyl group.

The "substituent" for $R^2$ is preferably an optionally substituted hydrocarbon group (e.g., a hydrocarbon group optionally having substituent(s) selected from Substituent Group A, and a non-aromatic heterocyclic group having oxo group(s)), or an optionally substituted heterocyclic group (e.g., a heterocyclic group optionally having substituent(s) selected from Substituent Group A), more preferably (1) an optionally substituted $C_{1-6}$ alkyl group (e.g., a $C_{1-6}$ alkyl group optionally having substituent(s) selected from Substituent Group A, and a non-aromatic heterocyclic group (preferably a 3- to 14-membered non-aromatic heterocyclic group) having oxo group(s)),
(2) an optionally substituted $C_{3-10}$ cycloalkyl group (e.g., a $C_{3-10}$ cycloalkyl group optionally having substituent(s) selected from Substituent Group A), or
(3) an optionally substituted non-aromatic heterocyclic group (preferably a 3- to 14-membered non-aromatic heterocyclic group) (e.g., a non-aromatic heterocyclic group (preferably a 3- to 14-membered non-aromatic heterocyclic group) optionally having substituent(s) selected from Substituent Group A).

In one embodiment, $R^2$ is preferably an optionally substituted $C_{1-6}$ alkyl group (e.g., a $C_{1-6}$ alkyl group optionally having substituent(s) selected from Substituent Group A).

In another embodiment, $R^2$ is preferably
(1) an optionally substituted $C_{1-6}$ alkyl group (e.g., a $C_{1-6}$ alkyl group optionally having substituent(s) selected from Substituent Group A, and a non-aromatic heterocyclic group (preferably a 3- to 14-membered non-aromatic heterocyclic group) having oxo group(s)),
(2) an optionally substituted $C_{3-10}$ cycloalkyl group (e.g., a $C_{3-10}$ cycloalkyl group optionally having substituent(s) selected from Substituent Group A), or
(3) an optionally substituted non-aromatic heterocyclic group (preferably a 3- to 14-membered non-aromatic heterocyclic group) (e.g., a non-aromatic heterocyclic group (preferably a 3- to 14-membered non-aromatic heterocyclic group) optionally having substituent(s) selected from Substituent Group A).

$R^2$ is more preferably
(1) a $C_{1-6}$ alkyl group (e.g., methyl, ethyl) optionally substituted by 1 to 3 substituents selected from
  (i) a $C_{1-6}$ alkoxy-carbonyl group (e.g., methoxycarbonyl),
  (ii) a $C_{1-6}$ alkylsulfonyl group (e.g., methylsulfonyl),
  (iii) a carbamoyl group,
  (iv) a cyano group,
  (v) a non-aromatic heterocyclic group (preferably a 3- to 14-membered non-aromatic heterocyclic group, more preferably a 3- to 8-membered monocyclic non-aromatic heterocyclic group) (e.g., pyrrolidinyl, tetrahydrofuryl, oxetanyl) optionally substituted by 1 to 3 oxo groups, and
  (vi) a halogen atom (e.g., a fluorine atom),
(2) a $C_{3-10}$ cycloalkyl group (e.g., cyclopentyl) optionally substituted by 1 to 3 hydroxy groups, or
(3) a non-aromatic heterocyclic group (preferably a 3- to 14-membered non-aromatic heterocyclic group, more preferably a 3- to 8-membered monocyclic non-aromatic heterocyclic group) (e.g., oxetanyl).

$R^2$ is further more preferably a $C_{1-6}$ alkyl group (e.g., methyl).

$R^3$ and $R^4$ are independently a hydrogen atom or a substituent, or $R^3$ and $R^4$ in combination optionally form an optionally substituted ring.

Examples of the "substituent" for $R^3$ or $R^4$ include those similar to the "substituent" exemplified in the present specification.

The "substituent" for $R^3$ or $R^4$ is preferably an optionally substituted hydrocarbon group (e.g., a hydrocarbon group optionally having substituent(s) selected from Substituent Group A), more preferably an optionally substituted $C_{1-6}$ alkyl group (e.g., a $C_{1-6}$ alkyl group optionally having substituent(s) selected from Substituent Group A).

Examples of the "ring" of the "optionally substituted ring" formed by $R^3$ and $R^4$ include a $C_{3-10}$ cycloalkane, a $C_{3-10}$ cycloalkene and a non-aromatic heterocycle (preferably a 3- to 14-membered non-aromatic heterocycle).

The "ring" of the "optionally substituted ring" formed by $R^3$ and $R^4$ optionally has 1 to 3 substituents selected from Substituent Group A at substitutable position(s). When the number of the substituents is plural, the respective substituents may be the same or different.

$R^3$ and $R^4$ are preferably independently a hydrogen atom or a substituent.

$R^3$ and $R^4$ are more preferably independently a hydrogen atom or an optionally substituted $C_{1-6}$ alkyl group (e.g., a $C_{1-6}$ alkyl group optionally having substituent(s) selected from Substituent Group A).

In one embodiment, $R^3$ and $R^4$ are further more preferably independently a hydrogen atom or a $C_{1-6}$ alkyl group (e.g., methyl).

In another embodiment, $R^3$ and $R^4$ are further more preferably independently
(1) a hydrogen atom, or
(2) a $C_{1-6}$ alkyl group (e.g., methyl) optionally substituted by 1 to 3 substituents selected from an amino group optionally mono- or di-substituted by $C_{1-6}$ alkyl group(s) (e.g., methyl).

Still more preferably, one of $R^3$ and $R^4$ is a hydrogen atom, and the other is
(1) a hydrogen atom, or
(2) a $C_{1-6}$ alkyl group (e.g., methyl) optionally substituted by 1 to 3 substituents selected from an amino group optionally mono- or di-substituted by $C_{1-6}$ alkyl group(s) (e.g., methyl).

Still further more preferably, one of $R^3$ and $R^4$ is a hydrogen atom, and the other is a hydrogen atom or a $C_{1-6}$ alkyl group (e.g., methyl).

$R^3$ and $R^4$ are particularly preferably both hydrogen atoms.

$R^5$ and $R^6$ are independently a hydrogen atom or a substituent, or $R^5$ and $R^6$ in combination optionally form an optionally substituted ring.

In one embodiment, examples of the "substituent" for $R^5$ or $R^6$ include those similar to the "substituent" exemplified in the present specification.

The "substituent" for $R^5$ or $R^6$ is preferably
(1) an optionally substituted hydroxy group,
(2) an optionally substituted hydrocarbon group (e.g., a hydrocarbon group optionally having substituent(s) selected from Substituent Group A),
(3) an optionally substituted amino group, or
(4) an optionally substituted heterocyclic group (e.g., a heterocyclic group optionally having substituent(s) selected from Substituent Group A),
more preferably
(1) a hydroxy group,
(2) an optionally substituted $C_{1-6}$ alkyl group (e.g., a $C_{1-6}$ alkyl group optionally having substituent(s) selected from Substituent Group A),
(3) an optionally substituted $C_{1-6}$ alkoxy group (e.g., a $C_{1-6}$ alkoxy group optionally having substituent(s) selected from Substituent Group A),
(4) an amino group optionally mono- or di-substituted by substituent(s) selected from
  (i) an optionally substituted $C_{1-6}$ alkyl group (e.g., a $C_{1-6}$ alkyl group optionally having substituent(s) selected from Substituent Group A),
  (ii) an optionally substituted $C_{1-6}$ alkyl-carbonyl group (e.g., a $C_{1-6}$ alkyl-carbonyl group optionally having substituent(s) selected from Substituent Group A), and
  (iii) an optionally substituted $C_{1-6}$ alkylsulfonyl group (e.g., a $C_{1-6}$ alkylsulfonyl group optionally having substituent(s) selected from Substituent Group A), or
(5) an optionally substituted non-aromatic heterocyclic group (preferably a 3- to 14-membered non-aromatic heterocyclic group) (e.g., a non-aromatic heterocyclic group (preferably a 3- to 14-membered non-aromatic heterocyclic group) optionally having substituent(s) selected from Substituent Group A).

In another embodiment, examples of the "substituent" for $R^5$ or $R^6$ include a halogen atom, a cyano group, a nitro group, an optionally substituted hydrocarbon group (the "hydrocarbon group" is optionally substituted by substituent(s) selected from (1) Substituent Group A, and (2) an amino group mono- or di-substituted by substituent(s) selected from (a) a $C_{1-6}$ alkyl group, (b) a $C_{3-10}$ cycloalkyl group optionally substituted by 1 to 3 halogen atoms, (c) a non-aromatic heterocyclic group (preferably a 3- to 14-membered non-aromatic heterocyclic group), (d) a $C_{1-6}$ alkylsulfonyl group, and (e) a $C_{3-10}$ cycloalkyl-carbonyl group), an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group, and an optionally substituted silyl group.

The "substituent" for $R^5$ or $R^6$ is preferably
(1) an optionally substituted hydroxy group,
(2) an optionally substituted hydrocarbon group (e.g., a hydrocarbon group optionally having substituent(s) selected from (1) Substituent Group A, and (2) an amino group mono- or di-substituted by substituent(s) selected from (a) a $C_{1-6}$ alkyl group, (b) a $C_{3-10}$ cycloalkyl group optionally substituted by 1 to 3 halogen atoms, (c) a non-aromatic heterocyclic group (preferably a 3- to 14-membered non-aromatic heterocyclic group), (d) a $C_{1-6}$ alkylsulfonyl group, and (e) a $C_{3-10}$ cycloalkyl-carbonyl group),
(3) an optionally substituted amino group,
(4), an optionally substituted heterocyclic group (e.g., a heterocyclic group optionally having substituent(s) selected from Substituent Group A), or
(5) an acyl group,
more preferably
(1) a hydroxy group,
(2) an optionally substituted $C_{1-6}$ alkyl group (e.g., a $C_{1-6}$ alkyl group optionally having substituent(s) selected from (1) Substituent Group A, and (2) an amino group mono- or di-substituted by substituent(s) selected from (a) a $C_{1-6}$ alkyl group, (b) a $C_{3-10}$ cycloalkyl group optionally substituted by 1 to 3 halogen atoms, (c) a non-aromatic heterocyclic group (preferably a 3- to 14-membered non-aromatic heterocyclic group), (d) a $C_{1-6}$ alkylsulfonyl group, and (e) a $C_{3-10}$ cycloalkyl-carbonyl group),
(3) an optionally substituted $C_{1-6}$ alkoxy group (e.g., a $C_{1-6}$ alkoxy group optionally having substituent(s) selected from Substituent Group A),
(4) an amino group optionally mono- or di-substituted by substituent(s) selected from
  (i) an optionally substituted $C_{1-6}$ alkyl group (e.g., a $C_{1-6}$ alkyl group optionally having substituent(s) selected from Substituent Group A),
  (ii) an optionally substituted $C_{1-6}$ alkyl-carbonyl group (e.g., a $C_{1-6}$ alkyl-carbonyl group optionally having substituent(s) selected from Substituent Group A), and
  (iii) an optionally substituted $C_{1-6}$ alkylsulfonyl group (e.g., a $C_{1-6}$ alkylsulfonyl group optionally having substituent(s) selected from Substituent Group A),
(5) an optionally substituted non-aromatic heterocyclic group (preferably a 3- to 14-membered non-aromatic heterocyclic group) (e.g., a non-aromatic heterocyclic group (preferably a 3- to 14-membered non-aromatic heterocyclic group) optionally having substituent(s) selected from Substituent Group A),
(6) a carboxy group, or
(7) a carbamoyl group optionally mono- or di-substituted by $C_{1-6}$ alkyl group(s).

Examples of the "ring" of the "optionally substituted ring" formed by $R^5$ and $R^6$ include a $C_{3-10}$ cycloalkane, a $C_{3-10}$ cycloalkene and a non-aromatic heterocycle (preferably a 3- to 14-membered non-aromatic heterocycle), and preferable examples thereof include a $C_{3-10}$ cycloalkane and a non-aromatic heterocycle (preferably a 3- to 14-membered non-aromatic heterocycle).

The "ring" of the "optionally substituted ring" formed by $R^5$ and $R^6$ optionally has 1 to 3 substituents selected from Substituent Group A at substitutable position(s). When the number of the substituents is plural, the respective substituents may be the same or different.

In one embodiment, $R^5$ and $R^6$ are preferably independently a hydrogen atom or a substituent.

$R^5$ and $R^6$ are more preferably independently
(1) a hydrogen atom,
(2) a hydroxy group,
(3) an optionally substituted $C_{1-6}$ alkyl group (e.g., a $C_{1-6}$ alkyl group optionally having substituent(s) selected from Substituent Group A),
(4) an optionally substituted $C_{1-6}$ alkoxy group (e.g., a $C_{1-6}$ alkoxy group optionally having substituent(s) selected from Substituent Group A), (5) an amino group optionally mono- or di-substituted by substituent(s) selected from
  (i) an optionally substituted $C_{1-6}$ alkyl group (e.g., a $C_{1-6}$ alkyl group optionally having substituent(s) selected from Substituent Group A),
  (ii) an optionally substituted $C_{1-6}$ alkyl-carbonyl group (e.g., a $C_{1-6}$ alkyl-carbonyl group optionally having substituent(s) selected from Substituent Group A), and
  (iii) an optionally substituted $C_{1-6}$ alkylsulfonyl group (e.g., a $C_{1-6}$ alkylsulfonyl group optionally having substituent(s) selected from Substituent Group A), or
(6) an optionally substituted non-aromatic heterocyclic group (preferably a 3- to 14-membered non-aromatic heterocyclic group) (e.g., a non-aromatic heterocyclic group (preferably a 3- to 14-membered non-aromatic heterocyclic group) optionally having substituent(s) selected from Substituent Group A).

$R^5$ and $R^6$ are further more preferably independently
(1) a hydrogen atom,
(2) a hydroxy group,
(3) a $C_{1-6}$ alkyl group (e.g., methyl) optionally substituted by 1 to 3 substituents selected from
  (i) a hydroxy group, and
  (ii) an amino group optionally mono- or di-substituted by $C_{1-6}$ alkyl group(s) (e.g., methyl, ethyl),
(4) a $C_{1-6}$ alkoxy group (e.g., methoxy),
(5) an amino group optionally mono- or di-substituted by substituent(s) selected from
  (i) a $C_{1-6}$ alkyl group (e.g., methyl, ethyl),
  (ii) a $C_{1-6}$ alkyl-carbonyl group (e.g., acetyl), and
  (iii) a $C_{1-6}$ alkylsulfonyl group (e.g., methylsulfonyl), or
(6) a non-aromatic heterocyclic group (preferably a 3- to 14-membered non-aromatic heterocyclic group, more preferably a 3- to 8-membered monocyclic non-aromatic heterocyclic group) (e.g., morpholinyl).

Still more preferably, one of $R^5$ and $R^6$ is a hydrogen atom, and the other is
(1) a hydrogen atom,
(2) a hydroxy group,
(3) a $C_{1-6}$ alkyl group (e.g., methyl) optionally substituted by 1 to 3 substituents selected from
  (i) a hydroxy group, and
  (ii) an amino group optionally mono- or di-substituted by $C_{1-6}$ alkyl group(s) (e.g., methyl, ethyl),
(4) a $C_{1-6}$ alkoxy group (e.g., methoxy),
(5) an amino group optionally mono- or di-substituted by substituent(s) selected from
  (i) a $C_{1-6}$ alkyl group (e.g., methyl, ethyl),
  (ii) a $C_{1-6}$ alkyl-carbonyl group (e.g., acetyl), and
  (iii) a $C_{1-6}$ alkylsulfonyl group (e.g., methylsulfonyl), or
(6) a non-aromatic heterocyclic group (preferably a 3- to 14-membered non-aromatic heterocyclic group, more preferably a 3- to 8-membered monocyclic non-aromatic heterocyclic group) (e.g., morpholinyl).

Particularly preferably, one of $R^5$ and $R^6$ is a hydrogen atom, and the other is
(1) a hydrogen atom,
(2) a hydroxy group,
(3) a $C_{1-6}$ alkyl group (e.g., methyl) optionally substituted by amino group(s) optionally mono- or di-substituted by $C_{1-6}$ alkyl group(s) (e.g., methyl), or
(4) an amino group optionally mono- or di-substituted by $C_{1-6}$ alkyl group(s) (e.g., methyl).

In another embodiment, $R^5$ and $R^6$ are preferably independently
(1) a hydrogen atom,
(2) a hydroxy group,
(3) an optionally substituted $C_{1-6}$ alkyl group (e.g., a $C_{1-6}$ alkyl group optionally having substituent(s) selected from (1) Substituent Group A, and (2) an amino group mono- or di-substituted by substituent(s) selected from (a) a $C_{1-6}$ alkyl group, (b) a $C_{3-10}$ cycloalkyl group optionally substituted by 1 to 3 halogen atoms, (c) a non-aromatic heterocyclic group (preferably a 3- to 14-membered non-aromatic heterocyclic group), (d) a $C_{1-6}$ alkylsulfonyl group, and (e) a $C_{3-10}$ cycloalkyl-carbonyl group),
(4) an optionally substituted $C_{1-6}$ alkoxy group (e.g., a $C_{1-6}$ alkoxy group optionally having substituent(s) selected from Substituent Group A),
(5) an amino group optionally mono- or di-substituted by substituent(s) selected from
  (i) an optionally substituted $C_{1-6}$ alkyl group (e.g., a $C_{1-6}$ alkyl group optionally having substituent(s) selected from Substituent Group A),
  (ii) an optionally substituted $C_{1-6}$ alkyl-carbonyl group (e.g., a $C_{1-6}$ alkyl-carbonyl group optionally having substituent(s) selected from Substituent Group A), and
  (iii) an optionally substituted $C_{1-6}$ alkylsulfonyl group (e.g., a $C_{1-6}$ alkylsulfonyl group optionally having substituent(s) selected from Substituent Group A),
(6) an optionally substituted non-aromatic heterocyclic group (preferably a 3- to 14-membered non-aromatic heterocyclic group) (e.g., a non-aromatic heterocyclic group (preferably a 3- to 14-membered non-aromatic heterocyclic group) optionally having substituent(s) selected from Substituent Group A),
(7) a carboxy group, or
(8) a carbamoyl group optionally mono- or di-substituted by $C_{1-6}$ alkyl group(s), or
$R^5$ and $R^6$ in combination optionally form.
(1) an optionally substituted non-aromatic heterocycle (preferably a 3- to 14-membered non-aromatic heterocycle) (e.g., a non-aromatic heterocycle (preferably a 3- to 14-membered non-aromatic heterocycle) optionally having substituent(s) selected from Substituent Group A), or
(2) an optionally substituted $C_{3-10}$ cycloalkane (e.g., a $C_{3-10}$ cycloalkane optionally having substituent(s) selected from Substituent Group A).

$R^5$ and $R^6$ are more preferably independently
(1) a hydrogen atom,
(2) a hydroxy group,
(3) a $C_{1-6}$ alkyl group (e.g., methyl) optionally substituted by 1 to 3 substituents selected from
  (i) a hydroxy group,
  (ii) an amino group optionally mono- or di-substituted by substituent(s) selected from
    (a) a $C_{1-6}$ alkyl group (e.g., methyl, ethyl) optionally substituted by 1 to 3 halogen atoms (e.g., a fluorine atom),
    (b) a $C_{3-13}$ cycloalkyl group (e.g., cyclopropyl, cyclobutyl) optionally substituted by 1 to 3 halogen atoms (e.g., a fluorine atom),
    (c) a non-aromatic heterocyclic group (preferably a 3- to 14-membered non-aromatic heterocyclic group, more preferably a 3- to 8-membered monocyclic non-aromatic heterocyclic group) (e.g., oxetanyl),
    (d) a $C_{1-6}$ alkylsulfonyl group (e.g., methylsulfonyl),
    (e) a $C_{1-6}$ alkyl-carbonyl group (e.g., acetyl), and
    (f) a $C_{3-10}$ cycloalkyl-carbonyl group (e.g., cyclopropylcarbonyl),
  (iii) a halogen atom (e.g., a fluorine atom),
  (iv) a $C_{1-6}$ alkylsulfanyl group (e.g., methylsulfanyl),
  (v) a $C_{1-6}$ alkylsulfinyl group (e.g., methylsulfinyl), and
  (vi) a $C_{1-6}$ alkylsulfonyl group (e.g., methylsulfonyl), (4) a $C_{1-6}$ alkoxy group (e.g., methoxy),
(5) an amino group optionally mono- or di-substituted by substituent(s) selected from
　(i) a $C_{1-6}$ alkyl group (e.g., methyl, ethyl),
　(ii) a $C_{1-6}$ alkyl-carbonyl group (e.g., acetyl), and
　(iii) a $C_{1-6}$ alkylsulfonyl group (e.g., methylsulfonyl),
(6) a non-aromatic heterocyclic group (preferably a 3- to 14-membered non-aromatic heterocyclic group, more preferably a 3- to 8-membered monocyclic non-aromatic heterocyclic group) (e.g., morpholinyl),
(7) a carboxy group, or
(8) a carbamoyl group optionally mono- or di-substituted by $C_{1-6}$ alkyl group(s) (e.g., methyl), or
$R^5$ and $R^6$ in combination optionally form
(1) a non-aromatic heterocycle (preferably a 3- to 14-membered non-aromatic heterocycle, more preferably a 3- to 8-membered monocyclic non-aromatic heterocycle) (e.g., tetrahydrofuran), or
(2) a $C_{3-10}$ cycloalkane (e.g., cyclopentane).

Further more preferably, one of $R^5$ and $R^6$ is a hydrogen atom or a $C_{1-6}$ alkyl group (e.g., methyl), and the other is
(1) a hydrogen atom,
(2) a hydroxy group,
(3) a $C_{1-6}$ alkyl group (e.g., methyl) optionally substituted by 1 to 3 substituents selected from
　(i) a hydroxy group,
　(ii) an amino group optionally mono- or di-substituted by substituent(s) selected from
　　(a) a $C_{1-6}$ alkyl group (e.g., methyl, ethyl) optionally substituted by 1 to 3 halogen atoms (e.g., a fluorine atom),
　　(b) a $C_{3-10}$ cycloalkyl group (e.g., cyclopropyl, cyclobutyl) optionally substituted by 1 to 3 halogen atoms (e.g., a fluorine atom),
　　(c) a non-aromatic heterocyclic group (preferably a 3- to 14-membered non-aromatic heterocyclic group, more preferably a 3- to 8-membered monocyclic non-aromatic heterocyclic group) (e.g., oxetanyl),
　　(d) a $C_{1-6}$ alkylsulfonyl group (e.g., methylsulfonyl),
　　(e) a $C_{1-6}$ alkyl-carbonyl group (e.g., acetyl), and
　　(f) a $C_{3-10}$ cycloalkyl-carbonyl group (e.g., cyclopropylcarbonyl),
　(iii) a halogen atom (e.g., a fluorine atom),
　(iv) a $C_{1-6}$ alkylsulfanyl group (e.g., methylsulfanyl),
　(v) a $C_{1-6}$ alkylsulfinyl group (e.g., methylsulfinyl), and
　(vi) a $C_{1-6}$ alkylsulfonyl group (e.g., methylsulfonyl),
(4) a $C_{1-6}$ alkoxy group (e.g., methoxy),
(5) an amino group optionally mono- or di-substituted by substituent(s) selected from
　(i) a $C_{1-6}$ alkyl group (e.g., methyl, ethyl),
　(ii) a $C_{1-6}$ alkyl-carbonyl group (e.g., acetyl), and
　(iii) a $C_{1-6}$ alkylsulfonyl group (e.g., methylsulfonyl),
(6) a non-aromatic heterocyclic group (preferably a 3- to 14-membered non-aromatic heterocyclic group, more preferably a 3- to 8-membered monocyclic non-aromatic heterocyclic group) (e.g., morpholinyl),
(7) a carboxy group, or
(8) a carbamoyl group optionally mono- or di-substituted by $C_{1-6}$ alkyl group(s) (e.g., methyl), or
$R^5$ and $R^6$ in combination optionally form
(1) a non-aromatic heterocycle (preferably a 3- to 14-membered non-aromatic heterocycle, more preferably a 3- to 8-membered monocyclic non-aromatic heterocycle) (e.g., tetrahydrofuran), or
(2) a $C_{3-10}$ cycloalkane (e.g., cyclopentane).

Still more preferably, one of $R^5$ and $R^6$ is a hydrogen atom, and the other is
(1) a hydrogen atom,
(2) a hydroxy group,
(3) a $C_{1-6}$ alkyl group (e.g., methyl) optionally substituted by 1 to 3 substituents selected from
　(i) an amino group optionally mono- or di-substituted by $C_{1-6}$ alkyl group(s) (e.g., methyl), and
　(ii) a hydroxy group, or
(4) an amino group optionally mono- or di-substituted by $C_{1-6}$ alkyl group(s) (e.g., methyl).

Particularly preferably, one of $R^5$ and $R^6$ is a hydrogen atom, and the other is
(1) a hydrogen atom,
(2) a $C_{1-6}$ alkyl group (e.g., methyl) optionally substituted by amino group(s) optionally mono- or di-substituted by $C_{1-6}$ alkyl group(s) (e.g., methyl), or
(3) an amino group optionally mono- or di-substituted by $C_{1-6}$ alkyl group(s) (e.g., methyl).

Especially, $R^5$ and $R^6$ are particularly preferably both hydrogen atoms.

X is $CR^7R^8$, $NR^9$, O or S.
X is preferably $CR^7R^8$, $NR^9$ or O.
X is more preferably $CR^7R^8$ or $NR^9$.
In one embodiment, X is further more preferably $CR^7R^8$.
In another embodiment, X is further more preferably $NR^9$.
$R^7$ and $R^8$ are independently a hydrogen atom or a substituent, or $R^7$ and $R^8$ in combination optionally form an optionally substituted ring.

Examples of the "substituent" for $R^7$ or $R^8$ include those similar to the "substituent" exemplified in the present specification.

In one embodiment, the "substituent" for $R^7$ or $R^8$ is preferably
(1) a cyano group, or
(2) an optionally substituted hydrocarbon group (e.g., a hydrocarbon group optionally having substituent(s) selected from Substituent Group A),
more preferably
(1) a cyano group, or
(2) an optionally substituted $C_{1-6}$ alkyl group (e.g., a $C_{1-6}$ alkyl group optionally having substituent(s) selected from Substituent Group A).

In another embodiment, the "substituent" for $R^7$ or $R^8$ is preferably
(1) a cyano group,
(2) an optionally substituted hydrocarbon group (e.g., a hydrocarbon group optionally having substituent(s) selected from Substituent Group A), or
(3) an optionally substituted hydroxy group,
more preferably
(1) a cyano group,
(2) an optionally substituted $C_{1-6}$ alkyl group (e.g., a $C_{1-6}$ alkyl group optionally having substituent(s) selected from Substituent Group A), or
(3) a hydroxy group.

Examples of the "ring" of the "optionally substituted ring" formed by $R^7$ and $R^8$ include a $C_{3-10}$ cycloalkane, a $C_{3-10}$ cycloalkene and a non-aromatic heterocycle (preferably a 3- to 14-membered non-aromatic heterocycle), and preferable examples thereof include a $C_{3-10}$ cycloalkane and a non-aromatic heterocycle (preferably a 3- to 14-membered non-aromatic heterocycle).

In one embodiment, the "ring" of the "optionally substituted ring" formed by $R^7$ and $R^8$ optionally has 1 to 3 substituents selected from Substituent Group A at substitutable position(s). When the number of the substituents is plural, the respective substituents may be the same or different.

In another embodiment, the "ring" of the "optionally substituted ring" formed by $R^7$ and $R^8$ optionally has 1 to 3 substituents selected from Substituent Group A and a $C_{7-16}$ aralkyl group at substitutable position(s). When the number of the substituents is plural, the respective substituents may be the same or different.

In one embodiment, $R^7$ and $R^8$ are preferably independently a hydrogen atom or a substituent.

$R^7$ and $R^8$ are more preferably independently
(1) a hydrogen atom,
(2) a cyano group, or
(3) an optionally substituted $C_{1-6}$ alkyl group (e.g., a $C_{1-6}$ alkyl group optionally having substituent(s) selected from Substituent Group A).

$R^7$ and $R^8$ are further more preferably independently
(1) a hydrogen atom,
(2) a cyano group, or
(3) a $C_{1-6}$ alkyl group (e.g., methyl, ethyl).

In another embodiment, $R^7$ and $R^8$ are preferably independently
(1) a hydrogen atom,
(2) a cyano group,
(3) an optionally substituted $C_{1-6}$ alkyl group (e.g., a $C_{1-6}$ alkyl group optionally having substituent(s) selected from Substituent Group A), or
(4) a hydroxy group, or
$R^7$ and $R^8$ in combination optionally form
(1) an optionally substituted $C_{3-10}$ cycloalkane (e.g., a $C_{3-10}$ cycloalkane optionally having substituent(s) selected from Substituent Group A), or
(2) an optionally substituted non-aromatic heterocycle (preferably a 3- to 14-membered non-aromatic heterocycle) (e.g., a non-aromatic heterocycle (preferably a 3- to 14-membered non-aromatic heterocycle) optionally having substituent(s) selected from Substituent Group A and a $C_{7-16}$ aralkyl group).

$R^7$ and $R^8$ are more preferably independently
(1) a hydrogen atom,
(2) a cyano group,
(3) a $C_{1-6}$ alkyl group (e.g., methyl, ethyl) optionally substituted by 1 to 3 hydroxy groups, or
(4) a hydroxy group, or
$R^7$ and $R^8$ in combination optionally form
(1) a $C_{3-10}$ cycloalkane (e.g., cyclohexane) optionally substituted by 1 to 3 substituents selected from
  (i) an oxo group, and
  (ii) a hydroxy group, or
(2) a non-aromatic heterocycle (preferably a 3- to 14-membered non-aromatic heterocycle, more preferably a 3- to 8-membered monocyclic non-aromatic heterocycle) (e.g., pyrrolidine, piperidine) optionally substituted by 1 to 3 $C_{7-15}$ aralkyl groups (e.g., benzyl).

$R^7$ and $R^8$ are further more preferably independently
(1) a hydrogen atom, or
(2) a $C_{1-6}$ alkyl group (e.g., methyl).

$R^9$ is a hydrogen atom or a substituent.

Examples of the "substituent" for $R^9$ include those similar to the "substituent" exemplified in the present specification.

In one embodiment, the "substituent" for $R^9$ is preferably an optionally substituted hydrocarbon group (e.g., a hydrocarbon group optionally having substituent(s) selected from Substituent Group A), more preferably an optionally substituted $C_{1-6}$ alkyl group (e.g., a $C_{1-6}$ alkyl group optionally having substituent(s) selected from Substituent Group A).

In another embodiment, the "substituent" for $R^9$ is preferably an optionally substituted hydrocarbon group, more preferably
(1) an optionally substituted $C_{1-6}$ alkyl group (e.g., a $C_{1-6}$ alkyl group optionally having substituent(s) selected from Substituent Group A),
(2) an optionally substituted $C_{2-6}$ alkenyl group (e.g., a $C_{2-6}$ alkenyl group optionally having substituent(s) selected from Substituent Group A), or
(3) an optionally substituted $C_{7-16}$ aralkyl group (e.g., a $C_{7-16}$ aralkyl group optionally having substituent(s) selected from Substituent Group A).

In one embodiment, $R^9$ is preferably an optionally substituted $C_{1-6}$ alkyl group (e.g., a $C_{1-6}$ alkyl group optionally having substituent(s) selected from Substituent Group A).

$R^9$ is more preferably a $C_{1-6}$ alkyl group (e.g., methyl, ethyl) optionally substituted by 1 to 3 substituents selected from
(1) a hydroxy group, and
(2) a $C_{1-6}$ alkoxy group (e.g., methoxy) optionally substituted by 1 to 3 $C_{6-14}$ aryl groups (e.g., phenyl).

In another embodiment, $R^9$ is preferably a hydrogen atom or an optionally substituted $C_{1-6}$ alkyl group (e.g., a $C_{1-6}$ alkyl group optionally having substituent(s) selected from Substituent Group A).

$R^9$ is more preferably
(1) a hydrogen atom, or
(2) a $C_{1-6}$ alkyl group (e.g., methyl, ethyl) optionally substituted by 1 to 3 substituents selected from
  (i) a hydroxy group, and
  (ii) a $C_{1-6}$ alkoxy group (e.g., methoxy) optionally substituted by 1 to 3 $C_{6-14}$ aryl groups (e.g., phenyl).

In yet another embodiment, $R^9$ is preferably
(1) a hydrogen atom,
(2) an optionally substituted $C_{1-6}$ alkyl group (e.g., a $C_{1-6}$ alkyl group optionally having substituent(s) selected from Substituent Group A),
(3) an optionally substituted $C_{2-6}$ alkenyl group (e.g., a $C_{2-6}$ alkenyl group optionally having substituent(s) selected from Substituent Group A), or
(4) an optionally substituted $C_{7-16}$ aralkyl group (e.g., a $C_{7-16}$ aralkyl group optionally having substituent(s) selected from Substituent Group A).

$R^9$ is more preferably
(1) a hydrogen atom, or
(2) a $C_{1-6}$ alkyl group (e.g., methyl, ethyl, propyl, isopropyl) optionally substituted by 1 to 3 substituents selected from
  (i) a hydroxy group,
  (ii) a $C_{1-6}$ alkoxy group (e.g., methoxy) optionally substituted by 1 to 3 $C_{6-14}$ aryl groups (e.g., phenyl), and
  (iii) an amino group optionally mono- or di-substituted by $C_{1-6}$ alkyl group(s) (e.g., methyl),
(3) a $C_{2-6}$ alkenyl group (e.g., allyl), or
(4) a $C_{7-16}$ aralkyl group (e.g., benzyl) optionally substituted by 1 to 3 $C_{1-6}$ alkoxy groups (e.g., methoxy).

$R^9$ is further more preferably
(1) a hydrogen atom, or
(2) a $C_{1-6}$ alkyl group (e.g., methyl, ethyl, propyl, preferably methyl, ethyl) optionally substituted by 1 to 3 hydroxy groups.

Preferable examples of compound (1) include the following compounds:

[Compound A-1]

Compound (I) wherein $R^1$ is an aromatic heterocyclic group (preferably a 5- to 14-membered aromatic heterocyclic group) or a $C_{6-14}$ aryl group, each of which is optionally substituted by 1 to 3 substituents selected from (1) an optionally substituted $C_{1-6}$ alkyl group (e.g., a $C_{1-6}$ alkyl group optionally having substituent(s) selected from Substituent Group A), (2) an optionally substituted $C_{6-14}$ aryl group (e.g., a $C_{6-14}$ aryl group optionally having substituent(s) selected from Substituent Group A), (3) an optionally substituted heterocyclic group (e.g., a heterocyclic group optionally having substituent(s) selected from Substituent Group A (the substituent is optionally further substituted by substituent(s) selected from Substituent Group A)), (4) a $C_{3-10}$ cycloalkylsulfonyl group, (5) a $C_{1-6}$ alkyl-carbonyl group, and (6) an aromatic heterocyclylsulfonyl group (preferably a 5- to 14-membered aromatic heterocyclylsulfonyl group);

$R^2$ is an optionally substituted $C_{1-6}$ alkyl group (e.g., a $C_{1-6}$ alkyl group optionally having substituent(s) selected from Substituent Group A);

$R^3$ and $R^4$ are independently a hydrogen atom or an optionally substituted $C_{1-6}$ alkyl group (e.g., a $C_{1-6}$ alkyl group optionally having substituent(s) selected from Substituent Group A);

$R^5$ and $R^6$ are independently (1) a hydrogen atom, (2) a hydroxy group, (3) an optionally substituted $C_{1-6}$ alkyl group (e.g., a $C_{1-6}$ alkyl group optionally having substituent(s) selected from Substituent Group A), (4) an optionally substituted $C_{1-6}$ alkoxy group (e.g., a $C_{1-6}$ alkoxy group optionally having substituent(s) selected from Substituent Group A), (5) an amino group optionally mono- or di-substituted by substituent(s) selected from (i) an optionally substituted $C_{1-6}$ alkyl group (e.g., a $C_{1-6}$ alkyl group optionally having substituent(s) selected from Substituent Group A), (ii) an optionally substituted $C_{1-6}$ alkyl-carbonyl group (e.g., a $C_{1-6}$ alkyl-carbonyl group optionally having substituent(s) selected from Substituent Group A), and (iii) an optionally substituted $C_{1-6}$ alkylsulfonyl group (e.g., a $C_{1-6}$ alkylsulfonyl group optionally having substituent(s) selected from Substituent Group A), or (6) an optionally substituted non-aromatic heterocyclic group (preferably a 3- to 14-membered non-aromatic heterocyclic group) (e.g., a non-aromatic heterocyclic group (preferably a 3- to 14-membered non-aromatic heterocyclic group) optionally having substituent(s) selected from Substituent Group A);

X is $CR^7R^8$, $NR^9$ or O;

$R^7$ and $R^8$ are independently (1) a hydrogen atom, (2) a cyano group, or (3) an optionally substituted $C_{1-6}$ alkyl group (e.g., a $C_{1-6}$ alkyl group optionally having substituent(s) selected from Substituent Group A); and $R^9$ is an optionally substituted $C_{1-6}$ alkyl group (e.g., a $C_{1-6}$ alkyl group optionally having substituent(s) selected from Substituent Group A).

[Compound A-2]

Compound (I) wherein $R^1$ is an aromatic heterocyclic group (preferably a 5- to 14-membered aromatic heterocyclic group) or a $C_{6-14}$ aryl group, each of which is optionally substituted by 1 to 3 substituents selected from (1) an optionally substituted $C_{1-6}$ alkyl group (e.g., a $C_{1-6}$ alkyl group optionally having substituent(s) selected from Substituent Group A), (2) an optionally substituted $C_{6-14}$ aryl group (e.g., a $C_{6-14}$ aryl group optionally having substituent(s) selected from Substituent Group A), (3) an optionally substituted heterocyclic group (e.g., a heterocyclic group optionally having substituent(s) selected from Substituent Group A (the substituent is optionally further substituted by substituent(s) selected from Substituent Group A)), (4) a $C_{3-10}$ cycloalkylsulfonyl group, (5) a $C_{1-6}$ alkyl-carbonyl group, and (6) an aromatic heterocyclylsulfonyl group (preferably a 5- to 14-membered aromatic heterocyclylsulfonyl group);

$R^2$ is an optionally substituted $C_{1-6}$ alkyl group (e.g., a $C_{1-6}$ alkyl group optionally having substituent(s) selected from Substituent Group A);

$R^3$ and $R^4$ are independently a hydrogen atom or an optionally substituted $C_{1-6}$ alkyl group (e.g., a $C_{1-6}$ alkyl group optionally having substituent(s) selected from Substituent Group A);

$R^5$ and $R^6$ are independently (1) a hydrogen atom, (2) a hydroxy group, (3) an optionally substituted $C_{1-6}$ alkyl group (e.g., a $C_{1-6}$ alkyl group optionally having substituent(s) selected from Substituent Group A), (4) an optionally substituted $C_{1-6}$ alkoxy group (e.g., a $C_{1-6}$ alkoxy group optionally having substituent(s) selected from Substituent Group A), (5) an amino group optionally mono- or di-substituted by substituent(s) selected from (i) an optionally substituted $C_{1-6}$ alkyl group (e.g., a $C_{1-6}$ alkyl group optionally having substituent(s) selected from Substituent Group A), (ii) an optionally substituted $C_{1-6}$ alkyl-carbonyl group (e.g., a $C_{1-6}$ alkyl-carbonyl group optionally having substituent(s) selected from Substituent Group A), and (iii) an optionally substituted $C_{1-6}$ alkylsulfonyl group (e.g., a $C_{1-6}$ alkylsulfonyl group optionally having substituent(s) selected from Substituent Group A), or (6) an optionally substituted non-aromatic heterocyclic group (preferably a 3- to 14-membered non-aromatic heterocyclic group) (e.g., a non-aromatic heterocyclic group (preferably a 3- to 14-membered non-aromatic heterocyclic group) optionally having substituent(s) selected from Substituent Group A);

X is $CR^7R^6$, $NR^9$ or O;

$R^7$ and $R^8$ are independently (1) a hydrogen atom, (2) a cyano group, or (3) an optionally substituted $C_{1-6}$ alkyl group (e.g., a $C_{1-6}$ alkyl group optionally having substituent(s) selected from Substituent Group A); and $R^9$ is a hydrogen atom or an optionally substituted $C_{1-6}$ alkyl group (e.g., a $C_{1-6}$ alkyl group optionally having substituent(s) selected from Substituent Group A).

[Compound A-3]
Compound (I) wherein
$R^1$ is an aromatic heterocyclic group (preferably a 5- to 14-membered aromatic heterocyclic group) or a $C_{6-14}$ aryl group, each of which is optionally substituted by 1 to 3 substituents selected from
(1) a halogen atom,
(2) an optionally substituted $C_{1-6}$ alkyl group (e.g., a $C_{1-6}$ alkyl group optionally having substituent(s) selected from Substituent Group A),
(3) an optionally substituted $C_{6-14}$ aryl group (e.g., a $C_{6-14}$ aryl group optionally having substituent(s) selected from Substituent Group A),
(4) an optionally substituted heterocyclic group (e.g., a heterocyclic group optionally having substituent(s) selected from Substituent Group A and a thioxo group (the substituent is optionally further substituted by substituent(s) selected from Substituent Group A, an azido group and a mono- or di-$C_{1-6}$ alkylamino group (the alkyl is substituted by substituent(s) selected from a $C_{3-10}$ cycloalkyl group and a halogen atom))),
(5) a $C_{3-10}$ cycloalkylsulfonyl group,
(6) a $C_{1-6}$ alkyl-carbonyl group,
(7) an aromatic heterocyclylsulfonyl group (preferably a 5- to 14-membered aromatic heterocyclylsulfonyl group), and
(8) a halogenated sulfanyl group;
$R^2$ is
(1) an optionally substituted $C_{1-6}$ alkyl group (e.g., a $C_{1-6}$ alkyl group optionally having substituent(s) selected from Substituent Group A, and a non-aromatic heterocyclic group (preferably a 3- to 14-membered non-aromatic heterocyclic group) having oxo group(s)),
(2) an optionally substituted $C_{3-10}$ cycloalkyl group (e.g., a $C_{3-10}$ cycloalkyl group optionally having substituent(s) selected from Substituent Group A), or
(3) an optionally substituted non-aromatic heterocyclic group (preferably a 3- to 14-membered non-aromatic heterocyclic group) (e.g., a non-aromatic heterocyclic group (preferably a 3- to 14-membered non-aromatic heterocyclic group) optionally having substituent(s) selected from Substituent Group A);
$R^3$ and $R^4$ are independently a hydrogen atom or an optionally substituted $C_{1-6}$ alkyl group (e.g., a $C_{1-6}$ alkyl group optionally having substituent(s) selected from Substituent Group A);
$R^5$ and $R^6$ are independently
(1) a hydrogen atom,
(2) a hydroxy group,
(3) an optionally substituted $C_{1-6}$ alkyl group (e.g., a $C_{1-6}$ alkyl group optionally having substituent(s) selected from (1) Substituent Group A, and (2) an amino group mono- or di-substituted by substituent(s) selected from (a) a $C_{1-5}$ alkyl group, (b) a $C_{3-10}$ cycloalkyl group optionally substituted by 1 to 3 halogen atoms, (c) a non-aromatic heterocyclic group (preferably a 3- to 14-membered non-aromatic heterocyclic group), (d) a $C_{1-6}$ alkylsulfonyl group, and (e) a $C_{3-10}$ cycloalkyl-carbonyl group),
(4) an optionally substituted $C_{1-6}$ alkoxy group (e.g., a $C_{1-6}$ alkoxy group optionally having substituent(s) selected from Substituent Group A),
(5) an amino group optionally mono- or di-substituted by substituent(s) selected from
(i) an optionally substituted $C_{1-6}$ alkyl group (e.g., a $C_{1-6}$ alkyl group optionally having substituent(s) selected from Substituent Group A),
(ii) an optionally substituted $C_{1-6}$ alkyl-carbonyl group (e.g., a $C_{1-6}$ alkyl-carbonyl group optionally having substituent(s) selected from Substituent Group A), and
(iii) an optionally substituted $C_{1-6}$ alkylsulfonyl group (e.g., a $C_{1-6}$ alkylsulfonyl group optionally having substituent(s) selected from Substituent Group A),
(6) an optionally substituted non-aromatic heterocyclic group (preferably a 3- to 14-membered non-aromatic heterocyclic group) (e.g., a non-aromatic heterocyclic group (preferably a 3- to 14-membered non-aromatic heterocyclic group) optionally having substituent(s) selected from Substituent Group A),
(7) a carboxy group, or
(8) a carbamoyl group optionally mono- or di-substituted by $C_{1-6}$ alkyl group(s), or
$R^5$ and $R^6$ in combination optionally form
(1) an optionally substituted non-aromatic heterocycle (preferably a 3- to 14-membered non-aromatic heterocycle) (e.g., a non-aromatic heterocycle (preferably a 3- to 14-membered non-aromatic heterocycle) optionally having substituent(s) selected from Substituent Group A), or
(2) an optionally substituted $C_{3-10}$ cycloalkane (e.g., a $C_{3-10}$ cycloalkane optionally having substituent(s) selected from Substituent Group A);
X is $CR^7R^8$, $NR^9$, O or S;
$R^7$ and $R^8$ are independently
(1) a hydrogen atom,
(2) a cyano group,
(3) an optionally substituted $C_{1-6}$ alkyl group (e.g., a $C_{1-6}$ alkyl group optionally having substituent(s) selected from Substituent Group A), or
(4) a hydroxy group, or
$R^7$ and $R^8$ in combination optionally form
(1) an optionally substituted $C_{3-10}$ cycloalkane (e.g., a $C_{3-10}$ cycloalkane optionally having substituent(s) selected from Substituent Group A), or
(2) an optionally substituted non-aromatic heterocycle (preferably a 3- to 14-membered non-aromatic heterocycle) (e.g., a non-aromatic heterocycle (preferably a 3- to 14-membered non-aromatic heterocycle) optionally having substituent(s) selected from Substituent Group A and a $C_{7-16}$ aralkyl group); and
$R^9$ is
(1) a hydrogen atom,
(2) an optionally substituted $C_{1-6}$ alkyl group (e.g., a $C_{1-6}$ alkyl group optionally having substituent(s) selected from Substituent Group A),
(3) an optionally substituted $C_{2-6}$ alkenyl group (e.g., a $C_{2-6}$ alkenyl group optionally having substituent(s) selected from Substituent Group A), or
(4) an optionally substituted $C_{7-16}$ aralkyl group (e.g., a $C_{7-16}$ aralkyl group optionally having substituent(s) selected from Substituent Group A).
[Compound B-1]
Compound (I) wherein
$R^1$ is
(1) an aromatic heterocyclic group (preferably a 5- to 14-membered aromatic heterocyclic group, more preferably a 5- to 6-membered monocyclic aromatic heterocyclic group, a 8- to 14-membered fused polycyclic aromatic heterocyclic group) (e.g., oxazolyl, thiazolyl, thienyl, pyrazolyl, pyridyl, imidazopyridyl (e.g., imidazo[1,5-a]pyridyl), imidazopyridazinyl (e.g., imidazo[1,2-b]pyridazinyl), pyrazolopyrimidinyl (e.g., pyrazolo[1,5-a]pyrimidinyl)) optionally substituted by 1 to 3 substituents selected from
(i) a $C_{1-6}$ alkyl group (e.g., methyl, ethyl, isopropyl) optionally substituted by 1 to 3 substituents selected from
(a) a halogen atom (e.g., a fluorine atom), and
(b) a hydroxy group, (ii) a $C_{6-14}$ aryl group (e.g., phenyl) optionally substituted by 1 to 3 halogen atoms (e.g., a fluorine atom),
(iii) an aromatic heterocyclic group (preferably a 5- to 14-membered aromatic heterocyclic group, more preferably a 5- to 6-membered monocyclic aromatic heterocyclic group) (e.g., pyridyl, thienyl) optionally substituted by amino group(s) optionally mono- or di-substituted by $C_{1-6}$ alkyl group(s) (e.g., ethyl) optionally substituted by 1 to 3 halogen atoms (e.g., a fluorine atom),
(iv) a non-aromatic heterocyclic group (preferably a 3- to 14-membered non-aromatic heterocyclic group, more preferably a 3- to 8-membered monocyclic non-aromatic heterocyclic group) (e.g., morpholinyl) optionally substituted by 1 to 3 $C_{1-6}$ alkyl groups (e.g., methyl),
(v) a $C_{3-10}$ cycloalkylsulfonyl group (e.g., cyclopentylsulfonyl), and
(vi) a $C_{1-6}$ alkyl-carbonyl group (e.g., acetyl), or
(2) a $C_{6-14}$ aryl group (e.g., phenyl) optionally substituted by 1 to 3 substituents selected from
(i) a $C_{1-6}$ alkyl group (e.g., methyl),
(ii) a $C_{3-10}$ cycloalkylsulfonyl group (e.g., cyclopentylsulfonyl), and
(iii) an aromatic heterocyclylsulfonyl group (preferably a 5- to 14-membered aromatic heterocyclylsulfonyl group, more preferably a 5- to 6-membered monocyclic aromatic heterocyclylsulfonyl group) (e.g., thiazolylsulfonyl);
$R^2$ is a $C_{1-6}$ alkyl group (e.g., methyl);
$R^3$ and $R^4$ are independently a hydrogen atom or a $C_{1-6}$ alkyl group (e.g., methyl);
$R^5$ and $R^6$ are independently
(1) a hydrogen atom,
(2) a hydroxy group,
(3) a $C_{1-6}$ alkyl group (e.g., methyl) optionally substituted by 1 to 3 substituents selected from
(i) a hydroxy group, and
(ii) an amino group optionally mono- or di-substituted by $C_{1-6}$ alkyl group(s) (e.g., methyl, ethyl),
(4) a $C_{1-6}$ alkoxy group (e.g., methoxy),
(5) an amino group optionally mono- or di-substituted by substituent(s) selected from
(i) a $C_{1-6}$ alkyl group (e.g., methyl, ethyl),
(ii) a $C_{1-6}$ alkyl-carbonyl group (e.g., acetyl), and
(iii) a $C_{1-6}$ alkylsulfonyl group (e.g., methylsulfonyl), or
(6) a non-aromatic heterocyclic group (preferably a 3- to 14-membered non-aromatic heterocyclic group, more preferably a 3- to 8-membered monocyclic non-aromatic heterocyclic group) (e.g., morpholinyl);
X is $CR^7R^8$, $NR^9$ or O;
$R^7$ and $R^8$ are independently
(1) a hydrogen atom,
(2) a cyano group, or
(3) a $C_{1-6}$ alkyl group (e.g., methyl, ethyl); and
$R^9$ is a $C_{1-6}$ alkyl group (e.g., methyl, ethyl) optionally substituted by 1 to 3 substituents selected from
(1) a hydroxy group, and
(2) a $C_{1-6}$ alkoxy group (e.g., methoxy) optionally substituted by 1 to 3 $C_{6-14}$ aryl groups (e.g., phenyl).

[Compound B-2]
Compound (I) wherein
$R^1$ is
(1) an aromatic heterocyclic group (preferably a 5- to 14-membered aromatic heterocyclic group, more preferably a 5- to 6-membered monocyclic aromatic heterocyclic group, a 8- to 14-membered fused polycyclic aromatic heterocyclic group) (e.g., oxazolyl, thiazolyl, thienyl, pyrazolyl, pyridyl, imidazopyridyl (e.g., imidazo[1,5-a]pyridyl), imidazopyridazinyl (e.g., imidazo[1,2-b]pyridazinyl), pyrazolopyrimidinyl (e.g., pyrazolo[1,5-a]pyrimidinyl)) optionally substituted by 1 to 3 substituents selected from
(i) a $C_{1-6}$ alkyl group (e.g., methyl, ethyl, isopropyl) optionally substituted by 1 to 3 substituents selected from
(a) a halogen atom (e.g., a fluorine atom), and
(b) a hydroxy group,
(ii) a $C_{6-14}$ aryl group (e.g., phenyl) optionally substituted by 1 to 3 halogen atoms (e.g., a fluorine atom),
(iii) an aromatic heterocyclic group (preferably a 5- to 14-membered aromatic heterocyclic group, more preferably a 5- to 6-membered monocyclic aromatic heterocyclic group) (e.g., pyridyl, thienyl) optionally substituted by amino group(s) optionally mono- or di-substituted by $C_{1-6}$ alkyl group(s) (e.g., methyl, ethyl) optionally substituted by 1 to 3 substituents selected from
(a) a halogen atom (e.g., a fluorine atom), and
(b) a $C_{3-10}$ cycloalkyl group (e.g., cyclopropyl),
(iv) a non-aromatic heterocyclic group (preferably a 3- to 14-membered non-aromatic heterocyclic group, more preferably a 3- to 8-membered monocyclic non-aromatic heterocyclic group) (e.g., morpholinyl) optionally substituted by 1 to 3 $C_{1-5}$ alkyl groups (e.g., methyl),
(v) a $C_{3-10}$ cycloalkylsulfonyl group (e.g., cyclopentylsulfonyl), and
(vi) a $C_{1-6}$ alkyl-carbonyl group (e.g., acetyl), or
(2) a $C_{6-14}$ aryl group (e.g., phenyl) optionally substituted by 1 to 3 substituents selected from
(i) a $C_{1-6}$ alkyl group (e.g., methyl),
(ii) a $C_{3-10}$ cycloalkylsulfonyl group (e.g., cyclopentylsulfonyl), and
(iii) an aromatic heterocyclylsulfonyl group (preferably a 5- to 14-membered aromatic heterocyclylsulfonyl group, more preferably a 5- to 6-membered monocyclic aromatic heterocyclylsulfonyl group) (e.g., thiazolylsulfonyl);
$R^2$ is a $C_{1-6}$ alkyl group (e.g., methyl);
$R^3$ and $R^4$ are independently a hydrogen atom or a $C_{1-6}$ alkyl group (e.g., methyl);
$R^5$ and $R^6$ are independently
(1) a hydrogen atom,
(2) a hydroxy group,
(3) a $C_{1-6}$ alkyl group (e.g., methyl) optionally substituted by 1 to 3 substituents selected from
(i) a hydroxy group, and
(ii) an amino group optionally mono- or di-substituted by $C_{1-6}$ alkyl group(s) (e.g., methyl, ethyl),
(4) a $C_{1-6}$ alkoxy group (e.g., methoxy),
(5) an amino group optionally mono- or di-substituted by substituent(s) selected from
(i) a $C_{1-6}$ alkyl group (e.g., methyl, ethyl),
(ii) a $C_{1-6}$ alkyl-carbonyl group (e.g., acetyl), and
(iii) a $C_{1-6}$ alkylsulfonyl group (e.g., methylsulfonyl), or
(6) a non-aromatic heterocyclic group (preferably a 3- to 14-membered non-aromatic heterocyclic group, more preferably a 3- to 8-membered monocyclic non-aromatic heterocyclic group) (e.g., morpholinyl);
X is $CR^7R^8$, $NR^9$ or O;
$R^7$ and $R^8$ are independently
(1) a hydrogen atom,
(2) a cyano group, or
(3) a $C_{1-6}$ alkyl group (e.g., methyl, ethyl); and
$R^9$ is
(1) a hydrogen atom, or
(2) a $C_{1-6}$ alkyl group (e.g., methyl, ethyl) optionally substituted by 1 to 3 substituents selected from
(i) a hydroxy group, and
(ii) a $C_{1-6}$ alkoxy group (e.g., methoxy) optionally substituted by 1 to 3 $C_{6-14}$ aryl groups (e.g., phenyl).

[Compound B-3]
Compound (I) wherein
$R^1$ is an aromatic heterocyclic group (preferably a 5- to 14-membered aromatic heterocyclic group, more preferably a 5- to 6-membered monocyclic aromatic heterocyclic group, a 8- to 14-membered fused polycyclic aromatic heterocyclic group) (e.g., oxazolyl, thiazolyl, thienyl, pyrazolyl, pyridyl, imidazopyridyl (e.g., imidazo[1,5-a]pyridyl), imidazopyridazinyl (e.g., imidazo[1,2-b]pyridazinyl), pyrazolopyrimidinyl (e.g., pyrazolo[1,5-a]pyrimidinyl)), or a $C_{6-14}$ aryl group (e.g., phenyl), each of which is optionally substituted by 1 to 3 substituents selected from
  (1) a halogen atom (e.g., a fluorine atom),
  (2) a $C_{1-6}$ alkyl group (e.g., methyl, ethyl, isopropyl) optionally substituted by 1 to 3 substituents selected from
    (i) a halogen atom (e.g., a fluorine atom), and
    (ii) a hydroxy group,
  (3) a $C_{6-14}$ aryl group (e.g., phenyl) optionally substituted by 1 to 3 halogen atoms (e.g., a fluorine atom),
  (4) an aromatic heterocyclic group (preferably a 5- to 14-membered aromatic heterocyclic group, more preferably a 5- to 6-membered monocyclic aromatic heterocyclic group, a 8- to 14-membered fused polycyclic aromatic heterocyclic group) (e.g., pyridyl, thienyl, pyrimidinyl, imidazolyl, pyrazolyl, tetrazolyl, benzimidazolyl (e.g., 1H-benzimidazolyl), thiazolyl) optionally substituted by 1 to 3 substituents selected from
    (i) an amino group optionally mono- or di-substituted by $C_{1-6}$ alkyl group(s) (e.g., methyl, ethyl) optionally substituted by 1 to 3 substituents selected from
      (a) a halogen atom (e.g., a fluorine atom), and
      (b) a $C_{3-10}$ cycloalkyl group (e.g., cyclopropyl),
    (ii) a halogen atom (e.g., a chlorine atom),
    (iii) a $C_{1-6}$ alkoxy group (e.g., methoxy),
    (iv) a cyano group,
    (v) a $C_{1-6}$ alkyl group (e.g., methyl, ethyl) optionally substituted by 1 to 3 substituents selected from
      (a) an azido group,
      (b) an amino group optionally mono- or di-substituted by $C_{1-6}$ alkyl group(s) (e.g., methyl, ethyl) optionally substituted by 1 to 3 substituents selected from a halogen atom (e.g., a fluorine atom) and a $C_{3-10}$ cycloalkyl group (e.g., cyclopropyl),
      (c) a hydroxy group, and
      (d) a halogen atom (e.g., a fluorine atom),
    (vi) a formyl group,
    (vii) a carboxy group,
    (viii) a carbamoyl group,
    (ix) a $C_{3-10}$ cycloalkyl group (e.g., cyclopropyl), and
    (x) a non-aromatic heterocyclic group (preferably a 3- to 14-membered non-aromatic heterocyclic group, more preferably a 3- to 8-membered monocyclic non-aromatic heterocyclic group) (e.g., dioxolanyl (e.g., 1,3-dioxolanyl)),
  (5) a non-aromatic heterocyclic group (preferably a 3- to 14-membered non-aromatic heterocyclic group, more preferably a 3- to 8-membered monocyclic non-aromatic heterocyclic group, a 9- to 14-membered fused polycyclic non-aromatic heterocyclic group, a 7- to 14-membered spiro heterocyclic group) (e.g., morpholinyl, dihydropyranyl (e.g., 3,6-dihydro-2H-pyranyl), tetrahydropyranyl, dihydropyridyl (e.g., 1,2-dihydropyridyl), dihydrobenzofuranyl (e.g., 2,3-dihydrobenzofuranyl), imidazolidinyl, pyrrolidinyl, dihydroisoxazolyl (e.g., 4,5-dihydroisoxazolyl), dihydropyrrolopyrazolyl (e.g., 5,6-dihydropyrrolo[3,4-c] pyrazolyl), piperazinyl, triazaspirononyl (e.g., 1,3,7-triazaspiro[4.4]nonyl), thiadiazaspirononyl (e.g., 7-thia-1,3-diazaspiro[4.4]nonyl), dioxidothiadiazaspirononyl (e.g., 7,7-dioxido-7-thia-1,3-diazaspiro[4.4]nonyl)) optionally substituted by 1 to 3 substituents selected from
    (i) a $C_{1-6}$ alkyl group (e.g., methyl, ethyl) optionally substituted by 1 to 3 substituents selected from
      (a) a hydroxy group,
      (b) an amino group optionally mono- or di-substituted by $C_{1-6}$ alkyl group(s) (e.g., methyl),
      (c) a cyano group, and
      (d) a $C_{6-14}$ aryl group (e.g., phenyl),
    (ii) an oxo group,
    (iii) a hydroxy group,
    (iv) a carbamoyl group, and
    (v) a thioxo group,
  (6) a $C_{3-10}$ cycloalkylsulfonyl group (e.g., cyclopentylsulfonyl),
  (7) a $C_{1-6}$ alkyl-carbonyl group (e.g., acetyl),
  (8) an aromatic heterocyclylsulfonyl group (preferably a 5- to 14-membered aromatic heterocyclylsulfonyl group, more preferably a 5- to 6-membered monocyclic aromatic heterocyclylsulfonyl group) (e.g., thiazolylsulfonyl), and
  (9) a halogenated thio group (e.g., pentafluorothio);
$R^2$ is
  (1) a $C_{1-6}$ alkyl group (e.g., methyl, ethyl) optionally substituted by 1 to 3 substituents selected from
    (i) a $C_{1-6}$ alkoxy-carbonyl group (e.g., methoxycarbonyl),
    (ii) a $C_{1-6}$ alkylsulfonyl group (e.g., methylsulfonyl),
    (iii) a carbamoyl group,
    (iv) a cyano group,
    (v) a non-aromatic heterocyclic group (preferably a 3- to 14-membered non-aromatic heterocyclic group, more preferably a 3- to 8-membered monocyclic non-aromatic heterocyclic group) (e.g., pyrrolidinyl, tetrahydrofuryl, oxetanyl) optionally substituted by 1 to 3 oxo groups, and
    (vi) a halogen atom (e.g., a fluorine atom),
  (2) a $C_{3-10}$ cycloalkyl group (e.g., cyclopentyl) optionally substituted by 1 to 3 hydroxy groups, or
  (3) a non-aromatic heterocyclic group (preferably a 3- to 14-membered non-aromatic heterocyclic group, more preferably a 3- to 8-membered monocyclic non-aromatic heterocyclic group) (e.g., oxetanyl);
$R^3$ and $R^4$ are independently
  (1) a hydrogen atom, or
  (2) a $C_{1-6}$ alkyl group (e.g., methyl) optionally substituted by 1 to 3 substituents selected from an amino group optionally mono- or di-substituted by $C_{1-6}$ alkyl group(s) (e.g., methyl);
$R^5$ and $R^6$ are independently
  (1) a hydrogen atom,
  (2) a hydroxy group,
  (3) a $C_{1-6}$ alkyl group (e.g., methyl) optionally substituted by 1 to 3 substituents selected from
    (i) a hydroxy group,
    (ii) an amino group optionally mono- or di-substituted by substituent(s) selected from
      (a) a $C_{1-6}$ alkyl group (e.g., methyl, ethyl) optionally substituted by 1 to 3 halogen atoms (e.g., a fluorine atom),
      (b) a $C_{3-10}$ cycloalkyl group (e.g., cyclopropyl, cyclobutyl) optionally substituted by 1 to 3 halogen atoms (e.g., a fluorine atom),
      (c) a non-aromatic heterocyclic group (preferably a 3- to 14-membered non-aromatic heterocyclic group, more preferably a 3- to 8-membered monocyclic non-aromatic heterocyclic group) (e.g., oxetanyl),
  (d) a $C_{1-6}$ alkylsulfonyl group (e.g., methylsulfonyl),
  (e) a $C_{1-6}$ alkyl-carbonyl group (e.g., acetyl), and
  (f) a $C_{3-10}$ cycloalkyl-carbonyl group (e.g., cyclopropylcarbonyl),
  (iii) a halogen atom (e.g., a fluorine atom),
  (iv) a $C_{1-6}$ alkylsulfanyl group (e.g., methylsulfanyl),
  (v) a $C_{1-6}$ alkylsulfinyl group (e.g., methylsulfinyl), and
  (vi) a $C_{1-6}$ alkylsulfonyl group (e.g., methylsulfonyl),
(4) a $C_{1-6}$ alkoxy group (e.g., methoxy),
(5) an amino group optionally mono- or di-substituted by substituent(s) selected from
  (i) a $C_{1-6}$ alkyl group (e.g., methyl, ethyl),
  (ii) a $C_{1-6}$ alkyl-carbonyl group (e.g., acetyl), and
  (iii) a $C_{1-6}$ alkylsulfonyl group (e.g., methylsulfonyl),
(6) a non-aromatic heterocyclic group (preferably a 3- to 14-membered non-aromatic heterocyclic group, more preferably a 3- to 8-membered monocyclic non-aromatic heterocyclic group) (e.g., morpholinyl),
(7) a carboxy group, or
(8) a carbamoyl group optionally mono- or di-substituted by $C_{1-6}$ alkyl group(s) (e.g., methyl), or
$R^5$ and $R^6$ in combination optionally form
(1) a non-aromatic heterocycle (preferably a 3- to 14-membered non-aromatic heterocycle, more preferably a 3- to 8-membered monocyclic non-aromatic heterocycle) (e.g., tetrahydrofuran), or
(2) a $C_{3-10}$ cycloalkane (e.g., cyclopentane);
X is $CR^7R^9$, $NR^9$, O or S;
$R^7$ and $R^8$ are independently
(1) a hydrogen atom,
(2) a cyano group,
(3) a 01-6 alkyl group (e.g., methyl, ethyl) optionally substituted by 1 to 3 hydroxy groups, or
(4) a hydroxy group, or
$R^7$ and $R^8$ in combination optionally form
(1) a $C_{3-10}$ cycloalkane (e.g., cyclohexane) optionally substituted by 1 to 3 substituents selected from
  (i) an oxo group, and
  (ii) a hydroxy group, or
(2) a non-aromatic heterocycle (preferably a 3- to 14-membered non-aromatic heterocycle, more preferably a 3- to 8-membered monocyclic non-aromatic heterocycle) (e.g., pyrrolidine, piperidine) optionally substituted by 1 to 3 $C_{7-16}$ aralkyl groups (e.g., benzyl); and
$R^9$ is
(1) a hydrogen atom, or
(2) a $C_{1-6}$ alkyl group (e.g., methyl, ethyl, propyl, isopropyl) optionally substituted by 1 to 3 substituents selected from
  (i) a hydroxy group,
  (ii) a $C_{1-6}$ alkoxy group (e.g., methoxy) optionally substituted by 1 to 3 $C_{6-14}$ aryl groups (e.g., phenyl), and
  (iii) an amino group optionally mono- or di-substituted by $C_{1-6}$ alkyl group(s) (e.g., methyl),
(3) a $C_{2-6}$ alkenyl group (e.g., allyl), or
(4) a $C_{7-16}$ aralkyl group (e.g., benzyl) optionally substituted by 1 to 3 $C_{1-6}$ alkoxy groups (e.g., methoxy).
[Compound B-4]
  Compound (I) wherein
$R^1$ is
(1) an aromatic heterocyclic group (preferably a 5- to 14 membered aromatic heterocyclic group, more preferably a 5- to 6-membered monocyclic aromatic heterocyclic group, a 8- to 14-membered fused polycyclic aromatic heterocyclic group) (e.g., oxazolyl, thiazolyl, thienyl, pyrazolyl, pyridyl, imidazopyridyl (e.g., imidazo[1,5-a]pyridyl), imidazopyridazinyl (e.g., imidazo[1,2-b]pyridazinyl), pyrazolopyrimidinyl (e.g., pyrazolo[1,5-a]pyrimidinyl)) optionally substituted by 1 to 3 substituents selected from
  (i) a $C_{1-6}$ alkyl group (e.g., methyl, ethyl, isopropyl) optionally substituted by 1 to 3 substituents selected from
    (a) a halogen atom (e.g., a fluorine atom), and
    (b) a hydroxy group,
  (ii) a $C_{6-14}$ aryl group (e.g., phenyl) optionally substituted by 1 to 3 halogen atoms (e.g., a fluorine atom),
  (iii) an aromatic heterocyclic group (preferably a 5- to 14-membered aromatic heterocyclic group, more preferably a 5- to 6-membered monocyclic aromatic heterocyclic group) (e.g., pyridyl, thienyl, pyrimidinyl, pyrazolyl, thiazolyl, imidazolyl) optionally substituted by 1 to 3 substituents selected from
    (a) an amino group optionally mono- or di-substituted by $C_{1-6}$ alkyl group(s) (e.g., methyl, ethyl) optionally substituted by 1 to 3 substituents selected from
      (I) a halogen atom (e.g., a fluorine atom), and
      (II) a $C_{3-10}$ cycloalkyl group (e.g., cyclopropyl),
    (b) a halogen atom (e.g., a chlorine atom),
    (c) a $C_{1-6}$ alkoxy group (e.g., methoxy),
    (d) a cyano group,
    (e) a $C_{1-6}$ alkyl group (e.g., methyl, ethyl) optionally substituted by 1 to 3 substituents selected from
      (I) an azido group,
      (II) an amino group optionally mono- or di-substituted by $C_{1-6}$ alkyl group(s) (e.g., methyl, ethyl) optionally substituted by 1 to 3 substituents selected from a halogen atom (e.g., a fluorine atom) and a $C_{3-10}$ cycloalkyl group (e.g., cyclopropyl),
      (III) a hydroxy group, and
      (IV) a halogen atom (e.g., a fluorine atom),
    (f) a formyl group,
    (g) a carboxy group,
    (h) a carbamoyl group,
    (i) a $C_{3-10}$ cycloalkyl group (e.g., cyclopropyl), and
    (j) a non-aromatic heterocyclic group (preferably a 3- to 14-membered non-aromatic heterocyclic group, more preferably a 3- to 8-membered monocyclic non-aromatic heterocyclic group) (e.g., dioxolanyl (e.g., 1,3-dioxolanyl)),
  (iv) a non-aromatic heterocyclic group (preferably a 3- to 14-membered non-aromatic heterocyclic group, more preferably a 3- to 8-membered monocyclic non-aromatic heterocyclic group, a 9- to 14-membered fused polycyclic non-aromatic heterocyclic group, a 7- to 14-membered spiro heterocyclic group) (e.g., morpholinyl, dihydropyranyl (e.g., 3,6-dihydro-2H-pyranyl), tetrahydropyranyl, dihydropyridyl (e.g., 1,2-dihydropyridyl), dihydrobenzofuranyl (e.g., 2,3-dihydrobenzofuranyl), imidazolidinyl, pyrrolidinyl, dihydroisoxazolyl (e.g., 4,5-dihydroisoxazolyl), dihydropyrrolopyrazolyl (e.g., 5,6-dihydropyrrolo[3,4-c]pyrazolyl), piperazinyl, triazaspirononyl (e.g., 1,3,7-triazaspiro[4.4]nonyl), thiadiazaspirononyl (e.g., 7-thia-1,3-diazaspiro[4.4]nonyl), dioxidothiadiazaspirononyl (e.g., 7,7-dioxido-7-thia-1,3-diazaspiro[4.4]nonyl)) optionally substituted by 1 to 3 substituents selected from
    (a) a $C_{1-6}$ alkyl group (e.g., methyl, ethyl) optionally substituted by 1 to 3 substituents selected from
      (I) a hydroxy group,
      (II) an amino group optionally mono- or di-substituted by $C_{1-6}$ alkyl group(s) (e.g., methyl),
      (III) a cyano group, and
      (IV) a $C_{6-14}$ aryl group (e.g., phenyl),
    (b) an oxo group,
    (c) a hydroxy group,
    (d) a carbamoyl group, and
    (e) a thioxo group, (v) a $C_{3-10}$ cycloalkylsulfonyl group (e.g., cyclopentylsulfonyl), and
(vi) a $C_{1-6}$ alkyl-carbonyl group (e.g., acetyl), or
(2) a $C_{6-14}$ aryl group (e.g., phenyl) optionally substituted by 1 to 3 substituents selected from
  (i) a halogen atom (e.g., a fluorine atom),
  (ii) a $C_{1-6}$ alkyl group (e.g., methyl),
  (iii) an aromatic heterocyclic group (preferably a 5- to 14-membered aromatic heterocyclic group, more preferably a 5- to 6-membered monocyclic aromatic heterocyclic group, a 8- to 14-membered fused polycyclic aromatic heterocyclic group) (e.g., imidazolyl, pyrazolyl, tetrazolyl, benzimidazolyl (e.g., 1H-benzimidazolyl)),
  (iv) a $C_{3-10}$ cycloalkylsulfonyl group (e.g., cyclopentylsulfonyl),
  (v) an aromatic heterocyclylsulfonyl group (preferably a 5- to 14-membered aromatic heterocyclylsulfonyl group, more preferably a 5- to 6-membered monocyclic aromatic heterocyclylsulfonyl group) (e.g., thiazolylsulfonyl),
  (vi) a halogenated thio group (e.g., pentafluorothio), and
  (vii) a non-aromatic heterocyclic group (preferably a 3- to 14-membered non-aromatic heterocyclic group, more preferably a 3- to 8-membered monocyclic non-aromatic heterocyclic group, a 7- to 14-membered spiro heterocyclic group) (e.g., imidazolidinyl, triazaspirononyl (e.g., 1,3,7-triazaspiro[4.4]nonyl)) optionally substituted by 1 to 3 substituents selected from
    (a) a $C_{1-6}$ alkyl group (e.g., methyl) optionally substituted by 1 to 3 amino groups, and
    (b) an oxo group;
$R^2$ is
(1) a $C_{1-6}$ alkyl group (e.g., methyl, ethyl) optionally substituted by 1 to 3 substituents selected from
  (i) a $C_{1-6}$ alkoxy-carbonyl group (e.g., methoxycarbonyl),
  (ii) a $C_{1-6}$ alkylsulfonyl group (e.g., methylsulfonyl),
  (iii) a carbamoyl group,
  (iv) a cyano group,
  (v) a non-aromatic heterocyclic group (preferably a 3- to 14-membered non-aromatic heterocyclic group, more preferably a 3- to 8-membered monocyclic non-aromatic heterocyclic group) (e.g., pyrrolidinyl, tetrahydrofuryl, oxetanyl) optionally substituted by 1 to 3 oxo groups, and
  (vi) a halogen atom (e.g., a fluorine atom),
(2) a $C_{3-10}$ cycloalkyl group (e.g., cyclopentyl) optionally substituted by 1 to 3 hydroxy groups, or
(3) a non-aromatic heterocyclic group (preferably a 3- to 14-membered non-aromatic heterocyclic group, more preferably a 3- to 8-membered monocyclic non-aromatic heterocyclic group) (e.g., oxetanyl);
one of $R^3$ and $R^4$ is a hydrogen atom, and the other is
(1) a hydrogen atom, or
(2) a $C_{1-6}$ alkyl group (e.g., methyl) optionally substituted by 1 to 3 substituents selected from an amino group optionally mono- or di-substituted by $C_{1-6}$ alkyl group(s) (e.g., methyl);
one of $R^5$ and $R^6$ is a hydrogen atom or a $C_{1-6}$ alkyl group (e.g., methyl), and the other is
(1) a hydrogen atom,
(2) a hydroxy group,
(3) a $C_{1-6}$ alkyl group (e.g., methyl) optionally substituted by 1 to 3 substituents selected from
  (i) a hydroxy group,
  (ii) an amino group optionally mono- or di-substituted by substituent(s) selected from
    (a) a $C_{1-6}$ alkyl group (e.g., methyl, ethyl) optionally substituted by 1 to 3 halogen atoms (e.g., a fluorine atom),
    (b) a $C_{3-10}$ cycloalkyl group (e.g., cyclopropyl, cyclobutyl) optionally substituted by 1 to 3 halogen atoms (e.g., a fluorine atom),
    (c) a non-aromatic heterocyclic group (preferably a 3- to 14-membered non-aromatic heterocyclic group, more preferably a 3- to 8-membered monocyclic non-aromatic heterocyclic group) (e.g., oxetanyl),
    (d) a $C_{1-6}$ alkylsulfonyl group (e.g., methylsulfonyl),
    (e) a $C_{1-6}$ alkyl-carbonyl group (e.g., acetyl), and
    (f) a $C_{3-10}$ cycloalkyl-carbonyl group (e.g., cyclopropylcarbonyl),
  (iii) a halogen atom (e.g., a fluorine atom),
  (iv) a $C_{1-6}$ alkylsulfanyl group (e.g., methylsulfanyl),
  (v) a $C_{1-6}$ alkylsulfinyl group (e.g., methylsulfinyl), and
  (vi) a $C_{1-6}$ alkylsulfonyl group (e.g., methylsulfonyl),
(4) a $C_{1-6}$ alkoxy group (e.g., methoxy),
(5) an amino group optionally mono- or di-substituted by substituent(s) selected from
  (i) a $C_{1-6}$ alkyl group (e.g., methyl, ethyl),
  (ii) a $C_{1-6}$ alkyl-carbonyl group (e.g., acetyl), and
  (iii) a $C_{1-6}$ alkylsulfonyl group (e.g., methylsulfonyl),
(6) a non-aromatic heterocyclic group (preferably a 3- to 14-membered non-aromatic heterocyclic group, more preferably a 3- to 8-membered monocyclic non-aromatic heterocyclic group) (e.g., morpholinyl),
(7) a carboxy group, or
(8) a carbamoyl group optionally mono- or di-substituted by $C_{1-6}$ alkyl group(s) (e.g., methyl), or
$R^5$ and $R^6$ in combination optionally form
(1) a non-aromatic heterocycle (preferably a 3- to 14-membered non-aromatic heterocycle, more preferably a 3- to 8-membered monocyclic non-aromatic heterocycle) (e.g., tetrahydrofuran), or
(2) a $C_{3-10}$ cycloalkane (e.g., cyclopentane);
X is $CR^7R^8$, $NR^9$, O or S;
$R^7$ and $R^8$ are independently
(1) a hydrogen atom,
(2) a cyano group,
(3) a $C_{1-6}$ alkyl group (e.g., methyl, ethyl) optionally substituted by 1 to 3 hydroxy groups, or
(4) a hydroxy group, or
$R^7$ and $R^8$ in combination optionally form
(1) a $C_{3-10}$ cycloalkane (e.g., cyclohexane) optionally substituted by 1 to 3 substituents selected from
  (i) an oxo group, and
  (ii) a hydroxy group, or
(2) a non-aromatic heterocycle (preferably a 3- to 14-membered non-aromatic heterocycle, more preferably a 3- to 8-membered monocyclic non-aromatic heterocycle) (e.g., pyrrolidine, piperidine) optionally substituted by 1 to 3 $C_{7-16}$ aralkyl groups (e.g., benzyl); and
$R^9$ is
(1) a hydrogen atom, or
(2) a $C_{1-6}$ alkyl group (e.g., methyl, ethyl, propyl, isopropyl) optionally substituted by 1 to 3 substituents selected from
  (i) a hydroxy group,
  (ii) a $C_{1-6}$ alkoxy group (e.g., methoxy) optionally substituted by 1 to 3 $C_{6-14}$ aryl groups (e.g., phenyl), and
  (iii) an amino group optionally mono- or di-substituted by $C_{1-6}$ alkyl group(s) (e.g., methyl),
(3) a $C_{2-6}$ alkenyl group (e.g., allyl), or
(4) a $C_{7-16}$ aralkyl group (e.g., benzyl) optionally substituted by 1 to 3 $C_{1-6}$ alkoxy groups (e.g., methoxy).

[Compound C-1]
Compound (I) wherein
$R^1$ is
(1) an aromatic heterocyclic group (preferably a 5- to 14-membered aromatic heterocyclic group, more preferably a 5- to 6-membered monocyclic aromatic heterocyclic group)

(e.g., oxazolyl, pyridyl, pyrazolyl) optionally substituted by 1 to 3 substituents selected from
  (i) a $C_{1-6}$ alkyl group (e.g., methyl) optionally substituted by 1 to 3 halogen atoms (e.g., a fluorine atom),
  (ii) an aromatic heterocyclic group (preferably a 5- to 14-membered aromatic heterocyclic group, more preferably a 5- to 6-membered monocyclic aromatic heterocyclic group) (e.g., pyridyl, pyrazolyl) optionally substituted by 1 to 3 substituents selected from
    (a) an amino group optionally mono- or di-substituted by $C_{1-6}$ alkyl group(s) (e.g., methyl, ethyl) optionally substituted by 1 to 3 substituents selected from
      (I) a halogen atom (e.g., a fluorine atom), and
      (II) a $C_{3-10}$ cycloalkyl group (e.g., cyclopropyl), and
    (b) a $C_{1-6}$ alkyl group (e.g., methyl) optionally substituted by 1 to 3 amino groups, and
  (iii) a non-aromatic heterocyclic group (preferably a 3- to 14-membered non-aromatic heterocyclic group, more preferably a 3- to 8-membered monocyclic non-aromatic heterocyclic group, a 7- to 14-membered spiro heterocyclic group) (e.g., imidazolidinyl, triazaspirononyl (e.g., 1,3,7-triazaspiro[4.4]nonyl)) optionally substituted by 1 to 3 substituents selected from
    (a) a $C_{1-6}$ alkyl group (e.g., methyl) optionally substituted by 1 to 3 amino groups, and
    (b) an oxo group, or
(2) a $C_{6-14}$ aryl group (e.g., phenyl) optionally substituted by 1 to 3 $C_{1-6}$ alkyl groups (e.g., methyl);
$R^2$ is a $C_{1-6}$ alkyl group (e.g., methyl);
one of $R^3$ and $R^4$ is a hydrogen atom, and the other is a hydrogen atom or a $C_{1-6}$ alkyl group (e.g., methyl);
one of $R^5$ and $R^6$ is a hydrogen atom, and the other is
(1) a hydrogen atom,
(2) a hydroxy group,
(3) a $C_{1-6}$ alkyl group (e.g., methyl) optionally substituted by 1 to 3 substituents selected from
  (i) an amino group optionally mono- or di-substituted by $C_{1-6}$ alkyl group(s) (e.g., methyl), and
  (ii) a hydroxy group, or
(4) an amino group optionally mono- or di-substituted by $C_{1-6}$ alkyl group(s) (e.g., methyl);
X is $CR^7R^9$, $NR^9$ or O;
$R^7$ and $R^8$ are independently
(1) a hydrogen atom, or
(2) a $C_{1-6}$ alkyl group (e.g., methyl); and
$R^9$ is
(1) a hydrogen atom, or
(2) a $C_{1-6}$ alkyl group (e.g., methyl, ethyl, propyl) optionally substituted by 1 to 3 hydroxy groups.
[Compound D-1]
  Compound (I) wherein
$R^1$ is an aromatic heterocyclic group (preferably a 5- to 14-membered aromatic heterocyclic group, more preferably a 5- to 6-membered monocyclic aromatic heterocyclic group) (e.g., oxazolyl) optionally substituted by aromatic heterocyclic group(s) (preferably a 5- to 14-membered aromatic heterocyclic group, more preferably a 5- to 6-membered monocyclic aromatic heterocyclic group) (e.g., pyridyl) optionally substituted by amino group(s) optionally mono- or di-substituted by $C_{1-6}$ alkyl group(s) (e.g., ethyl) optionally substituted by 1 to 3 halogen atoms (e.g., a fluorine atom);
$R^2$ is a $C_{1-6}$ alkyl group (e.g., methyl);
$R^3$ and $R^4$ are both hydrogen atoms;
one of $R^5$ and $R^6$ is a hydrogen atom, and the other is
(1) a hydrogen atom,
(2) a hydroxy group,
(3) a $C_{1-6}$ alkyl group (e.g., methyl) optionally substituted by amino group(s) optionally mono- or di-substituted by $C_{1-6}$ alkyl group(s) (e.g., methyl), or
(4) an amino group optionally mono- or di-substituted by $C_{1-6}$ alkyl group(s) (e.g., methyl);
X is $CR^7R^8$; and
$R^7$ and $R^8$ are independently
(1) a hydrogen atom, or
(2) a $C_{1-6}$ alkyl group (e.g., methyl).
[Compound D-2]
  Compound (I) wherein
$R^1$ is an aromatic heterocyclic group (preferably a 5- to 14-membered aromatic heterocyclic group, more preferably a 5- to 6-membered monocyclic aromatic heterocyclic group) (e.g., oxazolyl) optionally substituted by aromatic heterocyclic group(s) (preferably a 5- to 14-membered aromatic heterocyclic group, more preferably a 5- to 6-membered monocyclic aromatic heterocyclic group) (e.g., pyridyl) optionally substituted by amino group(s) optionally mono- or di-substituted by $C_{1-6}$ alkyl group(s) (e.g., methyl, ethyl) optionally substituted by 1 to 3 substituents selected from
  (1) a halogen atom (e.g., a fluorine atom), and
  (2) a $C_{3-10}$ cycloalkyl group (e.g., cyclopropyl);
$R^2$ is a $C_{1-6}$ alkyl group (e.g., methyl);
$R^3$ and $R^4$ are both hydrogen atoms;
one of $R^5$ and $R^6$ is a hydrogen atom, and the other is
(1) a hydrogen atom,
(2) a $C_{1-6}$ alkyl group (e.g., methyl) optionally substituted by amino group(s) optionally mono- or di-substituted by $C_{1-6}$ alkyl group(s) (e.g., methyl), or
(3) an amino group optionally mono- or di-substituted by $C_{1-6}$ alkyl group(s) (e.g., methyl);
X is $CR^7R^8$ or $NR^9$;
$R^7$ and $R^8$ are independently
(1) a hydrogen atom, or
(2) a $C_{1-6}$ alkyl group (e.g., methyl); and
$R^9$ is
(1) a hydrogen atom, or
(2) a $C_{1-6}$ alkyl group (e.g., methyl, ethyl) optionally substituted by 1 to 3 hydroxy groups.
[Compound E-1]
  Compound (I) wherein
$R^1$ is an aromatic heterocyclic group (preferably a 5- to 14-membered aromatic heterocyclic group, more preferably a 5- to 6-membered monocyclic aromatic heterocyclic group) (e.g., oxazolyl) optionally substituted by aromatic heterocyclic group(s) (preferably a 5- to 14-membered aromatic heterocyclic group, more preferably a 5- to 6-membered monocyclic aromatic heterocyclic group) (e.g., pyridyl) optionally substituted by amino group(s) optionally mono- or di-substituted by $C_{1-6}$ alkyl group(s) (e.g., methyl, ethyl) optionally substituted by 1 to 3 halogen atoms (e.g., a fluorine atom);
$R^2$ is a $C_{1-6}$ alkyl group (e.g., methyl);
$R^3$ and $R^4$ are both hydrogen atoms;
$R^5$ and $R^6$ are both hydrogen atoms;
X is $CR^7R^8$ or $NR^9$;
$R^7$ and $R^8$ are independently
(1) a hydrogen atom, or
(2) a $C_{1-6}$ alkyl group (e.g., methyl); and
$R^9$ is
(1) a hydrogen atom, or
(2) a $C_{1-6}$ alkyl group (e.g., methyl, ethyl) optionally substituted by 1 to 3 hydroxy groups.
[Compound F-1]
  Compound (I) wherein
$R^1$ is an aromatic heterocyclic group (preferably a 5- to 14-membered aromatic heterocyclic group, more preferably a 5- to 6-membered monocyclic aromatic heterocyclic group) (e.g., oxazolyl) optionally substituted by aromatic heterocyclic group(s) (preferably a 5- to 14-membered aromatic heterocyclic group, more preferably a 5- to 6-membered monocyclic aromatic heterocyclic group) (e.g., pyridyl) optionally substituted by amino group(s) optionally mono- or di-substituted by $C_{1-6}$ alkyl group(s) (e.g., methyl, ethyl) optionally substituted by 1 to 3 halogen atoms (e.g., a fluorine atom);

$R^2$ is a $C_{1-6}$ alkyl group (e.g., methyl);

$R^3$ and $R^4$ are both hydrogen atoms;

$R^5$ and $R^6$ are both hydrogen atoms;

X is $NR^9$; and $R^9$ is (1) a hydrogen atom, or (2) a $C_{1-6}$ alkyl group (e.g., methyl, ethyl) optionally substituted by 1 to 3 hydroxy groups.

[Compound G-1]

N-(3-(3-(2-hydroxyethyl)-2-oxoimidazolidin-1-yl)-1-methyl-1H-pyrazol-4-yl)-2-(2-((2,2,2-trifluoroethyl)amino)pyridin-4-yl)-1,3-oxazole-4-carboxamide or a salt thereof; or N-(1-methyl-3-(2-oxoimidazolidin-1-yl)-1H-pyrazol-4-yl)-2-(2-((2,2,2-trifluoroethyl)amino)pyridin-4-yl)-1,3-oxazole-4-carboxamide or a salt thereof.

[Compound H-1]

N-(1-methyl-3-((3S)-3-methyl-2-oxopyrrolidin-1-yl)-1H-pyrazol-4-yl)-2-(2-((2,2,2-trifluoroethyl)amino)pyridin-4-yl)-1,3-oxazole-4-carboxamide or a salt thereof.

When compound (I) is in a form of a salt, examples thereof include metal salts, an ammonium salt, salts with organic base, salts with inorganic acid, salts with organic acid, salts with basic or acidic amino acid, and the like. Preferable examples of the metal salt include alkali metal salts such as sodium salt, potassium salt and the like; alkaline earth metal salts such as calcium salt, magnesium salt, barium salt and the like; an aluminum salt, and the like. Preferable examples of the salt with organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of the salt with inorganic acid include salts with hydrochloric acid, hydrobromic acid, nitric acid, sulfuric acid, phosphoric acid and the like. Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of the salt with basic amino acid include salts with arginine, lysine, ornithine and the like. Preferable examples of the salt with acidic amino acid include salts with aspartic acid, glutamic acid and the like.

Of these, a pharmaceutically acceptable salt is preferable. For example, when a compound has an acidic functional group, examples thereof include inorganic salts such as alkali metal salts (e.g., sodium salt, potassium salt etc.), alkaline earth metal salts (e.g., calcium salt, magnesium salt etc.) and the like, ammonium salt etc., and when a compound has a basic functional group, examples thereof include salts with inorganic acid such as hydrochloric acid, hydrobromic acid, nitric acid, sulfuric acid, phosphoric acid and the like, and salts with organic acid such as acetic acid, phthalic acid, fumaric acid, oxalic acid, tartaric acid, maleic acid, citric acid, succinic acid, methanesulfonic acid, benzenesulfonic acid, p-toluenesulfonic acid and the like.

[Production Method]

The production method of the compound of the present invention is explained below.

The raw material compound and reagent used and the compound obtained in each step in the following production method may be each in a form of a salt, and examples of such salt include those similar to the salts of the compound of the present invention and the like.

When the compound obtained in each step is a free form, it can be converted to the objective salt according to a method known per se. When the compound obtained in each step is a salt, it can be converted to the objective free form or the other salt according to a method known per se.

The compound obtained in each step can be used directly as the reaction mixture or as a crude product for the next reaction. Alternatively, the compound obtained in each step can be isolated and purified from a reaction mixture according to a method known per se, for example, a separation means such as concentration, crystallization, recrystallization, distillation, solvent extraction, fractional distillation, column chromatography and the like.

When the raw material compound and reagent used in each step are commercially available, the commercially available product can also be used directly.

In the reaction in each step, while the reaction time varies depending on the kind of the reagent and solvent to be used, it is generally 1 min-48 hr, preferably 10 min-8 hr, unless otherwise specified.

In the reaction in each step, while the reaction temperature varies depending on the kind of the reagent and solvent to be used, it is generally −78° C.-300° C., preferably −78° C.-150° C., unless otherwise specified.

In the reaction in each step, while the pressure varies depending on the kind of the reagent and solvent to be used, it is generally 1 atm-20 atm, preferably 1 atm-3 atm, unless otherwise specified.

Microwave synthesizer such as Initiator manufactured by Biotage and the like may be used for the reaction in each step. While the reaction temperature varies depending on the kind of the reagent and solvent to be used, it is generally room temperature—300° C., preferably 50° C.-250° C., unless otherwise specified. While the reaction time varies depending on the kind of the reagent and solvent to be used, it is generally 1 min-48 hr, preferably 1 min-8 hr, unless otherwise specified.

In the reaction in each step, the reagent is used in an amount of 0.5 equivalents-20 equivalents, preferably 0.8 equivalents-5 equivalents, relative to the substrate, unless otherwise specified. When the reagent is used as a catalyst, the reagent is used in an amount of 0.001 equivalent-1 equivalent, preferably 0.01 equivalent-0.2 equivalent, relative to the substrate. When the reagent is used as a reaction solvent, the reagent is used in a solvent amount.

Unless otherwise specified, the reaction in each step is carried out without solvent, or by dissolving or suspending the raw material compound in a suitable solvent. Examples of the solvent include those described in Examples and the following solvents.

alcohols: methanol, ethanol, tert-butyl alcohol, 2-methoxyethanol and the like;

ethers: diethyl ether, diphenyl ether, tetrahydrofuran, 1,2-dimethoxyethane and the like;

aromatic hydrocarbons: chlorobenzene, toluene, xylene and the like;

saturated hydrocarbons: cyclohexane, hexane and the like;

amides: N,N-dimethylformamide, N-methylpyrrolidone and the like;

halogenated hydrocarbons: dichloromethane, carbon tetrachloride and the like;

nitriles: acetonitrile and the like;

sulfoxides: dimethyl sulfoxide and the like;

aromatic organic bases: pyridine and the like;

anhydrides: acetic anhydride and the like;

organic acids: formic acid, acetic acid, trifluoroacetic acid and the like;

inorganic acids: hydrochloric acid, sulfuric acid and the like;
esters: ethyl acetate and the like;
ketones: acetone, methyl ethyl ketone and the like;
water.

The above-mentioned solvent can be used in a mixture of two or more kinds thereof in an appropriate ratio.

When a base is used for the reaction in each step, examples thereof include those described in Examples and the following bases.
inorganic bases: sodium hydroxide, magnesium hydroxide and the like;
basic salts: sodium carbonate, calcium carbonate, sodium hydrogen carbonate and the like;
organic bases: triethylamine, diethylamine, pyridine, 4-dimethylaminopyridine, N,N-dimethylaniline, 1,4-diazabicyclo[2.2.2]octane, 1,8-diazabicyclo[5.4.0]-7-undecene, imidazole, piperidine and the like;
metal alkoxides: sodium ethoxide, potassium tert-butoxide and the like;
alkali metal hydrides: sodium hydride and the like;
metal amides: sodium amide, lithium diisopropylamide, lithium hexamethyldisilazide and the like;
organic lithiums: n-butyllithium and the like.

When an acid or an acid catalyst is used for the reaction in each step, examples thereof include those described in Examples and the following acids and acid catalysts.
inorganic acids: hydrochloric acid, sulfuric acid, nitric acid, hydrobromic acid, phosphoric acid and the like;
organic acids: acetic acid, trifluoroacetic acid, citric acid, p-toluenesulfonic acid, 10-camphorsulfonic acid and the like;
Lewis acid: boron trifluoride diethyl ether complex, zinc iodide, anhydrous aluminum chloride, anhydrous zinc chloride, anhydrous iron chloride and the like.

Unless otherwise specified, the reaction in each step is carried out according to a method known per se, for example, the method described in Jikken Kagaku Kouza, 5th Edition, vol. 13-19 (the Chemical Society of Japan ed.); Shin Jikken Kagaku Kouza, vol. 14-15 (the Chemical Society of Japan ed.); Fine Organic Chemistry, Revised 2nd Edition (L. F. Tietze, Th. Eicher, Nankodo); Organic Name Reactions, the Reaction Mechanism and Essence, Revised Edition (Hideo Togo, Kodansha); ORGANIC SYNTHESES Collective Volume I-VII (John Wiley & Sons Inc); Modern Organic Synthesis in the Laboratory A Collection of Standard Experimental Procedures (Jie Jack Li, OXFORD UNIVERSITY); Comprehensive Heterocyclic Chemistry III, Vol. 1-Vol. 14 (Elsevier Japan); Strategic Applications of Named Reactions in Organic Synthesis (translated by Kiyoshi Tomioka, Kagakudojin); Comprehensive Organic Transformations (VCH Publishers Inc.), 1989, or the like, or the method described in Examples.

In each step, the protection or deprotection reaction of an functional group is carried out according to a method known per se, for example, the method described in "Protective Groups in Organic Synthesis, 4th Ed", Wiley-Interscience, Inc., 2007 (Theodora W. Greene, Peter G. M. Wuts); "Protecting Groups 3rd Ed." Thieme, 2004 (P. J. Kocienski), or the like, or the method described in Examples.

Examples of the protected hydroxy group of an alcohol and a phenol include ether groups such as methoxymethyl ether, benzyl ether, t-butyldimethylsilyl ether, tetrahydropyranyl ether and the like; carboxylate groups such as acetate and the like; sulfonate groups such as methanesulfonate and the like; carbonate groups such as t-butyl carbonate and the like, and the like.

Examples of the protected carbonyl group of an aldehyde include acetal groups such as dimethyl acetal and the like; cyclic acetal groups such as cyclic 1,3-dioxane and the like, and the like.

Examples of the protected carbonyl group of a ketone include ketal groups such as dimethyl ketal and the like; cyclic ketal groups such as cyclic 1,3-dioxane and the like; oxime groups such as O-methyloxime and the like; hydrazone groups such as N,N-dimethylhydrazone and the like, and the like.

Examples of the protected carboxyl group include ester groups such as methyl ester and the like; amide groups such as N,N-dimethylamide and the like, and the like.

Examples of the protected thiol group include ether groups such as benzylthio ether and the like; ester groups such as thioacetate, thiocarbonate, thiocarbamate and the like, and the like.

Examples of the protected amino group and aromatic heterocycle (e.g., imidazole, pyrrole, indole etc.) include carbamate groups such as benzyl carbamate and the like; amide groups such as acetamide and the like; alkyl amine groups such as N-triphenylmethylamine and the like; sulfonamide groups such as methanesulfonamide and the like, and the like.

The protecting groups can be removed according to a method known per se, for example, by employing a method using acid, base, ultraviolet rays, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide) and the like, a reduction method, and the like.

When reduction reaction is carried out in each step, examples of the reducing agent to be used include metal hydrides such as lithium aluminum hydride, sodium triacetoxyborohydride, sodium cyanoborohydride, diisobutylaluminium hydride (DIBAL-H), sodium borohydride, tetramethylammonium triacetoxyborohydride and the like; boranes such as borane tetrahydrofuran complex and the like; Raney nickel; Raney cobalt; hydrogen; formic acid and the like. When carbon-carbon double bond or triple bond is reduced, a method using a catalyst such as palladium-carbon, Lindlar's catalyst and the like may be employed.

When oxidation reaction is carried out in each step, examples of the oxidizing agent to be used include peroxides such as m-chloroperbenzoic acid (MCPBA), hydrogen peroxide, t-butylhydroperoxide and the like; perchlorates such as tetrabutylammonium perchlorate and the like; chlorates such as sodium chlorate and the like; chlorites such as sodium chlorite and the like; periodic acids such as sodium periodate and the like; hypervalent iodine reagents such as iodosylbenzene and the like; reagents containing manganese such as manganese dioxide, potassium permanganate and the like; leads such as lead tetraacetate and the like; reagents containing chromium such as pyridinium chlorochromate (PCC), pyridinium dichromate (PDC), Jones reagent and the like; halogen compounds such as N-bromosuccinimide (NBS) and the like; oxygen; ozone; sulfur trioxide-pyridine complex; osmium tetroxide; selenium dioxide; 2,3-dichloro-5,6-dicyano-1,4-benzoquinone (DDQ) and the like.

When radical cyclization reaction is carried out in each step, examples of the radical initiator to be used include azo compounds such as azobisisobutyronitrile (AIBN) and the like; water-soluble radical initiators such as 4-4'-azobis-4-cyanopentanoic acid (ACPA) and the like; triethylboron in the presence of air or oxygen; benzoyl peroxide and the like. Examples of the radical reagent to be used include tributylstannane, tristrimethylsilylsilane, 1,1,2,2-tetraphenyldisilane, diphenylsilane, samarium iodide and the like.

When Wittig reaction is carried out in each step, examples of the Wittig reagent to be used include alkylidene phosphoranes and the like. The alkylidene phosphoranes can be prepared according to a method known per se, for example, by reacting a phosphonium salt with a strong base.

When Horner-Emmons reaction is carried out in each step, examples of the reagent to be used include phosphonoacetates such as methyl dimethylphosphonoacetate, ethyl diethylphosphonoacetate and the like; and bases such as alkali metal hydrides, organic lithiums and the like.

When Friedel-Crafts reaction is carried out in each step, a combination of a Lewis acid and an acid chloride or a combination of a Lewis acid and an alkylating agent (e.g., an alkyl halide, an alcohol, an olefin etc.) is used as a reagent. Alternatively, an organic acid or an inorganic acid can also be used instead of a Lewis acid, and an anhydride such as acetic anhydride and the like can also be used instead of an acid chloride.

When aromatic nucleophilic substitution reaction is carried out in each step, a nucleophile (e.g., an amine, imidazole etc.) and a base (e.g., a basic salt, an organic base etc.) are used as a reagent.

When nucleophilic addition reaction by a carbo anion, nucleophilic 1,4-addition reaction (Michael addition reaction) by a carbo anion or nucleophilic displacement reaction by a carbo anion is carried out in each step, examples of the base to be used for generation of the carbo anion include organic lithiums, metal alkoxides, inorganic bases, organic bases and the like.

When Grignard reagent is carried out in each step, examples of the Grignard reagent to be used include arylmagnesium halides such as phenylmagnesium bromide and the like; and alkylmagnesium halides such as methylmagnesium bromide and the like. The Grignard reagent can be prepared according to a method known per se, for example, by reacting an alkyl halide or an aryl halide with a metal magnesium in an ether or tetrahydrofuran as a solvent.

When Knoevenagel condensation reaction is carried out in each step, a compound having an activated methylene group with two electron withdrawing groups (e.g., malonic acid, diethyl malonate, malononitrile etc.) and a base (e.g., an organic base, a metal alkoxide, an inorganic base) are used as a reagent.

When Vilsmeier-Haack reaction is carried out in each step, phosphoryl chloride and an amide derivative (e.g., N,N-dimethylformamide etc.) are used as a reagent.

When azidation reaction of an alcohol, an alkyl halide or a sulfonate is carried out in each step, examples of the azidating agent to be used include diphenylphosphorylazide (DPPA), trimethylsilylazide, sodium azide and the like. For example, for the azidation reaction of an alcohol, a method using diphenylphosphorylazide and 1,8-diazabicyclo[5.4.0]undec-7-ene (DBU), a method using trimethylsilylazide and a Lewis acid, and the like are employed.

When reductive amination reaction is carried out in each step, examples of the reducing agent to be used include sodium triacetoxyborohydride, sodium cyanoborohydride, hydrogen, formic acid and the like. When the substrate is an amine compound, examples of the carbonyl compound to be used include paraformaldehyde, aldehydes such as acetaldehyde and the like, and ketones such as cyclohexanone and the like. When the substrate is a carbonyl compound, examples of the amine to be used include ammonia, primary amines such as methylamine and the like; secondary amines such as dimethylamine and the like, and the like.

When Mitsunobu reaction is carried out in each step, an azodicarboxylate (e.g., diethyl azodicarboxylate (DEAD), diisopropyl azodicarboxylate (DIAD) etc.) and triphenylphosphine are used as a reagent.

When esterification reaction, amidation reaction or ureation reaction is carried out in each step, examples of the reagent to be used include acyl halides such as acid chlorides, acid bromides and the like; activated carboxylic acids such as anhydrides, activated esters, sulfates and the like. Examples of the activating agent of the carboxylic acid include carbodiimide condensing agents such as 1-ethyl-3-(3-dimethylaminopropyl)carbodiimide hydrochloride (WSCD) and the like; triazine condensing agents such as 4-(4,6-dimethoxy-1,3,5-triazin-2-yl)-4-methylmorpholinium chloride n-hydrate (DMT-MM) and the like; carbonate condensing agents such as 1,1-carbonyldiimidazole (CDI) and the like; diphenylphosphoryl azide (DPPA); benzotriazol-1-yloxy-trisdimethylaminophosphonium salt (BOP reagent); 2-chloro-1-methyl-pyridinium iodide (Mukaiyama reagent); thionyl chloride; lower alkyl haloformates such as ethyl chloroformate and the like; O-(7-azabenzotriazol-1-yl)-N,N,N',N'-tetramethyluronium hexafluorophosphate (HATU); sulfuric acid; combinations thereof and the like. When carbodiimide condensing agent is used, an additive such as 1-hydroxybenzotriazole (HOBt), N-hydroxysuccinimide (HOSu), dimethylaminopyridine (DMAP) and the like may be added to the reaction system.

When coupling reaction is carried out in each step, examples of the metal catalyst to be used include palladium compounds such as palladium(II) acetate, tetrakis(triphenylphosphine)palladium(0), dichlorobis(triphenylphosphine)palladium(II), dichlorobis(triethylphosphine)palladium(II), tris(dibenzylideneacetone)dipalladium(0), 1,1'-bis(diphenylphosphino)ferrocene palladium(II) chloride, palladium(II) acetate and the like; nickel compounds such as tetrakis(triphenylphosphine)nickel(0) and the like; rhodium compounds such as tris(triphenylphosphine)rhodium(III) chloride and the like; cobalt compounds; copper compounds such as copper oxide, copper(I) iodide and the like; platinum compounds and the like. In addition, a base can be added to the reaction system, and examples thereof include inorganic bases, basic salts and the like.

When thiocarbonylation reaction is carried out in each step, phosphorus pentasulfide is typically used as the thiocarbonylating agent. Alternatively, a reagent having a 1,3,2,4-dithiadiphosphetane-2,4-disulfide structure (e.g., 2,4-bis(4-methoxyphenyl-1,3,2,4-dithiadiphosphetane-2,4-disulfide (Lowesson reagent) etc.) can also be used instead of phosphorus pentasulfide.

When Wohl-Ziegler reaction is carried out in each step, examples of the halogenating agent to be used include N-iodosuccinimide, N-bromosuccinimide (NBS), N-chlorosuccinimide (NCS), bromine, sulfuryl chloride and the like. In addition, the reaction can be accelerated by subjecting a radical initiator such as heat, light, benzoyl peroxide, azobisisobutyronitrile and the like to the reaction system reaction.

When halogenation reaction of a hydroxy group is carried out in each step, examples of the halogenating agent to be used include hydrohalic acids and acid halides of inorganic acids, specifically, hydrochloric acid, thionyl chloride, phosphorus oxychloride and the like for chlorination, 48% hydrobromic acid and the like for bromination. In addition, a method of producing an alkyl halide by reacting an alcohol with triphenylphosphine and carbon tetrachloride or carbon tetrabromide or the like can be employed. Alternatively, a method of producing an alkyl halide via two step comprising converting an alcohol to the corresponding sulfonate, and then reacting the sulfonate with lithium bromide, lithium chloride or sodium iodide can also be employed.

When Arbuzov reaction is carried out in each step, examples of the reagent to be used include alkyl halides such as ethyl bromoacetate and the like; and phosphites such as triethyl phosphite, tri(isopropyl) phosphite and the like.

When sulfonate esterification reaction is carried out in each step, examples of the sulfonating agent to be used include methanesulfonyl chloride, p-toluenesulfonyl chloride, methanesulfonic anhydride, p-toluenesulfonic anhydride and the like.

When hydrolysis reaction is carried out in each step, an acid or a base is used as a reagent. For acid hydrolysis reaction of t-butyl ester, formic acid, triethylsilane and the like may be added to reductively-trap t-butyl cation which is by-produced.

When dehydration reaction is carried out in each step, examples of the dehydrating agent to be used include sulfuric acid, diphosphorus pentaoxide, phosphorus oxychloride, N,N'-dicyclohexylcarbodiimide, alumina, polyphosphoric acid and the like.

When nitration reaction is carried out in each step, examples of the nitrating agent to be used include nitric acid, fuming nitric acid, copper nitrate and the like. The nitrating agent is activated by conc. sulfuric acid, acetic anhydride and the like.

When halogenation reaction is carried out in each step, examples of the halogenating agent to be used include N-iodosuccinimide, N-bromosuccinimide (NBS), N-chlorosuccinimide (NCS), iodine monochloride, iodine, bromine, sulfuryl chloride and the like. In this reaction, an additive such as trifluoroacetic acid and the like may be used for the purpose of the activation of the halogenating agent.

Acylation reaction is carried out by amidation reaction, ureation reaction, carbamation reaction, thiocarbamation reaction or the like. Examples of the reagent to be used for carbamation reaction or thiocarbamation reaction include carbonate condensing agents (e.g., triphosgene, 1,1-carbonyldiimidazole (CDI) etc.), chlorocarbonates, chlorothiocarbonates, isothiocyanates and the like.

Cyclization reaction is carried out by Mitsunobu reaction or alkylation reaction. A base is used as a reagent for alkylation reaction.

Compound (I) can be produced from compound (1) according to the method shown in Scheme A or a method analogous thereto, or the methods described in Examples.

Compound (3) and compound (4) can be produced from compound (1) according to the method shown in Scheme B or a method analogous thereto, or the methods described in Examples.

In each reaction, when the raw material compound or intermediate has an amino group, a carboxyl group or a hydroxy group as a substituent, these groups may be protected by a protecting group generally used in peptide chemistry and the like. In this case, by removing the protecting group as necessary after the reaction, the objective compound can be obtained.

Scheme A

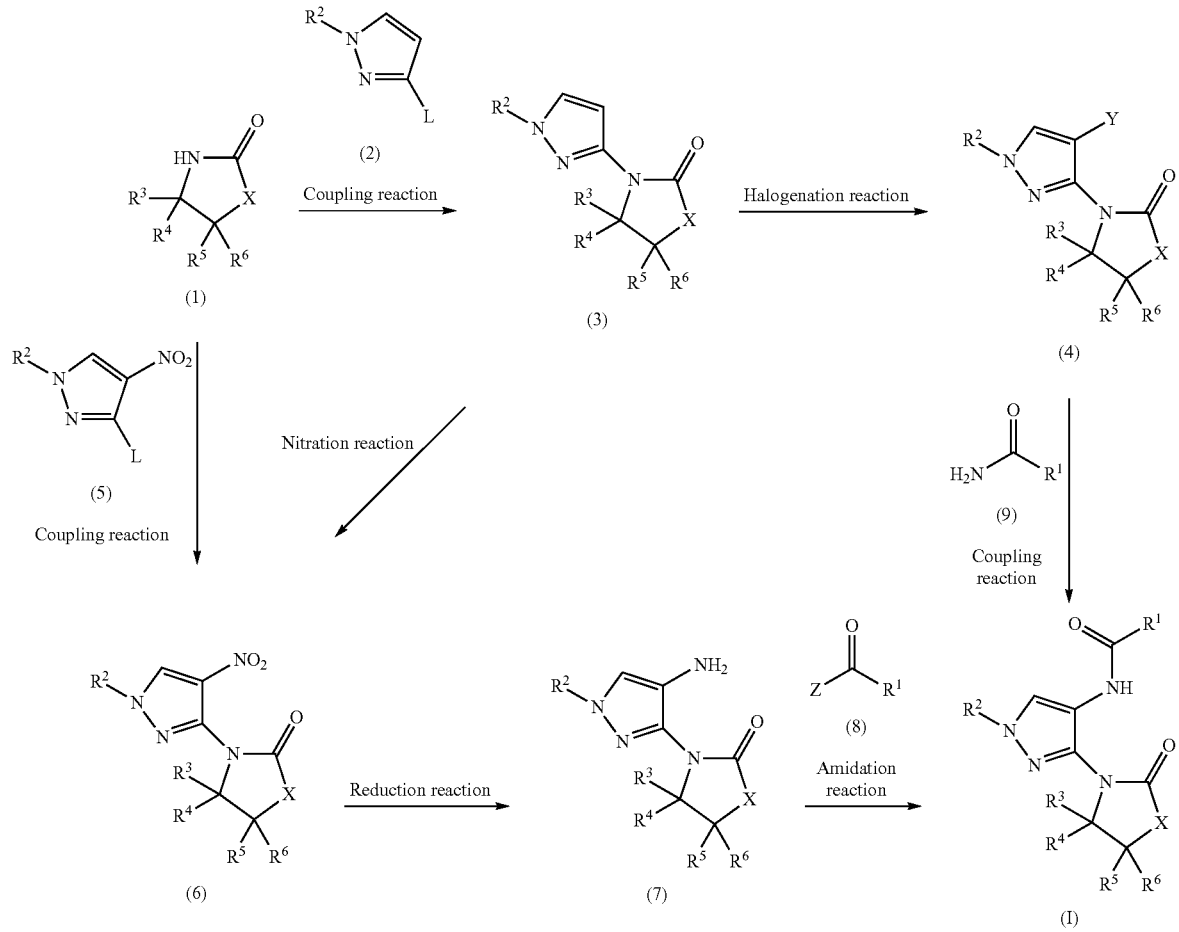

-continued
Scheme B

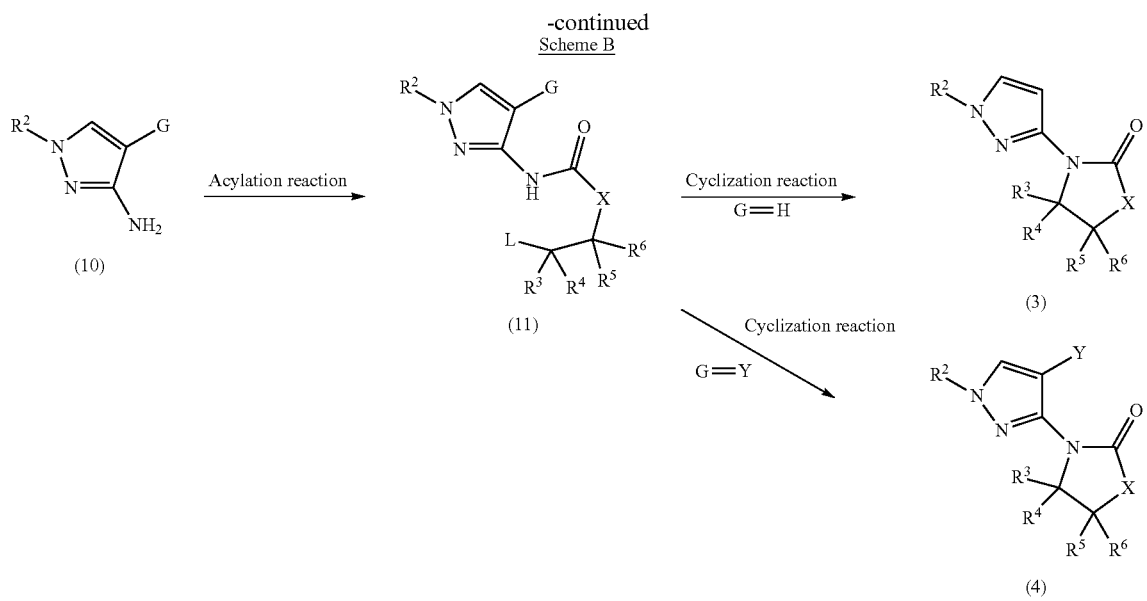

wherein X, $R^1$, $R^2$, $R^3$, $R^4$, $R^5$ and $R^6$ are each as defined above, L is a leaving group, G is a hydrogen atom or a halogen atom, Y is a halogen atom, and Z is a hydroxy group or a leaving group.

Examples of the "leaving group" for L include a halogen atom (preferably an iodine atom, a bromine atom, a chlorine atom), a sulfonyloxy group and the like.

Examples of the "leaving group" for Z include a halogen atom (preferably an iodine atom, a bromine atom, a chlorine atom), an alkoxy group, an alkylsulfonyloxy group, a succinimidooxy group, a pentafluorophenoxy group and the like.

The "halogen atom" for G or Y is preferably an iodine atom, a bromine atom or a chlorine atom.

Each of compound (1), compound (2), compound (5), compound (8), compound (9) and compound (10) may be commercially available products, or can also be produced according to a method known per se or a method analogous thereto.

In each intermediate, $R^3$, $R^4$, $R^5$ and $R^6$, and $R^7$, $R^8$ and $R^9$ in X can be each modified to the other substituent according to a method known per se or a method analogous thereto.

When compound (I) has an optical isomer, a stereoisomer, a regioisomer or a rotamer, these are also encompassed in compound (I), and can be obtained as a single product according to a synthesis method and separation method known per se (e.g., concentration, solvent extraction, column chromatography, recrystallization etc.). For example, when compound (I) has an optical isomer, the optical isomer resolved from the compound is also encompassed in compound (I).

The optical isomer can be produced according to a method known per se. Specifically, the optical isomer is obtained using an optically active synthetic intermediate or by subjecting the racemic final product to an optical resolution according to a known method.

The method of optical resolution may be a method known per se, such as a fractional recrystallization method, a chiral column method, a diastereomer method etc.

1) Fractional Recrystallization Method

A method wherein a salt of a racemate with an optically active compound (e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine etc.) is formed, which is separated by a fractional recrystallization method, and if desired, a neutralization step to give a free optical isomer.

2) Chiral Column Method

A method wherein a racemate or a salt thereof is applied to a column (a chiral column) for separation of an optical isomer to allow separation. In the case of a liquid chromatography, for example, a mixture of the optical isomers is applied to a chiral column such as ENANTIO-OVM (manufactured by Tosoh Corporation), CHIRAL series (manufactured by Daicel Chemical Industries, Ltd.) and the like, and developed with water, various buffers (e.g., phosphate buffer, etc.) and organic solvents (e.g., ethanol, methanol, 2-propanol, acetonitrile, trifluoroacetic acid, diethylamine, etc.) as an eluent, solely or in admixture to separate the optical isomer. In the case of a gas chromatography, for example, a chiral column such as CP-Chirasil-DeX CB (manufactured by GL Sciences Inc.) and the like is used to allow separation.

3) Diastereomer Method

A method wherein a racemic mixture is prepared into a diastereomeric mixture by chemical reaction with an optically active reagent, which is made into a single substance by a typical separation means (e.g., a fractional recrystallization method, a chromatography method etc.) and the like, and is subjected to a chemical treatment such as hydrolysis and the like to separate an optically active reagent moiety, whereby an optical isomer is obtained. For example, when compound (I) contains hydroxy or primary or secondary amino in a molecule, the compound and an optically active organic acid (e.g., MTPA [α-methoxy-α-(trifluoromethyl)phenylacetic acid], (−)-menthoxyacetic acid etc.) and the like are subjected to condensation reaction to give diastereomers of the ester compound or the amide compound, respectively. When compound (I) has a carboxyl group, the compound and an optically active amine or an optically active alcohol reagent are subjected to condensation reaction to give diastereomers of the amide compound or the ester compound, respectively. The separated diastereomer is converted to an optical isomer of the original compound by acid hydrolysis or base hydrolysis.

Compound (I) may be a crystal.

The crystal of compound (I) can be produced according to a crystallization method known per se.

Examples of the crystallization method include crystallization method from a solution, crystallization method from vapor, crystallization method from a melt, and the like.

The "crystallization method from a solution" is typically a method of shifting a non-saturated state to supersaturated state by varying factors involved in solubility of compounds (solvent composition, pH, temperature, ionic strength, redox state, etc.) or the amount of solvent. Specific examples thereof include a concentration method, a slow cooling method, a reaction method (a diffusion method, an electrolysis method), a hydrothermal growth method, a flux method and the like. Examples of the solvent to be used include aromatic hydrocarbons (e.g., benzene, toluene, xylene, etc.), halogenated hydrocarbons (e.g., dichloromethane, chloroform, etc.), saturated hydrocarbons (e.g., hexane, heptane, cyclohexane, etc.), ethers (e.g., diethyl ether, diisopropyl ether, tetrahydrofuran, dioxane, etc.), nitriles (e.g., acetonitrile, etc.), ketones (e.g., acetone, etc.), sulfoxides (e.g., dimethyl sulfoxide, etc.), acid amides (e.g., N,N-dimethylformamide, etc.), esters (e.g., ethyl acetate, etc.), alcohols (e.g., methanol, ethanol, 2-propanol, etc.), water and the like. These solvents are used alone or in a combination of two or more at a suitable ratio (e.g., 1:1 to 1:100 (a volume ratio)). Where necessary, a seed crystal can be used.

The "crystallization method from vapor" is, for example, a vaporization method (a sealed tube method, a gas stream method), a gas phase reaction method, a chemical transportation method and the like.

The "crystallization method from a melt" is, for example, a normal freezing method (a pulling method, a temperature gradient method, a Bridgman method), a zone melting method (a zone leveling method, a floating zone method), a special growth method (a VLS method, a liquid phase epitaxy method) and the like.

Preferable examples of the crystallization method include a method comprising dissolving compound (I) in a suitable solvent (e.g., alcohols such as methanol, ethanol etc.) at 20° C. to 120° C., and cooling the obtained solution to a temperature (e.g., 0-50° C., preferably 0-20° C.) not higher than the dissolution temperature, and the like.

The thus-obtained crystals of the present invention can be isolated, for example, by filtration and the like.

An analysis method of the obtained crystal is generally a method of crystal analysis by powder X-ray diffraction. As a method of determining crystal orientation, a mechanical method or an optical method and the like can also be used.

The crystal of compound (I) obtained by the above-mentioned production method has high purity, high quality, and low hygroscopicity, is not denatured even after a long-term preservation under general conditions, and is extremely superior in the stability. In addition, it is also superior in the biological properties (e.g., pharmacokinetics (absorption, distribution, metabolism, excretion), efficacy expression etc.) and is extremely useful as a medicament.

The prodrug of compound (I) means a compound which is converted to compound (I) with a reaction due to an enzyme, gastric acid and the like under the physiological condition in the living body, that is, a compound which is converted to compound (I) by enzymatic oxidation, reduction, hydrolysis and the like; a compound which is converted to compound (I) by hydrolysis and the like due to gastric acid, and the like.

Examples of the prodrug for compound (I) include a compound obtained by subjecting an amino group in compound (I) to acylation, alkylation or phosphorylation [e.g., a compound obtained by subjecting an amino group in compound (I) to eicosanoylation, alanylation, pentylaminocarbonylation, (5-methyl-2-oxo-1,3-dioxolen-4-yl)methoxycarbonylation, tetrahydrofurylation, pyrrolidylmethylation, pivaloyloxymethylation, tert-butylation, and the like]; a compound obtained by subjecting a hydroxy group in compound (I) to acylation, alkylation, phosphorylation or boration (e.g., a compound obtained by subjecting a hydroxy group in compound (I) to acetylation, palmitoylation, propanoylation, pivaloylation, succinylation, fumarylation, alanylation or dimethylaminomethylcarbonylation, and the like); a compound obtained by subjecting a carboxyl group in compound (I) to esterification or amidation (e.g., a compound obtained by subjecting a carboxyl group in compound (I) to ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation, and the like) and the like. These compounds can be produced from compound (I) according to a method known per se.

The prodrug of compound (I) may also be one which is converted to compound (I) under physiological conditions as described in "IYAKUHIN no KAIHATSU (Development of Pharmaceuticals)", Vol. 7, Design of Molecules, p. 163-198, Published by HIROKAWA SHOTEN (1990).

In the present specification, compound (I) and the prodrug of compound (I) are sometimes collectively abbreviated as "the compound of the present invention".

Compound (I) may be a hydrate, a non-hydrate, a solvate or a non-solvate.

Compound (I) also encompasses a compound labeled with an isotope (e.g., $^3H$, $^{14}C$, $^{35}S$, $^{125}I$ etc.) and the like.

Compound (I) also encompasses a deuterium conversion form wherein $^1H$ is converted to $^2H(D)$.

Compound (I) also encompasses a tautomer thereof.

Compound (I) may be a pharmaceutically acceptable cocrystal or a salt thereof. The cocrystal or a salt thereof means a crystalline substance constituted with two or more special solids at room temperature, each having different physical properties (e.g., structure, melting point, melting heat, hygroscopicity, solubility and stability etc.). The cocrystal or a salt thereof can be produced according to a cocrystallization a method known per se.

Compound (I) may also be used as a PET tracer.

Since the compound of the present invention has superior IRAK-4 inhibitory activity, it is also useful as safe medicaments based on such action.

In addition, since the compound of the present invention has TLR1-9 (excluding TLR3) inhibitory action as well as IL-1R inhibitory action, IL-18R inhibitory action and IL-33R inhibitory action, it is also useful as safe medicaments based on such action.

For example, the medicament of the present invention containing the compound of the present invention can be used for a mammal (e.g., mouse, rat, hamster, rabbit, cat, dog, bovine, sheep, monkey, human etc.) as a prophylactic or therapeutic agent for IRAK-4 associated diseases, more specifically, the diseases described in (1)-(4) below.

(1) inflammatory diseases (e.g., acute pancreatitis, chronic pancreatitis, asthma, adult respiratory distress syndrome, chronic obstructive pulmonary disease (COPD), inflammatory bone disease, inflammatory pulmonary disease, inflammatory bowel disease, celiac disease, hepatitis, systemic inflammatory response syndrome (SIRS), postoperative or posttraumatic inflammation, pneumonia (idiopathic interstitial pneumonia including idiopathic pulmonary fibrosis (IPF), etc.), nephritis, meningitis, cystitis, pharyngolaryngitis, gastric mucosal injury, central nervous system diseases (neurodegenerative diseases such as Alzheimer's disease etc., depression etc.), spondylitis, arthritis, dermatitis, chronic pneumonia, bronchitis, pulmonary infarction, silicosis, pulmonary sarcoidosis, ischemia-reperfusion injury, gout (e.g., acute gout etc.), hay fever, acute kidney injury, cryopyrin-associated periodic syndrome (CAPS) etc.), (2) autoimmune diseases (e.g., psoriasis, rheumatoid arthritis, inflammatory bowel disease (e.g., Crohn's disease, ulcerative colitis etc.), Sjogren's syndrome, Behcet's disease, multiple sclerosis, systemic lupus erythematosus, ankylopoietic spondylarthritis, polymyositis, dermatomyositis (DM), polyarteritis nodosa (PN), mixed connective tissue disease (MCTD), scleroderma, profundus lupus erythematosus, chronic thyroiditis, Hashimoto's thyroiditis, Graves' disease, autoimmune gastritis, type I and type II diabetes, autoimmune hemolytic anemia, autoimmune neutropenia, thrombocytopenia, atopic dermatitis, chronic active hepatitis, myasthenia gravis, organ transplant rejection, graft versus host disease, Addison's disease, abnormal immunoresponse, arthritis, dermatitis, radiodermatitis, lupus nephritis etc.), (3) osteoarticular degenerative disease (e.g., rheumatoid arthritis, osteoporosis, osteoarthritis etc.), (4) neoplastic diseases [e.g., malignant tumor, angiogenesis glaucoma, infantile hemangioma, multiple myeloma, acute myeloblastic leukemia, chronic sarcoma, chronic myelogenous leukemia, metastasis melanoma, Kaposi's sarcoma, vascular proliferation, cachexia, metastasis of the breast cancer, cancer (e.g., colorectal cancer (e.g., familial colorectal cancer, hereditary nonpolyposis colorectal cancer, gastrointestinal stromal tumor etc.), lung cancer (e.g., non-small cell lung cancer, small cell lung cancer, malignant mesothelioma etc.), mesothelioma, pancreatic cancer (e.g., pancreatic duct cancer etc.), gastric cancer (e.g., papillary adenocarcinoma, mucinous adenocarcinoma, adenosquamous carcinoma etc.), breast cancer (e.g., invasive ductal carcinoma, ductal carcinoma in situ, inflammatory breast cancer etc.), ovarian cancer (e.g., ovarian epithelial carcinoma, extragonadal germ cell tumor, ovarian germ cell tumor, ovarian low malignant potential tumor etc.), prostate cancer (e.g., hormone-dependent prostate cancer, non-hormone dependent prostate cancer etc.), liver cancer (e.g., primary liver cancer, extrahepatic bile duct cancer etc.), thyroid cancer (e.g., medullary thyroid carcinoma etc.), kidney cancer (e.g., renal cell carcinoma, transitional cell carcinoma in kidney and urinary duct etc.), uterine cancer, brain tumor (e.g., pineal astrocytoma, pilocytic astrocytoma, diffuse astrocytoma, anaplastic astrocytoma etc.), melanoma, sarcoma, urinary bladder cancer, hematologic cancer and the like including multiple myeloma, hypophyseal adenoma, glioma, acoustic neurinoma, retinoblastoma, pharyngeal cancer, laryngeal cancer, cancer of the tongue, thymoma, esophagus cancer, duodenal cancer, colorectal cancer, rectal cancer, hepatoma, pancreatic endocrine tumor, bile duct cancer, gallbladder cancer, penile cancer, urinary duct cancer, testis tumor, vulvar cancer, cervix cancer, endometrial cancer, uterus sarcoma, cholionic disease, vaginal cancer, skin cancer, fungoid mycosis, basal cell tumor, soft tissue sarcoma, malignant lymphoma, Hodgkin's disease, myelodysplastic syndrome, acute lymphocytic leukemia, chronic lymphocytic leukemia, adult T cell leukemia, chronic bone marrow proliferative disease, pancreatic endocrine tumor, fibrous histiocytoma, leiomyosarcoma, rhabdomyosarcoma, cancer of unknown primary, activated B-cell like diffuse large B-cell lymphoma (ABC-DLBCL))], (5) pain (e.g., neuropathic pain, diabetic pain, muscle fibrosis, postoperative pain, cancer pain, inflammatory pain, migraine, nerve pain, muscular pain etc.).

The medicament of the present invention can be preferably used as an agent for the prophylaxis or treatment of autoimmune diseases, inflammatory disease, osteoarticular degenerative disease or neoplastic disease, particularly preferably psoriasis, rheumatoid arthritis, inflammatory bowel disease (preferably Crohn's disease or ulcerative colitis), Sjogren's syndrome, Behcet's disease, multiple sclerosis, or systemic lupus erythematosus.

In another embodiment, the medicament of the present invention can be preferably used as an agent for the prophylaxis or treatment of autoimmune disease and/or inflammatory disease, particularly preferably multiple sclerosis; systemic lupus erythematosus, gout or hay fever.

Here, the above-mentioned "prophylaxis" of a disease means, for example, administration of a medicament containing the compound of the present invention to patients who are expected to have a high risk of the onset due to some factor relating to the disease but have not developed the disease or patients who have developed the disease but do not have a subjective symptom, or administration of a medicament containing the compound of the present invention to patients who are feared to show recurrence of the disease after treatment of the disease.

The medicament of the present invention shows superior pharmacokinetics (e.g., a half-life of the drug in plasma), low toxicity (e.g., HERG inhibition, CYP inhibition, CYP induction, cytotoxicity etc.), and decreased adverse effect (e.g., drug interaction, weight loss etc.). The compound of the present invention can be directly used as a medicament, or as the medicament of the present invention by producing a pharmaceutical composition by mixing with a pharmaceutically acceptable carrier by a means known per se and generally used in a production method of pharmaceutical preparations. The medicament of the present invention can be orally or parenterally administered safely to mammals (e.g., humans, monkeys, cows, horses, pigs, mice, rats, hamsters, rabbits, cats, dogs, sheep, goats etc.).

A medicament containing the compound of the present invention can be safely administered solely or by mixing with a pharmacologically acceptable carrier according to a method known per se (e.g., the method described in the Japanese Pharmacopoeia etc.) as the production method of a pharmaceutical preparation, and in the form of, for example, tablet (including sugar-coated tablet, film-coated tablet, sublingual tablet, orally disintegrating tablet, buccal etc.), pill, powder, granule, capsule (including soft capsule, microcapsule), troche, syrup, liquid, emulsion, suspension, release control preparation (e.g., immediate-release preparation, sustained-release preparation, sustained-release microcapsule), aerosol, film (e.g., orally disintegrating film, oral mucosa-adhesive film), injection (e.g., subcutaneous injection, intravenous injection, intramuscular injection, intraperitoneal injection), drip infusion, transdermal absorption type preparation, cream, ointment, lotion, adhesive preparation, suppository (e.g., rectal suppository, vaginal suppository), pellet, nasal preparation, pulmonary preparation (inhalant), eye drop and the like, orally or parenterally (e.g., intravenous, intramuscular, subcutaneous, intraorgan, intranasal, intradermal, instillation, intracerebral, intrarectal, intravaginal, intraperitoneal and intratumor administrations, administration to the vicinity of tumor, and direct administration to the lesion).

The content of the compound of the present invention in the medicament of the present invention is about 0.01 to 100% by weight of the entire medicament. The dose varies depending on administration subject, administration route, disease and the like. For example, for oral administration to patients (body weight about 60 kg) with psoriasis, rheumatoid arthritis, inflammatory bowel disease, Sjogren's syndrome, Behcet's disease, multiple sclerosis or systemic lupus erythematosus, about 0.01 mg/kg body weight—about 500 mg/kg body weight, preferably about 0.1 mg/kg body weight— about 50 mg/kg body weight, more preferably about 1 mg/kg body weight—about 30 mg/kg body weight of an active ingredient (compound (I)) can be administered once to several portions per day.

The pharmaceutically acceptable carrier, which may be used for the production of the medicament of the present invention, may be exemplified by various organic or inorganic carrier materials that are conventionally used as preparation materials, for example, excipient, lubricant, binding agent and disintegrant for solid preparations; or solvent, solubilizing agent, suspending agent, isotonic agent, buffering agent, soothing agent and the like for liquid preparations. Furthermore, when necessary, ordinary additives such as preservative, antioxidant, colorant, sweetening agent, adsorbent, wetting agent and the like can be also used as appropriate in an appropriate amount.

When the compound of the present invention is used as an ointment, the ointment is prepared by mixing the compound of the present invention with a general ointment base so that the concentration is adjusted to about 0.001 to 3% (W/W), preferably about 0.01 to 1% (W/W). The preparation of ointment preferably comprises a powderization step of the compound of the present invention, and a sterilization step of the formulation. The ointment is administered once to four times a day depending on condition of the patient.

Examples of the ointment base include purified lanolin, white vaseline, macrogol, plastibase, liquid paraffin and the like.

Examples of the excipient include lactose, white sugar, D-mannitol, starch, corn starch, crystalline cellulose, light anhydrous silicic acid and the like.

Examples of the lubricant include magnesium stearate, calcium stearate, talc, colloidal silica and the like.

Examples of the binding agent include crystalline cellulose, white sugar, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of the disintegrant include starch, carboxymethylcellulose, carboxymethylcellulose calcium, carboxymethylstarch sodium, L-hydroxypropylcellulose and the like.

Examples of the solvent include water for injection, alcohol, propylene glycol, Macrogol, sesame oil, corn oil, olive oil and the like.

Examples of the solubilizing agent include polyethylene glycol, propylene glycol, D-mannitol, benzyl benzoate, ethanol, trisaminomethane, cholesterol, triethanolamine, sodium carbonate, sodium citrate and the like.

Examples of the suspending agent include surfactants such as stearyl triethanolamine, sodium lauryl sulfate, laurylaminopropionic acid, lecithin, benzalkonium chloride, benzetonium chloride, glycerin monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like; and the like.

Examples of the isotonic agent include glucose, D-sorbitol, sodium chloride, glycerin, D-mannitol and the like.

Examples of the buffering agent include buffer solutions such as phosphates, acetates, carbonates, citrates and the like.

Examples of the soothing agent include benzyl alcohol and the like.

Examples of the preservative include parahydroxybenzoates, chlorobutanol, benzyl alcohol, phenylethyl alcohol, dehydroacetic acid, sorbic acid and the like.

Examples of the antioxidant include sulfites, ascorbic acid, α-tocopherol and the like.

Examples of the colorant include water-soluble food tar color (e.g., food colors such as Food Color Red No. 2 and No. 3, Food Color Yellow No. 4 and No. 5, Food Color Blue No. 1 and No. 2 etc.), water-insoluble lake dye (e.g., aluminum salt of the aforementioned water-soluble food tar color etc.), natural dye (e.g., β-carotene, chlorophyll, ferric oxide red etc.) and the like.

Examples of the sweetening agent include saccharin sodium, dipotassium glycyrrhizinate, aspartame, stevia and the like.

Examples of the adsorbent include porous starch, calcium silicate (trade name: Florite RE), magnesium alumino metasilicate (trade name: Neusilin), light anhydrous silicic acid (trade name: Sylysia) and the like.

Examples of the wetting agent include propylene glycol monostearate, sorbitan monooleate, diethylene glycol monolaurate, polyoxyethylenelauryl ether and the like.

For the prophylaxis or treatment of various diseases, the compound of the present invention can also be used together with other drugs. In the following, a medicament to be used when the compound of the present invention is used together with other drug is referred to as "the combination agent of the present invention".

For example, when the compound of the present invention is used as a IRAK-4 inhibitor, TLR1-9 (excluding TLR3) inhibitor, IL-1R inhibitor, IL-18R inhibitor or IL-33R inhibitor, it can be used in combination with the following drugs.

(1) Non-Steroidal Anti-Inflammatory Drug (NSAIDs)
(i) Classical NSAIDs
alcofenac, aceclofenac, sulindac, tolmetin, etodolac, fenoprofen, thiaprofenic acid, meclofenamic acid, meloxicam, tenoxicam, lornoxicam, nabumeton, acetaminophen, phenacetin, ethenzamide, sulpyrine, antipyrine, migrenin, aspirin, mefenamic acid, flufenamic acid, diclofenac sodium, loxoprofen sodium, phenylbutazone, indomethacin, ibuprofen, ketoprofen, naproxen, oxaprozin, flurbiprofen, fenbufen, pranoprofen, floctafenine, piroxicam, epirizole, tiaramide hydrochloride, zaltoprofen, gabexate mesylate, camostat mesylate, ulinastatin, colchicine, probenecid, sulfinpyrazone, benzbromarone, allopurinol, sodium aurothiomalate, hyaluronate sodium, sodium salicylate, morphine hydrochloride, salicylic acid, atropine, scopolamine, morphine, pethidine, levorphanol, oxymorphone or a salt thereof and the like.
(ii) cyclooxygenase inhibitor (COX-1 selective inhibitor, COX-2 selective inhibitor etc.)
salicylic acid derivatives (e.g., celecoxib, aspirin), etoricoxib, valdecoxib, diclofenac, indomethacin, loxoprofen and the like.
(iii) nitric oxide-releasing NSAIDs.
(iv) JAK inhibitor
tofacitinib, ruxolitinib and the like.
(2) Disease-Modifying Anti-Rheumatic Drugs (DMARDs)
(i) Gold preparation
auranofin and the like.
(ii) penicillamine
D-penicillamine and the like.
(iii) aminosalicylic acid preparation
sulfasalazine, mesalazine, olsalazine, balsalazide and the like.
(iv) antimalarial drug
chloroquine and the like.
(v) pyrimidine synthesis inhibitor
leflunomide and the like.
(vi) prograf
(3) Anti-Cytokine Drug
(I) Protein Drug
(i) TNF inhibitor
etanercept, infliximab, adalimumab, certolizumab pegol, golimumab, PASSTNF-α, soluble TNF-α receptor, TNF-α binding protein, anti-TNF-α antibody and the like.

(ii) interleukin-1 inhibitor
  anakinra (interleukin-1 receptor antagonist), soluble interleukin-1 receptor and the like.
(iii) interleukin-6 inhibitor
  tocilizumab (anti-interleukin-6 receptor antibody), anti-interleukin-6 antibody and the like.
(iv) interleukin-10 drug
  interleukin-10 and the like.
(v) interleukin-12/23 inhibitor
  ustekinumab, briakinumab (anti-interleukin-12/23 antibody) and the like.
(II) Non-Protein Drug
(i) MAPK inhibitor
  BMS-582949 and the like.
(ii) gene modulator
  inhibitor of molecule involved in signal transduction, such as NF-κ, NF-κB, IKK-1, IKK-2, AP-1 and the like, and the like.
(iii) cytokine production inhibitor
  iguratimod, tetomilast and the like.
(iv) TNF-α converting enzyme inhibitor
(v) interleukin-1β converting enzyme inhibitor
  VX-765 and the like.
(vi) interleukin-6 antagonist
  HMPL-004 and the like.
(vii) interleukin-8 inhibitor
  IL-8 antagonist, CXCR1 & CXCR2 antagonist, reparixin and the like.
(viii) chemokine antagonist
  CCR9 antagonist (CCX-282, CCX-025), MCP-1 antagonist and the like.
(ix) interleukin-2 receptor antagonist
  denileukin, diftitox and the like.
(x) therapeutic vaccines
  TNF-α vaccine and the like.
(xi) gene therapy drug
  gene therapy drugs aiming at promoting the expression of gene having an anti-inflammatory action such as interleukin-4, interleukin-10, soluble interleukin-1 receptor, soluble TNF-α receptor and the like.
(xii) antisense compound
  ISIS 104838 and the like.
(4) Integrin Inhibitor
  natalizumab, vedolizumab, AJM300, TRK-170, E-6007 and the like.
(5) Immunomodulator (Immunosuppressant)
  methotrexate, cyclophosphamide, MX-68, atiprimod dihydrochloride, BMS-188667, CKD-461, rimexolone, cyclosporine, tacrolimus, gusperimus, azathiopurine, anti-lymphocyte serum, freeze-dried sulfonated normal immunoglobulin, erythropoietin, colony stimulating factor, interleukin, interferon and the like.
(6) Steroid
  dexamethasone, hexestrol, methimazole; betamethasone, triamcinolone, triamcinolone acetonide, fluocinonide, fluocinolone acetonide, predonisolone, methylpredonisolone, cortisone acetate, hydrocortisone, fluorometholone, beclomethasone dipropionate, estriol and the like.
(7) Angiotensin Converting Enzyme Inhibitor
  enalapril, captopril, ramipril, lisinopril, cilazapril, perindopril and the like.
(8) Angiotensin II Receptor Antagonist
  candesartan, candesartan cilexetil, azilsartan, azilsartan medoxomil, valsartan, irbesartan, olmesartan, eprosartan and the like.
(9) Diuretic Drug
  hydrochlorothiazide, spironolactone, furosemide, indapamide, bendrofluazide, cyclopenthiazide and the like.
(10) Cardiotonic Drug
  digoxin, dobutamine and the like.
(11) β Receptor Antagonist
  carvedilol, metoprolol, atenolol and the like.
(12) Ca Sensitizer
  MCC-135 and the like.
(13) Ca Channel Antagonist
  nifedipine, diltiazem, verapamil and the like.
(14) Anti-Platelet Drug, Anticoagulator
  heparin, aspirin, warfarin and the like.
(15) HMG-CoA Reductase Inhibitor
  atorvastatin, simvastatin and the like.
(16) Contraceptive
(i) sex hormone or derivatives thereof
  gestagen or a derivative thereof (progesterone, 17α-hydroxy progesterone, medroxyprogesterone, medroxyprogesterone acetate, norethisterone, norethisterone enanthate, norethindrone, norethindrone acetate, norethynodrel, levonorgestrel, norgestrel, ethynodiol diacetate, desogestrel, norgestimate, gestodene, progestin, etonogestrel, drospirenone, dienogest, trimegestone, nestorone, chlormadinone acetate, mifepristone, nomegestrol acetate, Org-30659, TX-525, EMM-310525) or a combination agent of a gestagen or a derivative thereof and an estrogen or a derivative thereof (estradiol, estradiol benzoate, estradiol cypionate, estradiol dipropionate, estradiol enanthate, estradiol hexahydrobenzoate, estradiol phenylpropionate, estradiol undecanoate, estradiol valerate, estrone, ethinylestradiol, mestranol) and the like.
(ii) antiestrogen
  ormeloxifene, mifepristone, Org-33628 and the like.
(iii) spermatocide
  ushercell and the like.
(17) Others
(i) T cell inhibitors
(ii) inosine monophosphate dehydrogenase (IMPDH) inhibitor
  mycophenolate mofetil and the like.
(iii) adhesion molecule inhibitor
  ISIS-2302, selectin inhibitor, ELAM-1, VCAM-1, ICAM-1 and the like.
(iv) thalidomide
(v) cathepsin inhibitor
(vi) matrix metalloprotease (MMPs) inhibitor
  V-85546 and the like.
(vii) glucose-6-phosphate dehydrogenase inhibitor
(viii) Dihydroorotate dehydrogenase (DHODH) inhibitor
(ix) phosphodiesterase IV (PDE IV) inhibitor
  roflumilast, CG-1088 and the like.
(x) phospholipase $A_2$ inhibitor
(xi) iNOS inhibitor
  VAS-203 and the like.
(xii) microtubule stimulating drug
  paclitaxel and the like.
(xiii) microtuble inhibitor
  reumacon and the like.
(xiv) MHC class II antagonist
(xv) prostacyclin agonist
  iloprost and the like.
(xvi) CD4 antagonist
  zanolimumab and the like.
(xvii) CD23 antagonist
(xviii) LTB4 receptor antagonist
  DW-1305 and the like.

(xix) 5-lipoxygenase inhibitor
  zileuton and the like.
(xx) cholinesterase inhibitor
  galanthamine and the like.
(xxi) tyrosine kinase inhibitor
  Tyk2 inhibitor (WO2010142752) and the like.
(xxii) cathepsin B inhibitor
(xxiii) adenosine deaminase inhibitor
  pentostatin and the like.
(xxiv) osteogenesis stimulator
(xxv) dipeptidylpeptidase inhibitor
(xxvi) collagen agonist
(xxvii) capsaicin cream
(xxviii) hyaluronic acid derivative
  synvisc (hylan G-F 20), orthovisc and the like.
(xxix) glucosamine sulfate
(xxx) amiprilose
(xxxi) CD-20 inhibitor
  rituximab, ibritumomab, tositumomab, ofatumumab and the like.
(xxxii) BAFF inhibitor
  belimumab, tabalumab, atacicept, A-623 and the like.
(xxxiii) CD52 inhibitor
  alemtuzumab and the like.
(xxxiv) IL-17 inhibitor
  secukinumab (AIN-457), LY-2439821, AMG827 and the like.

Other concomitant drugs besides the above-mentioned include, for example, antibacterial agent, antifungal agent, antiprotozoal agent, antibiotic, antitussive and expectorant drug, sedative, anesthetic, antiulcer drug, antiarrhythmic agent, hypotensive diuretic drug, anticoagulant, tranquilizer, antipsychotic, antitumor drug, hypolipidemic drug, muscle relaxant, antiepileptic drug, antidepressant, antiallergic drug, cardiac stimulants, therapeutic drug for arrhythmia, vasodilator, vasoconstrictor, hypotensive diuretic, therapeutic drug for diabetes, antinarcotic, vitamin, vitamin derivative, anti-asthmatic, therapeutic agent for pollakisuria/anischuria, antipruritic drug, therapeutic agent for atopic dermatitis, therapeutic agent for allergic rhinitis, hypertensor, endotoxin-antagonist or -antibody, signal transduction inhibitor, inhibitor of inflammatory mediator activity, antibody to inhibit inflammatory mediator activity, inhibitor of anti-inflammatory mediator activity, antibody to inhibit anti-inflammatory mediator activity and the like. Specific examples thereof include the following.

(1) Antibacterial Agent
(i) sulfa drug
  sulfamethizole, sulfisoxazole, sulfamonomethoxine, salazosulfapyridine, silver sulfadiazine and the like.
(ii) quinolone antibacterial agent
  nalidixic acid, pipemidic acid trihydrate, enoxacin, norfloxacin, ofloxacin, tosufloxacin tosylate, ciprofloxacin hydrochloride, lomefloxacin hydrochloride, sparfloxacin, fleroxacin and the like.
(iii) antiphthisic
  isoniazid, ethambutol (ethambutol hydrochloride), p-aminosalicylic acid (calcium p-aminosalicylate), pyrazinamide, ethionamide, protionamide, rifampicin, streptomycin sulfate, kanamycin sulfate, cycloserine and the like.
(iv) antiacidfast bacterium drug
  diaphenylsulfone, rifampicin and the like.
(v) antiviral drug
  idoxuridine, acyclovir, vidarabine, gancyclovir and the like.
(vi) anti-HIV agent
  zidovudine, didanosine, zalcitabine, indinavir sulfate ethanolate, ritonavir and the like.
(vii) antispirochetele
(viii) antibiotic
  tetracycline hydrochloride, ampicillin, piperacillin, gentamicin, dibekacin, kanendomycin, lividomycin, tobramycin, amikacin, fradiomycin, sisomicin, tetracycline, oxytetracycline, rolitetracycline, doxycycline, ticarcillin, cephalothin, cephapirin, cephaloridine, cefaclor, cephalexin, cefroxadine, cefadroxil, cefamandole, cefotoam, cefuroxime, cefotiam, cefotiam hexetil, cefuroxime axetil, cefdinir, cefditoren pivoxil, ceftazidime, cefpiramide, cefsulodin, cefinenoxime, cefpodoxime proxetil, cefpirome, cefozopran, cefepime, cefsulodin, cefinenoxime, cefinetazole, cefminox, cefoxitin, cefbuperazone, latamoxef, flomoxef, cefazolin, cefotaxime, cefoperazone, ceftizoxime, moxalactam, thienamycin, sulfazecin, aztreonam or a salt a salt thereof, griseofulvin, lankacidin-group [Journal of Antibiotics (J. Antibiotics), 38, 877-885 (1985)], azole compound [2-[(1R,2R)-2-(2,4-difluorophenyl)-2-hydroxy-1-methyl-3-(1H-1,2,4-triazol-1-yl)propyl]-4-[4-(2,2,3,3-tetrafluoropropoxy)phenyl]-3(2H,4H)-1,2,4-triazolone, fluconazole, itraconazole and the like] and the like.

(2) Antifungal Agent
(i) polyethylene antibiotic (e.g., amphotericin B, nystatin, trichomycin)
(ii) griseofulvin, pyrrolnitrin and the like
(iii) cytosine metabolism antagonist (e.g., flucytosine)
(iv) imidazole derivative (e.g., econazole, clotrimazole, miconazole nitrate, bifonazole, croconazole)
(v) triazole derivative (e.g., fluconazole, itraconazole)
(vi) thiocarbamic acid derivative (e.g., trinaphthol) and the like.

(3) Antiprotozoal Agent
  metronidazole, tinidazole, diethylcarbamazine citrate, quinine hydrochloride, quinine sulfate and the like.

(4) Antitussive and Expectorant Drug
  ephedrine hydrochloride, noscapine hydrochloride, codeine phosphate, dihydrocodeine phosphate, isoproterenol hydrochloride, methylephedrine hydrochloride, alloclamide, chlophedianol, picoperidamine, cloperastine, protokylol, isoproterenol, salbutamol, terbutaline, oxymetebanol, morphine hydrochloride, dextromethorphan hydrobromide, oxycodone hydrochloride, dimemorfan phosphate, tipepidine hibenzate, pentoxyverine citrate, clofedanol hydrochloride, benzonatate, guaifenesin, bromhexine hydrochloride, ambroxol hydrochloride, acetylcysteine, ethyl cysteine hydrochloride, carbocysteine and the like.

(5) Sedative
  chlorpromazine hydrochloride, atropine sulfate, phenobarbital, barbital, amobarbital, pentobarbital, thiopental sodium, thiamylal sodium, nitrazepam, estazolam, flurazepam, haloxazolam, triazolam, flunitrazepam, bromovalerylurea, chloral hydrate, triclofos sodium and the like.

(6) Anesthetic
(6-1) Local Anesthetic
  cocaine hydrochloride, procaine hydrochloride, lidocaine, dibucaine hydrochloride, tetracaine hydrochloride, mepivacaine hydrochloride, bupivacaine hydrochloride, oxybuprocaine hydrochloride, ethyl aminobenzoate, oxethazaine and the like.
(6-2) General Anesthetic
(i) inhalation anesthetic (e.g., ether, halothane, nitrous oxide, isoflurane, enflurane), (ii) intravenous anesthetic (e.g., ketamine hydrochloride, droperidol, thiopental sodium, thiamylal sodium, pentobarbital) and the like.

(7) Antiulcer Drug histidine hydrochloride, lansoprazole, metoclopramide, pirenzepine, cimetidine, ranitidine, famotidine, urogastrone, oxethazaine, proglumide, omeprazole, sucralfate, sulpiride, cetraxate, gefarnate, aldioxa, teprenone, prostaglandin and the like.

(8) Antiarrhythmic Agent (i) sodium channel blocker (e.g., quinidine, procainamide, disopyramide, ajmaline, lidocaine, mexiletine, phenyloin), (ii) β-blocker (e.g., propranolol, alprenolol, bufetolol hydrochloride, oxprenolol, atenolol, acebutolol, metoprolol, bisoprolol, pindolol, carteolol, arotinolol hydrochloride), (iii) potassium channel blocker (e.g., amiodarone), (iv) calcium channel blocker (e.g., verapamil, diltiazem) and the like.

(9) Hypotensive Diuretic Drug hexamethonium bromide, clonidine hydrochloride, hydrochlorothiazide, trichlormethiazide, furosemide, ethacrynic acid, bumetanide, mefruside, azosemide, spironolactone, potassium canrenoate, triamterene, amiloride, acetazolamide, D-mannitol, isosorbide, aminophylline and the like.

(10) Anticoagulant heparin sodium, sodium citrate, activated protein C, tissue factor pathway inhibitor, antithrombin III, dalteparin sodium, warfarin potassium, argatroban, gabexate, ozagrel sodium, ethyl icosapentate, beraprost sodium, alprostadil, ticlopidine hydrochloride, pentoxifylline, dipyridamole, tisokinase, urokinase, streptokinase and the like.

(11) Tranquilizer diazepam, lorazepam, oxazepam, chlordiazepoxide, medazepam, oxazolam, cloxazolam, clotiazepam, bromazepam, etizolam, fludiazepam, hydroxyzine and the like.

(12) Antipsychotic chlorpromazine hydrochloride, prochlorperazine, trifluoperazine, thioridazine hydrochloride, perphenazine maleate, fluphenazine enanthate, prochlorperazine maleate, levomepromazine maleate, promethazine hydrochloride, haloperidol, bromperidol, spiperone, reserpine, clocapramine hydrochloride, sulpiride, zotepine and the like.

(13) Antitumor Drug

6-O—(N-chloroacetylcarbamoyl)fumagillol, bleomycin, methotrexate, actinomycin D, mitomycin C, daunorubicin, adriamycin, neocarzinostatin, cytosine arabinoside, fluorouracil, tetrahydrofuryl-5-fluorouracil, picibanil, lentinan, levamisole, bestatin, azimexon, glycyrrhizin, doxorubicin hydrochloride, aclarubicin hydrochloride, bleomycin hydrochloride, peplomycin sulfate, vincristine sulfate, vinblastine sulfate, irinotecan hydrochloride, cyclophosphamide, melphalan, busulfan, thiotepa, procarbazine hydrochloride, cisplatin, azathioprine, mercaptopurine, tegafur, carmofur, cytarabine, methyltestosterone, testosterone propionate, testosterone enanthate, mepitiostane, fosfestrol, chlormadinone acetate, leuprorelin acetate, buserelin acetate and the like.

(14) Hypolipidemic Drug clofibrate, ethyl 2-chloro-3-[4-(2-methyl-2-phenylpropoxy)phenyl]propionate [Chemical and Pharmaceutical Bulletin, 1990, 38, 2792-2796], pravastatin, simvastatin, probucol, bezafibrate, clinofibrate, nicomol, cholestyramine, dextran sulfate sodium and the like.

(15) Muscle Relaxant pridinol, tubocurarine, pancuronium, tolperisone hydrochloride, chlorphenesin carbamate, baclofen, chlormezanone, mephenesin, chlorzoxazone, eperisone, tizanidine and the like.

(16) Antiepileptic Drug phenyloin, ethosuximide, acetazolamide, chlordiazepoxide, trimethadione, carbamazepine, phenobarbital, primidone, sulthiame, sodium valproate, clonazepam; diazepam, nitrazepam and the like.

(17) Antidepressant imipramine, clomipramine, noxiptiline, phenelzine, amitriptyline hydrochloride, nortriptyline hydrochloride, amoxapine, mianserin hydrochloride, maprotiline hydrochloride, sulpiride, fluvoxamine maleate, trazodone hydrochloride and the like.

(18) Antiallergic Drug diphenhydramine, chlorpheniramine, tripelennamine, metodilamine, clemizole, diphenylpyraline, methoxyphenamine, sodium cromoglicate, tranilast, repirinast, amlexanox, ibudilast, ketotifen, terfenadine, mequitazine, azelastine hydrochloride, epinastine, ozagrel hydrochloride, pranlukast hydrate, seratrodast and the like.

(19) Cardiac Stimulants trans-π-oxocamphor, terephyllol, aminophylline, etilefrine, dopamine, dobutamine, denopamine, vesnarinone, aminone, pimobendan, ubidecarenone, digitoxin, digoxin, methyldigoxin, lanatoside C, G-strophanthin and the like.

(20) Vasodilator oxyfedrine, diltiazem, tolazoline, hexobendine, bamethan, clonidine, methyldopa, guanabenz and the like.

(21) Vasoconstrictor dopamine, dobutamine, denopamine and the like.

(22) Hypotensive Diuretic hexamethonium bromide, pentolinium, mecamylamine, ecarazine, clonidine, diltiazem, nifedipine and the like.

(23) Therapeutic Drug for Diabetes tolbutamide, chlorpropamide, acetohexamide, glibenclamide, tolazamide, acarbose, epalrestat, troglitazone, glucagon, glymidine, glipizide, phenformin, buformin, metformin and the like.

(24) Antinarcotic levallorphan, nalorphine, naloxone or a salt thereof and the like.

(25) Liposoluble Vitamins (i) vitamin A: vitamin $A_1$, vitamin $A_2$ and retinol palmitate (ii) vitamin D: vitamin $D_1$, $D_2$, $D_3$, $D_4$ and $D_5$ (iii) vitamin E: α-tocopherol, β-tocopherol, γ-tocopherol, δ-tocopherol, dl-α-tocopherol nicotinate (iv) vitamin K: vitamin $K_1$, $K_2$, $K_3$ and $K_4$ (v) folic acid (vitamin M) and the like.

(26) Vitamin Derivative various derivatives of vitamins, for example, vitamin $D_3$ derivatives such as 5,6-trans-cholecalciferol, 2,5-hydroxycholecalciferol, 1-α-hydroxycholecalciferol and the like, vitamin $D_2$ derivatives such as 5,6-trans-ergocalciferol and the like, and the like.

(27) Antiasthmatic isoprenaline hydrochloride, salbutamol sulfate, procaterol hydrochloride, terbutaline sulfate, trimetoquinol hydrochloride, tulobuterol hydrochloride, orciprenaline sulfate, fenoterol hydrobromide, ephedrine hydrochloride, ipratropium bromide, oxitropium bromide, flutropium bromide, theophylline, aminophylline, sodium cromoglicate, tranilast, repirinast, amlexanox, ibudilast, ketotifen, terfenadine, mequitazine, azelastine, epinastine, ozagrel hydrochloride, pranikast hydrate, seratrodast, dexamethasone, prednisolone, hydrocortisone, hydrocortisone sodium succinate, beclometasone dipropionate and the like.

(28) Therapeutic Agent for Pollakisuria/Anischuria flavoxate hydrochloride and the like.

(29) Therapeutic Agent for Atopic Dermatitis sodium cromoglicate and the like.

(30) Therapeutic Agent for Allergic Rhinitis sodium cromoglicate, chlorpheniramine maleate, alimemazine tartrate, clemastine fumarate, homochlorcyclizine hydrochloride, fexofenadine, mequitazine and the like.

(31) Hypertensor dopamine, dobutamine, denopamine, digitoxin, digoxin, methyldigoxin, lanatoside C, G-strophanthin and the like.

(32) Others hydroxycam, diacerein, megestrol acetate, nicergoline, prostaglandins and the like.

For combined use, the administration time of the compound of the present invention and the concomitant drug is not restricted, and the compound of the present invention or the concomitant drug can be administered to an administration subject simultaneously, or may be administered at different times. The dosage of the concomitant drug may be determined according to the dose clinically used, and can be appropriately selected depending on an administration subject, administration route, disease, combination and the like.

The administration form of the combined use is not particularly limited, and the compound of the present invention and a concomitant drug only need to be combined on administration. Examples of such administration mode include the following:

(1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like.

The mixing ratio of the compound of the present invention and a concomitant drug in the combination agent of the present invention can be appropriately selected based on the subject of administration, administration route, disease and the like.

For example, while the content of the compound of the present invention in the combination agent of the present invention varies depending on the preparation form, it is generally about 0.01-100 wt %, preferably about 0.1-50 wt %, more preferably about 0.5-20 wt %, of the whole preparation.

The content of the concomitant drug in the combination agent of the present invention varies depending on the preparation form, and generally about 0.01 to 100% by weight, preferably about 0.1 to 50% by weight, further preferably about 0.5 to 20% by weight, of the entire preparation.

While the content of the additive such as a carrier and the like in the combination agent of the present invention varies depending on the form of a preparation, it is generally about 1 to 99.99% by weight, preferably about 10 to 90% by weight, based on the preparation.

When the compound of the present invention and the concomitant drug are separately prepared, the same content may be adopted.

The dose of the combination agent varies depending on the kind of the compound of the present invention, administration route, symptom, age of patients and the like. For example, for oral administration to patients (body weight about 60 kg) with psoriasis, rheumatoid arthritis, inflammatory bowel disease, Sjogren's syndrome, Behcet's disease, multiple sclerosis or systemic lupus erythematosus, about 0.1 mg/kg body weight—about 50 mg/kg body weight, preferably about 1 mg/kg body weight—about 30 mg/kg body weight, of compound (I) can be administered once to several portions per day.

The dose of the pharmaceutical composition of the present invention as a sustained-release preparation varies depending on the kind and content of compound (I), dosage form, period of sustained drug release, subject animal of administration (e.g., mammals such as mouse, rat, hamster, guinea pig, rabbit, cat, dog, bovine, horse, swine, sheep, monkey, human etc.), and administration object. For example, for application by parenteral administration, about 0.1 to about 100 mg of compound (I) needs to be released from the administered preparation per 1 week.

Any amount of the concomitant drug can be adopted as long as the side effects do not cause a problem. The daily dosage in terms of the concomitant drug varies depending on the severity, age, sex, body weight, sensitivity difference of the subject, administration period, interval, and nature, pharmacology, kind of the pharmaceutical preparation, kind of effective ingredient, and the like, and not particularly restricted, and the amount of a drug is, in the case of oral administration for example, generally about 0.001 to 2000 mg, preferably about 0.01 to 500 mg, further preferably about 0.1 to 100 mg, per 1 kg of a mammal and this is generally administered once to 4-times, divided in a day.

When the combination agent of the present invention is administered, the compound of the present invention and the concomitant drug can be administered simultaneously, or may be administered in a staggered manner. When administered at a time interval, the interval varies depending on the effective ingredient, dosage form and administration method, and, for example, when the concomitant drug is administered first, a method in which the compound of the present invention is administered within time range of from 1 minute to 3 days, preferably from 10 minutes to 1 day, more preferably from 15 minutes to 1 hour, after administration of the concomitant drug is an example. When the compound of the present invention is administered first, a method in which the concomitant drug is administered within time range of from 1 minute to 1 day, preferably from 10 minutes to 6 hours, more preferably from 15 minutes to 1 hour after administration of the compound of the present invention is an example.

EXAMPLES

The present invention is explained in detail in the following by referring to Examples, Experimental Examples and Formulation Examples, which are not to be construed as limitative, and the invention may be changed within the scope of the present invention.

In the following Examples, the "room temperature" generally means about 10° C. to about 35° C. The ratios indicated for mixed solvents are volume mixing ratios, unless otherwise specified. % means wt %, unless otherwise specified.

In silica gel column chromatography, NH means use of aminopropylsilane-bound silica gel, and Diol means use of 3-(2,3-dihydroxypropoxy)propylsilane-bound silica gel. In HPLC (high performance liquid chromatography), C18 means use of octadecyl-bound silica gel. The ratios of elution solvents are volume mixing ratios, unless otherwise specified.

In Examples, the following abbreviations are used.
mp: melting point
MS: mass spectrum
M: mol concentration
$CDCl_3$: deuterochloroform
$DMSO-d_6$: deuterodimethyl sulfoxide
$^1H$ NMR: proton nuclear magnetic resonance
LC/MS: liquid chromatograph mass spectrometer
ESI: Electron Spray Ionization
APCI: atmospheric pressure chemical ionization
DME: 1,2-dimethoxyethane
DMA: N,N-dimethylacetamide
HATU: 2-(7-azabenzotriazol-1-yl)-1,1,3,3-tetramethyluronium hexafluorophosphate
HOBt: 1-hydroxybenzotriazole
THF: tetrahydrofuran
DMF: N,N-dimethylformamide
TFA: trifluoroacetic acid
LHMDS: lithium hexamethyldisilazide
n-: normal
s-: secondary
t-: tertiary $^1H$ NMR was measured by Fourier-transform type NMR. For the analysis, ACD/SpecManager (trade name) and the like were used. Peaks with very mild protons such as a hydroxy group, an amino group and the like are not described.

MS was measured by LC/MS. As ionization method, ESI method or APCI method was used. The data indicates those actual measured value (found). Generally, molecular ion peaks ($[M+H]^+$, $[M-H]^-$ and the like) are observed. For example, in the case of a compound having a tert-butoxycarbonyl group, a peak after elimination of a tert-butoxycarbonyl group or tert-butyl group may be observed as a fragment ion. In the case of a compound having a hydroxy group, a peak after elimination of $H_2O$ may be observed as a fragment ion. In the case of a salt, a molecular ion peak or fragment ion peak of free form is generally observed.

The unit of sample concentration (c) for optical rotation ($[\alpha]_D$) is g/100 mL.

Elemental analysis value (Anal.) was described as calculated value (Calcd) and actual measured value (Found).

Example 1

N-(3-((4S)-4-hydroxy-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide hydrate A) (4S)-4-((tert-butyl(dimethyl)silyl)oxy)-1-(1-methyl-1H-pyrazol-3-yl)pyrrolidin-2-one A solution of 3-iodo-1-methyl-1H-pyrazole (1.7 g), (4S)-4-((tert-butyl(dimethyl)silyl)oxy)pyrrolidin-2-one (1.8 g), copper(I) iodide (315 mg), N1,N2-dimethylethane-1,2-diamine (0.36 mL) and tripotassium phosphate (3.5 g) in cyclopentyl methyl ether (34 mL) was stirred overnight at 120° C. The reaction mixture was diluted with ethyl acetate, washed with saturated aqueous ammonium chloride solution, water and saturated brine, and dried over anhydrous magnesium sulfate, and the solvent was evaporated under reduced pressure. The residue was purified by silica gel column chromatography (ethyl acetate/hexane) to give the title compound (2.1 g).

MS (ESI+): $[M+H]^+$: 295.9.

B) (4S)-4-((tert-butyl(dimethyl)silyl)oxy)-1-(1-methyl-4-nitro-1H-pyrazol-3-yl)pyrrolidin-2-one To a solution of (4S)-4-((tert-butyl(dimethyl)silyl)oxy)-1-(1-methyl-1H-pyrazol-3-yl)pyrrolidin-2-one (2.07 g) in acetic anhydride (21 mL) was added a solution of fuming nitric acid (0.58 mL) in acetic anhydride (21 mL), and the mixture was stirred under for 1.5 hr under ice-cooling. To the reaction mixture were added ice water and saturated aqueous sodium hydrogen carbonate solution, and the mixture was extracted with ethyl acetate. The extract was washed with saturated brine, and dried over anhydrous magnesium sulfate, and the solvent was evaporated under reduced pressure. The residue was purified by silica gel column chromatography (ethyl acetate/hexane) to give the title compound (1.9 g).

MS (ESI+): $[M+H]^+$: 341.0.

C) (4S)-1-(4-amino-1-methyl-1H-pyrazol-3-yl)-4-((tert-butyl(dimethyl)silyl)oxy)pyrrolidin-2-one A mixture of (4S)-4-((tert-butyl(dimethyl)silyl)oxy)-1-(1-methyl-4-nitro-1H-pyrazol-3-yl)pyrrolidin-2-one (2.7 g), 10% palladium-carbon (0.85 g), THF (27 mL) and methanol (27 mL) was stirred at room temperature for 2 hr under hydrogen atmosphere. The reaction mixture was filtered through a membrane filter, and the filtrate was concentrated under reduced pressure to give the title compound (2.3 g).

MS (ESI+): $[M+H]^+$: 310.9.

D) tert-butyl (4-bromopyridin-2-yl)carbamate

To a suspension of 4-bromopyridin-2-amine (45 g) in tert-butanol (336 mL) was added di-tert-butyl dicarbonate (84 mL) at room temperature, the mixture was stirred at 50° C. for 3 hr, and the precipitate was collected by filtration. The mother liquid was concentrated under reduced pressure, the residue was suspended in hexane, and the solid was collected by filtration. The collected solids were combined, washed with diisopropyl ether, and dried under reduced pressure to give the title compound (56 g). The filtrates were combined, and concentrated under reduced pressure, and the residue was purified by silica gel column chromatography (ethyl acetate/hexane) to give the title compound (6.4 g).

MS (ESI+). found: 217.0.

E) tert-butyl (4-bromopyridin-2-yl)(2,2,2-trifluoroethyl)carbamate

To a mixture of tert-butyl (4-bromopyridin-2-yl)carbamate (1.5 g), cesium carbonate (2.7 g) and DMF (15 mL) was added 2,2,2-trifluoroethyl trifluoromethanesulfonate (1.0 mL). The reaction mixture was stirred at room temperature for 15 hr, saturated aqueous ammonium chloride solution was added thereto, and the mixture was extracted with ethyl acetate. The extract was washed with saturated brine, and dried over anhydrous sodium sulfate, and the solvent was evaporated under reduced pressure. The residue was purified by silica gel column chromatography (ethyl acetate/hexane) to give the title compound (2.0 g).

¹H NMR (400 MHz, CDCl₃) δ 1.54 (9H, s), 4.78 (1H, d, J=8.8 Hz), 4.82 (1H, d, J=8.8 Hz), 7.23 (1H, dd, J=5.4, 1.7 Hz), 7.96 (1H, s), 8.17 (1H, d, J=5.4 Hz).

F) tert-butyl (4-(4,4,5,5-tetramethyl-1,3,2-dioxaborolan-2-yl)pyridin-2-yl) (2,2,2-trifluoroethyl)carbamate To a solution of tert-butyl (4-bromopyridin-2-yl)(2,2,2-trifluoroethyl)carbamate (2.0 g), bis(pinacolato)diboron (2.2 g) and potassium acetate (1.1 g) in DMF (30 mL) was added dichloro[1,1'-bis(diphenylphosphino)ferrocene]palladium (II) (394 mg). The reaction mixture was stirred at 80° C. for 2 hr under nitrogen atmosphere, diluted with ethyl acetate, washed with saturated aqueous ammonium chloride solution and saturated brine, and dried over anhydrous sodium sulfate, and the solvent was evaporated under reduced pressure. The residue was purified by silica gel column chromatography (Diol, ethyl acetate/hexane) to give the title compound (2.0 g).
¹H NMR (400 MHz, CDCl₃) δ 1.35 (12H, s), 1.52 (9H, s), 4.74 (1H, d, J=8.8 Hz), 4.76-4.80 (1H, m), 7.41 (1H, dd, J=4.8, 0.9 Hz), 7.91 (1H, s), 8.38 (1H, dd, J=4.6, 1.0 Hz).

G) ethyl 2-(2-((tert-butoxycarbonyl) (2,2,2-trifluoroethyl)amino)pyridin-4-yl)-1,3-oxazole-4-carboxylate To a mixture of tert-butyl (4-(4,4,5,5-tetramethyl-1,3,2-dioxaborolan-2-yl)pyridin-2-yl) (2,2,2-trifluoroethyl)carbamate (15 g), ethyl 2-bromo-1,3-oxazole-4-carboxylate (9.0 g), cesium carbonate (23 g), water (20 mL) and DME (80 mL) was added dichloro[1,1'-bis(diphenylphosphino)ferrocene]palladium(II) (1.3 g). The reaction mixture was stirred at 80° C. for 16 hr under nitrogen atmosphere, diluted with ethyl acetate, washed with saturated aqueous ammonium chloride solution and saturated brine, and dried over anhydrous sodium sulfate, and the solvent was evaporated under reduced pressure. The residue was purified by silica gel column chromatography (NH, ethyl acetate/hexane) to give the title compound (13 g).
MS (ESI+). found: 359.9.

H) 2-(2-((tert-butoxycarbonyl)(2,2,2-trifluoroethyl)amino)pyridin-4-yl)-1,3-oxazole-4-carboxylic acid To a solution of ethyl 2-(2-((tert-butoxycarbonyl) (2,2,2-trifluoroethyl)amino)pyridin-4-yl)-1,3-oxazole-4-carboxylate (13 g) in ethanol (100 mL) was added 2M aqueous sodium hydroxide solution (30 mL). The reaction mixture was stirred at room temperature for 16 hr, diluted with water, acidified with 1M hydrochloric acid, and extracted with ethyl acetate. The extract was washed with saturated brine, and dried over anhydrous sodium sulfate, and the solvent was evaporated under reduced pressure. The residue was washed with diisopropyl ether, and dried under reduced pressure to give the title compound (10 g).
¹H NMR (400 MHz, CDCl₃) δ 1.56 (9H, s), 4.83 (1H, d, J=8.8 Hz), 4.87 (1H, d, J=8.8 Hz), 7.77 (1H, dd, J=5.1, 1.5 Hz), 8.39 (1H, s), 8.44 (1H, s), 8.52 (1H, dd, J=5.1, 0.7 Hz).

I) tert-butyl (4-(4-((3-((4S)-4-((tert-butyl(dimethyl)silyl)oxy)-2-oxopyrrolidin-1-yl)-1-methyl-1H-pyrazol-4-yl)carbamoyl)-1,3-oxazol-2-yl)pyridin-2-yl) (2,2,2-trifluoroethyl)carbamate To a solution of (4S)-1-(4-amino-1-methyl-1H-pyrazol-3-yl)-4-((tert-butyl(dimethyl)silyl)oxy)pyrrolidin-2-one (2.3 g) and 2-(2-((tert-butoxycarbonyl) (2,2,2-trifluoroethyl) amino)pyridin-4-yl)-1,3-oxazole-4-carboxylic acid (2.9 g) in DMF (50 mL) were added HATU (3.4 g) and diisopropylethylamine (3.9 mL) under ice-cooling, and the mixture was stirred overnight at room temperature. The reaction mixture was diluted with water, and the mixture was extracted with ethyl acetate. The extract was washed with saturated brine, and dried over anhydrous magnesium sulfate, and the solvent was evaporated under reduced pressure. The residue was purified by silica gel column chromatography (ethyl acetate/hexane), and the obtained solid was washed with a mixed solvent of ethyl acetate/hexane (1:1), and dried under reduced pressure to give the title compound (3.3 g).
MS (ESI+): [M+H]⁺: 680.3.

J) N-(3-((4S)-4-hydroxy-2-oxopyrrolidin-1-yl)-1-methyl-1H-pyrazol-4-yl)-2-(2-((2,2,2-trifluoroethyl) amino)pyridin-4-yl)-1,3-oxazole-4-carboxamide hydrate A solution of tert-butyl (4-(4-((3-((4S)-4-((tert-butyl(dimethyl)silyl)oxy)-2-oxopyrrolidin-1-yl)-1-methyl-1H-pyrazol-4-yl)carbamoyl)-1,3-oxazol-2-yl)pyridin-2-yl) (2,2,2-trifluoroethyl)carbamate (3.3 g) and 4M hydrogen chloride ethyl acetate solution (30 mL) in methanol (8.0 mL) was stirred at room temperature for 1 hr. 4M Hydrogen chloride ethyl acetate solution (10 mL) was added to the reaction mixture, and the mixture was stirred at room temperature for additional 30 min. The reaction mixture was diluted with ethyl acetate (40 mL), and the precipitated solid was collected by filtration, washed with ethyl acetate, and dried under reduced pressure. A mixture of the obtained solid, Amberlyst A21 (registered trademark) (45 g) and methanol (300 mL) was stirred at room temperature for 15 min, the reaction mixture was filtered, and the filtrate was concentrated under reduced pressure. The residue was purified by silica gel column chromatography (methanol/ethyl acetate), and recrystallized from THF/ethyl acetate/hexane. The obtained solid (1.4 g) was suspended in water (150 mL), and the solution was stirred overnight at 50° C. The solid was collected by filtration, washed with water, and dried under reduced pressure to give the title compound (1.4 g).
¹H NMR (400 MHz, DMSO-d₆) δ 2.32-2.45 (1H, m), 2.96 (1H, dd, J=17.1, 6.1 Hz), 3.71 (1H, d, J=11.2 Hz), 3.81 (3H, s), 4.08 (1H, dd, J=11.2, 4.9 Hz), 4.17-4.31 (2H, m), 4.40-4.50 (1H, m), 5.42 (1H, d, J=3.7 Hz), 7.12-7.26 (2H, m), 7.65 (1H, t, J=6.6 Hz), 8.21-8.31 (2H, m), 8.89 (1H, s), 11.00 (1H, s). Anal. Calcd. C, 47.21; H, 4.17; N, 20.28% (C₁₉H₁₈N₇O₄F₃.H₂O).
Found. C, 47.46; H, 4.14; N, 20.33%.

Example 2

N-(1-methyl-3-(3-methyl-2-oxopyrrolidin-1-yl)-1H-pyrazol-4-yl)-2-(2-((2,2,2-trifluoroethyl)amino)pyridin-4-yl)-1,3-oxazole-4-carboxamide A) 3-methyl-1-(1-methyl-1H-pyrazol-3-yl)pyrrolidin-2-one To a solution of 1-(1-methyl-1H-pyrazol-3-yl)pyrrolidin-2-one (1.5 g) in THF (60 mL) was added 1.3 M LHMDS THF solution (7.3 mL) at −78° C., and the mixture was stirred at −78° C. for 1 hr. Iodomethane (0.60 mL) was added to the reaction mixture, and the mixture was stirred at room temperature for 4 hr. To the reaction mixture was added water, and the mixture was extracted with ethyl acetate. The extract was washed with saturated brine, and dried over anhydrous sodium sulfate, and the solvent was evaporated under reduced pressure. The residue was purified by silica gel column chromatography (ethyl acetate/hexane) to give the title compound (927 mg).

MS (ESI+): [M+H]$^+$: 179.8.

B) 3-methyl-1-(1-methyl-4-nitro-1H-pyrazol-3-yl) pyrrolidin-2-one

To a solution of 3-methyl-1-(1-methyl-1H-pyrazol-3-yl) pyrrolidin-2-one (97 mg) in acetic anhydride (1.2 mL) was added fuming nitric acid (45 μL) under ice-cooling, and the mixture was stirred under ice-cooling for 1.5 hr. The reaction mixture was poured into ice water, and the mixture was neutralized with saturated aqueous sodium hydrogen carbonate solution, and extracted with ethyl acetate. The extract was washed with saturated brine, and dried over anhydrous magnesium sulfate, and the solvent was evaporated under reduced pressure. The residue was purified by silica gel column chromatography (ethyl acetate/hexane) to give the title compound (53 mg).

MS (ESI+): [M+H]$^+$: 225.1.

C) tert-butyl (4-(4-((1-methyl-3-(3-methyl-2-oxopyrrolidin-1-yl)-1H-pyrazol-4-yl)carbamoyl)-1,3-oxazol-2-yl)pyridin-2-yl)(2,2,2-trifluoroethyl)carbamate A mixture of 3-methyl-1-(1-methyl-4-nitro-1H-pyrazol-3-yl)pyrrolidin-2-one (53 mg), 10% palladium-carbon (25 mg), THF (2.0 mL) and methanol (2.0 mL) was stirred at room temperature for 2 hr under hydrogen atmosphere. The reaction mixture was filtered through a membrane filter, and the filtrate was concentrated under reduced pressure. To a solution of the obtained residue, 2-(2-((tert-butoxycarbonyl)(2,2,2-trifluoroethyl)amino)pyridin-4-yl)-1,3-oxazole-4-carboxylic acid (92 mg) and HATU (108 mg) in DMF (2.0 mL) was added diisopropylethylamine (0.12 mL), and the mixture was stirred overnight at room temperature. The reaction mixture was diluted with water, and the mixture was extracted with ethyl acetate. The extract was washed with saturated brine, and dried over anhydrous magnesium sulfate, and the solvent was evaporated under reduced pressure. The residue was purified by silica gel column chromatography (ethyl acetate/hexane) to give the title compound (133 mg).

MS (ESI+). found: 464.2.

D) N-(1-methyl-3-(3-methyl-2-oxopyrrolidin-1-yl)-1H-pyrazol-4-yl)-2-(2-((2,2,2-trifluoroethyl)amino) pyridin-4-yl)-1,3-oxazole-4-carboxamide A mixture of tert-butyl (4-(4-((1-methyl-3-(3-methyl-2-oxopyrrolidin-1-yl)-1H-pyrazol-4-yl)carbamoyl)-1,3-oxazol-2-yl)pyridin-2-yl) (2,2,2-trifluoroethyl)carbamate (133 mg), 4M hydrogen chloride ethyl acetate solution (3.0 mL) and methanol (1.0 mL) was stirred at room temperature for 3 hr. The reaction mixture was concentrated under reduced pressure, and a mixture of the obtained solid, Amberlyst A21 (registered trademark) (200 mg) and methanol (5.0 mL) was stirred at room temperature for 5 min. The reaction mixture was filtered, and the filtrate was concentrated under reduced pressure. The residue was purified by silica gel column chromatography (ethyl acetate/hexane), and recrystallized from ethyl acetate/hexane to give the title compound (22 mg).

$^1$H NMR (400 MHz, DMSO-d$_6$) δ 1.25 (3H, d, J=7.1 Hz), 1.74-1.88 (1H, m), 2.31-2.43 (1H, m), 2.71-2.84 (1H, m), 3.76-3.91 (5H, m), 4.17-4.31 (2H, m), 7.15-7.23 (2H, m), 7.61 (1H, t, J=6.6 Hz), 8.21-8.28 (2H, m), 8.88 (1H, s), 10.97 (1H, s).

Example 3

N-(3-(4-((dimethylamino)methyl)-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide

A) 4-((benzyloxy)methyl)-1-(1-methyl-1H-pyrazol-3-yl)pyrrolidin-2-one

To a solution of 4-((benzyloxy)methyl)pyrrolidin-2-one (836 mg), 3-iodo-1-methyl-1H-pyrazole (856 mg), copper(I) iodide (80 mg) and tripotassium phosphate (1.7 g) in cyclopentyl methyl ether (20 mL) was added N1,N2-dimethylethane-1,2-diamine (87 μL). The reaction mixture was stirred at 120° C. for 22 hr, and diluted with ethyl acetate, and saturated aqueous ammonium chloride solution was added thereto. The extract was washed with saturated brine, and dried over anhydrous sodium sulfate, and the solvent was evaporated under reduced pressure. The residue was purified by silica gel column chromatography (ethyl acetate/hexane) to give the title compound (1.1 g).

MS (ESI+): [M+H]$^+$286.3.

B) 4-((benzyloxy)methyl)-1-(1-methyl-4-nitro-1H-pyrazol-3-yl)pyrrolidin-2-one To a mixture of fuming nitric acid (0.32 mL) and acetic anhydride (5.0 mL) was added 4-((benzyloxy)methyl)-1-(1-methyl-1H-pyrazol-3-yl)pyrrolidin-2-one (1.1 g) under ice-cooling. The reaction mixture was stirred under ice-cooling for 1 hr, water was added thereto, and the mixture was neutralized with 8M aqueous sodium hydroxide solution, and extracted with ethyl acetate. The extract was washed with saturated brine, and dried over anhydrous sodium sulfate, and the solvent was evaporated under reduced pressure. The residue was purified by silica gel column chromatography (ethyl acetate/hexane) to give the title compound (1.1 g).

MS (ESI+): [M+H]$^+$331.0.

C) tert-butyl (3-(4-((benzyloxy)methyl)-2-oxopyrrolidin-1-yl)-1-methyl-1H-pyrazol-4-yl)carbamate To a mixture of 4-((benzyloxy)methyl)-1-(1-methyl-4-nitro-1H-pyrazol-3-yl)pyrrolidin-2-one (1.1 g), di-tert-butyl dicarbonate (0.95 mL), triethylamine (0.71 mL), THF (8.0 mL) and methanol (8.0 mL) was added 10% palladium-carbon (156 mg). The reaction mixture was stirred at room temperature for 16 hr under hydrogen atmosphere. The reaction mixture was filtered, and the filtrate was concentrated under reduced pressure. The residue was purified by silica gel column chromatography (ethyl acetate/hexane) to give the title compound (1.0 g).

$^1$H NMR (400 MHz, CDCl$_3$) δ 1.48 (9H, s), 2.47 (1H, dd, J=17.4, 6.4 Hz), 2.70 (1H, dd, J=17.4, 9.0 Hz), 2.76-2.88 (1H, m), 3.52 (2H, d, J=6.4 Hz), 3.75 (3H, s), 3.80 (1H, dd, J=10.8, 5.9 Hz), 4.04 (1H, dd, J=10.8, 8.1 Hz), 4.54 (2H, s), 7.28-7.39 (5H, m), 7.76 (1H, s), 8.42 (1H, brs).

D) tert-butyl (4-(4-((3-(4-((benzyloxy)methyl)-2-oxopyrrolidin-1-yl)-1-methyl-1H-pyrazol-4-yl)carbamoyl)-1,3-oxazol-2-yl)pyridin-2-yl) (2,2,2-trifluoroethyl)carbamate To a solution of tert-butyl (3-(4-((benzyloxy)methyl)-2-oxopyrrolidin-1-yl)-1-methyl-1H-pyrazol-4-yl)carbamate (114 mg) in methanol (3.0 mL) was added 4M hydrogen chloride ethyl acetate solution (2.0 mL). The reaction mixture was stirred at room temperature for 2 hr, and the solvent was evaporated under reduced pressure. To a solution of the residue, HATU (128 mg) and 2-(2-((tert-butoxycarbonyl)(2,2,2-trifluoroethyl)amino)pyridin-4-yl)-1,3-oxazole-4-carboxylic acid (125 mg) in DMF (5.0 mL) was added diisopropylethylamine (0.15 mL). The reaction mixture was stirred at room temperature for 3 hr, saturated aqueous ammonium chloride solution was added thereto, and the mixture was extracted with ethyl acetate. The extract was washed with saturated brine, and dried over anhydrous sodium sulfate, and the solvent was evaporated under reduced pressure. The residue was purified by silica gel column chromatography (ethyl acetate/hexane) to give the title compound as a crude product. This compound was used for the next step without further purification.

E) tert-butyl (4-(4-((3-(4-(hydroxymethyl)-2-oxopyrrolidin-1-yl)-1-methyl-1H-pyrazol-4-yl)carbamoyl)-1,3-oxazol-2-yl)pyridin-2-yl) (2,2,2-trifluoroethyl)carbamate To a solution of tert-butyl (4-(4-((3-(4-((benzyloxy)methyl)-2-oxopyrrolidin-1-yl)-1-methyl-1H-pyrazol-4-yl)carbamoyl)-1,3-oxazol-2-yl)pyridin-2-yl)(2,2,2-trifluoroethyl)carbamate (191 mg) obtained in Step D of Example 3 in a mixed solvent of THF (3.0 mL) and methanol (5.0 mL) was added 10% palladium-carbon (41 mg). The reaction mixture was stirred at 60° C. for 6 hr under hydrogen atmosphere. The reaction mixture was filtered, and the filtrate was concentrated under reduced pressure. The residue was purified by silica gel column chromatography (NH, ethyl acetate/hexane) to give the title compound (96 mg).
MS (ESI+): [M+H]$^+$580.2.

F) tert-butyl (4-(4-((3-(4-formyl-2-oxopyrrolidin-1-yl)-1-methyl-1H-pyrazol-4-yl)carbamoyl)-1,3-oxazol-2-yl)pyridin-2-yl) (2,2,2-trifluoroethyl)carbamate To a solution of tert-butyl (4-(4-((3-(4-(hydroxymethyl)-2-oxopyrrolidin-1-yl)-1-methyl-1H-pyrazol-4-yl)carbamoyl)-1,3-oxazol-2-yl)pyridin-2-yl) (2,2,2-trifluoroethyl)carbamate (94 mg) in acetonitrile (3.0 mL) was added Dess-Martin periodinane (100 mg). The reaction mixture was stirred at room temperature for 4 hr, saturated aqueous ammonium chloride solution was added thereto, and the mixture was extracted with ethyl acetate. The extract was filtered through silica gel layer, and the solvent was evaporated under reduced pressure. The residue was used for the next step without further purification.

G) tert-butyl (4-(4-((3-(4-((dimethylamino)methyl)-2-oxopyrrolidin-1-yl)-1-methyl-1H-pyrazol-4-yl) carbamoyl)-1,3-oxazol-2-yl)pyridin-2-yl) (2,2,2-trifluoroethyl)carbamate To a solution of tert-butyl (4-(4-((3-(4-formyl-2-oxopyrrolidin-1-yl)-1-methyl-1H-pyrazol-4-yl)carbamoyl)-1,3-oxazol-2-yl)pyridin-2-yl) (2,2,2-trifluoroethyl)carbamate (94 mg) obtained in Step F of Example 3, 2M dimethylamine THF solution (0.12 mL) and acetic acid (14 µL) in THF (5.0 mL) was added sodium triacetoxyborohydride (69 mg). The reaction mixture was stirred at room temperature for 2 hr, saturated aqueous sodium hydrogen carbonate solution was added thereto, and the mixture was extracted with ethyl acetate. The extract was washed with saturated brine, and dried over anhydrous sodium sulfate, and the solvent was evaporated under reduced pressure. The residue was purified by silica gel column chromatography (ethyl acetate/hexane) to give the title compound (71 mg).
MS (ESI+): [M+H]$^+$607.0.

H) N-(3-(4-((dimethylamino)methyl)-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide To a solution of tert-butyl (4-(4-((3-(4-((dimethylamino)methyl)-2-oxopyrrolidin-1-yl)-1-methyl-1H-pyrazol-4-yl) carbamoyl)-1,3-oxazol-2-yl)pyridin-2-yl)(2,2,2-trifluoroethyl)carbamate (71 mg) in methanol (2.0 mL) was added 4M hydrogen chloride ethyl acetate solution (2.0 mL). The reaction mixture was stirred at room temperature for 16 hr, and the solvent was evaporated under reduced pressure. The residue was suspended in methanol, the suspension was basified with sodium methoxide, and the solvent was evaporated under reduced pressure. The residue was purified by silica gel column chromatography (NH, ethyl acetate/hexane) to give the title compound (51 mg).
$^1$H NMR (400 MHz, DMSO-d$_6$) δ 2.26-2.44 (3H, m), 2.65-2.79 (2H, m), 3.32 (6H, s), 3.66 (1H, dd, J=10.4, 5.5 Hz), 3.80 (3H, s), 3.91-3.99 (1H, m), 4.18-4.30 (2H, m), 7.16 (1H, dd, J=5.3, 1.3 Hz), 7.20 (1H, s), 7.64 (1H, t, J=6.6 Hz), 8.24 (1H, d, J=5.4 Hz), 8.26 (1H, s), 8.88 (1H, s), 11.03 (1H, s).

Example 4

N-(3-(4-((dimethylamino)methyl)-3,3-dimethyl-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide A) 4-((benzyloxy)methyl)-3,3-dimethyl-1-(1-methyl-1H-pyrazol-3-yl)pyrrolidin-2-one To a solution of 4-((benzyloxy)methyl)-1-(1-methyl-1H-pyrazol-3-yl)pyrrolidin-2-one (499 mg) and iodomethane (0.32 mL) in THF (10 mL) was added 1.3M LHMDS THF solution (3.3 mL) under ice-cooling. The reaction mixture was stirred under ice-cooling for 1 hr, saturated aqueous ammonium chloride solution was added thereto, and the mixture was extracted with ethyl acetate. The extract was washed with saturated brine, and dried over anhydrous sodium sulfate, and the solvent was evaporated under reduced pressure. The residue was purified by silica gel column chromatography (ethyl acetate/hexane) to give the title compound (459 mg).
MS (ESI+): [M+1-1]$^+$313.9.

B) 4-((benzyloxy)methyl)-3,3-dimethyl-1-(1-methyl-4-nitro-1H-pyrazol-3-yl)pyrrolidin-2-one To a mixture of 4-((benzyloxy)methyl)-3,3-dimethyl-1-(1-methyl-1H-pyrazol-3-yl)pyrrolidin-2-one (459 mg) and acetic anhydride (3.0 mL) was added fuming nitric acid (0.12 mL) under ice-cooling. The reaction mixture was stirred under ice-cooling for 1 hr, water was added thereto, and the mixture was neutralized with 8M aqueous sodium hydroxide solution, and extracted with ethyl acetate. The extract was washed with saturated brine, and dried over anhydrous sodium sulfate, and the solvent was evaporated under reduced pressure. The residue was purified by silica gel column chromatography (ethyl acetate/hexane) to give the title compound (343 mg).

MS (ESI+): [M+H]$^+$359.3.

C) tert-butyl (3-(4-hydroxymethyl-3,3-dimethyl-2-oxopyrrolidin-1-yl)-1-methyl-1H-pyrazol-4-yl)carbamate To a solution of 4-((benzyloxy)methyl)-3,3-dimethyl-1-(1-methyl-4-nitro-1H-pyrazol-3-yl)pyrrolidin-2-one (343 mg) and di-tert-butyl dicarbonate (0.27 mL) in methanol (10 mL) was added 10% palladium-carbon (107 mg). The reaction mixture was stirred at 50° C. for 4 hr under hydrogen atmosphere. The reaction mixture was filtered, and the filtrate was concentrated under reduced pressure. The residue was purified by silica gel column chromatography (ethyl acetate/hexane) to give the title compound (176 mg).

$^1$H NMR (300 MHz, CDCl$_3$) δ 1.15 (3H, s), 1.33 (3H, s), 1.49 (9H, s), 1.81-1.91 (1H, m), 2.35-2.49 (1H, m), 3.65 (1H, dd, J=10.6, 8.0 Hz), 3.73-3.78 (4H, m), 3.82-3.92 (1H, m), 3.99 (1H, dd, J=10.6, 8.0 Hz), 7.79 (1H, s), 8.63 (1H, brs).

D) tert-butyl (3-(4-formyl-3,3-dimethyl-2-oxopyrrolidin-1-yl)-1-methyl-1H-pyrazol-4-yl)carbamate To a solution of tert-butyl (3-(4-hydroxymethyl-3,3-dimethyl-2-oxopyrrolidin-1-yl)-1-methyl-1H-pyrazol-4-yl)carbamate (174 mg) in acetonitrile (5.0 mL) was added Dess-Martin periodinane (348 mg). The reaction mixture was stirred at room temperature for 3 hr, and diluted with ethyl acetate, and the mixture was washed with saturated aqueous sodium hydrogen carbonate solution. The extract was washed with saturated brine, and dried over anhydrous sodium sulfate, and the solvent was evaporated under reduced pressure. The residue was used for the next step without purification.

E) tert-butyl (3-(4-((dimethylamino)methyl)-3,3-dimethyl-2-oxopyrrolidin-1-yl)-1-methyl-1H-pyrazol-4-yl)carbamate To a solution of tert-butyl (3-(4-formyl-3,3-dimethyl-2-oxopyrrolidin-1-yl)-1-methyl-1H-pyrazol-4-yl)carbamate (173 mg) obtained in Step D of Example 4, 2M dimethylamine THF solution (0.39 mL) and acetic acid (30 µL) in THF (5.0 mL) was added sodium triacetoxyborohydride (220 mg). The reaction mixture was stirred at room temperature for 16 hr, saturated aqueous sodium hydrogen carbonate solution was added thereto, and the mixture was extracted with ethyl acetate. The extract was washed with saturated brine, and dried over anhydrous sodium sulfate, and the solvent was evaporated under reduced pressure. The residue was purified by silica gel column chromatography (NH, ethyl acetate/hexane), and then HPLC (C18, mobile phase: water/acetonitrile (containing 0.1% TFA)), and the obtained fraction was concentrated under reduced pressure to give the title compound (112 mg).

$^1$H NMR (400 MHz, CDCl$_3$) δ 1.09 (3H, s), 1.29 (3H, s), 1.48 (9H, s), 2.24 (6H, s), 2.32-2.43 (3H, m), 3.53-3.61 (1H, m), 3.74 (3H, s), 3.93-4.00 (1H, m), 7.78 (1H, s), 8.66 (1H, brs).

F) tert-butyl (4-(4-((3-(4-((dimethylamino)methyl)-3,3-dimethyl-2-oxopyrrolidin-1-yl)-1-methyl-1H-pyrazol-4-yl)carbamoyl)-1,3-oxazol-2-yl)pyridin-2-yl)(2,2,2-trifluoroethyl)carbamate To a solution of tert-butyl (3-(4-((dimethylamino)methyl)-3,3-dimethyl-2-oxopyrrolidin-1-yl)-1-methyl-1H-pyrazol-4-yl)carbamate (109 mg) in methanol (3.0 mL) was added 4M hydrogen chloride ethyl acetate solution (2.0 mL). The reaction mixture was stirred at room temperature for 3 hr, and the solvent was evaporated under reduced pressure. To a solution of the residue, HATU (140 mg) and 2-(2-((tert-butoxycarbonyl)(2,2,2-trifluoroethyl)amino)pyridin-4-yl)-1,3-oxazole-4-carboxylic acid (128 mg) in DMF (5.0 mL) was added diisopropylethylamine (0.16 mL). The reaction mixture was stirred at room temperature for 3 hr, saturated aqueous ammonium chloride solution was added thereto, and the mixture was extracted with ethyl acetate. The extract was washed with saturated brine, and dried over anhydrous sodium sulfate, and the solvent was evaporated under reduced pressure. The residue was purified by silica gel column chromatography (NH, ethyl acetate/hexane), and then silica gel column chromatography (methanol/ethyl acetate) to give the title compound (136 mg).

$^1$H NMR (400 MHz, CDCl$_3$) δ 1.15 (3H, s), 1.38 (3H, s), 1.55 (9H, s), 2.25 (6H, s), 2.34-2.51 (3H, m), 3.63 (1H, dd, J=10.6, 8.9 Hz), 3.82 (3H, s), 4.02 (1H, dd, J=10.9, 7.0 Hz), 4.82 (1H, d, J=8.8 Hz), 4.87 (1H, d, J=8.6 Hz), 7.76-7.80 (1H, m), 8.19 (1H, s), 8.31-8.36 (2H, m), 8.50 (1H, d, J=5.1 Hz), 11.33 (1H, s).

G) N-(3-(4-((dimethylamino)methyl)-3,3-dimethyl-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide To a solution of tert-butyl (4-(4-((3-(4-((dimethylamino)methyl)-3,3-dimethyl-2-oxopyrrolidin-1-yl)-1-methyl-1H-pyrazol-4-yl)carbamoyl)-1,3-oxazol-2-yl)pyridin-2-yl) (2,2,2-trifluoroethyl)carbamate (134 mg) in methanol (3.0 mL) was added 4M hydrogen chloride ethyl acetate solution (2.0 mL). The reaction mixture was stirred at room temperature for 20 hr, and the solvent was evaporated under reduced pressure. The residue was dissolved in ethyl acetate, and the solution was washed with saturated aqueous sodium hydrogen carbonate solution and saturated brine, and dried over anhydrous sodium sulfate, and the solvent was evaporated under reduced pressure. The residue was purified by silica gel column chromatography (NH, ethyl acetate/hexane), and then HPLC (C18, mobile phase: water/acetonitrile (containing 0.1% TFA)), and the obtained fraction was concentrated under reduced pressure to give the title compound (45 mg).

$^1$H NMR (400 MHz, CDCl$_3$) δ 1.16 (3H, s), 1.38 (3H, s), 2.25 (6H, s), 2.35-2.51 (3H, m), 3.59-3.67 (1H, m), 3.82 (3H, s), 3.97-4.06 (1H, m), 4.12-4.23 (2H, m), 4.83 (1H, t, J=6.8 Hz), 7.20-7.23 (1H, m), 7.34 (1H, dd, J=5.3, 1.3 Hz), 8.19 (1H, s), 8.26 (1H, dd, J=5.3, 0.6 Hz), 8.30 (1H, s), 11.31 (1H, s).

Example 5

N-(1-methyl-3-((4S)-4-(methylamino)-2-oxopyrrolidin-1-yl)-1H-pyrazol-4-yl)-2-(2-((2,2,2-trifluoroethyl)amino)pyridin-4-yl)-1,3-oxazole-4-carboxamide

A) 2-(1-methyl-4-nitro-1H-pyrazol-3-yl)-1H-isoindole-1,3(2H)-dione

To a solution of 1-methyl-1H-pyrazol-3-amine (1.5 g) in THF (75 mL) was added phthalic anhydride (2.2 g), and the mixture was stirred at room temperature for 1 hr. The reaction mixture was concentrated under reduced pressure, the residue was dissolved in acetic anhydride (50 mL), and the solution was stirred at 80° C. for 2 hr. The reaction mixture was ice-cooled, fuming nitric acid (0.68 mL) was added thereto, and the mixture was stirred under ice-cooling for 1 hr, and allowed to be warmed to room temperature. Fuming nitric acid (0.66 mL) was added thereto, and the mixture was stirred at room temperature for 20 min. The reaction mixture was cooled to 0° C., 8M aqueous sodium hydroxide solution was added thereto, and the resulting precipitate was collected by filtration to give the title compound (2.2 g).

$^1$H NMR (400 MHz, CDCl$_3$) δ 4.04 (3H, s), 7.84 (2H, dd, J=5.5, 3.1 Hz), 8.00 (2H, dd, J=5.5, 3.1 Hz), 8.28 (1H, s).

B) tert-butyl (3-(1,3-dioxo-1,3-dihydro-2H-isoindol-2-yl)-1-methyl-1H-pyrazol-4-yl)carbamate To a solution of 2-(1-methyl-4-nitro-1H-pyrazol-3-yl)-1H-isoindole-1,3(2H)-dione (2.2 g) in methanol (41 mL) were added 10% palladium-carbon (864 mg) and di-tert-butyl dicarbonate (2.8 mL), and the mixture was stirred overnight at room temperature under hydrogen atmosphere. The reaction mixture was filtered, and the filtrate was concentrated under reduced pressure. The residue was purified by silica gel column chromatography (ethyl acetate/hexane) to give the title compound (2.1 g).

MS (ESI+). found: 243.1.

C) tert-butyl (3-amino-1-methyl-1H-pyrazol-4-yl)carbamate

To a solution of tert-butyl (3-(1,3-dioxo-1,3-dihydro-2H-isoindol-2-yl)-1-methyl-1H-pyrazol-4-yl)carbamate (1.8 g) in methanol (26 mL) was added hydrazine monohydrate (0.38 mL), and the mixture was stirred at room temperature for 3 hr. The reaction mixture was concentrated, and the residue was purified by silica gel column chromatography (ethyl acetate/hexane) to give the title compound (1.1 g).

MS (ESI+). found: 157.1.

D) benzyl ((2S)-4-((4-((tert-butoxycarbonyl)amino)-1-methyl-1H-pyrazol-3-yl)amino)-1-hydroxy-4-oxobutan-2-yl)carbamate To a solution of tert-butyl (3-amino-1-methyl-1H-pyrazol-4-yl)carbamate (1.0 g), (3S)-3-(((benzyloxy)carbonyl)amino)-4-methoxy-4-oxobutanoic acid (1.5 g) and HATU (2.2 g) in DMF (24 mL) was added diisopropylethylamine (1.2 mL), and the mixture was stirred overnight at room temperature. The reaction mixture was poured into water, and the mixture was extracted with ethyl acetate. The extract was washed successively with saturated aqueous ammonium chloride solution, saturated aqueous sodium hydrogen carbonate solution and saturated brine, and dried over anhydrous magnesium sulfate, and the solvent was evaporated under reduced pressure to give a crude product (2.6 g). To a suspension of lithium borohydride (0.26 g) in THF (20 mL) was added a solution of the crude product (2.2 g) in methanol (10 mL) under ice-cooling, and the mixture was stirred at 0° C. for 1 hr. To the reaction mixture was added water, and the mixture was concentrated under reduced pressure. The residue was extracted with ethyl acetate, the extract was washed with saturated brine, and dried over anhydrous magnesium sulfate, and the solvent was evaporated under reduced pressure. The residue was purified by silica gel column chromatography (ethyl acetate/hexane) to give the title compound (1.6 g).

MS (ESI+): [M+H]$^+$448.7.

E) benzyl ((3S)-1-(4-((tert-butoxycarbonyl)amino)-1-methyl-1H-pyrazol-3-yl)-5-oxopyrrolidin-3-yl)carbamate To a mixture of benzyl ((2S)-4-((4-((tert-butoxycarbonyl)amino)-1-methyl-1H-pyrazol-3-yl)amino)-1-hydroxy-4-oxobutan-2-yl)carbamate (1.6 g), tri-n-butylphosphine (1.3 mL), toluene (18 mL) and THF (6.0 mL) was added 40% diethyl azodicarboxylate toluene solution (1.8 mL) under ice-cooling, and the mixture was stirred at 60° C. for 1 hr. The reaction mixture was concentrated under reduced pressure, and the residue was purified by silica gel column chromatography (ethyl acetate/hexane) to give the title compound (1.3 g).

MS (ESI+). found: 330.1.

F) benzyl ((3S)-1-(4-(((2-(2-((tert-butoxycarbonyl)(2,2,2-trifluoroethyl)amino)pyridin-4-yl)-1,3-oxazol-4-yl)carbonyl)amino)-1-methyl-1H-pyrazol-3-yl)-5-oxopyrrolidin-3-yl)carbamate A mixture of benzyl ((3S)-1-(4-((tert-butoxycarbonyl)amino)-1-methyl-1H-pyrazol-3-yl)-5-oxopyrrolidin-3-yl)carbamate (1.3 g) and 4M hydrogen chloride ethyl acetate solution (15 mL) was stirred at room temperature for 1.5 hr, and the solvent was evaporated under reduced pressure. To a solution of the residue, 2-(2-((tert-butoxycarbonyl)(2,2,2-trifluoroethyl)amino)pyridin-4-yl)-1,3-oxazole-4-carboxylic acid (1.2 g) and HATU (1.4 g) in DMF (16 mL) was added diisopropylethylamine (2.7 mL). The reaction mixture was stirred overnight at room temperature, and poured into water, and the mixture was extracted with ethyl acetate. The extract was washed successively with saturated aqueous sodium hydrogen carbonate solution and saturated brine, and dried over anhydrous magnesium sulfate, and the solvent was evaporated under reduced pressure. The residue was purified by silica gel column chromatography (ethyl acetate/hexane) to give the title compound (1.0 g).

MS (ESI+): [M+H]$^+$699.2.

G) tert-butyl (4-(4-((3-((4S)-4-amino-2-oxopyrrolidin-1-yl)-1-methyl-1H-pyrazol-4-yl)carbamoyl)-1,3-oxazol-2-yl)pyridin-2-yl)(2,2,2-trifluoroethyl)carbamate To a mixture of benzyl ((3S)-1-(4-(((2-(2-((tert-butoxycarbonyl)(2,2,2-trifluoroethyl)amino)pyridin-4-yl)-1,3-oxazol-4-yl)carbonyl)amino)-1-methyl-1H-pyrazol-3-yl)-5-oxopyrrolidin-3-yl)carbamate (1.0 g), THF (7.2 mL) and methanol (7.2 mL) was added 10% palladium-carbon (154 mg), and the mixture was stirred at room temperature for 1.5 hr under hydrogen atmosphere. The reaction mixture was filtered through Celite, and the filtrate was concentrated under reduced pressure to give the title compound (817 mg).

MS (ESI+): [M+H]$^+$565.1.

H) N-(1-methyl-3-((4S)-4-(methylamino)-2-oxopyrrolidin-1-yl)-1H-pyrazol-4-yl)-2-(2-((2,2,2-trifluoroethyl)amino)pyridin-4-yl)-1,3-oxazole-4-carboxamide To a solution of tert-butyl (4-(4-((3-((4S)-4-amino-2-oxopyrrolidin-1-yl)-1-methyl-1H-pyrazol-4-yl)carbamoyl)-1,3-oxazol-2-yl)pyridin-2-yl)(2,2,2-trifluoroethyl)carbamate (83 mg) in THF (0.73 mL) was added 37% formalin (32 μl), and the mixture was stirred at room temperature for 3 hr. The reaction mixture was ice-cooled, sodium borohydride (28 mg) and methanol (0.73 mL) were added thereto, and the mixture was stirred under ice-cooling for 1 hr. The reaction mixture was concentrated under reduced pressure, the residue was dissolved in TFA (0.70 mL), and the solution was stirred at room temperature for 20 min. The reaction mixture was concentrated under reduced pressure, and the residue was purified by silica gel column chromatography (NH, methanol/ethyl acetate), and recrystallized from ethyl acetate/hexane to give the title compound (19 mg).

$^1$H NMR (400 MHz, DMSO-$d_6$) δ 2.28 (3H, s), 2.38 (1H, dd, J=17.1, 3.7 Hz), 2.85 (1H, dd, J=17.1, 7.2 Hz), 3.35-3.41 (1H, m), 3.66 (1H, dd, J=10.6, 3.1 Hz), 3.81 (3H, s), 3.99 (1H, dd, J=10.6, 6.4 Hz), 4.17-4.31 (2H, m), 7.16 (1H, dd, J=5.3, 1.3 Hz), 7.20 (1H, s), 7.64 (1H, t, J=6.6 Hz), 8.25 (1H, d, J=5.3 Hz), 8.26 (1H, s), 8.88 (1H, s), 11.02 (1H, s).

Example 6

N-(1-methyl-3-(2-oxopyrrolidin-1-yl)-1H-pyrazol-4-yl)-2-(2-((2,2,2-trifluoroethyl)amino)pyridin-4-yl)-1,3-oxazole-4-carboxamide A) N-(4-bromo-1-methyl-1H-pyrazol-3-yl)-4-chlorobutanamide To a solution of 4-bromo-1-methyl-1H-pyrazol-3-amine (310 mg) and triethylamine (0.37 mL) in THF (8.8 mL) was added 4-chlorobutanoyl chloride (0.22 mL) under ice-cooling, and the mixture was stirred at 0° C. for 30 min. To the reaction mixture was added saturated aqueous ammonium chloride solution, and the mixture was extracted with ethyl acetate. The extract was washed with saturated brine, and dried over anhydrous magnesium sulfate, and the solvent was evaporated under reduced pressure to give the title compound (456 mg).

MS (ESI+): [M+H]$^+$280.0.

B) 1-(4-bromo-1-methyl-1H-pyrazol-3-yl)pyrrolidin-2-one

To a solution of N-(4-bromo-1-methyl-1H-pyrazol-3-yl)-4-chlorobutanamide (456 mg) in DMF (8.1 mL) was added a sodium hydride 60% dispersion in mineral oil (72 mg) under ice-cooling, and the mixture was stirred at 0° C. for 30 min. To the reaction mixture was added saturated aqueous ammonium chloride solution, and the mixture was extracted with ethyl acetate. The extract was washed successively with water and saturated brine, and dried over anhydrous sodium sulfate, and the solvent was evaporated under reduced pressure. The residue was purified by silica gel column chromatography (ethyl acetate/hexane) to give the title compound (114 mg).

MS (ESI+): [M+H]$^+$244.0.

C) tert-butyl (4-(4-carbamoyl-1,3-oxazol-2-yl)pyridin-2-yl) (2,2,2-trifluoroethyl)carbamate To a solution of 2-(2-((tert-butoxycarbonyl)(2,2,2-trifluoroethyl)amino)pyridin-4-yl)-1,3-oxazole-4-carboxylic acid (519 mg) and 1-hydroxybenzotriazole ammonium salt (306 mg) in DMF (6.7 mL) was added N-(3-(dimethylamino)propyl)-N'-ethylcarbodiimide hydrochloride (385 mg), and the mixture was stirred at room temperature for 2 hr. Diisopropyl ether was added thereto, and the precipitate was collected by filtration to give the title compound (519 mg).

MS (ESI−): [M−H]$^-$ 385.1.

D) tert-butyl (4-(4-((1-methyl-3-(2-oxopyrrolidin-1-yl)-1H-pyrazol-4-yl)carbamoyl)-1,3-oxazol-2-yl)pyridin-2-yl) (2,2,2-trifluoroethyl)carbamate A solution of 1-(4-bromo-1-methyl-1H-pyrazol-3-yl)pyrrolidin-2-one (59 mg), tert-butyl (4-(4-carbamoyl-1,3-oxazol-2-yl)pyridin-2-yl) (2,2,2-trifluoroethyl)carbamate (93 mg), copper(I) iodide (4.6 mg), N1,N2-dimethylethane-1,2-diamine (5.1 µL) and tripotassium phosphate (102 mg) in THF (1.2 mL) was stirred with microwave irradiation at 120° C. for 14 hr. The reaction mixture was poured into water, and the mixture was extracted with ethyl acetate. The extract was washed with saturated brine, and dried over anhydrous magnesium sulfate, and the solvent was evaporated under reduced pressure. The residue was purified by silica gel column chromatography (ethyl acetate/hexane) to give the title compound (8.7 mg).

MS (ESI+). found: 450.1.

E) N-(1-methyl-3-(2-oxopyrrolidin-1-yl)-1H-pyrazol-4-yl)-2-(2-((2,2,2-trifluoroethyl)amino)pyridin-4-yl)-1,3-oxazole-4-carboxamide tert-Butyl (4-(4-((1-methyl-3-(2-oxopyrrolidin-1-yl)-1H-pyrazol-4-yl)carbamoyl)-1,3-oxazol-2-yl)pyridin-2-yl) (2,2,2-trifluoroethyl)carbamate (8.7 mg) was dissolved in TFA (0.30 mL), and the solution was stirred at room temperature for 3 hr. The reaction mixture was concentrated under reduced pressure, and the residue was purified by silica gel column chromatography (NH, ethyl acetate/hexane) to give the title compound (4.5 mg).

Example 7

N-(3-(4-(hydroxymethyl)-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide A) 1-(4-bromo-1-methyl-1H-pyrazol-3-yl)-5-oxopyrrolidine-3-carboxylic acid To a solution of 4-bromo-1-methyl-1H-pyrazol-3-amine (312 mg) in a mixed solvent of water (2.0 mL) and toluene (2.0 mL) was added itaconic acid (245 mg). The reaction mixture was stirred at 120° C. for 5 hr, and the solvent was evaporated under reduced pressure. The residue was used for the next step without purification.

B) 1-(4-bromo-1-methyl-1H-pyrazol-3-yl)-4-(hydroxymethyl)pyrrolidin-2-one

To a solution of 1-(4-bromo-1-methyl-1H-pyrazol-3-yl)-5-oxopyrrolidine-3-carboxylic acid (511 mg) obtained in Step A of Example 7 in THF (3.0 mL) was added 1.1M borane-THF complex THF solution (5.0 mL) under ice-cooling. The reaction mixture was stirred at room temperature for 20 hr, and diluted with ethyl acetate. The diluted solution was washed with saturated brine, and dried over anhydrous sodium sulfate, and the solvent was evaporated under reduced pressure. The residue was purified by silica gel column chromatography (ethyl acetate/hexane) and (methanol/ethyl acetate) to give the title compound (84 mg).

MS (ESI+): [M+H]$^+$273.8.

C) 1-(4-bromo-1-methyl-1H-pyrazol-3-yl)-4-(((tert-butyl(dimethyl)silyl)oxy)methyl)pyrrolidin-2-one To a solution of 1-(4-bromo-1-methyl-1H-pyrazol-3-yl)-4-(hydroxymethyl)pyrrolidin-2-one (84 mg) and 1H-imidazole (27 mg) in DMF (3.0 mL) was added tert-butyldimethylchlorosilane (54 mg). The reaction mixture was stirred at room temperature for 20 hr, and diluted with ethyl acetate. The diluted solution was washed with water and saturated brine, and dried over anhydrous sodium sulfate, and the solvent was evaporated under reduced pressure. The residue was purified by silica gel column chromatography (ethyl acetate/hexane) to give the title compound (44 mg).
MS (ESI+): [M+H]$^+$388.0.

D) N-(3-(4-(hydroxymethyl)-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide The title compound (1.0 mg) was obtained in the same manner as in Step D of Example 6 and Step H of Example 3.

Example 8

N-(3-(3-cyano-2-oxopyrrolidin-1-yl)-1-methyl-1H-pyrazol-4-yl)-2-methyl-1,3-oxazole-4-carboxamide A) 1-(1-methyl-1H-pyrazol-3-yl)-2-oxopyrrolidine-3-carbonitrile To a solution of 1-methyl-1H-pyrazol-3-amine (223 mg) in cyclopentyl methyl ether (5.0 mL) was added ethyl 1-cyanocyclopropanecarboxylate (0.90 ml). The reaction mixture was stirred at 120° C. for 30 hr, and diluted with ethyl acetate. The diluted solution was washed with water and saturated brine, and dried over anhydrous sodium sulfate, and the solvent was evaporated under reduced pressure. The residue was purified by silica gel column chromatography (ethyl acetate/hexane) to give the title compound (237 mg).
MS (ESI+): [M+H]$^+$190.8.

B) N-(3-(3-cyano-2-oxopyrrolidin-1-yl)-1-methyl-1H-pyrazol-4-yl)-2-methyl-1,3-oxazole-4-carboxamide The title compound was obtained in the same manner as in Steps B, C and I of Example 1.

Example 9

N-(3-((4S)-4-hydroxy-2-oxopyrrolidin-1-yl)-1-methyl-1H-pyrazol-4-yl)-2-methyl-1,3-oxazole-4-carboxamide A) N-(3-((4S)-4-((tert-butyl(dimethyl)silyl)oxy)-2-oxopyrrolidin-1-yl)-1-methyl-1H-pyrazol-4-yl)-2-methyl-1,3-oxazole-4-carboxamide The title compound was obtained in the same manner as in Step I of Example 1.
MS (ESI+): [M+H]$^+$420.2.

B) N-(3-((4S)-4-hydroxy-2-oxopyrrolidin-1-yl)-1-methyl-1H-pyrazol-4-yl)-2-methyl-1,3-oxazole-4-carboxamide To a solution of N-(3-((4S)-4-((tert-butyl(dimethyl)silyl)oxy)-2-oxopyrrolidin-1-yl)-1-methyl-1H-pyrazol-4-yl)-2-methyl-1,3-oxazole-4-carboxamide (32 mg) in THF (2.0 mL) was added 1M tetra-n-butylammonium fluoride THF solution (0.15 mL), and the mixture was stirred at room temperature for 1.5 hr. The reaction mixture was diluted with water, and the mixture was extracted with ethyl acetate. The extract was washed with saturated brine, and dried over anhydrous magnesium sulfate, and the solvent was evaporated under reduced pressure. The residue was purified by silica gel column chromatography (methanol/ethyl acetate) to give the title compound (10 mg).

Example 11

N-(3-(3-cyano-3-ethyl-2-oxopyrrolidin-1-yl)-1-methyl-1H-pyrazol-4-yl)-2-methyl-1,3-oxazole-4-carboxamide A) 3-ethyl-1-(4-fluorobenzoyl)-2-oxopyrrolidine-3-carbonitrile To a solution of 1-(4-fluorobenzoyl)-2-oxopyrrolidine-3-carbonitrile (25 g) in DMF (215 mL) was added a sodium hydride 60% dispersion in mineral oil (6.5 g) under ice-cooling. The reaction mixture was stirred under ice-cooling for 1 hr, and iodoethane (17 mL) was added slowly thereto. The reaction mixture was stirred under ice-cooling for 2 hr, and poured into 10% aqueous citric acid solution, and the mixture was extracted with ethyl acetate. The extract was washed with saturated brine, and dried over anhydrous magnesium sulfate, and the solvent was evaporated under reduced pressure. The residue was purified by silica gel column chromatography (ethyl acetate/hexane) to give the title compound (23 g).
$^1$H NMR (400 MHz, CDCl$_3$) δ 1.19 (3H, t, J=7.5 Hz), 1.76-1.87 (1H, m), 2.06-2.17 (1H, m), 2.20-2.30 (1H, m), 2.63 (1H, dt, J=13.3, 6.5 Hz), 3.99-4.07 (2H, m), 7.08-7.17 (2H, m), 7.61-7.70 (2H, m).

B) 3-ethyl-2-oxopyrrolidine-3-carbonitrile

To a solution of 3-ethyl-1-(4-fluorobenzoyl)-2-oxopyrrolidine-3-carbonitrile (11 g) in THF (80 mL) was added octylamine (8.5 mL). The reaction mixture was stirred at room temperature for 60 hr, and the solvent was evaporated under reduced pressure. The residue was purified by silica gel column chromatography (ethyl acetate/hexane) to give the title compound (5.7 g).
$^1$H NMR (300 MHz, CDCl$_3$) δ 1.16 (3H, t, J=7.4 Hz), 1.70-1.84 (1H, m), 2.00-2.16 (1H, m), 2.22 (1H, ddd, J=13.5, 7.6, 6.4 Hz), 2.61 (1H, ddd, J=13.0, 7.7, 4.9 Hz), 3.34-3.46 (1H, m), 3.47-3.61 (1H, m), 6.63 (1H, brs).

C) N-(3-(3-cyano-3-ethyl-2-oxopyrrolidin-1-yl)-1-methyl-1H-pyrazol-4-yl)-2-methyl-1,3-oxazole-4-carboxamide The title compound was obtained in the same manner as in Steps A, B, C and I of Example 1.

Example 13-I

N-(3-(3,3-dimethyl-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide hydrochloride A) tert-butyl (4-(4-((3-(3,3-dimethyl-2-oxopyrrolidin-1-yl)-1-methyl-1H-pyrazol-4-yl)carbamoyl)-1,3-oxazol-2-yl)pyridin-2-yl)(2,2,2-trifluoroethyl)carbamate The title compound was obtained in the same manner as in Steps A-I of Example 1.
MS (ESI+). found: 478.2.

B) N-(3-(3,3-dimethyl-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide hydrochloride A solution of tert-butyl (4-(4-((3-(3,3-dimethyl-2-oxopyrrolidin-1-yl)-1-methyl-1H-pyrazol-4-yl)carbamoyl)-1,3-oxazol-2-yl)pyridin-2-yl)(2,2,2-trifluoroethyl)carbamate (280 mg) and 4M hydrogen chloride ethyl acetate solution (4.0 mL) in methanol (1.0 mL) was stirred at room temperature for 3 hr. The reaction mixture was diluted with ethyl acetate (3.0 mL), and the precipitated solid was collected by filtration, washed with ethyl acetate, and dried under reduced pressure to give the title compound (195 mg).

Example 13-II

N-(3-(3,3-dimethyl-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide hydrochloride hydrate A) 3,3-dimethyl-1-(1-methyl-1H-pyrazol-3-yl)pyrrolidin-2-one A solution of 3-iodo-1-methyl-1H-pyrazole (200 mg), 3,3-dimethylpyrrolidin-2-one (109 mg), copper(I) iodide (73 mg), N1,N2-dimethylethane-1,2-diamine (0.083 mL) and tripotassium phosphate (408 mg) in cyclopentyl methyl ether (4 mL) was stirred overnight at 120° C. To the reaction mixture was added saturated aqueous ammonium chloride solution, and the mixture was extracted with ethyl acetate. The extract was washed with saturated brine, and dried over anhydrous magnesium sulfate, and the solvent was evaporated under reduced pressure. The residue was purified by silica gel column chromatography (ethyl acetate/hexane) to give the title compound (170 mg).
MS (ESI+): [M+H]$^+$: 194.1

B) 3,3-dimethyl-1-(1-methyl-4-nitro-1H-pyrazol-3-yl)pyrrolidin-2-one

To a solution of 3,3-dimethyl-1-(1-methyl-1H-pyrazol-3-yl)pyrrolidin-2-one (170 mg) in acetic anhydride (2.1 mL) was added fuming nitric acid (0.073 mL) under ice-cooling, and the mixture was stirred under ice-cooling for 1.5 hr. The reaction mixture was poured into ice water, and the mixture was neutralized with saturated aqueous sodium hydrogen carbonate solution, and extracted with ethyl acetate. The extract was washed with saturated brine, and dried over anhydrous magnesium sulfate, and the solvent was evaporated under reduced pressure. The residue was purified by silica gel column chromatography (ethyl acetate/hexane) to give the title compound (170 mg).
MS (ESI+): [M+H]$^+$: 239.1

C) 1-(4-amino-1-methyl-1H-pyrazol-3-yl)-3,3-dimethylpyrrolidin-2-one

A mixture of 3,3-dimethyl-1-(1-methyl-4-nitro-1H-pyrazol-3-yl)pyrrolidin-2-one (170 mg), 10% palladium-carbon (76 mg), THF (2 mL) and methanol (2 mL) was stirred at room temperature for 2 hr under hydrogen atmosphere. The reaction mixture was filtered through a membrane filter, and the filtrate was concentrated under reduced pressure to give the title compound (140 mg).
MS (ESI+): [M+H]$^+$: 208.9.

D) tert-butyl (4-(4-((3-(3,3-dimethyl-2-oxopyrrolidin-1-yl)-1-methyl-1H-pyrazol-4-yl)carbamoyl)-1,3-oxazol-2-yl)pyridin-2-yl) (2,2,2-trifluoroethyl)carbamate To a solution of 1-(4-amino-1-methyl-1H-pyrazol-3-yl)-3,3-dimethylpyrrolidin-2-one (140 mg), 2-(2-((tert-butoxycarbonyl)(2,2,2-trifluoroethyl)amino)pyridin-4-yl)-1,3-oxazole-4-carboxylic acid (260 mg) and HATU (383 mg) in DMF (3 mL) was added diisopropylethylamine (0.352 mL), and the mixture was stirred overnight at room temperature. The reaction mixture was diluted with water (5 mL), and the precipitate was collected by filtration, washed with water, and dried under reduced pressure to give the title compound (280 mg).
MS (ESI+). found: 478.2.

E) N-(3-(3,3-dimethyl-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide hydrochloride hydrate A solution of tert-butyl (4-(4-((3-(3,3-dimethyl-2-oxopyrrolidin-1-yl)-1-methyl-1H-pyrazol-4-yl)carbamoyl)-1,3-oxazol-2-yl)pyridin-2-yl) (2,2,2-trifluoroethyl)carbamate (280 mg) and 4M hydrogen chloride ethyl acetate solution (4 mL) in methanol (1 mL) was stirred at room temperature for 3 hr. The reaction mixture was diluted with ethyl acetate (3 mL), and the precipitated solid was collected by filtration, washed with ethyl acetate, and dried under reduced pressure to give the title compound (195 mg).
$^1$H NMR (400 MHz, DMSO-d$_6$) δ 1.23 (6H, s), 2.05 (2H, t, J=7.0 Hz), 3.76-3.90 (5H, m), 4.32-4.49 (2H, m), 7.28 (1H, dd, J=5.9, 1.5 Hz), 7.44 (1H, s), 8.21-8.31 (2H, m), 8.51 (1H, brs), 8.96 (1H, s), 10.92 (1H, s).
Anal. Calcd. C, 47.42; H, 4.74; N, 18.43, Cl; 6.67% (C$_{21}$H$_{22}$F$_3$N$_7$O$_3$.HCl.H$_2$O).
Found. C, 47.20; H, 4.63; N, 18.32, Cl; 6.55%.

Example 14

N-(3-(4-((dimethylamino)methyl)-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide (optical isomer)

Racemic N-(3-(4-((dimethylamino)methyl)-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide (37 mg) was resolved by SFC (column: CHIRALPAK IC (trade name), 20 mmID×250 mL, manufactured by Daicel Chemical Industries, mobile phase: carbon dioxide/ethanol/diethylamine=740/260/1) to give the title compound (14 mg) having a shorter retention time.

The retention time was 3.93 min when the title compound was analyzed using SFC for analysis (column: CHIRALPAK IC (trade name), 4.6 mmID×150 mL, manufactured by Daicel Chemical Industries, mobile phase: carbon dioxide/ethanol/diethylamine=740/260/1, flow rate: A mL/min).

Example 15

N-(3-((4S)-4-methoxy-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide A) (4S)-4-hydroxy-1-(1-methyl-1H-pyrazol-3-yl)pyrrolidin-2-one To a solution of (4S)-4-((tert-butyl(dimethyl)silyl)oxy)pyrrolidin-2-one (158 mg) in THF (3.0 mL) was added 1M tetra-n-butylammonium fluoride THF solution (1.1 mL), and the mixture was stirred at room temperature for 2 hr. The reaction mixture was diluted with water, and the mixture was extracted with ethyl acetate and n-butanol. The extract was washed with saturated brine, and dried over anhydrous magnesium sulfate, and the solvent was evaporated under reduced pressure. The residue was purified by silica gel column chromatography (methanol/ethyl acetate) to give the title compound (97 mg).

MS (ESI+): [M+H]$^+$182.1.

B) (4S)-4-methoxy-1-(1-methyl-1H-pyrazol-3-yl) pyrrolidin-2-one

To a solution of (4S)-4-hydroxy-1-(1-methyl-1H-pyrazol-3-yl)pyrrolidin-2-one (97 mg) in THF (3.0 mL) was added a sodium hydride 60% dispersion in mineral oil (24 mg) under ice-cooling, and the mixture was stirred under ice-cooling for 10 min. Iodomethane (50 μL) was added to the reaction mixture under ice-cooling, and the mixture was stirred overnight at room temperature. The reaction mixture was diluted with water, and the mixture was extracted with ethyl acetate. The extract was washed with saturated brine, and dried over anhydrous magnesium sulfate, and the solvent was evaporated under reduced pressure. The residue was purified by silica gel column chromatography (methanol/ethyl acetate) to give the title compound (30 mg).

MS (ESI+): [M+H]$^+$196.1.

C) N-(3-((4S)-4-methoxy-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide The title compound was obtained in the same manner as in Steps B-J of Example 1.

Example 16

N-(3-((4S)-4-(dimethylamino)-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide

A) (S)-tert-butyl 2-((tert-butoxycarbonyl)amino)-4-((1-methyl-1H-pyrazol-3-yl)amino)-4-oxobutanoate To a solution of 1-methyl-1H-pyrazol-3-amine (0.336 g) and (3S)-4-tert-butoxy-3-((tert-butoxycarbonyl)amino)-4-oxobutanoic acid (1.0 g) in DMF (17.28 mL) were added HATU (1.577 g) and diisopropylethylamine (0.905 mL) under ice-cooling, and the mixture was stirred at room temperature for 2 hr. The reaction mixture was poured into saturated aqueous ammonium chloride solution, and the mixture was extracted with ethyl acetate. The extract was washed with saturated aqueous sodium hydrogen carbonate solution and saturated brine, and dried over anhydrous magnesium sulfate, and the solvent was evaporated under reduced pressure to give the title compound (1.17 g).

MS (ESI+). found: 257.1.

B) tert-butyl ((2S)-1-hydroxy-4-((1-methyl-1H-pyrazol-3-yl)amino)-4-oxobutan-2-yl)carbamate To a solution of (S)-tert-butyl 2-((tert-butoxycarbonyl)amino)-4-((1-methyl-1H-pyrazol-3-yl)amino)-4-oxobutanoate (1.17 g) in a mixed solvent of THF (10.6 mL)/methanol (5.29 mL) was added lithium borohydride (0.484 g), and the mixture was stirred at room temperature for 2 hr, and then at 60° C. for 3 hr. The reaction mixture was poured into saturated aqueous ammonium chloride solution, and the mixture was extracted with ethyl acetate. The extract was washed with saturated brine, and dried over anhydrous magnesium sulfate, and the solvent was evaporated under reduced pressure. The residue was purified by silica gel column chromatography (ethyl acetate/hexane) to give the title compound (0.553 g).

MS (ESI+). found: 243.1.

C) tert-butyl ((3S)-1-(1-methyl-1H-pyrazol-3-yl)-5-oxopyrrolidin-3-yl)carbamate To a solution of tert-butyl ((2S)-1-hydroxy-4-((1-methyl-1H-pyrazol-3-yl)amino)-4-oxobutan-2-yl)carbamate (553.0 mg) and tri-n-butylphosphine (0.924 mL) in a mixed solvent of toluene (9 mL)/THF (3 mL) was added 40% diethyl azodicarboxylate toluene solution (0.954 mL) under ice-cooling, and the mixture was stirred at 60° C. for 1 hr. The reaction mixture was concentrated under reduced pressure, and the residue was purified by silica gel column chromatography (ethyl acetate/hexane) to give the title compound (358 mg).

MS (ESI+): [M+H]$^+$: 281.2.

D) (4S)-4-(dimethylamino)-1-(1-methyl-4-nitro-1H-pyrazol-3-yl)pyrrolidin-2-one To a solution of tert-butyl ((3S)-1-(1-methyl-1H-pyrazol-3-yl)-5-oxopyrrolidin-3-yl)carbamate (340 mg) in ethyl acetate (1.2 mL) was added 4M hydrogen chloride ethyl acetate solution (6.0 mL), and the mixture was stirred at room temperature for 2 hr, and concentrated under reduced pressure. To a solution of the residue and 37% formalin (0.45 mL) in methanol (6.1 mL) was added sodium triacetoxyborohydride (1.3 g) under ice-cooling, and the mixture was stirred at 0° C. for 40 min. The reaction mixture was poured into 0.5M aqueous sodium hydroxide solution, and the mixture was extracted successively with ethyl acetate and s-butanol. The extracts were combined, and dried over anhydrous magnesium sulfate, and the solvent was evaporated under reduced pressure. The residue was dissolved in conc. sulfuric acid (4.0 mL), fuming nitric acid (0.25 mL) was added thereto under ice-cooling, and the mixture was stirred at room temperature for 2 hr. The reaction mixture was neutralized with 8M aqueous sodium hydroxide solution, and the mixture was extracted successively with ethyl acetate and s-butanol. The extracts were combined, and dried over anhydrous magnesium sulfate, and the solvent was evaporated under reduced pressure. The residue was purified by silica gel column chromatography (NH, ethyl acetate/hexane) to give the title compound (70 mg).

MS (ESI+): [M+H]$^+$254.1.

E) (4S)-1-(4-amino-1-methyl-1H-pyrazol-3-yl)-4-(dimethylamino)pyrrolidin-2-one A mixture of (4S)-4-(dimethylamino)-1-(1-methyl-4-nitro-1H-pyrazol-3-yl)pyrrolidin-2-one (69.9 mg), 10% palladium-carbon (24.9 mg) and methanol (1.38 mL) was stirred at room temperature for 1 hr under hydrogen atmosphere. The reaction mixture was filtered through Celite, and the filtrate was concentrated under reduced pressure to give the title compound (55.6 mg).

MS (ESI+): [M+H]$^+$: 224.1.

F) tert-butyl (4-(4-((3-((4S)-4-(dimethylamino)-2-oxopyrrolidin-1-yl)-1-methyl-1H-pyrazol-4-yl)carbamoyl)-1,3-oxazol-2-yl)pyridin-2-yl)(2,2,2-trifluoroethyl)carbamate To a solution of (4S)-1-(4-amino-1-methyl-1H-pyrazol-3-yl)-4-(dimethylamino)pyrrolidin-2-one (69.9 mg), 2-(2-((tert-butoxycarbonyl)(2,2,2-trifluoroethyl)amino)pyridin-4-yl)-1,3-oxazole-4-carboxylic acid (146 mg) and HATU (143 mg) in DMF (1.57 mL) was added diisopropylethylamine (0.082 mL), and the mixture was stirred at room temperature for 1.5 hr. The reaction mixture was poured into water, and the mixture was extracted with ethyl acetate. The extract was washed successively with water, saturated aqueous sodium hydrogen carbonate solution and saturated brine, and dried over anhydrous magnesium sulfate, and the solvent was evaporated under reduced pressure. The residue was purified by silica gel column chromatography (NH, ethyl acetate/hexane) to give the title compound (63.7 mg).

MS (ESI+): [M+H]$^+$593.3.

G) N-(3-((4S)-4-(dimethylamino)-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide A mixture of tert-butyl (4-(4-((3-((4S)-4-(dimethylamino)-2-oxopyrrolidin-1-yl)-1-methyl-1H-pyrazol-4-yl)carbamoyl)-1,3-oxazol-2-yl)pyridin-2-yl) (2,2,2-trifluoroethyl)carbamate (63.6 mg) and TFA (2 mL) was stirred at room temperature for 30 min, and concentrated under reduced pressure. The residue was dissolved in methanol, Amberlyst A21 was added thereto, and the mixture was stirred at room temperature for 30 min. The reaction mixture was filtered, and the filtrate was concentrated under reduced pressure. The residue was recrystallized from ethyl acetate/hexane to give the title compound (38.9 mg).

$^1$H NMR (400 MHz, DMSO-d$_6$) δ 2.18 (6H, brs), 2.58 (1H, dd, J=17.1, 7.3 Hz), 2.77 (1H, dd, J=17.1, 7.8 Hz), 3.11-3.27 (1H, m), 3.73 (1H, dd, J=10.4, 6.5 Hz), 3.81 (3H, s), 3.99 (1H, dd, J=10.4, 7.2 Hz), 4.13-4.33 (2H, m), 7.16 (1H, dd, J=5.4, 1.5 Hz), 7.20 (1H, dd, J=1.5, 0.5 Hz), 7.63 (1H, t, J=6.5 Hz), 8.24 (1H, dd, J=5.4, 0.5 Hz), 8.26 (1H, s), 8.89 (1H, s), 10.91 (1H, s).

Example 17

N-(3-((5S)-4-hydroxy-3,3,5-trimethyl-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide trifluoroacetate A) (5S)-4-((tert-butyl(dimethyl)silyl)oxy)-3,3,5-trimethyl-1-(1-methyl-4-nitro-1H-pyrazol-3-yl)pyrrolidin-2-one A solution of 3-iodo-1-methyl-4-nitro-1H-pyrazole (197 mg), (5S)-4-((tert-butyl(dimethyl)silyl)oxy)-3,3,5-trimethylpyrrolidin-2-one (200 mg), copper(I) iodide (30 mg), N1,N2-dimethylethane-1,2-diamine (33 μL) and tripotassium phosphate (330 mg) in cyclopentyl methyl ether (5.0 mL) was stirred overnight at 120° C. The reaction mixture was diluted with ethyl acetate, the mixture was washed with saturated aqueous ammonium chloride solution, water and saturated brine, and dried over anhydrous magnesium sulfate, and the solvent was evaporated under reduced pressure. The residue was purified by silica gel column chromatography (ethyl acetate/hexane) and then silica gel column chromatography (NH, ethyl acetate/hexane) to give the title compound (90 mg).

MS (ESI+): [M+H]$^+$383.2.

B) N-(3-((5S)-4-hydroxy-3,3,5-trimethyl-2-oxopyrrolidin-1-yl)-1-methyl-1H-pyrazol-4-yl)-2-(2-(methyl(2,2,2-trifluoroethyl)amino)pyridin-4-yl)-1,3-oxazole-4-carboxamide trifluoroacetate A mixture of (5S)-4-((tert-butyl(dimethyl)silyl)oxy)-3,3,5-trimethyl-1-(1-methyl-4-nitro-1H-pyrazol-3-yl)pyrrolidin-2-one (90 mg), 10% palladium-carbon (25 mg), THF (4.0 mL) and methanol (4.0 mL) was stirred at room temperature for 5 hr under hydrogen atmosphere. The reaction mixture was filtered through a membrane filter, and the filtrate was concentrated under reduced pressure. To a solution of the residue, 2-(2-((tert-butoxycarbonyl)(2,2,2-trifluoroethyl)amino)pyridin-4-yl)-1,3-oxazole-4-carboxylic acid (91 mg) and HATU (107 mg) in DMF (3.0 mL) was added diisopropylethylamine (0.12 mL), and the mixture was stirred overnight at room temperature. The reaction mixture was diluted with water, and the mixture was extracted with ethyl acetate. The extract was washed with saturated brine, and dried over anhydrous magnesium sulfate, and the solvent was evaporated under reduced pressure. The residue was purified by silica gel column chromatography (ethyl acetate/hexane). A solution of the obtained solid and 4M hydrogen chloride ethyl acetate solution (2.0 mL) in methanol (0.50 mL) was stirred at room temperature for 3 hr. The reaction mixture was concentrated under reduced pressure, and a solution of the obtained solid and Amberlyst A21 (registered trademark) (100 mg) in methanol (3.0 mL) was stirred at room temperature for 10 min. The reaction mixture was filtered, and the filtrate was concentrated under reduced pressure. The residue was purified by HPLC(C18, mobile phase: water/acetonitrile (containing 0.1% TFA)), and the obtained fraction was concentrated under reduced pressure to give the title compound (15 mg).

Example 18

N-(3-(4-((dimethylamino)methyl)-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide (optical isomer)

Racemic N-(3-(4-((dimethylamino)methyl)-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide 37 mg) was resolved by SFC (column: CHIRALPAK IC (trade name), 20 mmID×250 mL, manufactured by Daicel Chemical Industries, mobile phase: carbon dioxide/ethanol/diethylamine=740/260/1) to give the title compound (13 mg) having a longer retention time.

The retention time was 5.55 min when the title compound was analyzed using SFC for analysis (column: CHIRALPAK IC (trade name), 4.6 mmID×150 mL, manufactured by Daicel Chemical Industries, mobile phase: carbon dioxide/ethanol/diethylamine=740/260/1, flow rate: 4 mL/min).

Example 19

N-(3-(3,3-dimethyl-2-oxopyrrolidin-1-yl)-1-methyl-1H-pyrazol-4-yl)-2-(morpholin-4-yl)-1,3-oxazole-4-carboxamide Ethyl 2-bromo-1,3-oxazole-4-carboxylate (150 mg), morpholine (89 mg), potassium carbonate (188 mg) and copper iodide (I) (26 mg) were dissolved in DMF (5.0 mL) in a sealed tube, and the solution was stirred overnight at 125° C. under nitrogen atmosphere. The reaction mixture was diluted with ethyl acetate, and the mixture was washed three times with saturated aqueous ammonium chloride solution, dried over magnesium sulfate, and concentrated under reduced pressure. The residue was dissolved in THF (3 mL), 2M aqueous sodium hydroxide solution (0.68 mL) was added thereto, and the mixture was stirred at room temperature for 4 hr. The reaction mixture was acidified with 2M hydrochloric acid to adjust pH=3, and concentrated under reduced pressure. The residue, 1-(4-amino-1-methyl-1H-pyrazol-3-yl)-3,3-dimethylpyrrolidin-2-one (213 mg), HATU (389 mg) and triethylamine (0.29 mL) were dissolved in DMF (4.0 mL), and the solution was stirred overnight at room temperature. The reaction solution was diluted with ethyl acetate, and the mixture was washed three times with saturated aqueous ammonium chloride solution, dried over magnesium sulfate, and concentrated under reduced pressure. The residue was purified by silica gel column chromatography (ethyl acetate/hexane) to give the title compound (3.0 mg).

Example 20

N-(3-(3,3-dimethyl-2-oxopyrrolidin-1-yl)-1-methyl-1H-pyrazol-4-yl)-2-phenyl-1,3-oxazole-4-carboxamide A mixture of ethyl 2-phenyl-1,3-oxazole-4-carboxylate (86 mg), 2M aqueous sodium hydroxide solution (1.0 mL), THF (1.0 mL) and ethanol (1.0 mL) was stirred at room temperature for 1 hr. The reaction mixture was diluted with water, and the mixture was neutralized with 2M hydrochloric acid, and extracted with ethyl acetate. The extract was washed with saturated brine, and dried over anhydrous magnesium sulfate, and the solvent was evaporated under reduced pressure. To a solution of the obtained residue, 1-(4-amino-1-methyl-1H-pyrazol-3-yl)-3,3-dimethylpyrrolidin-2-one (82 mg) and HATU (181 mg) in DMF (2.0 mL) was added diisopropylethylamine (0.14 mL), and the mixture was stirred overnight at room temperature. The reaction mixture was diluted with water, and the mixture was extracted with ethyl acetate. The extract was washed with saturated brine, and dried over anhydrous magnesium sulfate, and the solvent was evaporated under reduced pressure. The residue was, purified by silica gel column chromatography (ethyl acetate/hexane), and recrystallized from ethyl acetate/hexane to give the title compound (14 mg).

Example 23

N-(3-(4-hydroxy-3,3-dimethyl-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide A) tert-butyl (4-(4-((3-(3,3-dimethyl-2,4-dioxopyrrolidin-1-yl)-1-methyl-1H-pyrazol-4-yl)carbamoyl)-1,3-oxazol-2-yl)pyridin-2-yl) (2,2,2-trifluoroethyl)carbamate The title compound was obtained in the same manner as in Steps A-I of Example 1.

B) tert-butyl (4-(4-((3-(4-hydroxy-3,3-dimethyl-2-oxopyrrolidin-1-yl)-1-methyl-1H-pyrazol-4-yl)carbamoyl)-1,3-oxazol-2-yl)pyridin-2-yl) (2,2,2-trifluoroethyl)carbamate To a mixture of tert-butyl (4-(4-((3-(3,3-dimethyl-2,4-dioxopyrrolidin-1-yl)-1-methyl-1H-pyrazol-4-yl)carbamoyl)-1,3-oxazol-2-yl)pyridin-2-yl) (2,2,2-trifluoroethyl)carbamate (40 mg) and ethanol (2.0 mL) was added sodium borohydride (3.8 mg), and the mixture was stirred at room temperature for 2 hr. The reaction was quenched with a few drops of saturated aqueous ammonium chloride solution, and diluted with ethyl acetate. The extract was washed three times with saturated brine, dried over magnesium sulfate, and concentrated under reduced pressure to give the title compound (32 mg).

MS (ESI+): [M+H]$^+$594.3.

C) N-(3-(4-hydroxy-3,3-dimethyl-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide The title compound was obtained in the same manner as in Step J of Example 1.

Example 28

N-(3-((4S)-4-acetamido-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide To a solution of tert-butyl (4-(4-((3-((4S)-4-amino-2-oxopyrrolidin-1-yl)-1-methyl-1H-pyrazol-4-yl)carbamoyl)-1,3-oxazol-2-yl)pyridin-2-yl) (2,2,2-trifluoroethyl)carbamate (51 mg) in pyridine (0.30 mL) was added acetic anhydride (0.15 mL), and the mixture was stirred at room temperature for 10 min. The reaction mixture was concentrated under reduced pressure, and the residue was purified by silica gel column chromatography (NH, ethyl acetate/methanol). The residue was dissolved in TFA (0.45 mL), and the solution was stirred at room temperature for 10 min. The reaction mixture was concentrated under reduced pressure, and the residue was purified by silica gel column chromatography (NH, methanol/ethyl acetate), and recrystallized from ethyl acetate/methanol/hexane to give the title compound (19 mg).

Example 29

N-(1-methyl-3-((4S)-4-((methylsulfonyl)amino)-2-oxopyrrolidin-1-yl)-1H-pyrazol-4-yl)-2-(2-((2,2,2-trifluoroethyl)amino)pyridin-4-yl)-1,3-oxazole-4-carboxamide To a solution of tert-butyl (4-(4-((3-((4S)-4-amino-2-oxopyrrolidin-1-yl)-1-methyl-1H-pyrazol-4-yl)carbamoyl)-1,3-oxazol-2-yl)pyridin-2-yl) (2,2,2-trifluoroethyl)carbamate (51 mg) in THF (0.45 mL) were added triethylamine (19 μL) and methanesulfonyl chloride (8.0 μL), and the mixture was stirred at room temperature for 1 hr. The reaction mixture was poured into water, and the mixture was extracted with ethyl acetate. The extract was washed with saturated brine, and dried over anhydrous magnesium sulfate, and the solvent was evaporated under reduced pressure. The residue was dissolved in TFA (0.45 mL), and the solution was stirred at room temperature for 20 min. The reaction mixture was concentrated under reduced pressure, and the residue was purified by silica gel column chromatography (NH, methanol/ethyl acetate), and recrystallized from ethyl acetate/methanol/hexane to give the title compound (24 mg).

Example 30

N-(3-((4S)-4-(diethylamino)-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide To a solution of tert-butyl (4-(4-((3-((4S)-4-amino-2-oxopyrrolidin-1-yl)-1-methyl-1H-pyrazol-4-yl)carbamoyl)-1,3-oxazol-2-yl)pyridin-2-yl)(2,2,2-trifluoroethyl)carbamate (82 mg) and acetaldehyde (32 mg) in THF (0.24 mL)/methanol (0.48 mL) was added sodium triacetoxyborohydride (154 mg), and the mixture was stirred at 0° C. for 2 hr. The reaction mixture was concentrated under reduced pressure, the residue was dissolved in TFA (0.70 mL), and the solution was stirred at room temperature for 20 min. The reaction mixture was concentrated under reduced pressure, and the residue was purified by silica gel column chromatography (NH, methanol/ethyl acetate), and recrystallized from ethyl acetate/hexane to give the title compound (34 mg).

Example 31

N-(1-methyl-3-((4S)-4-(morpholin-4-yl)-2-oxopyrrolidin-1-yl)-1H-pyrazol-4-yl)-2-(2-((2,2,2-trifluoroethyl)amino)pyridin-4-yl)-1,3-oxazole-4-carboxamide To a solution of tert-butyl (4-(4-((3-((4S)-4-amino-2-oxopyrrolidin-1-yl)-1-methyl-1H-pyrazol-4-yl)carbamoyl)-1,3-oxazol-2-yl)pyridin-2-yl)(2,2,2-trifluoroethyl)carbamate (79 mg) and sodium hydrogen carbonate (70 mg) in toluene (0.70 mL) was added 2,2'-dibromodiethyl ether (0.035 mL), and the mixture was stirred overnight at 100° C. The reaction mixture was poured into water, and the mixture was extracted with ethyl acetate. The extract was washed with saturated brine, and dried over anhydrous magnesium sulfate, and the solvent was evaporated under reduced pressure. The residue was dissolved in TFA (0.70 mL), and the solution was stirred at room temperature for 30 min. The reaction mixture was concentrated under reduced pressure, and the residue was purified by silica gel column chromatography (NH, methanol/ethyl acetate), and recrystallized from ethyl acetate/hexane to give the title compound (3.3 mg).

Example 32

N-(3-((4S)-4-(ethylamino)-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide To a solution of tert-butyl (4-(4-((3-((4S)-4-amino-2-oxopyrrolidin-1-yl)-1-methyl-1H-pyrazol-4-yl)carbamoyl)-1,3-oxazol-2-yl)pyridin-2-yl)(2,2,2-trifluoroethyl)carbamate (42 mg) in THF (1.0 mL) was added acetaldehyde (37 μL), and the mixture was stirred overnight at room temperature. Sodium borohydride (28 mg) and methanol (0.20 mL) were added thereto, and the mixture was stirred at room temperature for 1 hr, and concentrated under reduced pressure. The residue was dissolved in TFA (0.70 mL), and the solution was stirred at room temperature for 20 min. The reaction mixture was concentrated under reduced pressure, and the residue was purified by silica gel column chromatography (NH, methanol/ethyl acetate), and recrystallized from ethyl acetate/hexane to give the title compound (14 mg).

Example 33

N-(3-(4-amino-3,3-dimethyl-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide trifluoroacetate A) 1-(4-(((2-(2-((tert-butoxycarbonyl) (2,2,2-trifluoroethyl)amino)pyridin-4-yl)-1,3-oxazol-4-yl)carbonyl)amino)-1-methyl-1H-pyrazol-3-yl)-4,4-dimethyl-5-oxopyrrolidin-3-yl methanesulfonate tert-Butyl (4-(4-((3-(4-hydroxy-3,3-dimethyl-2-oxopyrrolidin-1-yl)-1-methyl-1H-pyrazol-4-yl)carbamoyl)-1,3-oxazol-2-yl)pyridin-2-yl)(2,2,2-trifluoroethyl)carbamate (40 mg) was dissolved in acetonitrile (2.0 mL), triethylamine (14 μL) and methanesulfonyl chloride (5.7 μL) were added thereto, and the mixture was stirred overnight at room temperature. The reaction solution was diluted with ethyl acetate, and the mixture was washed three times with saturated aqueous ammonium chloride solution, dried over anhydrous magnesium sulfate, and concentrated under reduced pressure. The residue was purified by silica gel column chromatography (ethyl acetate/hexane) to give the title compound (15 mg).
MS (ESI+): [M+H]$^+$672.2.

B) tert-butyl (4-(4-((3-(4-azido-3,3-dimethyl-2-oxopyrrolidin-1-yl)-1-methyl-1H-pyrazol-4-yl)carbamoyl)-1,3-oxazol-2-yl)pyridin-2-yl)(2,2,2-trifluoroethyl)carbamate 1-(4-(((2-(2-((tert-Butoxycarbonyl)(2,2,2-trifluoroethyl)amino)pyridin-4-yl)-1,3-oxazol-4-yl)carbonyl)amino)-1-methyl-1H-pyrazol-3-yl)-4,4-dimethyl-5-oxopyrrolidin-3-yl methanesulfonate (15 mg) was dissolved in DMF (0.50 mL), sodium azide (22 mg) and 18-crown-6 (5.9 mg) were added thereto, and the mixture was stirred at room temperature for 3 days. The reaction mixture was diluted with ethyl acetate, and the mixture was washed three times with saturated aqueous ammonium chloride solution, dried over anhydrous magnesium sulfate, and concentrated under reduced pressure. The residue was purified by silica gel column chromatography (ethyl acetate/hexane) to give the title compound (5.0 mg).
MS (ESI+): [M+H]$^+$619.1.

C) N-(3-(4-amino-3,3-dimethyl-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide trifluoroacetate tert-Butyl (4-(4-((3-(4-azido-3,3-dimethyl-2-oxopyrrolidin-1-yl)-1-methyl-1H-pyrazol-4-yl)carbamoyl)-1,3-oxazol-2-yl)pyridin-2-yl)(2,2,2-trifluoroethyl)carbamate (5.0 mg) was dissolved in methanol (2.0 mL). 10% Palladium-carbon (0.086 mg) was added thereto, and the mixture was stirred overnight at room temperature under hydrogen atmosphere. The reaction solution was diluted with methanol, and the mixture was filtered through Celite, and the filtrate was concentrated under reduced pressure. The residue was dissolved in TFA (0.50 mL), and the solution was stirred at room temperature for 20 min. The reaction mixture was concentrated under reduced pressure, and the residue was dissolved in a few drops of acetonitrile. Diisopropyl ether was added thereto, and the supernatant was removed to give the title compound (2.0 mg).

Example 34

N-(3-(3,3-dimethyl-2-oxopyrrolidin-1-yl)-1-methyl-1H-pyrazol-4-yl)-3-(1,3-thiazol-2-ylsulfonyl)benzamide

A) methyl 3-(1,3-thiazol-2-ylsulfanyl)benzoate

To a solution of methyl 3-sulfanylbenzoate (375 mg) and potassium carbonate (616 mg) in DMF (11 mL) was added 2-chloro-1,3-thiazole (533 mg), and the mixture was stirred overnight at 100° C., and cooled to room temperature. A sodium hydride 60% dispersion in mineral oil (89 mg) was added thereto, and the mixture was stirred at 100° C. for 3 hr. The reaction mixture was poured into water at room temperature, and the mixture was extracted with ethyl acetate. The extract was washed successively with water and saturated brine, and dried over anhydrous magnesium sulfate, and the solvent was evaporated under reduced pressure. The residue was purified by silica gel column chromatography (ethyl acetate/hexane) to give the title compound (76 mg).
MS (ESI+): [M+H]$^+$252.2.

B) methyl 3-(1,3-thiazol-2-ylsulfonyl)benzoate

To a solution of methyl 3-(1,3-thiazol-2-ylsulfanyl)benzoate (76 mg) in ethyl acetate (1.5 mL) was added m-chloroperbenzoic acid (225 mg), and the mixture was stirred overnight at room temperature. The reaction mixture was poured into saturated aqueous sodium hydrogen sulfite solution, and the mixture was extracted with ethyl acetate. The extract was washed successively with saturated aqueous sodium carbonate solution and saturated brine, and dried over anhydrous magnesium sulfate, and the solvent was evaporated under reduced pressure to give the title compound (82 mg).
$^1$H NMR (400 MHz, CDCl$_3$) δ 3.96 (3H, s), 7.65-7.71 (2H, m), 7.99 (1H, d, J=3.2 Hz), 8.29-8.35 (2H, m), 8.74 (1H, dd, J=1.5, 1.4 Hz).

C) 3-(1,3-thiazol-2-ylsulfonyl)benzoic acid

To a solution of methyl 3-(1,3-thiazol-2-ylsulfonyl)benzoate (82 mg) in methanol (1.5 mL) was added 1M aqueous sodium hydroxide solution (0.58 mL), and the mixture was stirred at room temperature for 2 hr. The reaction mixture was ice-cooled, 1M hydrochloric acid (1.0 mL) was added thereto, and the precipitate was collected by filtration to give the title compound (67 mg).
MS (ESI−): [M−H]$^-$ 268.0.

D) N-(3-(3,3-dimethyl-2-oxopyrrolidin-1-yl)-1-methyl-1H-pyrazol-4-yl)-3-(1,3-thiazol-2-ylsulfonyl)benzamide To a solution of 1-(4-amino-1-methyl-1H-pyrazol-3-yl)-3,3-dimethylpyrrolidin-2-one hydrochloride (30 mg) and 3-(1,3-thiazol-2-ylsulfonyl)benzoic acid (33.0 mg) in DMF (0.61 mL) were added HATU (56 mg) and diisopropylethylamine (43 μL). The reaction mixture was stirred overnight at room temperature, and poured into water, and the precipitate was collected by filtration, purified by silica gel column chromatography (NH, ethyl acetate/hexane), and recrystallized from ethyl acetate/hexane to give the title compound (40 mg).

Example 47

N-(1-methyl-3-((3R)-3-methyl-2-oxopyrrolidin-1-yl)-1H-pyrazol-4-yl)-2-(2-((2,2,2-trifluoroethyl)amino)pyridin-4-yl)-1,3-oxazole-4-carboxamide

A) methyl (3R)-3-methyl-4-((1-methyl-1H-pyrazol-3-yl)amino)-4-oxobutanoate

To a solution of (2R)-4-methoxy-2-methyl-4-oxobutanoic acid (0.30 mL) and DMF (20 μL) in THF (5.0 mL) was added oxalyl chloride (0.25 mL). The reaction mixture was stirred at room temperature for 3 hr, and 1-methyl-1H-pyrazol-3-amine (200 mg) and triethylamine (0.62 mL) were added thereto. The reaction mixture was stirred at room temperature for 15 hr, and extracted with ethyl acetate. The extract was washed with saturated aqueous ammonium chloride solution and saturated brine, and dried over anhydrous sodium sulfate, and the solvent was evaporated under reduced pressure. The residue was purified by silica gel column chromatography (ethyl acetate/hexane) to give the title compound (345 mg).
MS (ESI+): [M+H]$^+$226.2.

B) (2R)-4-hydroxy-2-methyl-N-(1-methyl-1H-pyrazol-3-yl)butanamide

To a solution of lithium borohydride (97 mg) in THF (5.0 mL) was added a solution of methyl (3R)-3-methyl-4-((1-methyl-1H-pyrazol-3-yl)amino)-4-oxobutanoate (240 mg) in methanol (1.0 mL) under ice-cooling. The reaction mixture was stirred at room temperature for 2 hr, saturated aqueous ammonium chloride solution was added thereto, and the mixture was extracted with ethyl acetate. The extract was washed with saturated brine, and dried over anhydrous sodium sulfate, and the solvent was evaporated under reduced pressure. The residue was purified by silica gel column chromatography (ethyl acetate/hexane) to give the title compound (208 mg).
MS (ESI+): [M+H]$^+$197.8.

C) (3R)-3-methyl-1-(1-methyl-1H-pyrazol-3-yl)pyrrolidin-2-one

To a solution of (2R)-4-hydroxy-2-methyl-N-(1-methyl-1H-pyrazol-3-yl)butanamide (216 mg) and tri-n-butylphosphine (0.54 mL) in THF (10 mL) was added 40% diethyl azodicarboxylate toluene solution (1.0 mL). The reaction mixture was stirred at room temperature for 15 hr, and diluted with ethyl acetate. The diluted solution was washed with saturated brine, and dried over anhydrous sodium sulfate, and the solvent was evaporated under reduced pressure. The residue was purified by silica gel column chromatography (ethyl acetate/hexane), and then HPLC (C18, mobile phase: water/acetonitrile (containing 0.1% TFA)), and to the obtained fraction was added ethyl acetate. The mixture was washed with saturated aqueous sodium carbonate solution and saturated brine, and dried over anhydrous sodium sulfate, and the solvent was concentrated under reduced pressure to give the title compound (97 mg).
MS (ESI+): [M+H]$^+$180.3.

D) N-(1-methyl-3-((3R)-3-methyl-2-oxopyrrolidin-1-yl)-1H-pyrazol-4-yl)-2-(2-((2,2,2-trifluoroethyl)amino)pyridin-4-yl)-1,3-oxazole-4-carboxamide The title compound was obtained in the same manner as in Step B of Example 1 and Steps C, D and H of Example 3.

Example 48

N-(1-methyl-3-(3-methyl-2-oxoimidazolidin-1-yl)-1H-pyrazol-4-yl)-2-(2-((2,2,2-trifluoroethyl)amino)pyridin-4-yl)-1,3-oxazole-4-carboxamide

A) 1-methyl-3-(1-methyl-1H-pyrazol-3-yl)imidazolidin-2-one

A solution of 3-iodo-1-methyl-1H-pyrazole (250 mg), 1-methylimidazolidin-2-one (120 mg), copper(I) iodide (46 mg), N1,N2-dimethylethane-1,2-diamine (0.052 mL) and tripotassium phosphate (510 mg) in cyclopentyl methyl ether (5 mL) was stirred overnight at 120° C. The reaction mixture was diluted with ethyl acetate, and the mixture was washed successively with saturated aqueous ammonium chloride solution, water and saturated brine. The extract was dried over anhydrous magnesium sulfate, and the filtrate was concentrated under reduced pressure. The residue was purified by silica gel column chromatography (ethyl acetate/hexane) to give the title compound (161 mg).

MS (ESI+): [M+H]$^+$: 180.8.

B) 1-methyl-3-(1-methyl-4-nitro-1H-pyrazol-3-yl)imidazolidin-2-one

To a solution of 1-methyl-3-(1-methyl-1H-pyrazol-3-yl)imidazolidin-2-one (161 mg) in acetic anhydride (2.1 mL) was added fuming nitric acid (0.074 mL) under ice-cooling, and the mixture was stirred for 1.5 hr under ice-cooling. The reaction mixture was poured into ice water, and the mixture was neutralized with saturated aqueous sodium hydrogen carbonate solution, and extracted with ethyl acetate. The extract was washed with saturated brine, and dried over anhydrous magnesium sulfate, and the solvent was evaporated under reduced pressure. The residue was purified by silica gel column chromatography (methanol/ethyl acetate) to give the title compound (101 mg).

MS (ESI+): [M+H]$^+$: 226.1.

C) tert-butyl (4-(4-((1-methyl-3-(3-methyl-2-oxoimidazolidin-1-yl)-1H-pyrazol-4-yl)carbamoyl)-1,3-oxazol-2-yl)pyridin-2-yl) (2,2,2-trifluoroethyl)carbamate A mixture of 1-methyl-3-(1-methyl-4-nitro-1H-pyrazol-3-yl)imidazolidin-2-one (101 mg), 10% palladium-carbon (47 mg), THF (2 mL) and methanol (2 mL) was stirred at room temperature for 2 hr under hydrogen atmosphere. The reaction mixture was filtered through a membrane filter, and the filtrate was concentrated under reduced pressure. To a solution of the residue, 2-(2-((tert-butoxycarbonyl)(2,2,2-trifluoroethyl)amino)pyridin-4-yl)-1,3-oxazole-4-carboxylic acid (174 mg) and HATU (205 mg) in DMF (3 mL) was added diisopropylethylamine (0.157 mL), and the mixture was stirred overnight at room temperature. The reaction mixture was diluted with water, and the mixture was extracted with ethyl acetate. The extract was washed with saturated brine, and dried over anhydrous magnesium sulfate, and the solvent was evaporated under reduced pressure. The residue was purified by silica gel column chromatography (ethyl acetate/hexane), and washed with ethyl acetate/hexane to give the title compound (138 mg).

MS (ESI+). found: 465.0.

D) N-(1-methyl-3-(3-methyl-2-oxoimidazolidin-1-yl)-1H-pyrazol-4-yl)-2-(2-((2,2,2-trifluoroethyl)amino)pyridin-4-yl)-1,3-oxazole-4-carboxamide A solution of tert-butyl (4-(4-((1-methyl-3-(3-methyl-2-oxoimidazolidin-1-yl)-1H-pyrazol-4-yl)carbamoyl)-1,3-oxazol-2-yl)pyridin-2-yl) (2,2,2-trifluoroethyl)carbamate (138 mg) and 4M hydrogen chloride ethyl acetate solution (2 mL) in methanol (1 mL) was stirred at room temperature for 2 hr. The reaction mixture was concentrated under reduced pressure, and the residue was dissolved in methanol (4 mL). Amberlyst A21 (300 mg) was added thereto, and the mixture was stirred at room temperature for 10 min, and filtered. The filtrate was concentrated under reduced pressure, and the residue was purified by silica gel column chromatography (ethyl acetate/hexane), and recrystallized from DMF/water to give the title compound (28 mg).

$^1$H NMR (400 MHz, DMSO-d$_6$) δ 2.88 (3H, s), 3.51-3.60 (2H, m), 3.77 (3H, s), 3.80-3.87 (2H, m), 4.17-4.32 (2H, m), 7.14-7.24 (2H, m), 7.59 (1H, t, J=6.5 Hz), 8.17-8.28 (2H, m), 8.86 (1H, s), 11.33 (1H, s).

Example 49

N-(3-(3,3-dimethyl-4-((methylamino)methyl)-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide The title compound was obtained in the same manner as in Steps G and H of Example 3.

MS (ESI+): [M+H]$^+$521.2.

Example 51

N-(3-(3,3-dimethyl-2-oxopyrrolidin-1-yl)-1-methyl-1H-pyrazol-4-yl)-2-(morpholin-4-yl)-1,3-thiazole-4-carboxamide

A) ethyl 2-(morpholin-4-yl)-1,3-thiazole-4-carboxylate

A mixture of morpholine (1.5 mL) and ethyl 2-bromo-1,3-thiazole-4-carboxylate (200 mg) was stirred overnight at 50° C. The reaction solution was poured into water, and the mixture was extracted with ethyl acetate. The extract was washed with saturated brine, dried over sodium sulfate, and concentrated under reduced pressure. The residue was purified by silica gel column chromatography (NH, ethyl acetate/hexane) to give the title compound (193 mg).

MS (ESI+): [M+H]$^+$242.8.

B) N-(3-(3,3-dimethyl-2-oxopyrrolidin-1-yl)-1-methyl-1H-pyrazol-4-yl)-2-(morpholin-4-yl)-1,3-thiazole-4-carboxamide To a solution of ethyl 2-(morpholin-4-yl)-1,3-thiazole-4-carboxylate (100 mg) in ethanol (6.0 mL) was added 1M aqueous sodium hydroxide solution (3.0 mL), and the mixture was stirred at room temperature for 44 hr, neutralized with 1M hydrochloric acid (3.0 mL), and concentrated under reduced pressure. To the residue were added 1-(4-amino-1-methyl-1H-pyrazol-3-yl)-3,3-dimethylpyrrolidin-2-one hydrochloride (50 mg), HATU (101 mg), DMF (6.0 mL) and triethylamine (57 μL), and the mixture was stirred at room temperature for 20 hr. The reaction mixture was diluted with ethyl acetate, and water was added thereto. The extract was washed with water and saturated brine, dried over sodium sulfate, and concentrated under reduced pressure. The residue was purified by silica gel column chromatography (NH, ethyl acetate/hexane), and the obtained solid was washed with a mixed solvent of diisopropyl ether/ethyl acetate, and dried under reduced pressure to give the title compound (69 mg).

Example 52

6-acetyl-N-(3-(3,3-dimethyl-2-oxopyrrolidin-1-yl)-1-methyl-1H-pyrazol-4-yl)pyridine-2-carboxamide To a solution of 1-(4-amino-1-methyl-1H-pyrazol-3-yl)-3,3-dimethylpyrrolidin-2-one hydrochloride (50 mg), 6-acetylpyridine-2-carboxylic acid (37 mg) and HATU (101 mg) in DMF (3.0 mL) was added ethyldiisopropylamine (71 µL) at room temperature, and the mixture was stirred for 20 hr. The reaction mixture was diluted with ethyl acetate, and water was added thereto. The extract was washed with water and saturated brine, dried over sodium sulfate, and concentrated under reduced pressure. The residue was purified by silica gel column chromatography (ethyl acetate/hexane) to give the title compound (74 mg).

Example 53

N-(3-(3,3-dimethyl-2-oxopyrrolidin-1-yl)-1-methyl-1H-pyrazol-4-yl)-6-(1-hydroxyethyl)pyridine-2-carboxamide To a mixture of 6-acetyl-N-(3-(3,3-dimethyl-2-oxopyrrolidin-1-yl)-1-methyl-1H-pyrazol-4-yl)pyridine-2-carboxamide (32 mg) and methanol (5.0 mL) was added sodium borohydride (5.3 mg) at room temperature, and the mixture was stirred at room temperature for 3 hr. The reaction mixture was diluted with ethyl acetate, and water was added thereto. The extract was washed with water and saturated brine, dried over sodium sulfate, and concentrated under reduced pressure. The residue was purified by silica gel column chromatography (NH, ethyl acetate/hexane), and the obtained solid was washed with diisopropyl ether, and dried under reduced pressure to give the title compound (25 mg).

Example 54

N-(3-(3,3-dimethyl-2-oxopyrrolidin-1-yl)-1-methyl-1H-pyrazol-4-yl)-6-(2-hydroxypropan-2-yl)pyridine-2-carboxamide To a mixture of 6-acetyl-N-(3-(3,3-dimethyl-2-oxopyrrolidin-1-yl)-1-methyl-1H-pyrazol-4-yl)pyridine-2-carboxamide (35 mg) and THF (3.0 mL) was added 3M methylmagnesium bromide diethyl ether solution (0.33 mL) at 0° C., and the mixture was stirred at room temperature for 4 hr. The reaction solution was diluted with ethyl acetate, and water was added thereto. The extract was washed with water and saturated brine, dried over sodium sulfate, and concentrated under reduced pressure. The residue was purified by silica gel column chromatography (NH, ethyl acetate/hexane), and the obtained solid was washed with diisopropyl ether, and dried under reduced pressure to give the title compound (14 mg).

Example 55

N-(1-methyl-3-(2-oxo-1,3-oxazolidin-3-yl)-1H-pyrazol-4-yl)-2-(2-((2,2,2-trifluoroethyl)amino)pyridin-4-yl)-1,3-oxazole-4-carboxamide A) 3-(1-methyl-1H-pyrazol-3-yl)-1,3-oxazolidin-2-one The title compound was obtained in the same manner as in Step A of Example 1.
MS (ESI+): [M+H]$^+$168.2.

B) 3-(1-methyl-4-nitro-1H-pyrazol-3-yl)-1,3-oxazolidin-2-one

To a solution of 3-(1-methyl-1H-pyrazol-3-yl)-1,3-oxazolidin-2-one (85 mg) in conc. sulfuric acid (2.5 mL) was added fuming nitric acid (32 µL) under ice-cooling, and the mixture was stirred at 0° C. for 2 hr. The reaction mixture was neutralized with 8M aqueous sodium hydroxide solution under ice-cooling, and extracted with ethyl acetate. The extract was washed with saturated brine, and dried over anhydrous magnesium sulfate, and the solvent was evaporated under reduced pressure. The residue was purified by silica gel column chromatography (methanol/ethyl acetate) to give the title compound (58 mg).
MS (ESI+): [M+H]$^+$213.1.

C) pentafluorophenyl 2-(2-((tert-butoxycarbonyl)(2,2,2-trifluoroethyl)amino)pyridin-4-yl)-1,3-oxazole-4-carboxylate To a solution of 2-(2-((tert-butoxycarbonyl)(2,2,2-trifluoroethyl)amino)pyridin-4-yl)oxazole-4-carboxylic acid (315 mg), pentafluorophenol (0.10 mL) and triethylamine (0.23 mL) in DMF (4.1 mL) was added HATU (371 mg), and the mixture was stirred at room temperature for 2 hr. The reaction mixture was poured into saturated aqueous ammonium chloride solution, and the mixture was extracted with ethyl acetate. The extract was washed successively with saturated aqueous sodium hydrogen carbonate solution and saturated brine, and dried over anhydrous magnesium sulfate, and the solvent was evaporated under reduced pressure. The residue was purified by silica gel column chromatography (ethyl acetate/hexane) to give the title compound (450 mg).
MS (ESI+). found. 497.9.

D) tert-butyl (4-(4-((1-methyl-3-(2-oxo-1,3-oxazolidin-3-yl)-1H-pyrazol-4-yl)carbamoyl)-1,3-oxazol-2-yl)pyridin-2-yl)(2,2,2-trifluoroethyl)carbamate A solution of 3-(1-methyl-4-nitro-1H-pyrazol-3-yl)-1,3-oxazolidin-2-one (58 mg), pentafluorophenyl 2-(2-((tert-butoxycarbonyl) (2,2,2-trifluoroethyl)amino)pyridin-4-yl)-1,3-oxazole-4-carboxylate (197 mg), 10% palladium-carbon (29 mg) and triethylamine (76 µL) in methanol (1.4 mL) was stirred overnight at room temperature under hydrogen atmosphere. The reaction mixture was filtered through Celite, and the filtrate was concentrated under reduced pressure. The residue was purified by silica gel column chromatography (ethyl acetate/hexane) to give the title compound (28 mg).
MS (ESI+): [M+H]$^+$552.2.

E) N-(1-methyl-3-(2-oxo-1,3-oxazolidin-3-yl)-1H-pyrazol-4-yl)-2-(2-((2,2,2-trifluoroethyl)amino)pyridin-4-yl)-1,3-oxazole-4-carboxamide The title compound was obtained in the same manner as in Step E of Example 6.

Example 56

N-(3-(3-(2-(benzyloxy)ethyl)-2-oxoimidazolidin-1-yl)-1-methyl-1H-pyrazol-4-yl)-2-(2-((2,2,2-trifluoroethyl)amino)pyridin-4-yl)oxazole-4-carboxamide A) 1-(2-(benzyloxy)ethyl)imidazolidin-2-one To a solution of imidazolidin-2-one (500 mg) in DMF (5.0 mL) was added a sodium hydride 60% dispersion in mineral oil (232 mg) under ice-cooling, and the mixture was stirred under ice-cooling for 20 min. ((2-Bromoethoxy)methyl)benzene (0.83 mL) was added to the reaction mixture, and the mixture was stirred overnight at room temperature. The reaction mixture was diluted with water, and the mixture was extracted with ethyl acetate. The extract was washed with saturated brine, and dried over anhydrous magnesium sulfate, and the solvent was evaporated under reduced pressure. The residue was purified by silica gel column chromatography (methanol/ethyl acetate) to give the title compound (388 mg).
MS (ESI+): [M+H]$^+$220.9.

B) tert-butyl (4-(4-((3-(3-(2-(benzyloxy)ethyl)-2-oxoimidazolidin-1-yl)-1-methyl-1H-pyrazol-4-yl)carbamoyl)-1,3-oxazol-2-yl)pyridin-2-yl)(2,2,2-trifluoroethyl)carbamate The title compound was obtained in the same manner as in Steps B-J of Example 1.
MS (ESI+): [M+H]$^+$685.3.

C) N-(3-(3-(2-(benzyloxy)ethyl)-2-oxoimidazolidin-1-yl)-1-methyl-1H-pyrazol-4-yl)-2-(2-((2,2,2-trifluoroethyl)amino)pyridin-4-yl)-1,3-oxazole-4-carboxamide A solution of tert-butyl (4-(4-((3-(3-(2-(benzyloxy)ethyl)-2-oxoimidazolidin-1-yl)-1-methyl-1H-pyrazol-4-yl)carbamoyl)oxazol-2-yl)pyridin-2-yl) (2,2,2-trifluoroethyl)carbamate (53 mg) in TFA (2.0 mL) was stirred at room temperature for 2 hr. The reaction mixture was concentrated under reduced pressure, and the residue was purified by silica gel column chromatography (NH, ethyl acetate/hexane), and recrystallized from ethyl acetate/hexane to give the title compound (23 mg).

Example 57-I

N-(3-(3-(2-hydroxyethyl)-2-oxoimidazolidin-1-yl)-1-methyl-1H-pyrazol-4-yl)-2-(2-((2,2,2-trifluoroethyl)amino)pyridin-4-yl)-1,3-oxazole-4-carboxamide A solution of tert-butyl (4-(4-((3-(3-(2-(benzyloxy)ethyl)-2-oxoimidazolidin-1-yl)-1-methyl-1H-pyrazol-4-yl)carbamoyl)-1,3-oxazol-2-yl)pyridin-2-yl)(2,2,2-trifluoroethyl)carbamate (400 mg) in TFA (4.0 mL) was stirred at room temperature for 3 hr, and the reaction mixture was concentrated under reduced pressure. A solution of the obtained residue and 20% palladium hydroxide-carbon (80 mg) in acetic acid (10 mL) was stirred at room temperature for 5 hr under hydrogen atmosphere (3 atm). The reaction mixture was filtered through a membrane filter, and the filtrate was concentrated under reduced pressure. The residue was purified by silica gel column chromatography (NH, methanol/ethyl acetate) and then silica gel column chromatography (methanol/ethyl acetate). The obtained solid was washed with a mixed solvent of ethyl acetate/hexane (1:1), and dried under reduced pressure to give the title compound (100 mg).

Example 57-II

N-(3-(3-(2-hydroxyethyl)-2-oxoimidazolidin-1-yl)-1-methyl-1H-pyrazol-4-yl)-2-(2-((2,2,2-trifluoroethyl)amino)pyridin-4-yl)-1,3-oxazole-4-carboxamide A) 1-(2-(benzyloxy)ethyl)-3-(1-methyl-1H-pyrazol-3-yl)imidazolidin-2-one To a solution of 1-methyl-1H-pyrazol-3-amine (10 g) in THF (100 mL) was added dropwise 1-chloro-2-(isocyanato)ethane (8.33 mL) under ice-cooling. The reaction mixture was stirred at room temperature for 30 min, and potassium t-butoxide (12.71 g) was added thereto under ice-cooling. The reaction mixture was stirred overnight at room temperature, and the solvent was evaporated under reduced pressure. To the residue was added water (100 mL), the mixture was stirred for 30 min, and the precipitate was collected by filtration, and washed with water. To a solution of the obtained solid and potassium t-butoxide (9.86 g) in DMF (127 mL) was added ((2-bromoethoxy)methyl)benzene (13.29 mL), and the mixture was stirred at 60° C. for 30 min. The reaction mixture was concentrated under reduced pressure, to the residue was added water, and the mixture was extracted with ethyl acetate. The extract was washed with saturated brine, and dried over anhydrous magnesium sulfate, and the solvent was evaporated under reduced pressure to give the title compound (21.3 g).
MS (ESI+): [M+H]$^+$: 301.3.

B) 1-(2-(benzyloxy)ethyl)-3-(1-methyl-4-nitro-1H-pyrazol-3-yl)imidazolidin-2-one To acetic anhydride (22 mL) was added fuming nitric acid (2.76 mL) under ice-cooling, and the mixture was stirred for 5 min. The obtained solution was added dropwise to a solution of 1-(2-(benzyloxy)ethyl)-3-(1-methyl-1H-pyrazol-3-yl)imidazolidin-2-one (10 g) in acetic anhydride (44 mL) under ice-cooling, and the mixture was stirred at 0° C. for 30 min. The reaction mixture was diluted with water, and the mixture was neutralized with 8M aqueous sodium hydroxide solution, and extracted with ethyl acetate. The extract was washed successively with saturated aqueous sodium hydrogen carbonate solution, water and saturated brine, and dried over anhydrous magnesium sulfate, and the solvent was evaporated under reduced pressure. The residue was purified by silica gel column chromatography (NH, ethyl acetate/hexane) to give the title compound (8.20 g).
MS (ESI+): [M+H]$^+$: 346.3.

C) tert-butyl (3-(3-(2-hydroxyethyl)-2-oxoimidazolidin-1-yl)-1-methyl-1H-pyrazol-4-yl)carbamate Under hydrogen atmosphere, a mixture of 1-(2-(benzyloxy)ethyl)-3-(1-methyl-4-nitro-1H-pyrazol-3-yl)imidazolidin-2-one (8.14 g), 10% palladium-carbon (2.508 g), di-tert-butyl dicarbonate (8.21 mL) and methanol (81.4 mL) was stirred at room temperature for 6 hr, and then at 60° C. for 2.5 hr. The reaction mixture was filtered through Celite, the filtrate was concentrated under reduced pressure, and the residue was purified by silica gel column chromatography (methanol/ethyl acetate) to give the title compound (7.65 g).
MS (ESI+): [M+H]$^+$: 326.2.

D) 1-(4-amino-1-methyl-1H-pyrazol-3-yl)-3-(2-hydroxyethyl)imidazolidin-2-one hydrochloride To tert-butyl (3-(3-(2-hydroxyethyl)-2-oxoimidazolidin-1-yl)-1-methyl-1H-pyrazol-4-yl)carbamate (7.65 g) was added 4M hydrogen chloride ethyl acetate solution (76.5 mL), and the mixture was stirred at room temperature for 30 min. The reaction mixture was concentrated under reduced pressure, to the residue was added methanol (30 mL), and the mixture was stirred for 10 min, and concentrated under reduced pressure to give the title compound (5.21 g).
MS (ESI+): [M+H]$^+$: 226.1.

E) tert-butyl (4-(4-((3-(3-(2-hydroxyethyl)-2-oxoimidazolidin-1-yl)-1-methyl-1H-pyrazol-4-yl)carbamoyl)-1,3-oxazol-2-yl)pyridin-2-yl) (2,2,2-trifluoroethyl)carbamate To a solution of 1-(4-amino-1-methyl-1H-pyrazol-3-yl)-3-(2-hydroxyethyl)imidazolidin-2-one hydrochloride (5.21 g), 2-(2-(((tert-butoxycarbonyl)(2,2,2-trifluoroethyl)amino)pyridin-4-yl)-1,3-oxazole-4-carboxylic acid (6.43 g), N-(3-(dimethylamino)propyl)-N'-ethylcarbodiimide hydrochloride (4.45 g) and 1-hydroxybenzotriazole hydrate (3.56 g) in DMF (64.3 mL) was added triethylamine (5.55 mL), and the mixture was stirred overnight at room temperature. To the reaction mixture were added 1-(4-amino-1-methyl-1H-pyrazol-3-yl)-3-(2-hydroxyethyl)imidazolidin-2-one hydrochloride (435 mg), N-(3-(dimethylamino)propyl)-N'-ethylcarbodiimide hydrochloride (318 mg), 1-hydroxybenzotriazole hydrate (254 mg) and triethylamine (0.463 ml), and the mixture was stirred at room temperature for 3 hr. The reaction was quenched with water, and the mixture was stirred at room temperature for 30 min. Water was added thereto again, and the mixture was stirred at room temperature for 30 min. The precipitate was collected by filtration, washed with water, and dried under reduced pressure to give the title compound (7.56 g).
MS (ESI+): [M+H]$^+$: 595.1.

F) N-(3-(3-(2-hydroxyethyl)-2-oxoimidazolidin-1-yl)-1-methyl-1H-pyrazol-4-yl)-2-(2-((2,2,2-trifluoroethyl)amino)pyridin-4-yl)-1,3-oxazole-4-carboxamide A mixture of tert-butyl (4-(4-((3-(3-(2-hydroxyethyl)-2-oxoimidazolidin-1-yl)-1-methyl-1H-pyrazol-4-yl)carbamoyl)-1,3-oxazol-2-yl)pyridin-2-yl)(2,2,2-trifluoroethyl)carbamate (1.00 g) and 3M hydrogen chloride in a mixed solvent (10 mL) of ethyl acetate/methanol (1:1) was stirred overnight at room temperature. The precipitate was collected by filtration, and the obtained solid was washed with ethyl acetate/methanol (9:1), and dried under reduced pressure. To the obtained solid were added 1N aqueous sodium hydroxide solution (2.39 ml) and water (4 ml), and the mixture was stirred at room temperature for 30 min, and then at 0° C. for 30 min. The precipitate was collected by filtration, washed with water, and dried under reduced pressure to give the title compound (531 mg).
$^1$H NMR (400 MHz, DMSO-d$_6$) δ 3.34-3.38 (2H, m), 3.58-3.68 (4H, m), 3.77 (3H, s), 3.80-3.87 (2H, m), 4.10-4.35 (2H, m), 4.86 (1H, brs), 7.07-7.25 (2H, m), 7.56 (1H, t, J=6.48 Hz), 8.12-8.30 (2H, m), 8.86 (1H, s), 11.26 (1H, s).

Example 58

N-(1-methyl-3-(2-oxoimidazolidin-1-yl)-1H-pyrazol-4-yl)-2-(2-((2,2,2-trifluoroethyl)amino)pyridin-4-yl)-1,3-oxazole-4-carboxamide hydrate A) tert-butyl 3-(1-methyl-1H-pyrazol-3-yl)-2-oxoimidazolidine-1-carboxylate To a solution of 1-methyl-1H-pyrazol-3-amine (500 mg) in THF (10 mL) was added dropwise 1-chloro-2-(isocyanato) ethane (0.442 mL) under ice-cooling. The reaction mixture was stirred at room temperature for 30 min, and potassium t-butoxide (635 mg) was added thereto under ice-cooling. The reaction mixture was stirred at 0° C. for 30 min, and then at room temperature for 1 hr, and di-tert-butyl dicarbonate (1.793 mL), triethylamine (1.076 mL) and 4-dimethylaminopyridine (62.9 mg) were added thereto under ice-cooling. The reaction mixture was stirred overnight at room temperature, saturated aqueous ammonium chloride solution was added thereto under ice-cooling, and the mixture was extracted with ethyl acetate. The extract was washed with water and saturated brine, and dried over anhydrous sodium sulfate, and the solvent was evaporated under reduced pressure. The residue was recrystallized from ethyl acetate/hexane, and washed with diisopropyl ether to give the title compound (910 mg).
$^1$H NMR (300 MHz, CDCl$_3$) δ 1.56 (9H, s), 3.80 (3H, s), 3.90 (4H, s), 6.72 (1H, d, J=2.6 Hz), 7.24 (1H, d, J=2.3 Hz)

B) tert-butyl 3-(1-methyl-4-nitro-1H-pyrazol-3-yl)-2-oxoimidazolidine-1-carboxylate To acetic anhydride (30 mL) was added fuming nitric acid (3.77 mL) under ice-cooling, and the mixture was stirred for 5 min. The obtained solution was added dropwise to a solution of tert-butyl 3-(1-methyl-1H-pyrazol-3-yl)-2-oxoimidazolidine-1-carboxylate (12.1 g) in acetic anhydride (60 mL) under ice-cooling, and the mixture was stirred at 0° C. for 30 min. The reaction mixture was diluted with water, and the mixture was neutralized with 8M aqueous sodium hydroxide solution, and extracted with ethyl acetate. The extract was washed successively with saturated aqueous sodium hydrogen carbonate solution, water and saturated brine, and dried over anhydrous magnesium sulfate, and the solvent was evaporated under reduced pressure. The residue was purified by silica gel column chromatography (NH, ethyl acetate/hexane) to give the title compound (11.3 g).
MS (ESI+). found: 256.1.

C) tert-butyl 3-(4-((tert-butoxycarbonyl)amino)-1-methyl-1H-pyrazol-3-yl)-2-oxoimidazolidine-1-carboxylate A solution of tert-butyl 3-(1-methyl-4-nitro-1H-pyrazol-3-yl)-2-oxoimidazolidine-1-carboxylate (11.1 g), 10% palladium-carbon (3.79 g) and di-tert-butyl dicarbonate (10.76 mL) in methanol (100 mL) was stirred at room temperature for 9 hr under hydrogen atmosphere. The reaction mixture was filtered through Celite, and the filtrate was concentrated under reduced pressure, and the residue was purified by silica gel column chromatography (ethyl acetate/hexane) to give the title compound. (7.61 g).
MS (ESI+). found: 270.1.

D) 1-(4-amino-1-methyl-1H-pyrazol-3-yl)imidazolidin-2-one hydrochloride tert-Butyl 3-(4-((tert-butoxycarbonyl)amino)-1-methyl-1H-pyrazol-3-yl)-2-oxoimidazolidine-1-carboxylate (7.61 g) was dissolved in 2M hydrogen chloride methanol solution (50 mL), and the mixture was stirred at 60° C. for 3 hr. The reaction mixture was ice-cooled, ethyl acetate (50 mL) was added thereto, and the precipitate was collected by filtration, and dried under reduced pressure to give the title compound (4.15 g).

MS (ESI+). found: 182.2.

E) tert-butyl (4-(4-((1-methyl-3-(2-oxoimidazolidin-1-yl)-1H-pyrazol-4-yl)carbamoyl)-1,3-oxazol-2-yl)pyridin-2-yl)(2,2,2-trifluoroethyl)carbamate To a solution of 1-(4-amino-1-methyl-1H-pyrazol-3-yl)-3,3-dimethylpyrrolidin-2-one hydrochloride (3.09 g), 2-(2-((tert-butoxycarbonyl)(2,2,2-trifluoroethyl)amino)pyridin-4-yl)-1,3-oxazole-4-carboxylic acid (5.50 g), N-(3-(dimethylamino)propyl)-N'-ethylcarbodiimide hydrochloride (3.27 g) and 1-hydroxybenzotriazole hydrate (2.39 g) in DMA (40 mL) was added triethylamine (3.96 mL), and the mixture was stirred at room temperature for 1 hr, and then at 50° C. for 3 hr. The reaction mixture was ice-cooled, and water was added thereto. The precipitate was collected by filtration, and washed successively with DMA/water (1/2), water and diisopropyl ether. The obtained solid was suspended in ethanol, and the suspension was stirred at room temperature for 15 min, and the solid was collected by filtration, and washed with ethanol to give the title compound (4.46 g).

MS (ESI+): [M+H]$^+$: 551.1.

F) N-(1-methyl-3-(2-oxoimidazolidin-1-yl)-1H-pyrazol-4-yl)-2-(2-((2,2,2-trifluoroethyl)amino)pyridin-4-yl)-1,3-oxazole-4-carboxamide hydrate tert-Butyl (4-(4-((1-methyl-3-(2-oxoimidazolidin-1-yl)-1H-pyrazol-4-yl)carbamoyl)-1,3-oxazol-2-yl)pyridin-2-yl)(2,2,2-trifluoroethyl)carbamate (4.40 g) was dissolved in a mixture of 4M hydrogen chloride ethyl acetate solution (20 mL) and 2M hydrogen chloride methanol solution (20 mL), and the mixture was stirred at 60° C. for 2 hr. To the reaction mixture was added ethyl acetate (20 mL), the mixture was cooled to room temperature, and the precipitate was collected by filtration. The obtained solid was suspended in ethyl acetate, the suspension was neutralized with saturated aqueous sodium hydrogen carbonate solution, and the insoluble solid was collected by filtration, and recrystallized from dimethyl sulfoxide/water to give a crude product (3.60 g).

$^1$H NMR (400 MHz, DMSO-d$_6$) δ 3.51 (2H, dd, J=9.2, 8.2 Hz), 3.77 (3H, s), 3.89 (2H, dd, J=9.2, 7.2 Hz), 4.18-4.30 (2H, m), 7.14 (1H, dd, J=5.3, 1.3 Hz), 7.19 (1H, dd, J=1.3, 1.0 Hz), 7.37 (1H, s), 7.60 (1H, t, J=6.5 Hz), 8.21 (1H, s), 8.23 (1H, d, J=5.4 Hz), 8.86 (1H, s), 11.35 (1H, s).

The crude product (2.63 g) was purified by HPLC(C18, mobile phase: water/acetonitrile (containing 0.1% TFA), and the solvent of the obtained fraction was evaporated under reduced pressure. The residue was dissolved in dimethyl sulfoxide, saturated aqueous sodium hydrogen carbonate solution was added dropwise thereto, and the mixture was stirred at room temperature for 30 min. The precipitate was collected by filtration, and the obtained crystals were recrystallized from dimethyl sulfoxide/water to give the title compound (2.19 g).

$^1$H NMR (400 MHz, DMSO-d$_6$) δ 3.51 (2H, dd, J=8.6, 7.0 Hz), 3.77 (3H, s), 3.89 (2H, dd, J=9.2, 7.0 Hz), 4.18-4.30 (2H, m), 7.14 (1H, dd, J=5.3, 1.3 Hz), 7.19 (1H, s), 7.37 (1H, s), 7.60 (1H, t, J=6.5 Hz), 8.21 (1H, s), 8.23 (1H, d, J=5.1 Hz), 8.86 (1H, s), 11.35 (1H, s).

Anal. Calcd. C, 46.10; H, 4.09; N, 23.92% (C$_{18}$H$_{17}$N$_8$O$_3$F$_3$.H$_2$O).

Found. C, 46.13; H, 4.08; N, 23.85%.

Example 59

2-(2-((cyclopropylmethyl)amino)pyridin-4-yl)-N-(3-(3-(2-hydroxyethyl)-2-oxoimidazolidin-1-yl)-1-methyl-1H-pyrazol-4-yl)-1,3-oxazole-4-carboxamide

A) tert-butyl (4-bromopyridin-2-yl)(cyclopropylmethyl)carbamate

To a mixture of tert-butyl (4-bromopyridin-2-yl)carbamate (46.1 g), a sodium hydride 60% dispersion in mineral oil (10.13 g), and DMF (338 mL) was added bromomethylcyclopropane (19.64 mL). The reaction mixture was stirred overnight at room temperature, and poured into a mixture of water/ethyl acetate, and the mixture was filtered. The organic layer of the filtrate was separated, washed with water and saturated brine, and dried over anhydrous magnesium sulfate, and the solvent was evaporated under reduced pressure. The residue was purified by silica gel column chromatography (ethyl acetate/hexane) to give the title compound (55.2 g).

MS (ESI+). found: 271.0.

B) tert-butyl (cyclopropylmethyl)(4-(4,4,5,5-tetramethyl-1,3,2-dioxaborolan-2-yl)pyridin-2-yl)carbamate A mixture of tert-butyl (4-bromopyridin-2-yl)(cyclopropylmethyl)carbamate (55.2 g), bis(pinacolato)diboron (55.7 g), dichloro[1,1'-bis(diphenylphosphino)ferrocene]palladium(II) dichloromethane complex (6.89 g), potassium acetate (33.1 g) and DMF (694 mL) was stirred overnight at 80° C. under nitrogen atmosphere, and poured into a mixture of water/ethyl acetate, and the mixture was filtered through Celite. The organic layer of the filtrate was separated, washed with saturated brine, and dried over anhydrous magnesium sulfate, and the solvent was evaporated under reduced pressure. The residue was purified by silica gel column chromatography (ethyl acetate/hexane) to give the title compound (58.4 g).

$^1$H NMR (400 MHz, CDCl$_3$) δ 0.14-0.21 (2H, m), 0.34-0.41 (2H, m), 1.05-1.16 (1H, m), 1.35 (12H, s), 1.51 (9H, s), 3.83 (2H, d, J=7.1 Hz), 7.34 (1H, dd, J=4.9, 0.9 Hz), 7.88 (1H, dd, J=1.0, 0.9 Hz), 8.39 (1H, dd, J=4.9, 1.0 Hz).

C) ethyl 2-(2-((tert-butoxycarbonyl)(cyclopropylmethyl)amino)pyridin-4-yl)-1,3-oxazole-4-carboxylate A mixture of tert-butyl (cyclopropylmethyl)(4-(4,4,5,5-tetramethyl-1,3,2-dioxaborolan-2-yl)pyridin-2-yl)carbamate (48.3 g), ethyl 2-bromo-1,3-oxazole-4-carboxylate (25.8 g), dichloro[1,1'-bis(diphenylphosphino)ferrocene]palladium(II) dichloromethane complex (4.79 g), potassium carbonate (32.4 g) and DME (489 mL)/water (98 mL) was stirred at 80° C. for 4 hr, and poured into water, and the mixture was extracted with ethyl acetate. The extract was washed with saturated brine, and dried over anhydrous magnesium sulfate, and the solvent was evaporated under reduced pressure. The residue was purified by silica gel column chromatography (ethyl acetate/hexane) to give the title compound (33.3 g).
MS (ESI+). found: 332.1.

D) 2-(2-((tert-butoxycarbonyl)(cyclopropylmethyl) amino)pyridin-4-yl)-1,3-oxazole-4-carboxylic acid A solution of ethyl 2-(2-((tert-butoxycarbonyl)(cyclopropylmethyl)amino)pyridin-4-yl)-1,3-oxazole-4-carboxylate (13.88 g) and 2M aqueous sodium hydroxide solution (140 mL) in a mixed solvent of ethanol (140 mL)/THF (140 mL) was stirred at room temperature for 4 hr, and neutralized with 2M hydrochloric acid, and the mixture was extracted with ethyl acetate. The extract was washed with saturated brine, and dried over anhydrous magnesium sulfate, and the solvent was evaporated under reduced pressure to give the title compound (12.32 g).
$^1$H NMR (400 MHz, DMSO-$d_6$) d 0.19-0.29 (2H, m), 0.37-0.47 (2H, m), 1.11-1.23 (1H, m), 1.51 (9H, s), 3.86 (2H, d, J=6.8 Hz), 7.65 (1H, dd, J=5.1, 1.5 Hz), 8.30 (1H, s), 8.56 (1H, dd, J=5.1, 0.7 Hz), 8.98 (1H, s), 13.37 (1H, brs).

E) tert-butyl (cyclopropylmethyl)(4-(4-((3-(3-(2-hydroxyethyl)-2-oxoimidazolidin-1-yl)-1-methyl-1H-pyrazol-4-yl)carbamoyl)-1,3-oxazol-2-yl)pyridin-2-yl)carbamate A solution of 1-(2-(benzyloxy)ethyl)-3-(1-methyl-4-nitro-1H-pyrazol-3-yl)imidazolidin-2-one (500 mg) and 20% palladium hydroxide-carbon (185 mg) in acetic acid (15 mL) was stirred at room temperature for 4 hr under hydrogen atmosphere (4 atm). The reaction mixture was filtered, and the filtrate was concentrated under reduced pressure. A mixture of the residue, 2-(2-((tert-butoxycarbonyl) (cyclopropylmethyl)amino)pyridin-4-yl)-1,3-oxazole-4-carboxylic acid (780 mg), N-(3-(dimethylamino)propyl)-N'-ethylcarbodiimide hydrochloride (277 mg), 1-hydroxybenzotriazole hydrate (222 mg) and triethylamine (0.605 mL) in DMF (6 mL) was stirred overnight at room temperature, and diluted with water, and the mixture was extracted with ethyl acetate. The extract was washed with saturated brine, and dried over magnesium sulfate, and the solvent was evaporated under reduced pressure. The residue was purified by silica gel column chromatography (NH, methanol/ethyl acetate) to give the title compound (208 mg).
MS (ESI+): [M+H]$^+$: 567.2.

F) 2-(2-((cyclopropylmethyl)amino)pyridin-4-yl)-N-(3-(3-(2-hydroxyethyl)-2-oxoimidazolidin-1-yl)-1-methyl-1H-pyrazol-4-yl)-1,3-oxazole-4-carboxamide A mixture of tert-butyl (cyclopropylmethyl)(4-(4-((3-(3-(2-hydroxyethyl)-2-oxoimidazolidin-1-yl)-1-methyl-1H-pyrazol-4-yl)carbamoyl)-1,3-oxazol-2-yl)pyridin-2-yl)carbamate (208 mg), 4M hydrogen chloride ethyl acetate solution (5 mL) and methanol (5 mL) was stirred at 50° C. for 1 hr, the reaction mixture was cooled, and the solvent was evaporated under reduced pressure. The residue was dissolved in water, and the solution was basified with saturated aqueous sodium hydrogen carbonate solution, and extracted with ethyl acetate. The extract was washed with saturated brine, and dried over anhydrous sodium sulfate, and the solvent was evaporated under reduced pressure. The residue was purified by silica gel column chromatography (NH, ethyl acetate/hexane) to give the title compound (130 mg).
$^1$H NMR (400 MHz, DMSO-$d_6$) δ 0.19-0.26 (2H, m), 0.42-0.49 (2H, m), 1.01-1.12 (1H, m), 3.17 (2H, t, J=6.2 Hz), 3.34-3.38 (2H, m), 3.58-3.69 (4H, m), 3.77 (3H, s), 3.80-3.88 (2H, m), 4.86 (1H, t, J=5.5 Hz), 6.98-7.04 (2H, m), 7.06 (1H, s), 8.14 (1H, d, J=5.1 Hz), 8.20 (1H, s), 8.83 (1H, s), 11.26 (1H, s).

Example 60

2-(2-((2,2-difluoroethyl)amino)pyridin-4-yl)-N-(3-(3-(2-hydroxyethyl)-2-oxoimidazolidin-1-yl)-1-methyl-1H-pyrazol-4-yl)-1,3-oxazole-4-carboxamide A) ethyl 2-(2-aminopyridin-4-yl)-1,3-oxazole-4-carboxylate To a mixture of 4-(4,4,5,5-tetramethyl-1,3,2-dioxaborolan-2-yl)pyridin-2-amine (4.28 g), ethyl 2-bromo-1,3-oxazole-4-carboxylate (4.28 g), potassium carbonate (5.38 g) and DME (78 mL)/water (19.45 mL) was added dichloro[1,1'-bis(diphenylphosphino)ferrocene]palladium(II) (0.712 g), and the mixture was stirred at 80° C. for 3 hr under argon atmosphere, poured into water, and extracted with ethyl acetate. The extract was washed with saturated brine, and dried over anhydrous magnesium sulfate, and the solvent was evaporated under reduced pressure. The residue was purified by silica gel column chromatography (NH, ethyl acetate/hexane) to give the title compound (1.42 g).
MS (ESI+): [M+H]$^+$: 234.0.

B) ethyl 2-(2-((tert-butoxycarbonyl)amino)pyridin-4-yl)-1,3-oxazole-4-carboxylate A mixture of ethyl 2-(2-aminopyridin-4-yl)-1,3-oxazole-4-carboxylate (75.9 mg), di-tert-butyl dicarbonate (0.151 mL) and tert-butanol (2.0 mL) was stirred at room temperature for 2 hr, and then at 50° C. for 15 hr, and concentrated under reduced pressure. The residue was purified by silica gel column chromatography (NH, ethyl acetate/hexane), and washed with diisopropyl ether to give the title compound (58.6 mg).
$^1$H NMR (400 MHz, CDCl$_3$) δ 1.42 (3H, t, J=7.2 Hz), 1.55 (9H, s), 4.44 (2H, q, J=7.1 Hz), 7.42 (1H, brs), 7.71 (1H, dd, J=5.3, 1.3 Hz), 8.32 (1H, s), 8.36 (1H, dd, J=5.4, 0.7 Hz), 8.57 (1H, s).

C) ethyl 2-(2-((tert-butoxycarbonyl) (2,2-difluoroethyl)amino)pyridin-4-yl)-1,3-oxazole-4-carboxylate To a solution of ethyl 2-(2-((tert-butoxycarbonyl)amino) pyridin-4-yl)-1,3-oxazole-4-carboxylate (58 mg) in DMF (2 mL) was added a sodium hydride 60% dispersion in mineral oil (9.05 mg), and then 2,2-difluoroethyl trifluoromethanesulfonate (74.5 mg) was added thereto. The reaction mixture was stirred at room temperature for 30 min, and diluted with ethyl acetate, and water was added thereto. The organic layer was separated, washed with water and saturated brine, and dried over anhydrous sodium sulfate, and the solvent was evaporated under reduced pressure. The residue was purified by silica gel column chromatography (ethyl acetate/hexane) to give the title compound (69.4 mg).
$^1$H NMR (400 MHz, CDCl$_3$) δ1.42 (3H, t, J=7.1 Hz), 1.56 (9H, s), 4.33-4.49 (4H, m), 5.99-6.34 (1H, m), 7.75 (1H, dd, J=5.1, 1.5 Hz), 8.33 (1H, s), 8.41 (1H, s), 8.47 (1H, d, J=5.1 Hz).

D) 2-(2-((tert-butoxycarbonyl) (2,2-difluoroethyl) amino)pyridin-4-yl)-1,3-oxazole-4-carboxylic acid To a solution of ethyl 2-(2-((tert-butoxycarbonyl)(2,2-difluoroethyl)amino)pyridin-4-yl)-1,3-oxazole-4-carboxylate (69.4 mg) in methanol (5 mL) was added 1M aqueous sodium hydroxide solution (1.5 mL), and the mixture was stirred for 45 min. The reaction mixture was neutralized with 1M hydrochloric acid, and the methanol was evaporated under reduced pressure. The residue was extracted with ethyl acetate, the extract was dried over anhydrous magnesium sulfate, and the solvent was evaporated under reduced pressure to give the title compound (57.1 mg).

$^1$H NMR (400 MHz, DMSO-$d_6$) δ1.51 (9H, s), 4.40 (2H, td, J=14.2, 4.3 Hz), 6.15-6.50 (1H, m), 7.70 (1H, dd, J=5.1, 1.2 Hz), 8.29 (1H, s), 8.58 (1H, dd, J=5.1, 0.7 Hz), 8.97 (1H, s), 13.38 (1H, brs).

E) tert-butyl (4-(4-((3-(3-(2-(benzyloxy)ethyl)-2-oxoimidazolidin-1-yl)-1-methyl-1H-pyrazol-4-yl)carbamoyl)-1,3-oxazol-2-yl)pyridin-2-yl)(2,2-difluoroethyl)carbamate To a solution of 1-(2-(benzyloxy)ethyl)-3-(1-methyl-4-nitro-1H-pyrazol-3-yl)imidazolidin-2-one (74 mg) in a mixed solvent of THF (3 mL)/methanol (3 mL) was added 10% palladium-carbon (22.8 mg), and the mixture was stirred at room temperature for 3 hr under hydrogen atmosphere. The reaction mixture was filtered, and the filtrate was concentrated under reduced pressure. The residue and 2-(2-((tert-butoxycarbonyl) (2,2-difluoroethyl)amino)pyridin-4-yl)-1,3-oxazole-4-carboxylic acid (30.9 mg) were dissolved in DMF (3 mL), and HATU (63.6 mg) was added thereto. The mixture was stirred at room temperature for 22 hr, and diluted with ethyl acetate, and water was added thereto. The organic layer was separated, washed with saturated brine, and dried over anhydrous sodium sulfate, and the solvent was evaporated under reduced pressure. The residue was purified by silica gel column chromatography (NH, ethyl acetate/hexane) to give the title compound (52.2 mg).

$^1$H NMR (400 MHz, CDCl$_3$) δ1.55 (9H, s), 3.55-3.65 (2H, m), 3.66-3.77 (4H, m), 3.81 (3H, s), 3.89-4.00 (2H, m), 4.39 (2H, td, J=13.3, 4.5 Hz), 4.55 (2H, s), 5.97-6.36 (1H, m), 7.21-7.36 (5H, m), 7.73 (1H, dd, J=5.1, 1.2 Hz), 8.19 (1H, s), 8.31 (1H, s), 8.35 (1H, s), 8.43 (1H, d, J=5.1 Hz), 11.60 (1H, s).

F) 2-(2-((2,2-difluoroethyl)amino)pyridin-4-yl)-N-(3-(3-(2-hydroxyethyl)-2-oxoimidazolidin-1-yl)-1-methyl-1H-pyrazol-4-yl)-1,3-oxazole-4-carboxamide A mixture of tert-butyl (4-(4-((3-(3-(2-(benzyloxy)ethyl)-2-oxoimidazolidin-1-yl)-1-methyl-1H-pyrazol-4-yl)carbamoyl)-1,3-oxazol-2-yl)pyridin-2-yl) (2,2-difluoroethyl)carbamate (52.2 mg) and TFA (3 mL) was stirred at room temperature for 3 hr, and concentrated. The residue was dissolved in acetic acid (5 ml), 20% palladium hydroxide-carbon (3.0 mg) was added thereto, and the mixture was stirred at room temperature for 2 hr under hydrogen atmosphere (3 atm), and filtered. The filtrate was concentrated under reduced pressure, and the residue was purified by silica gel column chromatography (NH, ethyl acetate/hexane), and washed with diisopropyl ether to give the title compound (17.9 mg).

$^1$H NMR (400 MHz, CDCl$_3$) δ 3.45-3.52 (2H, m), 3.65-3.74 (2H, m), 3.78-3.93 (5H, m), 3.93-4.00 (2H, m), 4.01-4.10 (2H, m), 4.86 (1H, t, J=5.7 Hz), 5.79-6.15 (2H, m), 7.09 (1H, dd, J=5.4, 1.2 Hz), 7.45 (1H, s), 8.18-8.23 (2H, m), 8.26 (1H, s), 11.47 (1H, s).

Example 61

N-(3-(4-((dimethylamino)methyl)-3,3-dimethyl-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide (optical isomer)

Racemic N-(3-(4-((dimethylamino)methyl)-3,3-dimethyl-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide (66 mg) was resolved by SFC (column: CHIRALPAK AD-H (trade name), 20 mmID×250 mL, manufactured by Daicel Chemical Industries, mobile phase: carbon dioxide/ethanol/diethylamine=860/140/1) to give the title compound (22 mg) having a shorter retention time.

The retention time was 4.60 min when the title compound was analyzed using SFC for analysis (column: CHIRALPAK AD (trade name), 4.6 mmID×150 mL, manufactured by Daicel Chemical Industries, mobile phase: carbon dioxide/ethanol/diethylamine=860/140/1, flow rate: 4 mL/min).

$^1$H NMR (400 MHz, CDCl$_3$) δ 1.16 (3H, s), 1.38 (3H, s), 2.26 (6H, s), 2.34-2.50 (3H, m), 3.59-3.67 (1H, m), 3.82 (3H, s), 3.98-4.06 (1H, m), 4.12-4.23 (2H, m), 4.84 (1H, t, J=6.7 Hz), 7.22 (1H, s), 7.34 (1H, dd, J=5.4, 1.2 Hz), 8.19 (1H, s), 8.26 (1H, d, J=5.1 Hz), 8.30 (1H, s), 11.30 (1H, s).

Example 62

N-(3-(4-((dimethylamino)methyl)-3,3-dimethyl-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide (optical isomer)

Racemic N-(3-(4-((dimethylamino)methyl)-3,3-dimethyl-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide (66 mg) was resolved by SFC (column: CHIRALPAK AD-H (trade name), 20 mmID×250 mL, manufactured by Daicel Chemical Industries, mobile phase: carbon dioxide/ethanol/diethylamine=860/140/1) to give the title compound (20 mg) having a longer retention time.

The retention time was 5.84 min when the title compound was analyzed using SFC for analysis (column: CHIRALPAK AD (trade name), 4.6 mmID×150 mL, manufactured by Daicel Chemical Industries, mobile phase: carbon dioxide/ethanol/diethylamine=860/140/1, flow rate: 4 mL/min).

$^1$H NMR (400 MHz, CDCl$_3$) δ 1.16 (3H, s), 1.38 (3H, s), 2.26 (6H, s), 2.34-2.50 (3H, m), 3.59-3.67 (1H, m), 3.82 (3H, s), 3.98-4.06 (1H, m), 4.12-4.23 (2H, m), 4.84 (1H, t, J=6.7 Hz), 7.22 (1H, s), 7.34 (1H, dd, J=5.4, 1.2 Hz), 8.19 (1H, s), 8.26 (1H, d, J=5.1 Hz), 8.30 (1H, s), 11.30 (1H, s).

Example 77

N-(1-methyl-3-((3S)-3-methyl-2-oxopyrrolidin-1-yl)-1H-pyrazol-4-yl)-2-(2-((2,2,2-trifluoroethyl)amino)pyridin-4-yl)-1,3-oxazole-4-carboxamide Racemic N-(1-methyl-3-(3-methyl-2-oxopyrrolidin-1-yl)-1H-pyrazol-4-yl)-2-(2-((2,2,2-trifluoroethyl)amino)pyridin-4-yl)-1,3-oxazole-4-carboxamide (399 mg) was resolved by HPLC (column: CHIRALPAK IA (trade name), 50 mmID×500 mL, manufactured by Daicel Chemical Industries, mobile phase: hexane/ethanol=500/500), and the compound (186.7 mg) having a shorter retention time was recrystallized from THF/diisopropyl ether to give the title compound (183.7 mg).

The retention time was 14.56 min when the title compound was analyzed using HPLC for analysis (column: CHIRALPAK IA (trade name), 4.6 mmID×250 mL, manufactured by Daicel Chemical Industries, mobile phase: hexane/ethanol=5/5, flow rate: 0.5 mL/min).

$^1$H NMR (400 MHz, CDCl$_3$) δ 1.38 (3H, d, J=7.1 Hz), 1.89 (1H, dq, J=12.6, 8.7 Hz), 2.40-2.50 (1H, m), 2.74-2.85 (1H, m), 3.83 (3H, s), 3.85-3.93 (1H, m), 3.94-4.02 (1H, m), 4.12-4.24 (2H, m), 4.84 (1H, t, J=6.6 Hz), 7.22 (1H, s), 7.35 (1H, dd, J=5.3, 1.3 Hz), 8.21 (1H, s), 8.27 (1H, d, J=4.6 Hz), 8.30 (1H, s), 11.35 (1H, s).

Example compounds produced according to the above-mentioned production methods or Examples or a method analogous thereto are shown in the following Tables 1-1 to 1-32. MS in the tables means actual measured value.

TABLE 1-1

| Example Number | IUPAC name | Structure | Salt | MS |
|---|---|---|---|---|
| 1 | N-(3-((4S)-4-hydroxy-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide | 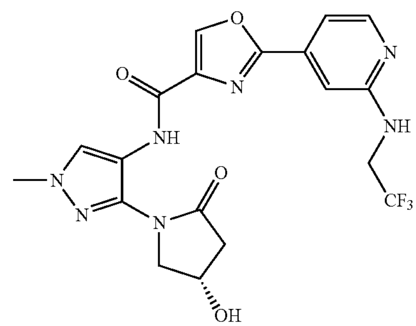 [SMILES: Cn1cc(NC(=O)c2coc(-c3ccnc(NCC(F)(F)F)c3)n2)c(N2C[C@@H](O)CC2=O)n1] | | 466.3 |
| 2 | N-(1-methyl-3-(3-methyl-2-oxopyrrolidin-1-yl)-1H-pyrazol-4-yl)-2-(2-((2,2,2-trifluoroethyl)amino)pyridin-4-yl)-1,3-oxazole-4-carboxamide | 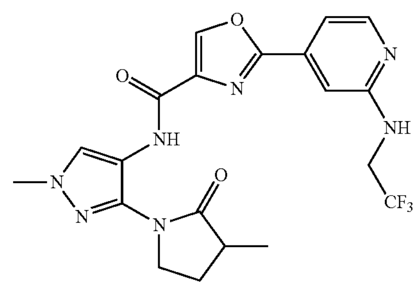 [SMILES: CC1CCN(c2nn(C)cc2NC(=O)c2coc(-c3ccnc(NCC(F)(F)F)c3)n2)C1=O] | | 464.2 |
| 3 | N-(3-(4-((dimethylamino)methyl)-2-oxopyrrolidin-1-yl)-1-methyl-1H-pyrazol-4-yl)-2-(2-((2,2-trifluoroethyl)amino)pyridin-4-yl)-1,3-oxazole-4-carboxamide | 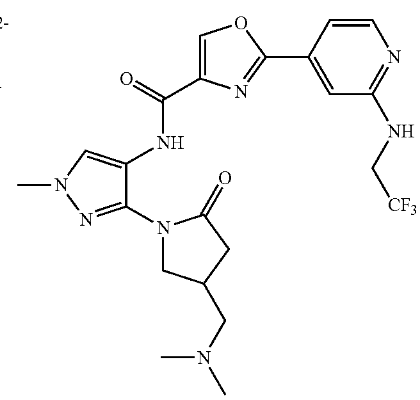 | | 507.0 |
| 4 | N-(3-(4-((dimethylamino)methyl)-3,3-dimethyl-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide | 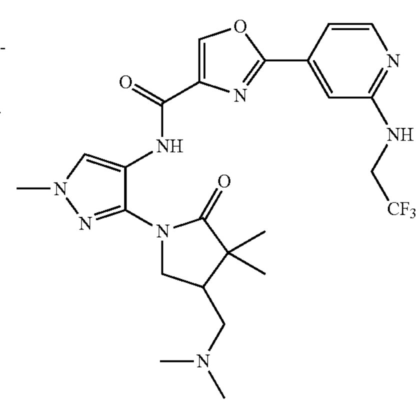 | | 535.2 |

TABLE 1-2

| | | | |
|---|---|---|---|
| 5 | N-(1-methyl-3-((4S)-4-(methylamino)-2-oxopyrrolidin-1-yl)-1H-pyrazol-4-yl)-2-(2-((2,2,2-trifluoroethyl)amino)pyridin-4-yl)-1,3-oxazole-4-carboxamide | | 479.4 |
| 6 | N-(1-methyl-3-(2-oxopyrrolidin-1-yl)-1H-pyrazol-4-yl)-2-(2-((2,2,2-trifluoroethyl)amino)pyridin-4-yl)-1,3-oxazole-4-carboxamide | | 450.1 |
| 7 | N-(3-(4-(hydroxymethyl)-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide | | 480.1 |
| 8 | N-(3-(3-cyano-2-oxopyrrolidin-1-yl)-1-methyl-1H-pyrazol-4-yl)-2-methyl-1,3-oxazole-4-carboxamide | | 315.1 |
| 9 | N-(3-((4S)-4-hydroxy-2-oxopyrrolidin-1-yl)-1-methyl-1H-pyrazol-4-yl)-2-methyl-1,3-oxazole-4-carboxamide | | 306.1 |

TABLE 1-2-continued

| | | | | |
|---|---|---|---|---|
| 11 | N-(3-(3-cyano-3-ethyl-2-oxopyrrolidin-1-yl)-1-methyl-1H-pyrazol-4-yl)-2-methyl-1,3-oxazole-4-carboxamide | 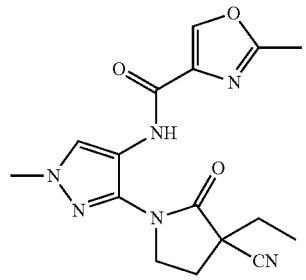 | | 343.0 |
| 12 | N-(3-(4-((dimethylamino)methyl)-2-oxopyrrolidin-1-yl)-1-methyl-1H-pyrazol-4-yl)-2-methyl-1,3-oxazole-4-carboxamide | 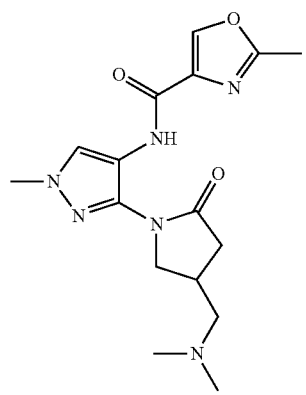 | | 347.0 |
| 13 | N-(3-(3,3-dimethyl-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide | 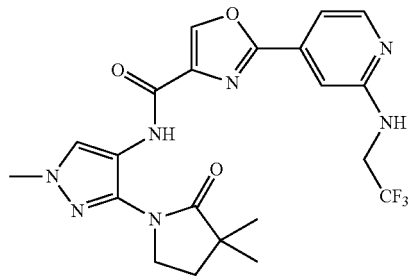 [SMILES: Cn1cc(NC(=O)c2coc(-c3ccnc(NCC(F)(F)F)c3)n2)c(N2CCC(C)(C)C2=O)n1] | HCl | 478.2 |
| 14 | N-(3-(4-((dimethylamino)methyl)-2-oxopyrrolidin-1-yl)-1-methyl-1H-pyrazol-4-yl)-2-((2,2,2-trifluoroethyl)amino)pyridin-4-yl)-1,3-oxazole-4-carboxamide (optical isomer) | 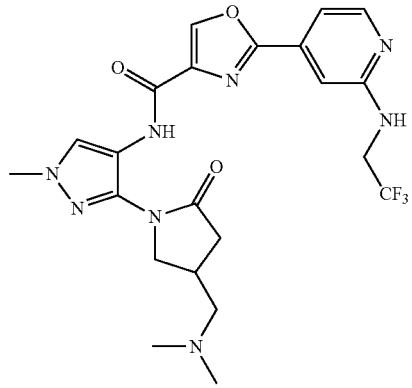 [SMILES: CN(C)CC1CC(=O)N(c2nn(C)cc2NC(=O)c2coc(-c3ccnc(NCC(F)(F)F)c3)n2)C1] | | 507.0 |

TABLE 1-3

| | | | | |
|---|---|---|---|---|
| 15 | N-(3-((4S)-4-methoxy-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide | | | 480.2 |
| 16 | N-(3-((4S)-4-(dimethylamino)-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide | | | 493.2 |
| 17 | N-(3-((5S)-4-hydroxy-3,3,5-trimethyl-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide | | CF3COOH | 508.2 |
| 18 | N-(3-(4-((dimethylamino)methyl)-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide (optical isomer) | | | 507.0 |

TABLE 1-3-continued

| 19 | N-(3-(3,3-dimethyl-2-oxopyrrolidin-1-yl)-1-methyl-1H-pyrazol-4-yl)-2-(morpholin-4-yl)-1,3-oxazole-4-carboxamide | | | 389.2 |
|---|---|---|---|---|
| 20 | N-(3-(3,3-dimethyl-2-oxopyrrolidin-1-yl)-1-methyl-1H-pyrazol-4-yl)-2-phenyl-1,3-oxazole-4-carboxamide | | | 380.2 |
| 22 | 2-(2,2-dimethylmorpholin-4-yl)-N-(3-(3,3-dimethyl-2-oxopyrrolidin-1-yl)-1-methyl-1H-pyrazol-4-yl)-1,3-oxazole-4-carboxamide | | | 417.2 |
| 23 | N-(3-(4-hydroxy-3,3-dimethyl-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide | | HCl | 494.2 |
| 24 | N-(3-(3,3-dimethyl-2-oxopyrrolidin-1-yl)-1-methyl-1H-pyrazol-4-yl)-2-(2-thienyl)-1,3-oxazole-4-carboxamide | | | 380.2 |

TABLE 1-4

| 25 | N-(3-(3,3-dimethyl-2-oxopyrrolidin-1-yl)-1-methyl-1H-pyrazol-4-yl)-2-(3-fluorophenyl)-1,3-oxazole-4-carboxamide | 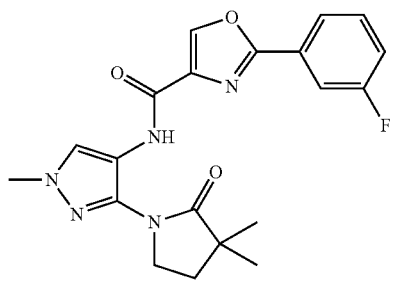 [SMILES: Cn1cc(NC(=O)c2coc(-c3cccc(F)c3)n2)c(N2CCC(C)(C)C2=O)n1] | 398.0 |
| --- | --- | --- | --- |
| 27 | N-(3-((4S)-4-amino-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide | 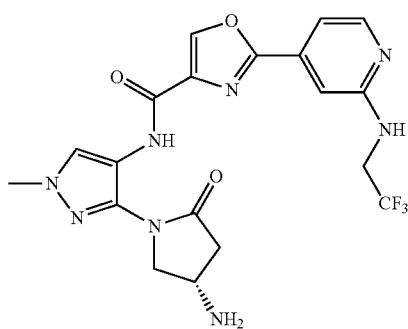 [SMILES: Cn1cc(NC(=O)c2coc(-c3ccnc(NCC(F)(F)F)c3)n2)c(N2C[C@@H](N)CC2=O)n1] | 465.3 |
| 28 | N-(3-((4S)-4-acetamido-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide | 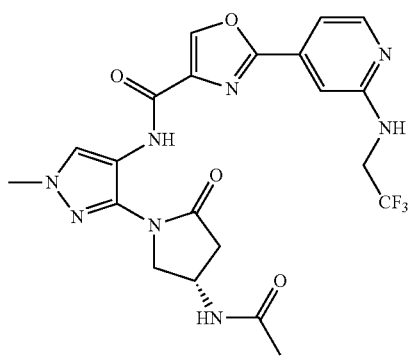 [SMILES: CC(=O)N[C@H]1CC(=O)N(c2nn(C)cc2NC(=O)c2coc(-c3ccnc(NCC(F)(F)F)c3)n2)C1] | 507.4 |
| 29 | N-(1-methyl-3-((4S)-4-((methylsulfonyl)amino)-2-oxopyrrolidin-1-yl)-1H-pyrazol-4-yl)-2-(2-((2,2,2-trifluoroethyl)amino)pyridin-4-yl)-1,3-oxazole-4-carboxamide | 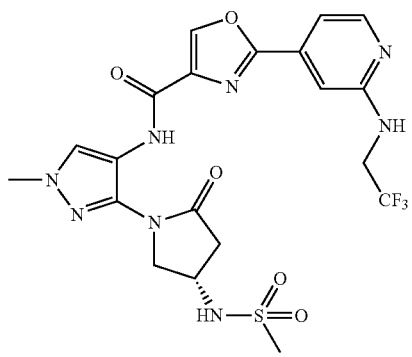 [SMILES: Cn1cc(NC(=O)c2coc(-c3ccnc(NCC(F)(F)F)c3)n2)c(N2C[C@@H](NS(C)(=O)=O)CC2=O)n1] | 543.4 |

TABLE 1-4-continued

| | | | |
|---|---|---|---|
| 30 | N-(3-((4S)-4-(diethylamino)-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide | 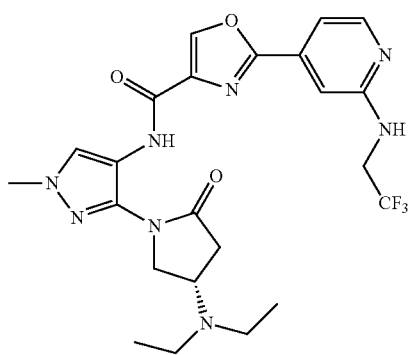 [SMILES: CCN(CC)[C@H]1CC(=O)N(c2nn(C)cc2NC(=O)c2coc(-c3ccnc(NCC(F)(F)F)c3)n2)C1] | 521.4 |
| 31 | N-(1-methyl-3-((4S)-4-(morpholin-4-yl)-2-oxopyrrolidin-1-yl)-1H-pyrazol-4-yl)-2-(2-((2,2,2-trifluoroethyl)amino)pyridin-4-yl)-1,3-oxazole-4-carboxamide | 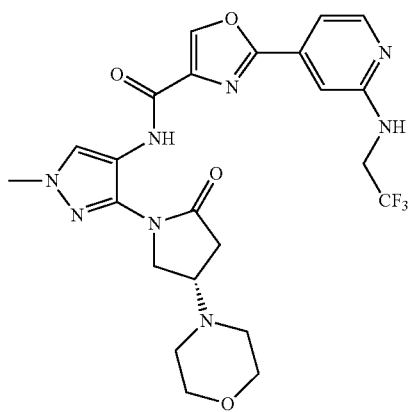 [SMILES: Cn1cc(NC(=O)c2coc(-c3ccnc(NCC(F)(F)F)c3)n2)c(N2C[C@@H](N3CCOCC3)CC2=O)n1] | 535.5 |
| 32 | N-(3-((4S)-4-(ethylamino)-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide | 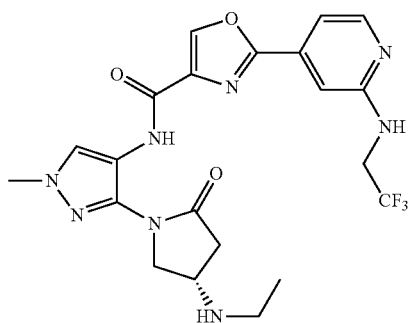 [SMILES: CCN[C@H]1CC(=O)N(c2nn(C)cc2NC(=O)c2coc(-c3ccnc(NCC(F)(F)F)c3)n2)C1] | 493.4 |
| 33 | N-(3-(4-amino-3,3-dimethyl-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide | 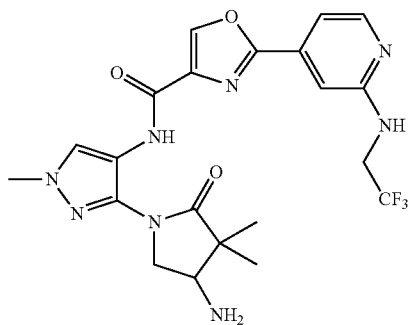 [SMILES: Cn1cc(NC(=O)c2coc(-c3ccnc(NCC(F)(F)F)c3)n2)c(N2CC(N)C(C)(C)C2=O)n1] | CF3COOH 493.1 |

TABLE 1-4-continued

| | | | |
|---|---|---|---|
| 34 | N-(3-(3,3-dimethyl-2-oxopyrrolidin-1-yl)-1-methyl-1H-pyrazol-4-yl)-3-(1,3-thiazol-2-ylsulfonyl)benzamide | 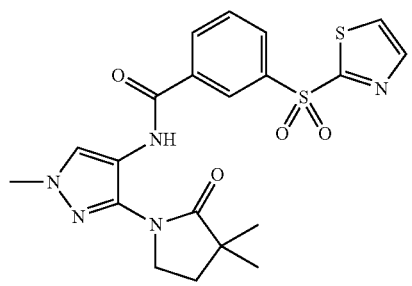 [SMILES: Cn1cc(NC(=O)c2cccc(S(=O)(=O)c3nccs3)c2)c(N2CCC(C)(C)C2=O)n1] | 460.3 |

TABLE 1-5

| | | | |
|---|---|---|---|
| 35 | 6-(cyclopentylsulfonyl)-N-(3-(3,3-dimethyl-2-oxopyrrolidin-1-yl)-1-methyl-1H-pyrazol-4-yl)pyridine-2-carboxamide | 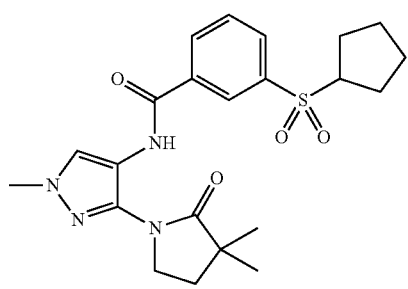 [SMILES: Cn1cc(NC(=O)c2cccc(S(=O)(=O)C3CCCC3)c2)c(N2CCC(C)(C)C2=O)n1] | 446.3 |
| 36 | N-(3-(3,3-dimethyl-2-oxopyrrolidin-1-yl)-1-methyl-1H-pyrazol-4-yl)-6-methylpyridine-2-carboxamide | 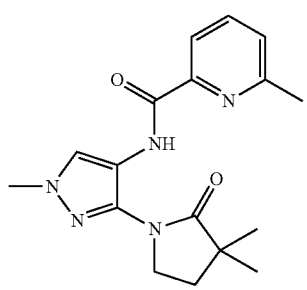 | 328.3 |
| 37 | N-(3-(3,3-dimethyl-2-oxopyrrolidin-1-yl)-1-methyl-1H-pyrazol-4-yl)-5-methylnicotinamide | 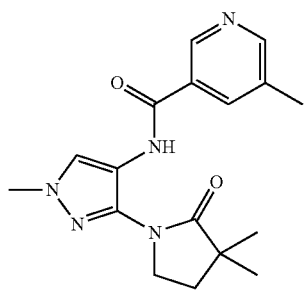 | 328.3 |
| 38 | N-(3-(3,3-dimethyl-2-oxopyrrolidin-1-yl)-1-methyl-1H-pyrazol-4-yl)-5-methylthiophene-3-carboxamide | 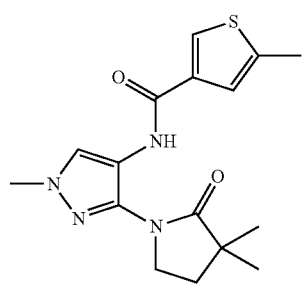 | 333.3 |

TABLE 1-5-continued

| | | | |
|---|---|---|---|
| 39 | N-(3-(3,3-dimethyl-2-oxopyrrolidin-1-yl)-1-methyl-1H-pyrazol-4-yl)-1-methyl-1H-pyrazole-3-carboxamide | 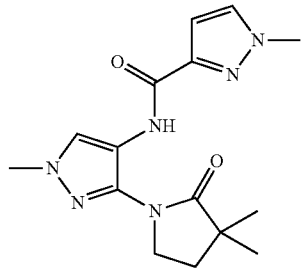 | 317.3 |
| 40 | 1-(difluoromethyl)-N-(3-(3,3-dimethyl-2-oxopyrrolidin-1-yl)-1-methyl-1H-pyrazol-4-yl)-1H-pyrazole-3-carboxamide | 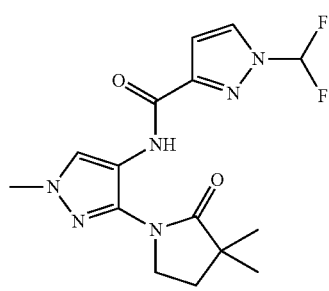 [SMILES: Cn1cc(NC(=O)c2ccn(C(F)F)n2)c(N2CCC(C)(C)C2=O)n1] | 353.3 |
| 41 | N-(3-(3,3-dimethyl-2-oxopyrrolidin-1-yl)-1-methyl-1H-pyrazol-4-yl)-2-(pyridin-4-yl)-1,3-thiazole-4-carboxamide | 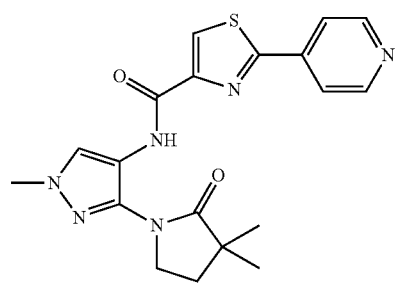 [SMILES: Cn1cc(NC(=O)c2csc(-c3ccncc3)n2)c(N2CCC(C)(C)C2=O)n1] | 397.3 |
| 42 | 3-(cyclopentylsulfonyl)-N-(3-(3,3-dimethyl-2-oxopyrrolidin-1-yl)-1-methyl-1H-pyrazol-4-yl)benzamide | 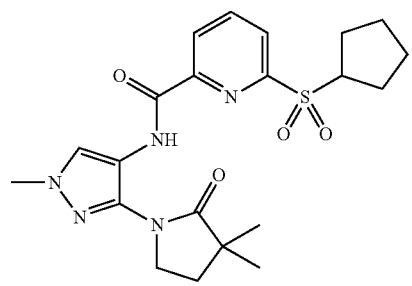 [SMILES: Cn1cc(NC(=O)c2cccc(S(=O)(=O)C3CCCC3)n2)c(N2CCC(C)(C)C2=O)n1] | 445.4 |
| 43 | N-(3-(3,3-dimethyl-2-oxopyrrolidin-1-yl)-1-methyl-1H-pyrazol-4-yl)imidazo[1,5-a]pyridine-7-carboxamide | 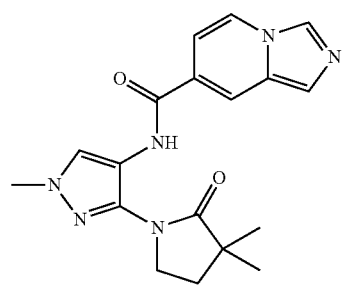 [SMILES: Cn1cc(NC(=O)c2ccn3cncc3c2)c(N2CCC(C)(C)C2=O)n1] | 353.3 |

TABLE 1-5-continued

| 44 | N-(3-(3,3-dimethyl-2-oxopyrrolidin-1-yl)-1-methyl-1H-pyrazol-4-yl)imidazo[1,2-b]pyridazine-3-carboxamide | 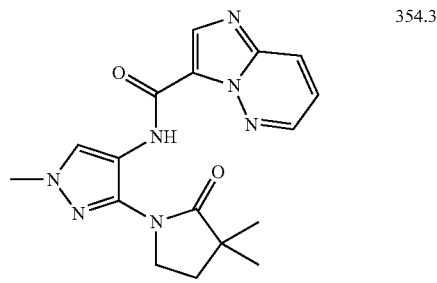 | 354.3 |

TABLE 1-6

| 45 | N-(3-(3,3-dimethyl-2-oxopyrrolidin-1-yl)-1-methyl-1H-pyrazol-4-yl)pyrazolo[1,5-a]pyrimidine-3-carboxamide | 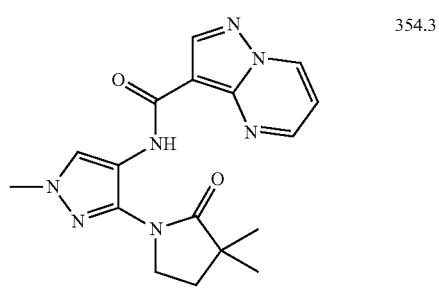 | 354.3 |
| 46 | N-(3-(3,3-dimethyl-2-oxopyrrolidin-1-yl)-1-methyl-1H-pyrazol-4-yl)-3-methylbenzamide | 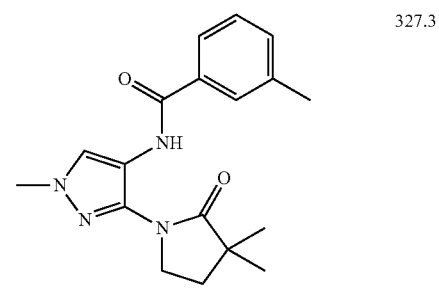 | 327.3 |
| 47 | N-(1-methyl-3-((3R)-3-methyl-2-oxopyrrolidin-1-yl)-1H-pyrazol-4-yl)-2-(2-((2,2,2-trifluoroethyl)amino)pyridin-4-yl)-1,3-oxazole-4-carboxamide | 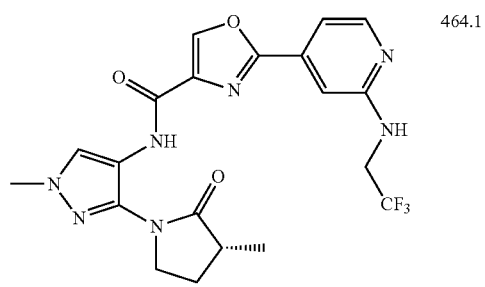 | 464.1 |
| 48 | N-(1-methyl-3-(3-methyl-2-oxoimidazolidin-1-yl)-1H-pyrazol-4-yl)-2-(2-((2,2,2-trifluoroethyl)amino)pyridin-4-yl)-1,3-oxazole-4-carboxamide | 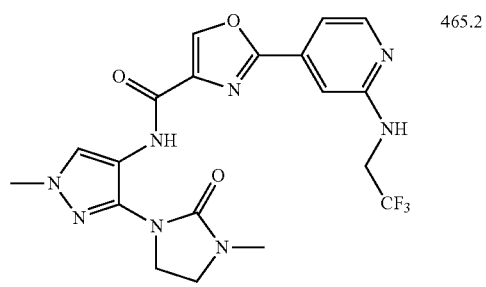 | 465.2 |

TABLE 1-6-continued

| 49 | N-(3-(3,3-dimethyl-4-((methylamino)methyl)-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide | | 521.2 |
| --- | --- | --- | --- |
| 50 | N-(3-(4-((diethylamino)methyl)-3,3-dimethyl-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide | | 563.3 |
| 51 | N-(3-(3,3-dimethyl-2-oxopyrrolidin-1-yl)-1-methyl-1H-pyrazol-4-yl)-2-(morpholin-4-yl)-1,3-thiazole-4-carboxamide | | 405.0 |
| 52 | 6-acetyl-N-(3-(3,3-dimethyl-2-oxopyrrolidin-1-yl)-1-methyl-1H-pyrazol-4-yl)pyridine-2-carboxamide | | 356.0 |
| 53 | N-(3-(3,3-dimethyl-2-oxopyrrolidin-1-yl)-1-methyl-1H-pyrazol-4-yl)-6-(1-hydroxyethyl)pyridine-2-carboxamide | | 358.0 |

TABLE 1-6-continued

| 54 | N-(3-(3,3-dimethyl-2-oxopyrrolidin-1-yl)-1-methyl-1H-pyrazol-4-yl)-6-(2-hydroxypropan-2-yl)pyridine-2-carboxamide | 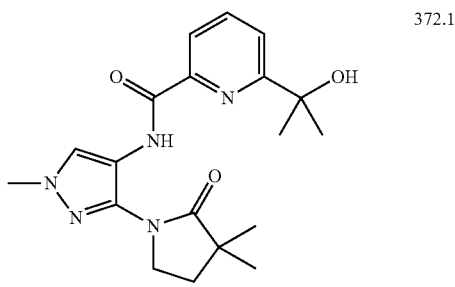 | 372.1 |

TABLE 1-7

| 55 | N-(1-methyl-3-(2-oxo-1,3-oxazolidin-3-yl)-1H-pyrazol-4-yl)-2-(2-((2,2,2-trifluoroethyl)amino)pyridin-4-yl)-1,3-oxazole-4-carboxamide | 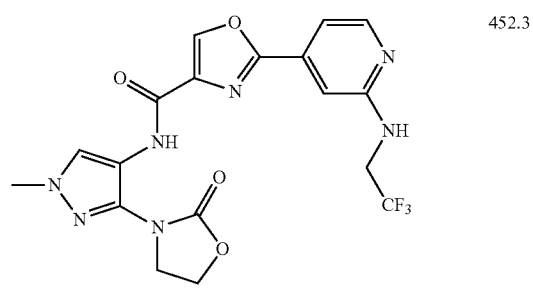 | 452.3 |
| 56 | N-(3-(3-(2-(benzyloxy)ethyl)-2-oxoimidazolidin-1-yl)-1-methyl-1H-pyrazol-4-yl)-2-(2-((2,2,2-trifluoroethyl)amino)pyridin-4-yl)-1,3-oxazole-4-carboxamide | 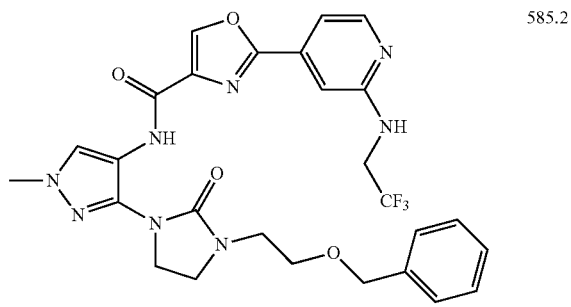 | 585.2 |
| 57 | N-(3-(3-(2-hydroxyethyl)-2-oxoimidazolidin-1-yl)-1-methyl-1H-pyrazol-4-yl)-2-(2-((2,2,2-trifluoroethyl)amino)pyridin-4-yl)-1,3-oxazole-4-carboxamide | 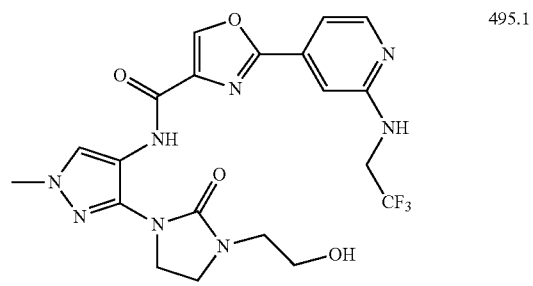 | 495.1 |

TABLE 1-8

| Example Number | IUPAC name | Structure | Salt | MS |
|---|---|---|---|---|
| 58 | N-(1-methyl-3-(2-oxoimidazolidin-1-yl)-1H-pyrazol-4-yl)-2-(2-((2,2,2-trifluoroethyl)amino)pyridin-4-yl)-1,3-oxazole-4-carboxamide | 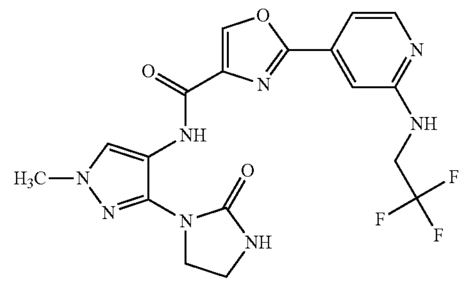 [SMILES: Cn1cc(NC(=O)c2coc(-c3ccnc(NCC(F)(F)F)c3)n2)c(N2CCNC2=O)n1] | | 451.0 |
| 59 | 2-(2-((cyclopropylmethyl)amino)pyridin-4-yl)-N-(3-(3-(2-hydroxyethyl)-2-oxoimidazolidin-1-yl)-1-methyl-1H-pyrazol-4-yl)-1,3-oxazole-4-carboxamide | 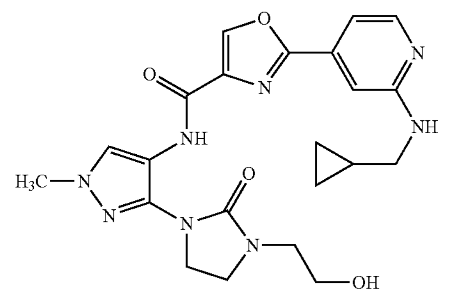 [SMILES: Cn1cc(NC(=O)c2coc(-c3ccnc(NCC4CC4)c3)n2)c(N2CCN(CCO)C2=O)n1] | | 467.1 |
| 60 | 2-(2-((2,2-difluoroethyl)amino)pyridin-4-yl)-N-(3-(3-(2-hydroxyethyl)-2-oxoimidazolidin-1-yl)-1-methyl-1H-pyrazol-4-yl)-1,3-oxazole-4-carboxamide | 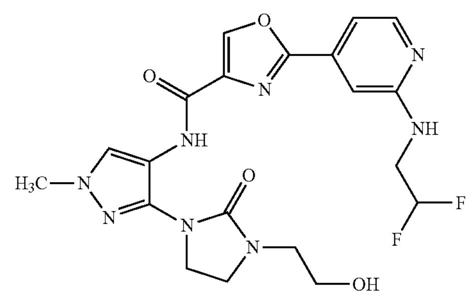 [SMILES: Cn1cc(NC(=O)c2coc(-c3ccnc(NCC(F)F)c3)n2)c(N2CCN(CCO)C2=O)n1] | | 477.2 |
| 61 | N-(3-(4-((dimethylamino)methyl)-3,3-dimethyl-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide (optical isomer) | 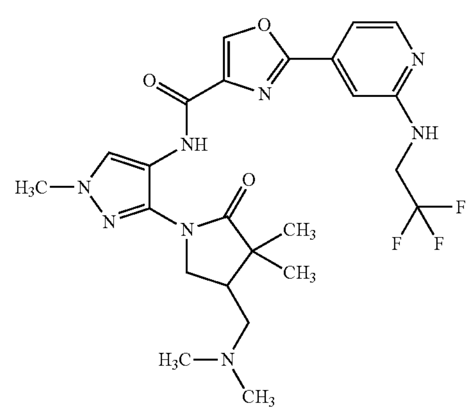 [SMILES: CN(C)CC1CN(c2nn(C)cc2NC(=O)c2coc(-c3ccnc(NCC(F)(F)F)c3)n2)C(=O)C1(C)C] | | 535.1 |

TABLE 1-8-continued

| Example Number | IUPAC name | Structure | Salt | MS |
|---|---|---|---|---|
| 62 | N-(3-(4-((dimethylamino)methyl)-3,3-dimethyl-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide (optical isomer) | 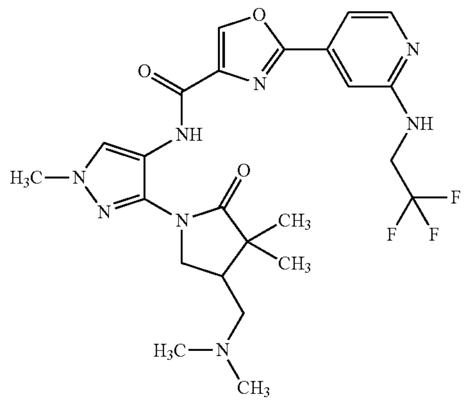 [SMILES: CN(C)CC1CN(c2nn(C)cc2NC(=O)c2coc(-c3ccnc(NCC(F)(F)F)c3)n2)C(=O)C1(C)C] | | 535.1 |

TABLE 1-9

| Example Number | IUPAC name | Structure | Salt | MS |
|---|---|---|---|---|
| 63 | 2-(3,6-dihydro-2H-pyran-4-yl)-N-(3-(3,3-dimethyl-2-oxopyrrolidin-1-yl)-1-methyl-1H-pyrazol-4-yl)-1,3-thiazole-4-carboxamide | 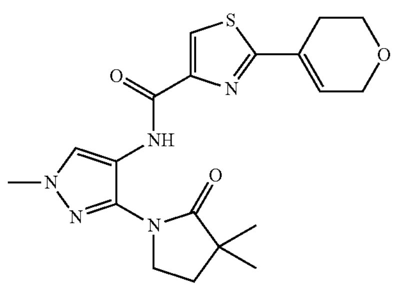 [SMILES: Cn1cc(NC(=O)c2csc(C3=CCOCC3)n2)c(N2CCC(C)(C)C2=O)n1] | | 402.1 |
| 64 | N-(3-(3,3-dimethyl-2-oxopyrrolidin-1-yl)-1-methyl-1H-pyrazol-4-yl)-2-(tetrahydro-2H-pyran-4-yl)-1,3-thiazole-4-carboxamide | 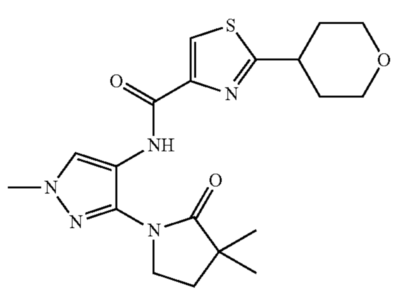 | | 404.1 |

TABLE 1-10

| 65 | N-(3-(3-(2-(dimethylamino)ethyl)-2-oxoimidazolidin-1-yl)-1-methyl-1H-pyrazol-4-yl)-2-(2-((2,2,2-trifluoroethyl)amino)pyridin-4-yl)-1,3-oxazole-4-carboxamide | 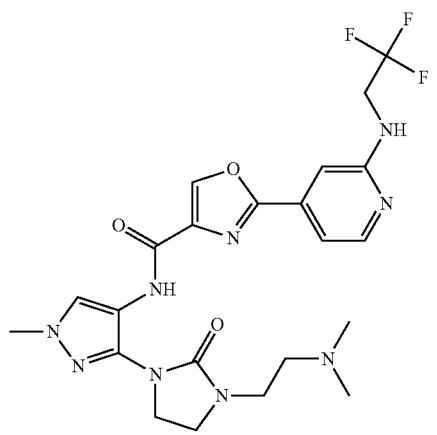 [SMILES: CN(C)CCN1CCN(c2nn(C)cc2NC(=O)c2coc(-c3ccnc(NCC(F)(F)F)c3)n2)C1=O] | 522.2 |
| --- | --- | --- | --- |
| 66 | methyl(3-(3,3-dimethyl-2-oxopyrrolidin-1-yl)-4-(((2-(2-((2,2,2-trifluoroethyl)amino)pyridin-4-yl)-1,3-oxazol-4-yl)carbonyl)amino)-1H-pyrazol-1-yl)acetate | 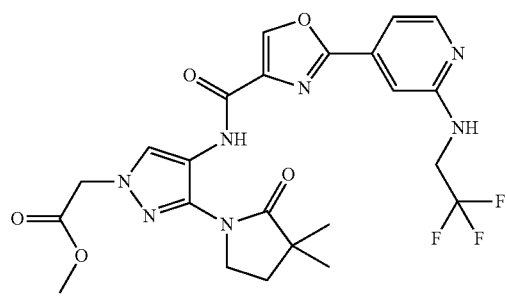 [SMILES: COC(=O)Cn1cc(NC(=O)c2coc(-c3ccnc(NCC(F)(F)F)c3)n2)c(N2CCC(C)(C)C2=O)n1] | 536.2 |
| 67 | N-(3-(3,3-dimethyl-2-oxopyrrolidin-1-yl)-1-((methylsulfonyl)methyl)-1H-pyrazol-4-yl)-2-(2-((2,2,2-trifluoroethyl)amino)pyridin-4-yl)-1,3-oxazole-4-carboxamide | 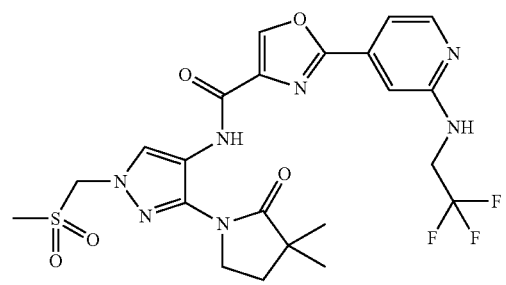 [SMILES: CC1(C)CCN(c2nn(CS(C)(=O)=O)cc2NC(=O)c2coc(-c3ccnc(NCC(F)(F)F)c3)n2)C1=O] | 556.1 |
| 68 | 2-(difluoromethyl)-N-(3-(3,3-dimethyl-2-oxopyrrolidin-1-yl)-1-methyl-1H-pyrazol-4-yl)-1,3-thiazole-4-carboxamide | 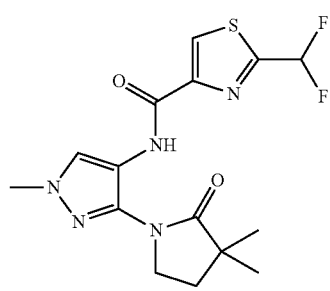 [SMILES: Cn1cc(NC(=O)c2csc(C(F)F)n2)c(N2CCC(C)(C)C2=O)n1] | 370.0 |
| 69 | N-(1-(2-amino-2-oxoethyl)-3-(3,3-dimethyl-2-oxopyrrolidin-1-yl)-1H-pyrazol-4-yl)-2-(2-((2,2,2-trifluoroethyl)amino)pyridin-4-yl)-1,3-oxazole-4-carboxamide | 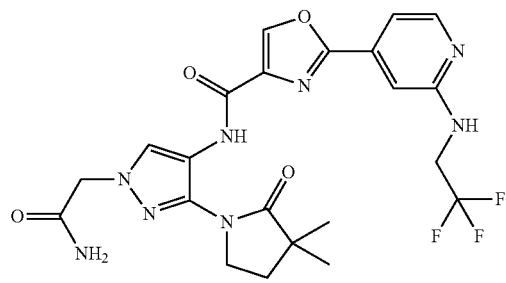 [SMILES: CC1(C)CCN(c2nn(CC(N)=O)cc2NC(=O)c2coc(-c3ccnc(NCC(F)(F)F)c3)n2)C1=O] | 521.1 |

TABLE 1-10-continued

| 71 | N-(1-methyl-3-(3-(2-(methylamino)ethyl)-2-oxoimidazolidin-1-yl)-1H-pyrazol-4-yl)-2-(2-((2,2,2-trifluoroethyl)amino)pyridin-4-yl)-1,3-oxazole-4-carboxamide | 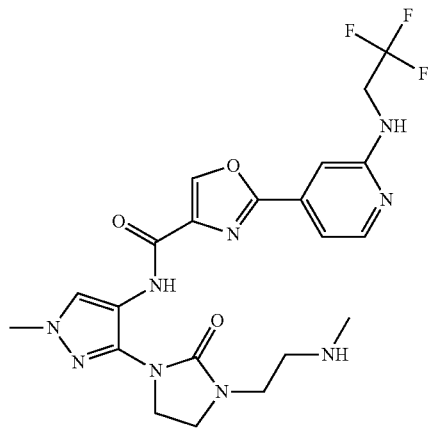 [SMILES: CNCCN1CCN(c2nn(C)cc2NC(=O)c2coc(-c3ccnc(NCC(F)(F)F)c3)n2)C1=O] | 2CF3COOH | 508.1 |

TABLE 1-11

| 72 | N-(3-(4-hydroxy-4-methyl-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide | 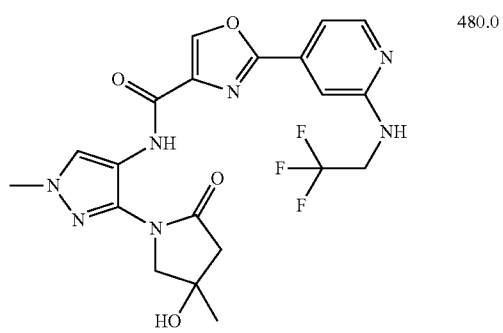 | 480.0 |
| 73 | N-(3-((2R)-2-((dimethylamino)methyl)-5-oxopyrrolidin-1-yl)-1-methyl-1H-pyrazol-4-yl)-2-(2-((2,2,2-trifluoroethyl)amino)pyridin-4-yl)-1,3-oxazole-4-carboxamide | 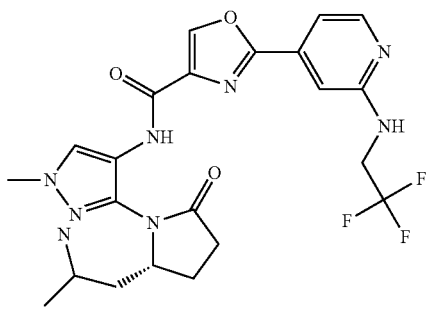 [SMILES: CC(N)C[C@H]1CCC(=O)N1c1nn(C)cc1NC(=O)c1coc(-c2ccnc(NCC(F)(F)F)c2)n1] | 507.1 |
| 74 | N-(3-(3-isopropyl-2-oxoimidazolidin-1-yl)-1-methyl-1H-pyrazol-4-yl)-2-(2-((2,2,2-trifluoroethyl)amino)pyridin-4-yl)-1,3-oxazole-4-carboxamide | 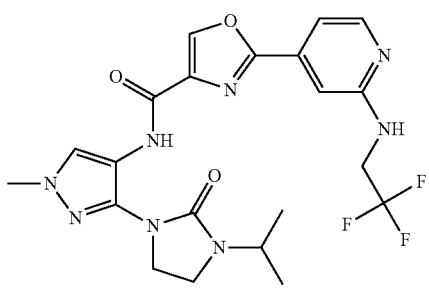 [SMILES: CC(C)N1CCN(c2nn(C)cc2NC(=O)c2coc(-c3ccnc(NCC(F)(F)F)c3)n2)C1=O] | 493.1 |

TABLE 1-11-continued

| 75 | N-(3-(1,8-dioxo-2-azaspiro[4.5]dec-2-yl)-1-methyl-1H-pyrazol-4-yl)-2-(2-((2,2,2-trifluoroethyl)amino)pyridin-4-yl)-1,3-oxazole-4-carboxamide | 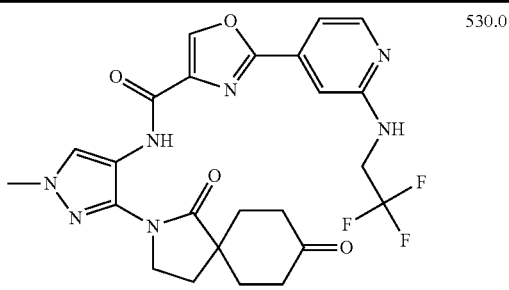 | 530.0 |
| --- | --- | --- | --- |
| 76 | 2-(2-aminopyridin-4-yl)-N-(3-(3,3-dimethyl-2-oxopyrrolidin-1-yl)-1-methyl-1H-pyrazol-4-yl)-1,3-thiazole-4-carboxamide | 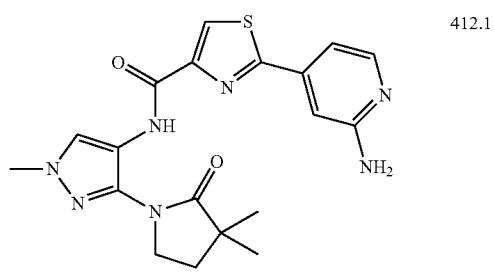 | 412.1 |
| 77 | N-(1-methyl-3-((3S)-3-methyl-2-oxopyrrolidin-1-yl)-1H-pyrazol-4-yl)-2-(2-((2,2,2-trifluoroethyl)amino)pyridin-4-yl)-1,3-oxazole-4-carboxamide | 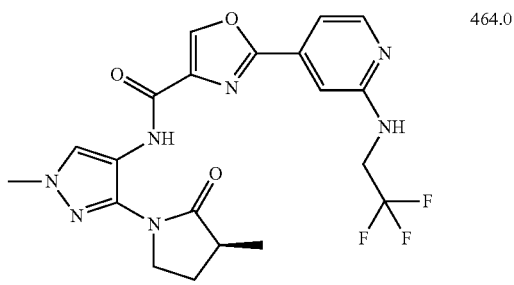 | 464.0 |
| 78 | 2-(2-chloropyridin-4-yl)-N-(3-(3,3-dimethyl-2-oxopyrrolidin-1-yl)-1-methyl-1H-pyrazol-4-yl)-1,3-thiazole-4-carboxamide | 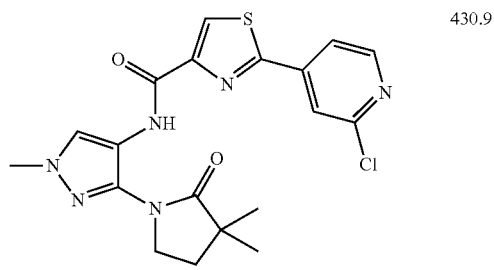 | 430.9 |

TABLE 1-12

| 79 | methyl 3-(3-(3,3-dimethyl-2-oxopyrrolidin-1-yl)-4-(((2-(2-((2,2,2-trifluoroethyl)amino)pyridin-4-yl)-1,3-oxazol-4-yl)carbonyl)amino)-1H-pyrazol-1-yl)propanoate | 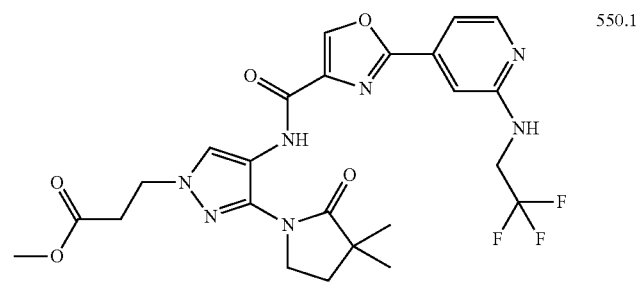 | 550.1 |
| --- | --- | --- | --- |

TABLE 1-12-continued

| | | | |
|---|---|---|---|
| 80 | N-(1-(3-amino-3-oxopropyl)-3-(3,3-dimethyl-2-oxopyrrolidin-1-yl)-1H-pyrazol-4-yl)-2-(2-((2,2,2-trifluoroethyl)amino)pyridin-4-yl)-1,3-oxazole-4-carboxamide | 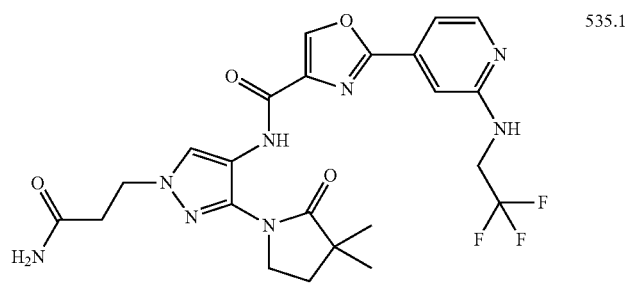 | 535.1 |
| 81 | N-(3-(3,3-dimethyl-2-oxopyrrolidin-1-yl)-1-methyl-1H-pyrazol-4-yl)-2-(2-methoxypyridin-4-yl)-1,3-oxazole-4-carboxamide | 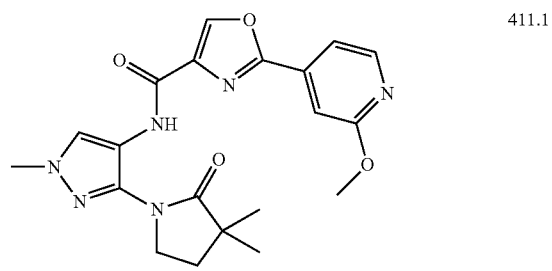 | 411.1 |
| 82 | 6-(difluoromethyl)-N-(3-(3,3-dimethyl-2-oxopyrrolidin-1-yl)-1-methyl-1H-pyrazol-4-yl)pyridine-2-carboxamide | 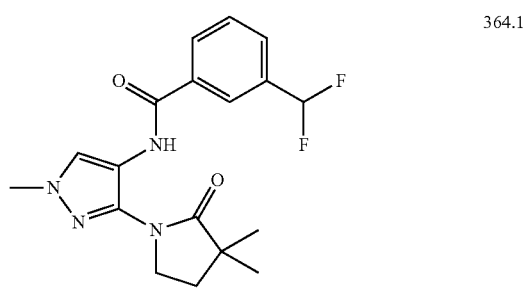 | 364.1 |
| 83 | N-(3-(3-(2-hydroxyethyl)-2-oxoimidazolidin-1-yl)-1-methyl-1H-pyrazol-4-yl)-2-(pyridin-4-yl)-1,3-thiazole-4-carboxamide | 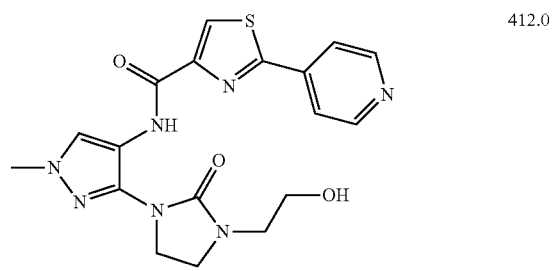 | 412.0 |
| 84 | N-(3-(8-hydroxy-1-oxo-2-azaspiro[4.5]dec-2-yl)-1-methyl-1H-pyrazol-4-yl)-2-(2-((2,2,2-trifluoroethyl)amino)pyridin-4-yl)-1,3-oxazole-4-carboxamide (single diastereomer) | 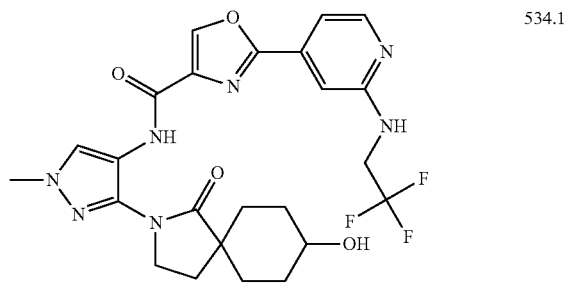 | 534.1 |

$^1$H NMR (400 MHz, DMSO-d6) d 1.19-1.37 (2H, m), 1.56-1.73 (4H, m), 1.80-1.91 (2H, m), 2.09 (2H, t, J = 7.1 Hz), 3.39-3.54 (1H, m), 3.76-3.86 (5H, m), 4.16-4.32 (2H, m), 4.63 (1H, d, J = 4.2 Hz), 7.12-7.23 (2H, m), 7.60 (1H, t, J = 6.6 Hz), 8.18-8.28 (2H, m), 8.88 (1H, s), 10.77 (1H, s).

TABLE 1-13

| | | | |
|---|---|---|---|
| 85 | N-(3-(8-hydroxy-1-oxo-2-azaspiro[4.5]dec-2-yl)-1-methyl-1H-pyrazol-4-yl)-2-(2-(((2,2,2-trifluoroethyl)amino)pyridin-4-yl)-1,3-oxazole-4-carboxamide (single diastereomer) | 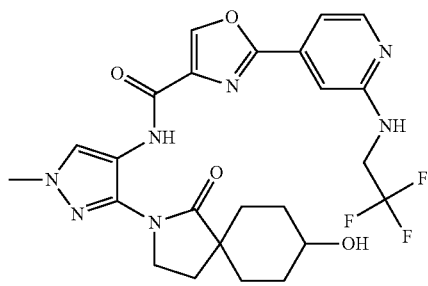 [SMILES: Cn1cc(NC(=O)c2coc(-c3ccnc(NCC(F)(F)F)c3)n2)c(N2CCC3(CCC(O)CC3)C2=O)n1] | 534.1 |

¹H NMR (400 MHz, DMSO-d6) d 1.28-1.46 (2H, m), 1.56-1.69 (2H, m), 1.79-1.92 (2H, m), 1.99-2.13) 4H, m), 3.69-3.95 (6H, m), 4.14-4.31 (2H, m), 4.74 (1H, d, J = 2.7 Hz), 7.15-7.29 (2H, m), 7.55 (1H, t, J = 6.6 Hz), 8.18-8.28 (2H, m), 8.88 (1H, s), 10.72-10.85 (1H, m).

| | | | |
|---|---|---|---|
| 86 | N-(3-(8-hydroxy-1-oxo-2-azaspiro[4.5]dec-2-yl)-1-methyl-1H-pyrazol-4-yl)-2-(pyridin-4-yl)-1,3-thiazole-4-carboxamide (diastereomer mixture) | 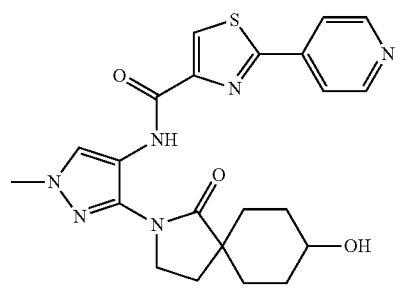 [SMILES: Cn1cc(NC(=O)c2csc(-c3ccncc3)n2)c(N2CCC3(CCC(O)CC3)C2=O)n1] | 453.0 |
| 87 | N-(3-(3,3-dimethyl-2-oxopyrrolidin-1-yl)-1-methyl-1H-pyrazol-4-yl)-2-(2-(methylamino)pyridin-4-yl)-1,3-thiazole-5-carboxamide | 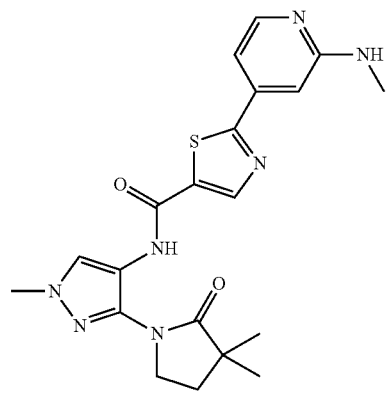 | 426.0 |
| 88 | N-(1-(2-cyanoethyl)-3-(3,3-dimethyl-2-oxopyrrolidin-1-yl)-1H-pyrazol-4-yl)-2-(2-(((2,2,2-trifluoroethyl)amino)pyridin-4-yl)-1,3-oxazole-4-carboxamide | 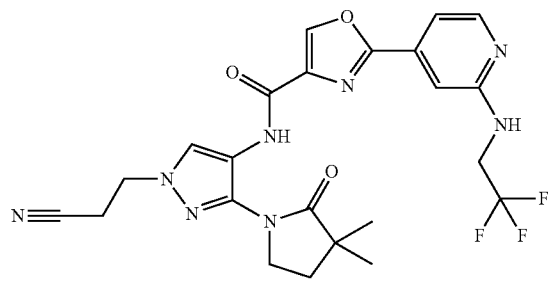 [SMILES: CC1(C)CCN(c2nn(CCC#N)cc2NC(=O)c2coc(-c3ccnc(NCC(F)(F)F)c3)n2)C1=O] | 517.1 |
| 89 | N-(1-(cyanomethyl)-3-(3,3-dimethyl-2-oxopyrrolidin-1-yl)-1H-pyrazol-4-yl)-2-(2-(((2,2,2-trifluoroethyl)amino)pyridin-4-yl)-1,3-oxazole-4-carboxamide | 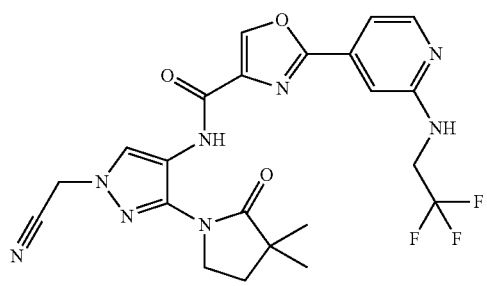 [SMILES: CC1(C)CCN(c2nn(CC#N)cc2NC(=O)c2coc(-c3ccnc(NCC(F)(F)F)c3)n2)C1=O] | 503.0 |

TABLE 1-13-continued

| 90 | N-(3-(3,3-dimethyl-2-oxopyrrolidin-1-yl)-1-(2-(2-oxopyrrolidin-1-yl)ethyl)-1H-pyrazol-4-yl)-2-(2-((2,2,2-trifluoroethyl)amino)pyridin-4-yl)-1,3-oxazole-4-carboxamide | 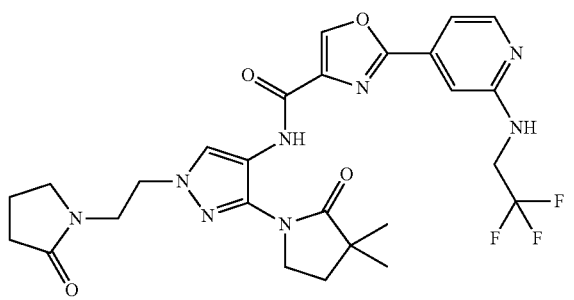 [SMILES: CC1(C)CCN(c2nn(CCN3CCCC3=O)cc2NC(=O)c2coc(-c3ccnc(NCC(F)(F)F)c3)n2)C1=O] | 575.1 |

TABLE 1-14

| 91 | N-(3-(3,3-dimethyl-2-oxopyrrolidin-1-yl)-1-(2-(methylsulfonyl)ethyl)-1H-pyrazol-4-yl)-2-(2-((2,2,2-trifluoroethyl)amino)pyridin-4-yl)-1,3-oxazole-4-carboxamide | 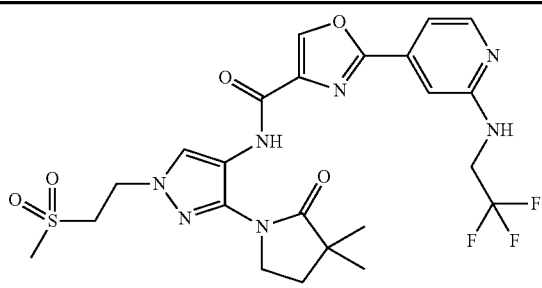 | 570.1 |
| 92 | N-(3-(7-benzyl-1-oxo-2,7-diazaspiro[4.4]non-2-yl)-1-methyl-1H-pyrazol-4-yl)-2-(2-((2,2,2-trifluoroethyl)amino)pyridin-4-yl)-1,3-oxazole-4-carboxamide | 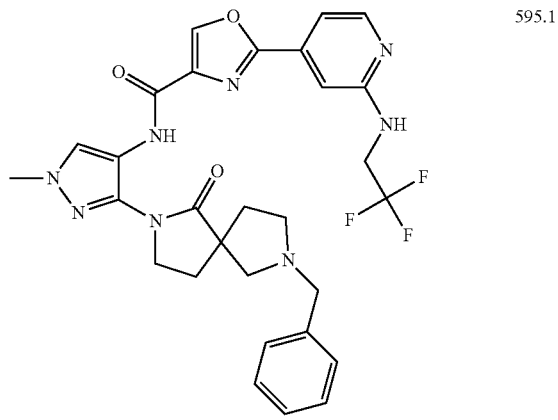 | 595.1 |
| 93 | 2-(2-(dimethylamino)pyridin-4-yl)-N-(3-(3,3-dimethyl-2-oxopyrrolidin-1-yl)-1-methyl-1H-pyrazol-4-yl)-1,3-thiazole-5-carboxamide | 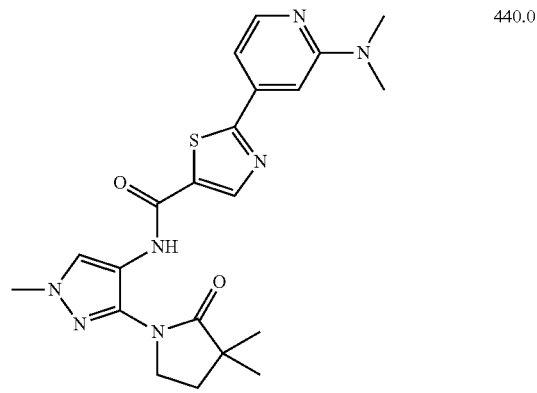 | 440.0 |

TABLE 1-14-continued

| 94 | N-(3-(3,3-dimethyl-2-oxopyrrolidin-1-yl)-1-(tetrahydrofuran-3-ylmethyl)-1H-pyrazol-4-yl)-2-(2-((2,2,2-trifluoroethyl)amino)pyridin-4-yl)-1,3-oxazole-4-carboxamide | 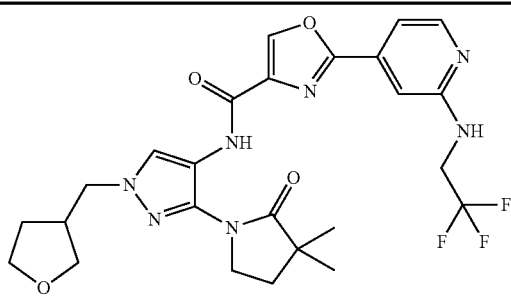 | 548.1 |
| 95 | N-(3-(3,3-dimethyl-2-oxopyrrolidin-1-yl)-1-(tetrahydrofuran-2-ylmethyl)-1H-pyrazol-4-yl)-2-(2-((2,2,2-trifluoroethyl)amino)pyridin-4-yl)-1,3-oxazole-4-carboxamide | 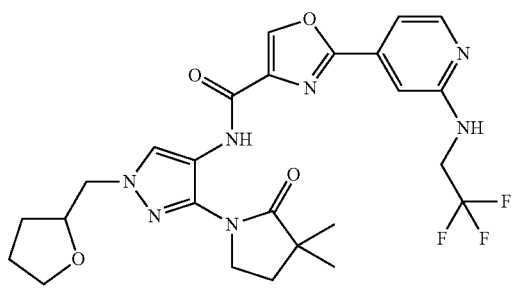 [SMILES: CC1(C)CCN(c2nn(CC3CCCO3)cc2NC(=O)c2coc(-c3ccnc(NCC(F)(F)F)c3)n2)C1=O] | 548.1 |
| 96 | N-(3-(3,3-dimethyl-2-oxopyrrolidin-1-yl)-1-methyl-1H-pyrazol-4-yl)-2-(2-oxo-1,2-dihydropyridin-4-yl)-1,3-oxazole-4-carboxamide | 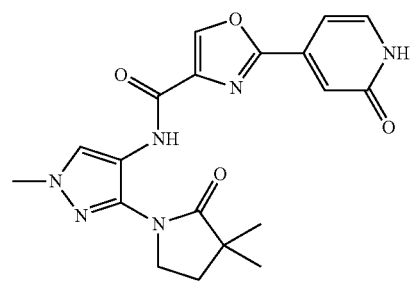 [SMILES: Cn1cc(NC(=O)c2coc(-c3cc[nH]c(=O)c3)n2)c(N2CCC(C)(C)C2=O)n1] | 397.1 |
| 97 | N-(3-(3,3-dimethyl-2-oxopyrrolidin-1-yl)-1-(2-hydroxycyclopentyl)-1H-pyrazol-4-yl)-2-(2-((2,2,2-trifluoroethyl)amino)pyridin-4-yl)-1,3-oxazole-4-carboxamide (transform) | 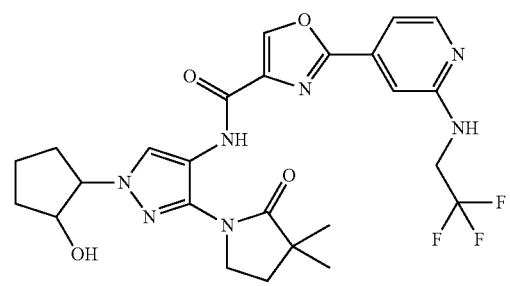 [SMILES: CC1(C)CCN(c2nn(C3CCCC3O)cc2NC(=O)c2coc(-c3ccnc(NCC(F)(F)F)c3)n2)C1=O] | 548,1 |

TABLE 1-15

| 98 | N-(3-(3-(2-hydroxyethyl)-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide | 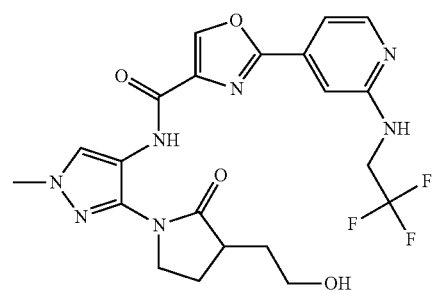 [SMILES: Cn1cc(NC(=O)c2coc(-c3ccnc(NCC(F)(F)F)c3)n2)c(N2CCC(CCO)C2=O)n1] | 494.0 |

TABLE 1-15-continued

| | | | | |
|---|---|---|---|---|
| 99 | N-(3-(3,3-diethyl-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide | 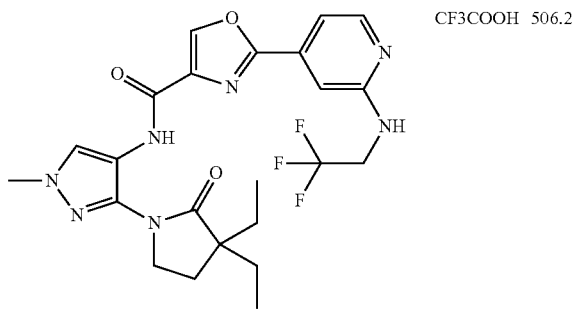 | CF3COOH | 506.2 |
| 100 | N-(3-((3S,4S)-4-hydroxy-3-methyl-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide | 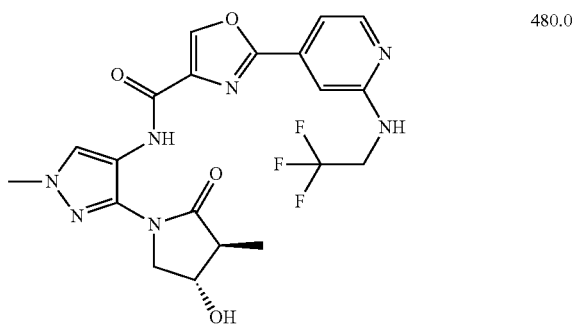 | | 480.0 |
| 101 | N-(3-(4-(hydroxymethyl)-3,3-dimethyl-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide | 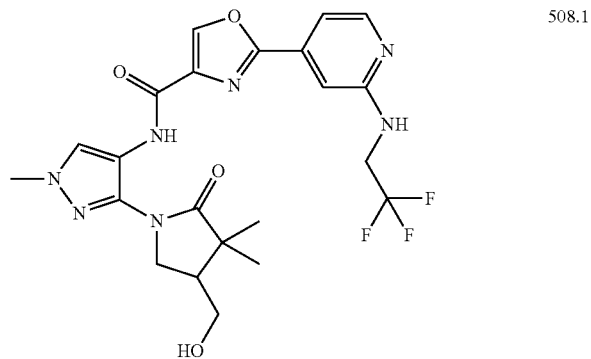 | | 508.1 |
| 102 | N-(3-(4-(hydroxymethyl)-3-methyl-2-oxoimidazolidin-1-yl)-1-methyl-1H-pyrazol-4-yl)-2-(2-((2,2,2-trifluoroethyl)amino)pyridin-4-yl)-1,3-oxazole-4-carboxamide | 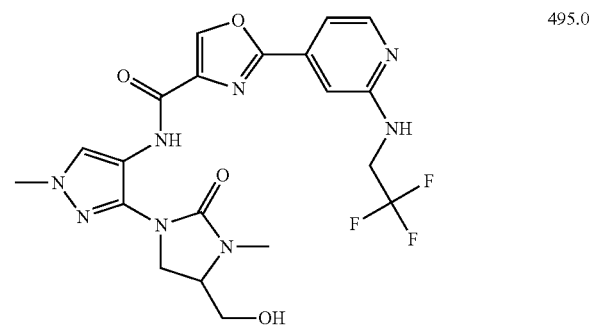 | | 495.0 |

TABLE 1-15-continued

| 103 | N-(3-(4-((dimethylaminomethyl)-3-methyl-2-oxoimidazolidin-1-yl)-1-methyl-1H-pyrazol-4-yl)-2-(2-((2,2,2-trifluoroethyl)amino)pyridin-4-yl)-1,3-oxazole-4-carboxamide | 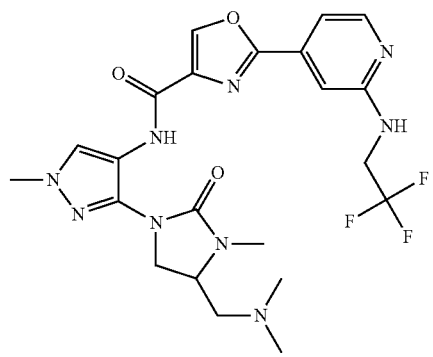 [SMILES: CN(C)CC1CN(c2nn(C)cc2NC(=O)c2coc(-c3ccnc(NCC(F)(F)F)c3)n2)C(=O)N1C] | | 522.1 |
| --- | --- | --- | --- | --- |
| 104 | N-(1-methyl-3-(1-oxo-2,7-diazaspiro[4.4]non-2-yl)-1H-pyrazol-4-yl)-2-(2-((2,2,2-trifluoroethyl)amino)pyridin-4-yl)-1,3-oxazole-4-carboxamide | 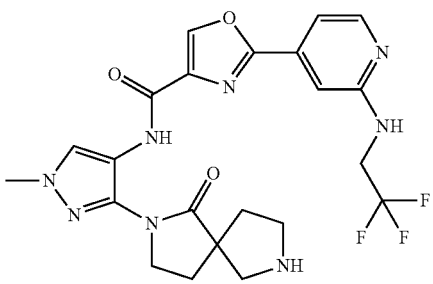 [SMILES: Cn1cc(NC(=O)c2coc(-c3ccnc(NCC(F)(F)F)c3)n2)c(N2CCC3(CCNC3)C2=O)n1] | CF3COOH | 505.0 |

TABLE 1-16

| 105 | 2-(2-cyanopyridin-4-yl)-N-(3-(3,3-dimethyl-2-oxopyrrolidin-1-yl)-1-methyl-1H-pyrazol-4-yl)-1,3-oxazole-4-carboxamide | 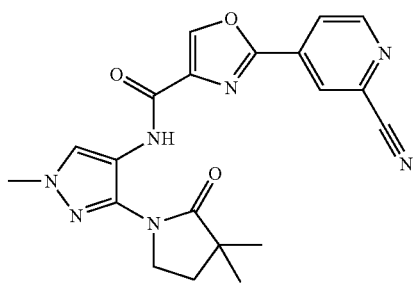 [SMILES: Cn1cc(NC(=O)c2coc(-c3ccnc(C#N)c3)n2)c(N2CCC(C)(C)C2=O)n1] | | 406.0 |
| --- | --- | --- | --- | --- |
| 106 | N-(3-(4-((cyclopropylamino)methyl)-3,3-dimethyl-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide | 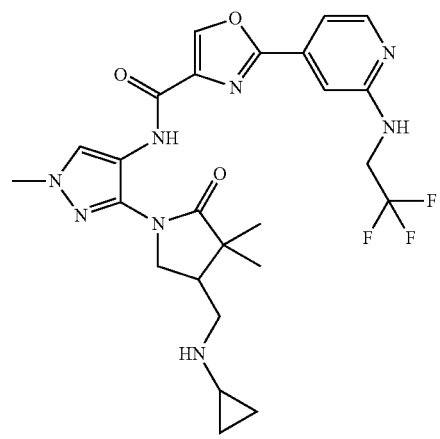 [SMILES: Cn1cc(NC(=O)c2coc(-c3ccnc(NCC(F)(F)F)c3)n2)c(N2CC(CNC3CC3)C(C)(C)C2=O)n1] | | 547.1 |

TABLE 1-16-continued

| | | | |
|---|---|---|---|
| 107 | N-(1-methyl-3-(8-oxo-2-oxa-7-azaspiro[4.4]non-7-yl)-1H-pyrazol-4-yl)-2-(2-((2,2,2-trifluoroethyl)amino)pyridin-4-yl)-1,3-oxazole-4-carboxamide | 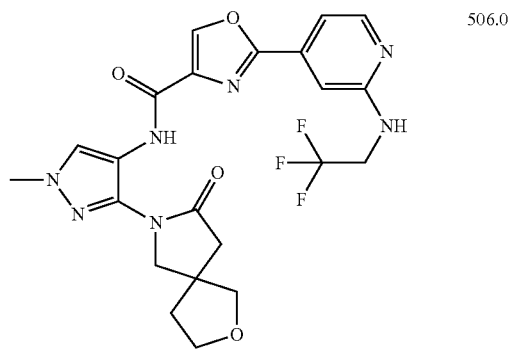 | 506.0 |
| 108 | N-(1-methyl-3-(3-oxo-2-azaspiro[4.4]non-2-yl)-1H-pyrazol-4-yl)-2-(2-((2,2,2-trifluoroethyl)amino)pyridin-4-yl)-1,3-oxazole-4-carboxamide | 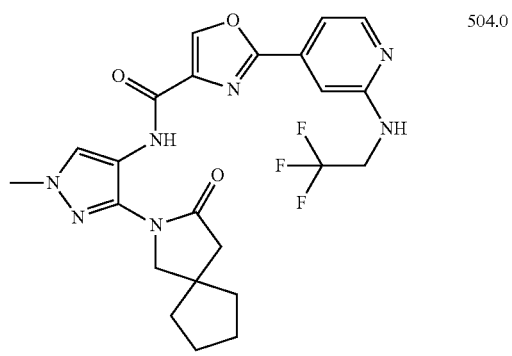 | 504.0 |
| 109 | N-(3-(3-(hydroxymethyl)-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide | 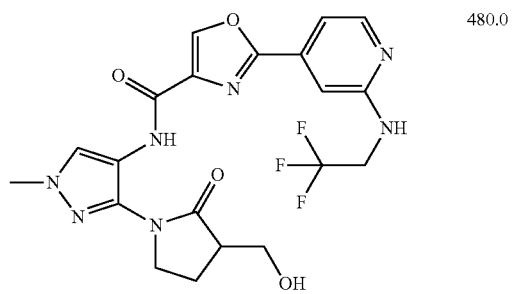 | 480.0 |
| 110 | N-(1-methyl-3-(3-methyl-4-((methylamino)methyl)-2-oxoimidazolidin-1-yl)-1H-pyrazol-4-yl)-2-(2-((2,2,2-trifluoroethyl)amino)pyridin-4-yl)-1,3-oxazole-4-carboxamide | 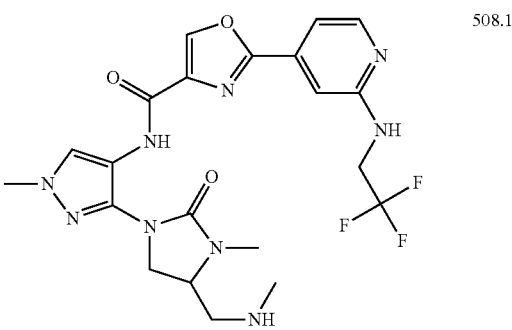 | 508.1 |
| 111 | N-(3-(3,3-dimethyl-2-oxopyrrolidin-1-yl)-1-ethyl-1H-pyrazol-4-yl)-2-(2-((2,2,2-trifluoroethyl)amino)pyridin-4-yl)-1,3-oxazole-4-carboxamide | 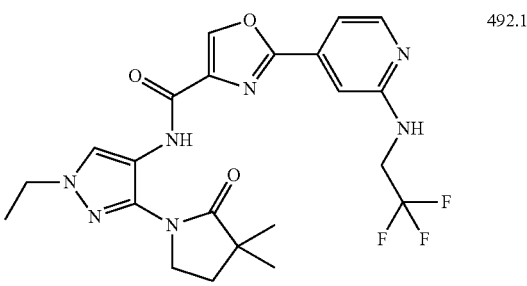 | 492.1 |

TABLE 1-17

| | | | |
|---|---|---|---|
| 112 | N-(3-(3-hydroxy-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide | 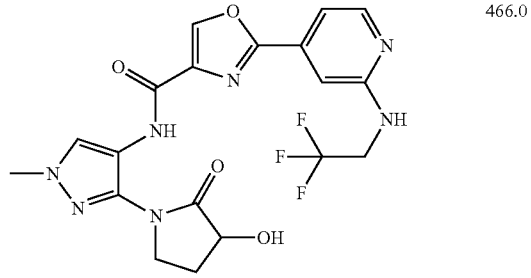 | 466.0 |
| 113 | N-(3-(3,3-dimethyl-2-oxopyrrolidin-1-yl)-1-(oxetan-3-yl)-1H-pyrazol-4-yl)-2-(2-((2,2,2-trifluoroethyl)amino)pyridin-4-yl)-1,3-oxazole-4-carboxamide | 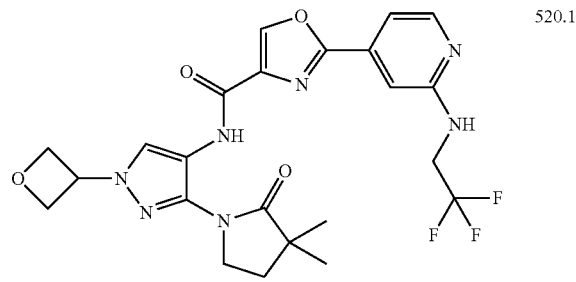 | 520.1 |
| 114 | N-(3-(3-(2-hydroxyethyl)-2-oxoimidazolidin-1-yl)-1-methyl-1H-pyrazol-4-yl)-2-phenyl-1,3-oxazole-5-carboxamide | 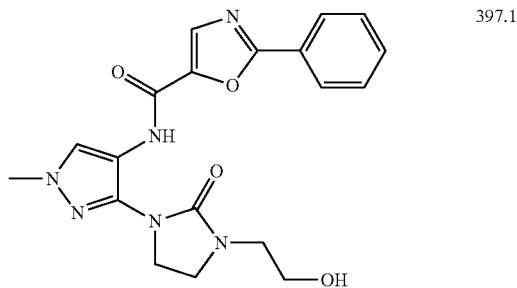 | 397.1 |
| 115 | N-(3-(3-(2-hydroxyethyl)-2-oxoimidazolidin-1-yl)-1-methyl-1H-pyrazol-4-yl)-2-(2-thienyl)-1,3-thiazole-4-carboxamide | 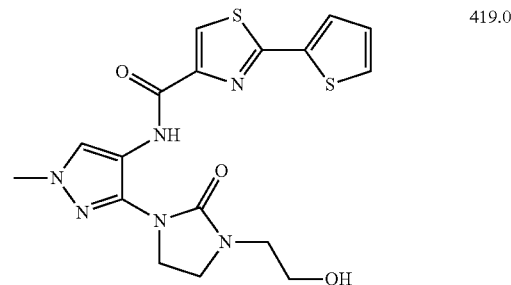 | 419.0 |
| 116 | N-(3-(3-(2-hydroxyethyl)-2-oxoimidazolidin-1-yl)-1-methyl-1H-pyrazol-4-yl)-5-(pyrimidin-4-yl)thiophene-3-carboxamide | 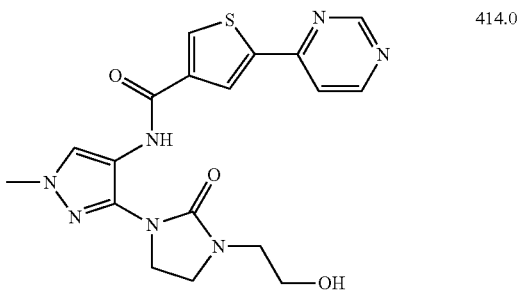 | 414.0 |

TABLE 1-17-continued

| | | | |
|---|---|---|---|
| 117 | 6-(difluoromethyl)-N-(3-(3-(2-hydroxyethyl)-2-oxoimidazolidin-1-yl)-1-methyl-1H-pyrazol-4-yl)pyridine-2-carboxamide | 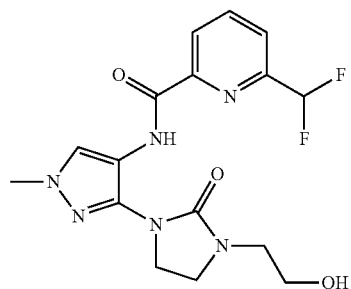 [SMILES: Cn1cc(NC(=O)c2cccc(C(F)F)n2)c(N2CCN(CCO)C2=O)n1] | 381.0 |
| 118 | N-(3-(3-(2-hydroxyethyl)-2-oxoimidazolidin-1-yl)-1-methyl-1H-pyrazol-4-yl)-3-(1H-imidazol-1-yl)benzamide | 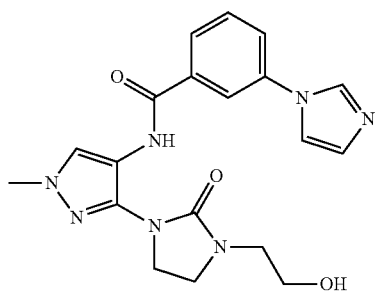 [SMILES: Cn1cc(NC(=O)c2cccc(-n3ccnc3)c2)c(N2CCN(CCO)C2=O)n1] | 396.1 |

TABLE 1-18

| | | | |
|---|---|---|---|
| 119 | N-(3-(3-(2-hydroxyethyl)-2-oxoimidazolidin-1-yl)-1-methyl-1H-pyrazol-4-yl)-3-(1H-pyrazol-3-yl)benzamide | 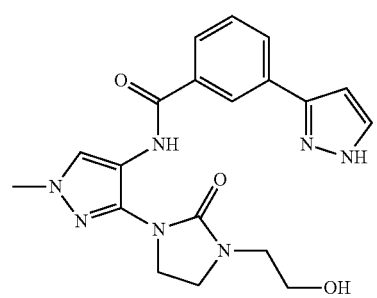 [SMILES: Cn1cc(NC(=O)c2cccc(-c3cc[nH]n3)c2)c(N2CCN(CCO)C2=O)n1] | 396.1 |
| 120 | N-(3-(3-(2-hydroxyethyl)-2-oxoimidazolidin-1-yl)-1-methyl-1H-pyrazol-4-yl)-3-(1H-tetrazol-1-yl)benzamide | 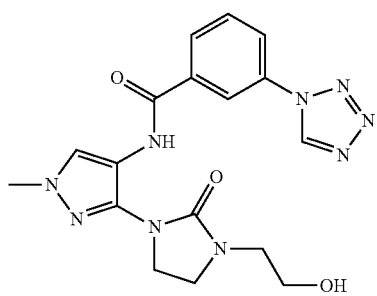 [SMILES: Cn1cc(NC(=O)c2cccc(-n3cnnn3)c2)c(N2CCN(CCO)C2=O)n1] | 398.0 |
| 121 | N-(3-(3-(2-hydroxyethyl)-2-oxoimidazolidin-1-yl)-1-methyl-1H-pyrazol-4-yl)-6-(morpholin-4-yl)pyridine-2-carboxamide | 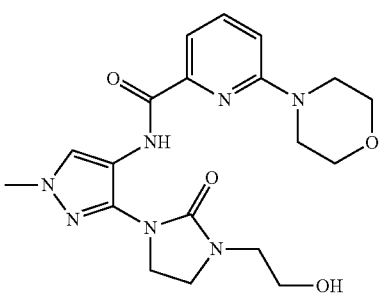 [SMILES: Cn1cc(NC(=O)c2cccc(N3CCOCC3)n2)c(N2CCN(CCO)C2=O)n1] | 416.1 |

TABLE 1-18-continued

| | | | |
|---|---|---|---|
| 122 | N-(3-(3,3-dimethyl-2-oxopyrrolidin-1-yl)-1-(oxetan-3-ylmethyl)-1H-pyrazol-4-yl)-2-(2-((2,2,2-trifluoroethyl)amino)pyridin-4-yl)-1,3-oxazole-4-carboxamide | 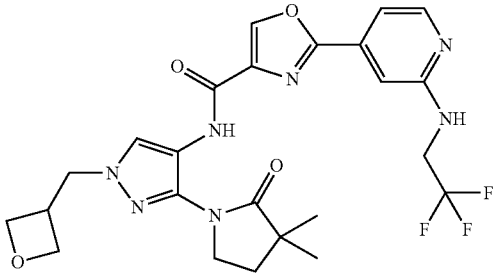 [SMILES: CC1(C)CCN(c2nn(CC3COC3)cc2NC(=O)c2coc(-c3ccnc(NCC(F)(F)F)c3)n2)C1=O] | 534.0 |
| 123 | N-(1-(2,2-difluoroethyl)-3-(3,3-dimethyl-2-oxopyrrolidin-1-yl)-1H-pyrazol-4-yl)-2-(2-((2,2,2-trifluoroethyl)amino)pyridin-4-yl)-1,3-oxazole-4-carboxamide | 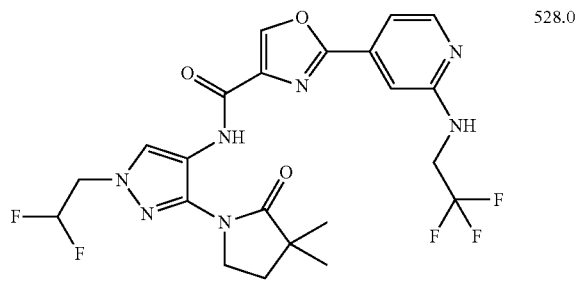 | 528.0 |
| 124 | N-(3-(4-((dimethylamino)methyl)-3-methyl-2-oxoimidazolidin-1-yl)-1-methyl-1H-pyrazol-4-yl)-2-(2-((2,2,2-trifluoroethyl)amino)pyridin-4-yl)-1,3-oxazole-4-carboxamide (optical isomer) | 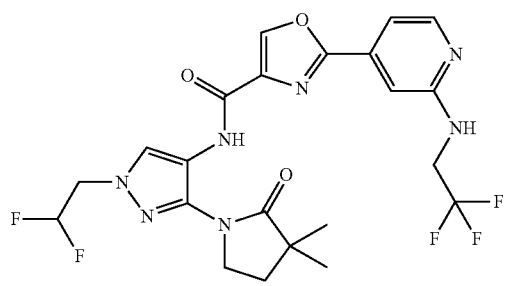 [SMILES: CC1(C)CCN(c2nn(CC(F)F)cc2NC(=O)c2coc(-c3ccnc(NCC(F)(F)F)c3)n2)C1=O] | 522.1 |

Retention time by HPLC for analysis (column: CHIRALPAK IC (trade name), 4.6 mmID × 250 mmL, manufactured by Daicel Chemical Industries, mobile phase: hexane/ethanol/diethylamine = 600/400/1, flow rate: 1.0 mL/min): 7.007 min

TABLE 1-19

| | | | |
|---|---|---|---|
| 125 | N-(3-(4-((dimethylamino)methyl)-3-methyl-2-oxoimidazolidin-1-yl)-1-methyl-1H-pyrazol-4-yl)-2-(2-((2,2,2-trifluoroethyl)amino)pyridin-4-yl)-1,3-oxazole-4-carboxamide (optical isomer) | 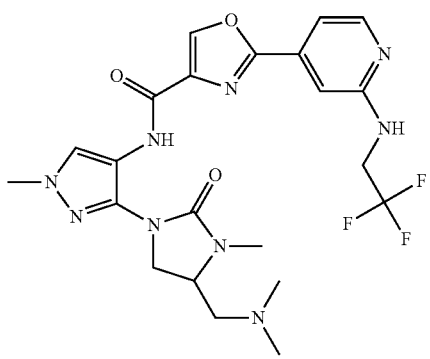 [SMILES: CN(C)CC1CN(c2nn(C)cc2NC(=O)c2coc(-c3ccnc(NCC(F)(F)F)c3)n2)C(=O)N1C] | 522.1 |

Retention time by HPLC for analysis (column: CHIRALPAK IC (trade name), 4.6 mmID × 250 mmL, manufactured by Daicel Chemical Industries, mobile phase: hexane/ethanol/diethylamine = 600/400/1, flow rate: 1.0 mL/min): 9.947 min TABLE 1-19-continued

| | | | |
|---|---|---|---|
| 126 | N-(1-methyl-3-(1-oxo-2,8-diazaspiro[4.5]dec-2-yl)-1H-pyrazol-4-yl)-2-(2-((2,2,2-trifluoroethyl)amino)pyridin-4-yl)-1,3-oxazole-4-carboxamide | 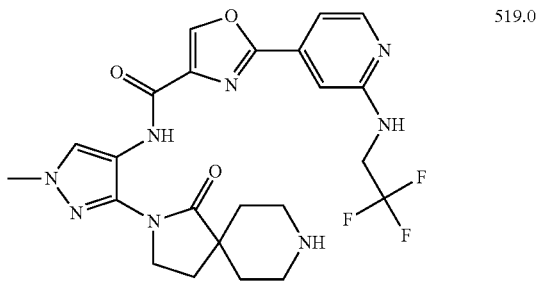 | 519.0 |
| 127 | 6-(4-(azidomethyl)-1H-pyrazol-1-yl)-N-(3-(3,3-dimethyl-2-oxopyrrolidin-1-yl)-1-methyl-1H-pyrazol-4-yl)pyridine-2-carboxamide | 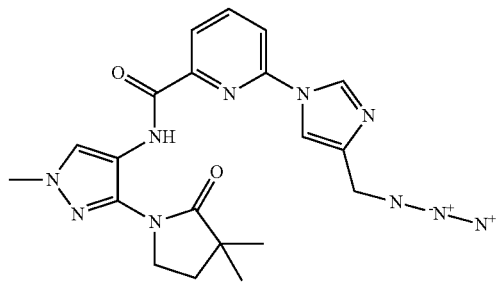 [SMILES: Cn1cc(NC(=O)c2cccc(-n3cnc(CNN[NH3+])c3)n2)c(N2CCC(C)(C)C2=O)n1] | 435.0 |
| 128 | 6-(4-(aminomethyl)-1H-pyrazol-1-yl)-N-(3-(3,3-dimethyl-2-oxopyrrolidin-1-yl)-1-methyl-1H-pyrazol-4-yl)pyridine-2-carboxamide | 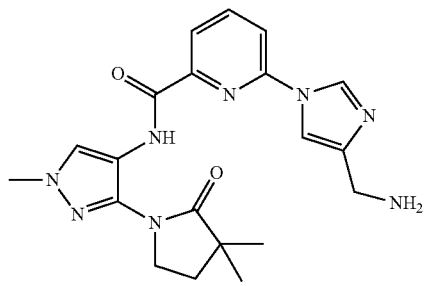 [SMILES: Cn1cc(NC(=O)c2cccc(-n3cnc(CN)c3)n2)c(N2CCC(C)(C)C2=O)n1] | 409.1 |
| 129 | 4,4-dimethyl-1-(1-methyl-4-(((2-(2-((2,2,2-trifluoroethyl)amino)pyridin-4-yl)-1,3-oxazol-4-yl)carbonyl)amino)-1H-pyrazol-3-yl)-5-oxopyrrolidine-3-carboxylic acid | 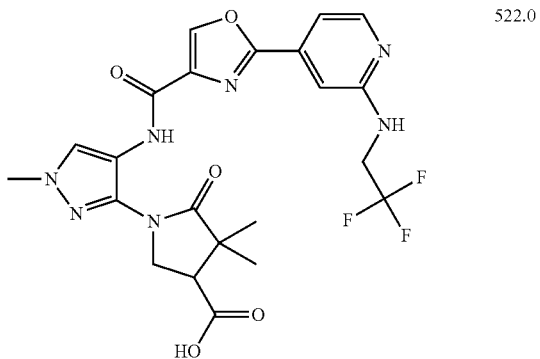 | 522.0 |
| 130 | N-(3-(3,3-dimethyl-4-(methylcarbamoyl)-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide | 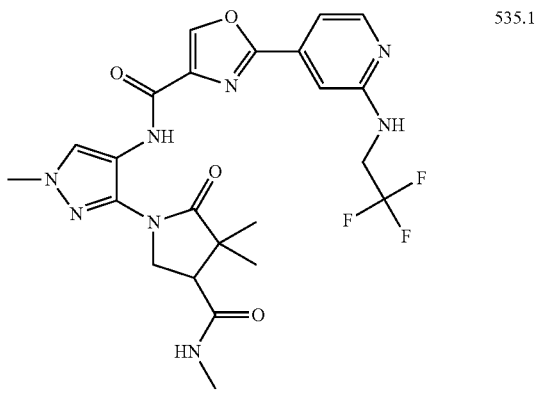 | 535.1 |

TABLE 1-20

| | | | |
|---|---|---|---|
| 131 | N-(3-(3-(2-hydroxyethyl)-2-oxoimidazolidin-1-yl)-1-methyl-1H-pyrazol-4-yl)-2-(2-methylpyridin-4-yl)-1,3-thiazole-4-carboxamide | 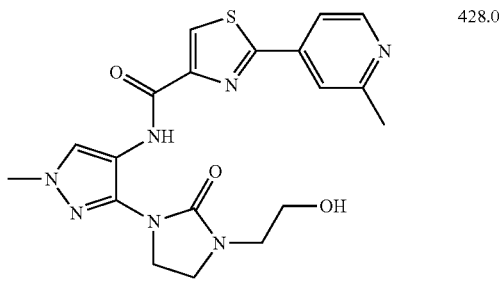 | 428.0 |
| 132 | N-(1-methyl-3-(2-oxo-1,3-thiazolidin-3-yl)-1H-pyrazol-4-yl)-2-(2-((2,2,2-trifluoroethyl)amino)pyridin-4-yl)-1,3-oxazole-4-carboxamide | 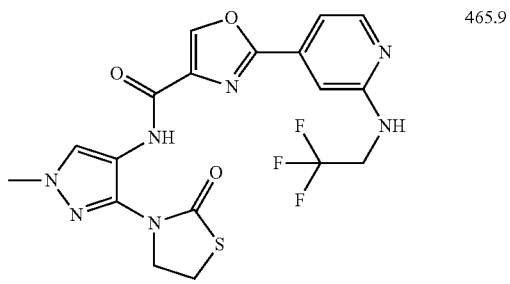 | 465.9 |
| 133 | 2-(2,3-dihydro-1-benzofuran-5-yl)-N-(3-(3-(2-hydroxyethyl)-2-oxoimidazolidin-1-yl)-1-methyl-1H-pyrazol-4-yl)-1,3-thiazole-4-carboxamide | 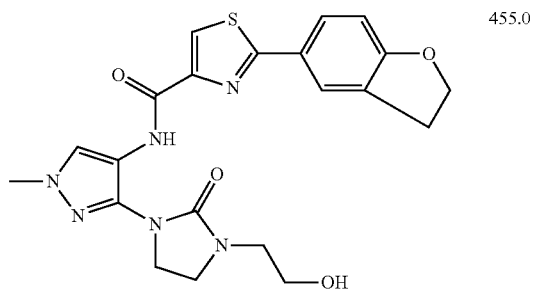 | 455.0 |
| 134 | N-(3-(3-(2-hydroxyethyl)-2-oxoimidazolidin-1-yl)-1-methyl-1H-pyrazol-4-yl)-3-(1H-pyrazol-4-yl)benzamide | 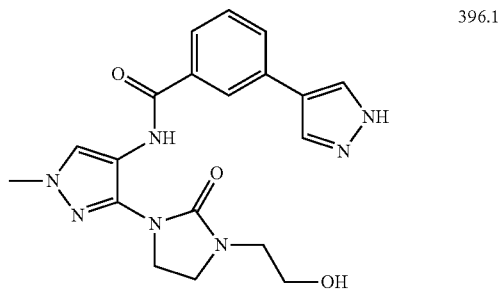 | 396.1 |
| 135 | N-(3-(3-(2-hydroxyethyl)-2-oxoimidazolidin-1-yl)-1-methyl-1H-pyrazol-4-yl)-3-(pentafluoro-lambda 6-sulfanyl)benzamide | 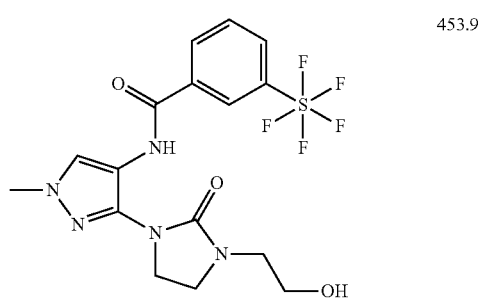 | 453.9 |

TABLE 1-20-continued

| 136 | 3-(1H-benzimidazol-2-yl)-N-(3-(3-(2-hydroxyethyl)-2-oxoimidazolidin-1-yl)-1-methyl-1H-pyrazol-4-yl)benzamide | 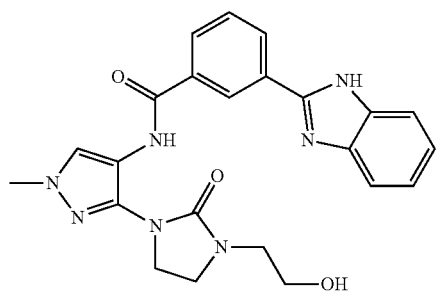 [SMILES: Cn1cc(NC(=O)c2cccc(-c3nc4ccccc4[nH]3)c2)c(N2CCN(CCO)C2=O)n1] | 446.0 |

TABLE 1-21

| 137 | N-(3-(3,3-dimethyl-4-((methylamino)methyl)-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide (optical isomer) | 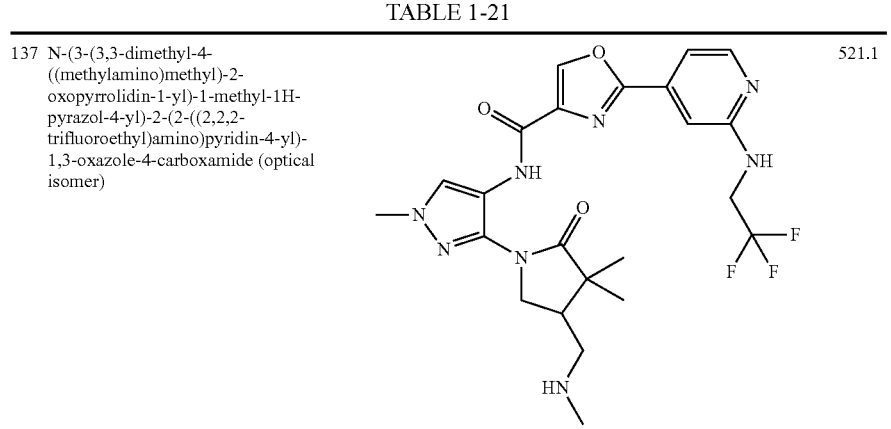 | 521.1 |

Retention time by SFC for analysis (column: CHIRALPAK IA (trade name), 4.6 mmID × 150 mmL, manufactured by Daicel Chemical Industries, mobile phase: carbon dioxide/methanol/acetonitrile/diethylamine = 600/200/200/1.2, flow rate: 4.0 mL/min): 1.116 min

| 138 | N-(3-(3,3-dimethyl-4-((methylamino)methyl)-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide (optical isomer) | 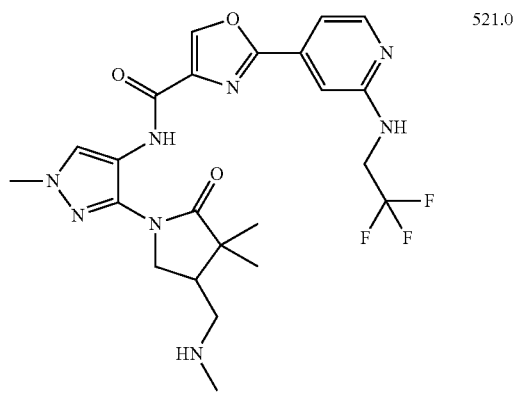 | 521.0 |

Retention time by SFC for analysis (column: CHIRALPAK IA (trade name , 4.6 mmID X 150 mmL, manufactured by Daicel Chemical Industries, mobile phase: carbon dioxide/methanol/acetonitrile/diethylamine = 600/200/200/1.2, flow rate: 4.0 mL/min): 1.917 min

| 139 | N-(3-(3,3-dimethyl-2-oxopyrrolidin-1-yl)-1-methyl-1H-pyrazol-4-yl)-2-(2-(ethylamino)pyridin-4-yl)-1,3-oxazole-4-carboxamide | 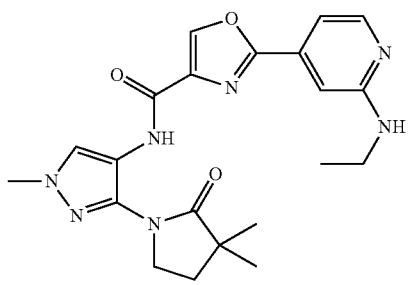 [SMILES: CCNc1cc(-c2nc(C(=O)Nc3cn(C)nc3N3CCC(C)(C)C3=O)co2)ccn1] | 424.0 |

TABLE 1-21-continued

| 140 | N-(3-(4-(((2,2-difluoroethyl)amino)methyl)-3,3-dimethyl-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide | 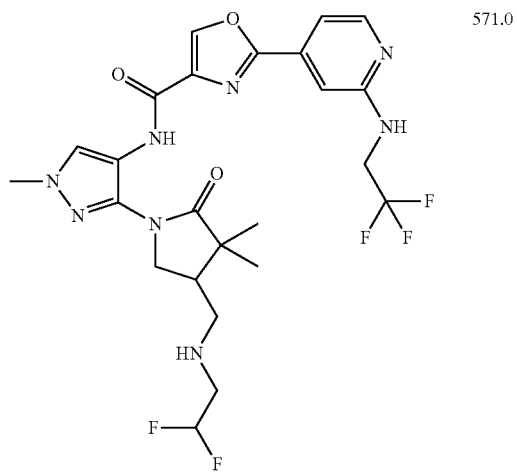 | 571.0 |
| 141 | N-(3-(3,3-dimethyl-2-oxo-4-(((2,2,2-trifluoroethyl)amino)methyl)pyrrolidin-1-yl)-1-methyl-1H-pyrazol-4-yl)-2-(2-((2,2,2-trifluoroethyl)amino)pyridin-4-yl)-1,3-oxazole-4-carboxamide | 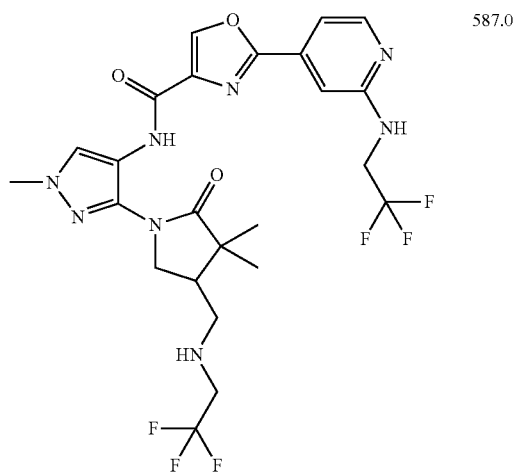 | 587.0 |
| 142 | N-(3-(4-carbamoyl-3,3-dimethyl-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide | 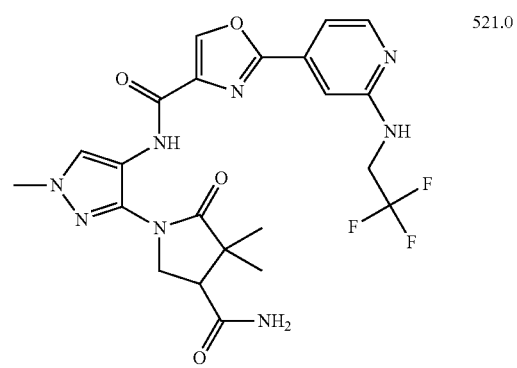 | 521.0 |

TABLE 1-22

| | | | |
|---|---|---|---|
| 143 | N-(3-(4-(difluoromethyl)-3,3-dimethyl-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide | 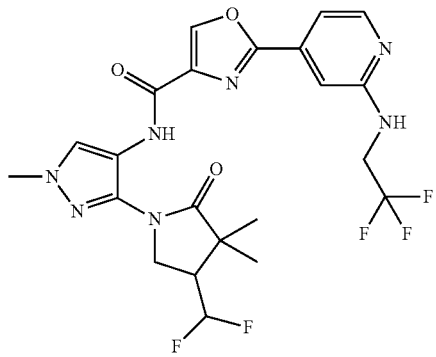 [SMILES: Cn1cc(NC(=O)c2coc(-c3ccnc(NCC(F)(F)F)c3)n2)c(N2CC(C(F)F)C(C)(C)C2=O)n1] | 528.0 |
| 144 | N-(3-(4-(((3,3-difluorocyclobutyl)amino)methyl)-3,3-dimethyl-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide | 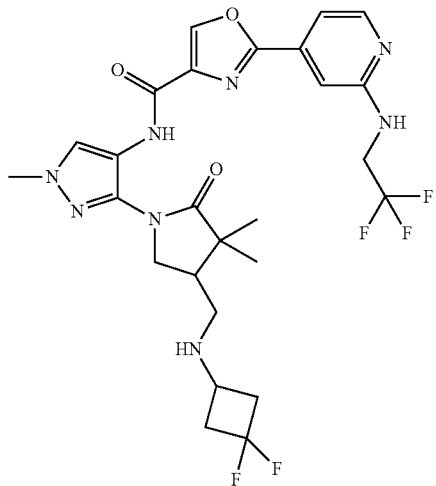 [SMILES: Cn1cc(NC(=O)c2coc(-c3ccnc(NCC(F)(F)F)c3)n2)c(N2CC(CNC3CC(F)(F)C3)C(C)(C)C2=O)n1] | 597.1 |
| 145 | N-(3-(3,3-dimethyl-2-oxopyrrolidin-1-yl)-1-methyl-1H-pyrazol-4-yl)-6-(4-(((2,2,2-trifluoroethyl)amino)methyl)-1H-pyrazol-1-yl)pyridine-2-carboxamide | 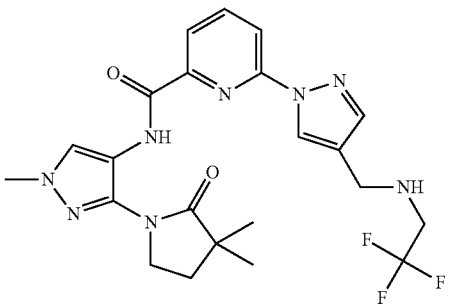 [SMILES: Cn1cc(NC(=O)c2cccc(-n3cc(CNCC(F)(F)F)cn3)n2)c(N2CCC(C)(C)C2=O)n1] | 491.0 |
| 146 | N-(3-(3,3-dimethyl-2-oxopyrrolidin-1-yl)-1-methyl-1H-pyrazol-4-yl)-6-(4-((ethylamino)methyl)-1H-pyrazol-1-yl)pyridine-2-carboxamide | 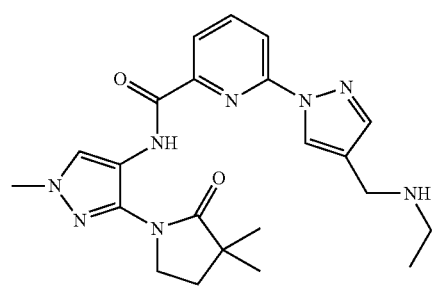 [SMILES: CCNCc1cnn(-c2cccc(C(=O)Nc3cn(C)nc3N3CCC(C)(C)C3=O)n2)c1] | CF3COOH 437.1 |

TABLE 1-22-continued

| | | | |
|---|---|---|---|
| 147 | 6-(4-(((cyclopropylmethyl)amino)methyl)-1H-pyrazol-1-yl)-N-(3-(3,3-dimethyl-2-oxopyrrolidin-1-yl)-1-methyl-1H-pyrazol-4-yl)pyridine-2-carboxamide | 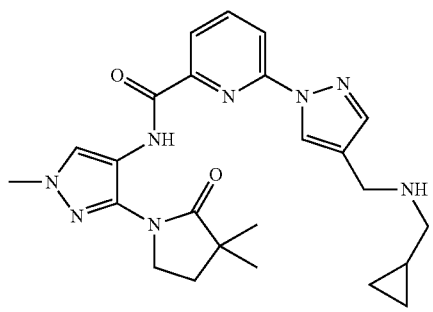 [SMILES: Cn1cc(NC(=O)c2cccc(-n3cc(CNCC4CC4)cn3)n2)c(N2CCC(C)(C)C2=O)n1] | CF3COOH 463.0 |
| 148 | N-(3-(3,3-dimethyl-4-((methylsulfonyl)methyl)-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide | 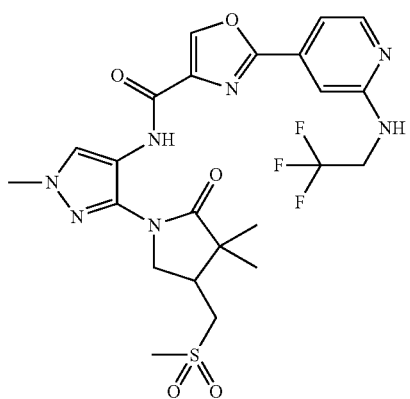 [SMILES: Cn1cc(NC(=O)c2coc(-c3ccnc(NCC(F)(F)F)c3)n2)c(N2CC(CS(C)(=O)=O)C(C)(C)C2=O)n1] | 570.0 |
| 149 | N-(3-(3,3-dimethyl-4-((methylsulfanyl)methyl)-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide | 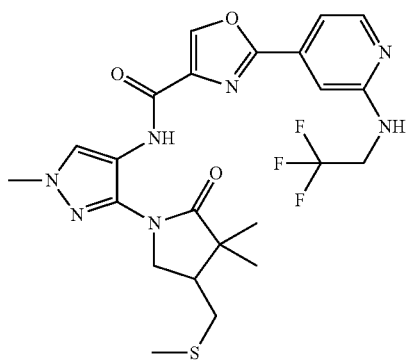 [SMILES: CSCC1CN(c2nn(C)cc2NC(=O)c2coc(-c3ccnc(NCC(F)(F)F)c3)n2)C(=O)C1(C)C] | 538.0 |

TABLE 1-23

| | | | |
|---|---|---|---|
| 150 | N-(3-(3,3-dimethyl-4-((methylsulfinyl)methyl)-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide | 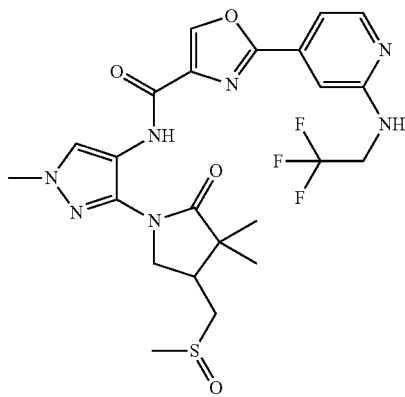 [SMILES: Cn1cc(NC(=O)c2coc(-c3ccnc(NCC(F)(F)F)c3)n2)c(N2CC(CS(C)=O)C(C)(C)C2=O)n1] | CF3COOH 554.0 |

TABLE 1-23-continued

| | | | |
|---|---|---|---|
| 151 | N-(3-(5-(hydroxymethyl)-2-oxo-1,3-oxazolidin-3-yl)-1-methyl-1H-pyrazol-4-yl)-2-(2-((2,2,2-trifluoroethyl)amino)pyridin-4-yl)-1,3-oxazole-4-carboxamide | 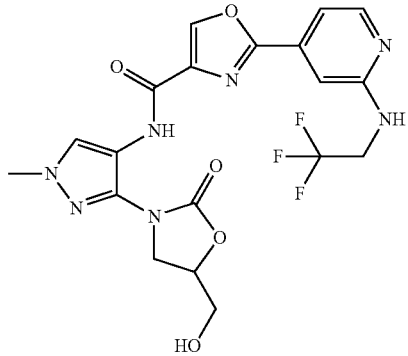 [SMILES: Cn1cc(NC(=O)c2coc(-c3ccnc(NCC(F)(F)F)c3)n2)c(N2CC(CO)OC2=O)n1] | 482.0 |
| 152 | N-(1-methyl-3-(5-((methylamino)methyl)-2-oxo-1,3-oxazolidin-3-yl)-1H-pyrazol-4-yl)-2-(2-((2,2,2-trifluoroethyl)amino)pyridin-4-yl)-1,3-oxazole-4-carboxamide | 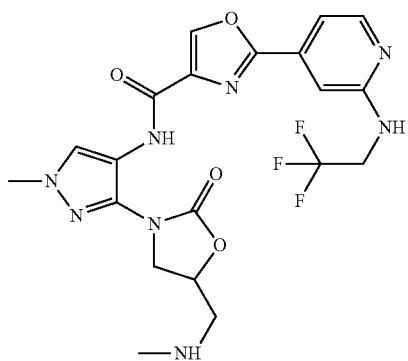 [SMILES: CNCC1CN(c2nn(C)cc2NC(=O)c2coc(-c3ccnc(NCC(F)(F)F)c3)n2)C(=O)O1] | 495.1 |
| 153 | N-(3-(5-((dimethylamino)methyl)-2-oxo-1,3-oxazolidin-3-yl)-1-methyl-1H-pyrazol-4-yl)-2-(2-((2,2,2-trifluoroethyl)amino)pyridin-4-yl)-1,3-oxazole-4-carboxamide | 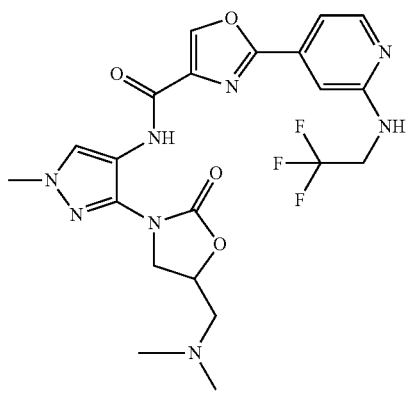 [SMILES: CN(C)CC1CN(c2nn(C)cc2NC(=O)c2coc(-c3ccnc(NCC(F)(F)F)c3)n2)C(=O)O1] | 509.2 |
| 154 | N-(3-(3,3-dimethyl-4-((oxetan-3-ylamino)methyl)-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide | 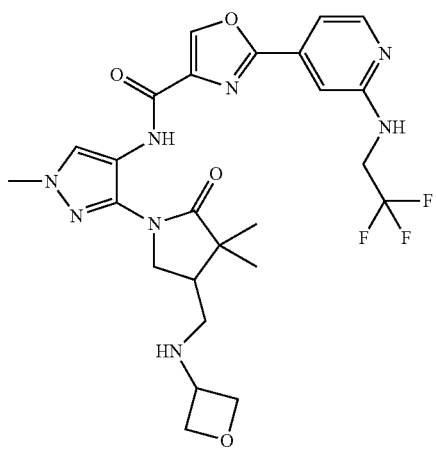 [SMILES: Cn1cc(NC(=O)c2coc(-c3ccnc(NCC(F)(F)F)c3)n2)c(N2CC(CNC3COC3)C(C)(C)C2=O)n1] | 563.2 |

TABLE 1-23-continued

| | | | |
|---|---|---|---|
| 155 | 6-(4-((dimethylamino)methyl)-1H-pyrazol-1-yl)-N-(3-(3,3-dimethyl-2-oxopyrrolidin-1-yl)-1-methyl-1H-pyrazol-4-yl)pyridine-2-carboxamide | 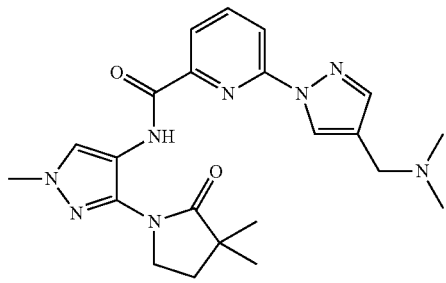 | 437.2 |
| 156 | N-(3-(3,3-dimethyl-4-(((methylsulfonyl)amino)methyl)-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide | 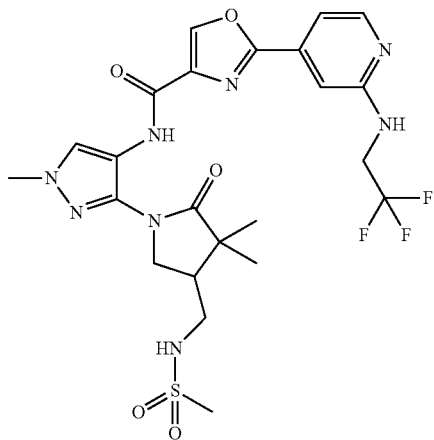 [SMILES: Cn1cc(NC(=O)c2coc(-c3ccnc(NCC(F)(F)F)c3)n2)c(N2CC(CNS(C)(=O)=O)C(C)(C)C2=O)n1] | 585.2 |

TABLE 1-24

| | | | |
|---|---|---|---|
| 157 | N-(3-(3,3-dimethyl-2-oxopyrrolidin-1-yl)-1-methyl-1H-pyrazol-4-yl)-6-(4-methyl-1H-pyrazol-1-yl)pyridine-2-carboxamide | 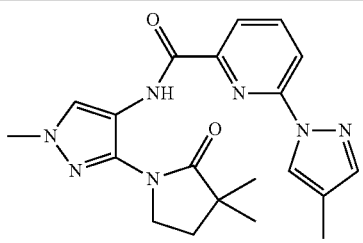 [SMILES: Cc1cnn(-c2cccc(C(=O)Nc3cn(C)nc3N3CCC(C)(C)C3=O)n2)c1] | 394.2 |
| 158 | N-(3-(3,3-dimethyl-2-oxopyrrolidin-1-yl)-1-methyl-1H-pyrazol-4-yl)-6-(4-formyl-1H-pyrazol-1-yl)pyridine-2-carboxamide | 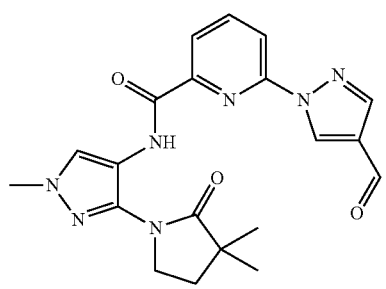 [SMILES: Cn1cc(NC(=O)c2cccc(-n3cc(C=O)cn3)n2)c(N2CCC(C)(C)C2=O)n1] | 408.1 |
| 159 | 1-(6-((3-(3,3-dimethyl-2-oxopyrrolidin-1-yl)-1-methyl-1H-pyrazol-4-yl)carbamoyl)pyridin-2-yl)-1H-pyrazole-4-carboxylic acid | 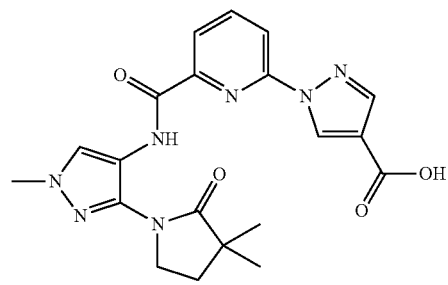 [SMILES: Cn1cc(NC(=O)c2cccc(-n3cc(C(=O)O)cn3)n2)c(N2CCC(C)(C)C2=O)n1] | 424.1 |

TABLE 1-24-continued

| | | | |
|---|---|---|---|
| 160 | N-(3-(3,3-dimethyl-2-oxopyrrolidin-1-yl)-1-methyl-1H-pyrazol-4-yl)-6-(4-(hydroxymethyl)-1H-pyrazol-1-yl)pyridine-2-carboxamide | 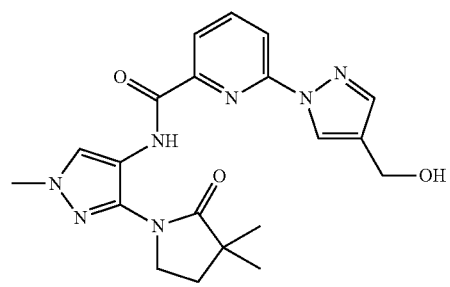 [SMILES: Cn1cc(NC(=O)c2cccc(-n3cc(CO)cn3)n2)c(N2CCC(C)(C)C2=O)n1] | 410.2 |
| 161 | N-(3-(3,3-dimethyl-2-oxopyrrolidin-1-yl)-1-methyl-1H-pyrazol-4-yl)-6-(4-(1-hydroxyethyl)-1H-pyrazol-1-yl)pyridine-2-carboxamide | 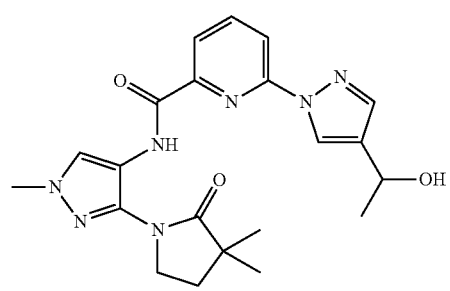 [SMILES: CC(O)c1cnn(-c2cccc(C(=O)Nc3cn(C)nc3N3CCC(C)(C)C3=O)n2)c1] | 424.2 |
| 162 | N-(3-(3,3-dimethyl-2-oxopyrrolidin-1-yl)-1-methyl-1H-pyrazol-4-yl)-6-(4-((methylamino)methyl)-1H-pyrazol-1-yl)pyridine-2-carboxamide | 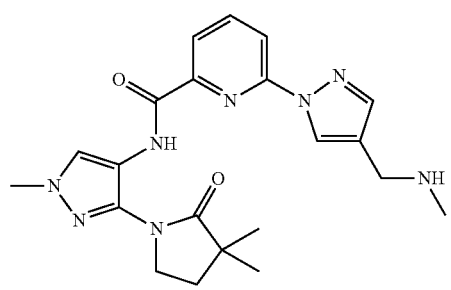 | 423.2 |
| 163 | 6-(4-carbamoyl-1H-pyrazol-1-yl)-N-(3-(3,3-dimethyl-2-oxopyrrolidin-1-yl)-1-methyl-1H-pyrazol-4-yl)pyridine-2-carboxamide | 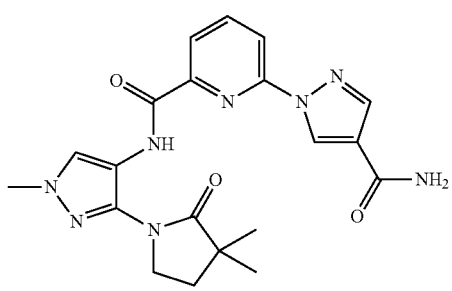 [SMILES: Cn1cc(NC(=O)c2cccc(-n3cc(C(N)=O)cn3)n2)c(N2CCC(C)(C)C2=O)n1] | 423.2 |

TABLE 1-25

| | | | |
|---|---|---|---|
| 164 | N-(3-(3-(2-hydroxypropyl)-2-oxoimidazolidin-1-yl)-1-methyl-1H-pyrazol-4-yl)-2-(2-((2,2,2-trifluoroethyl)amino)pyridin-4-yl)-1,3-oxazole-4-carboxamide | 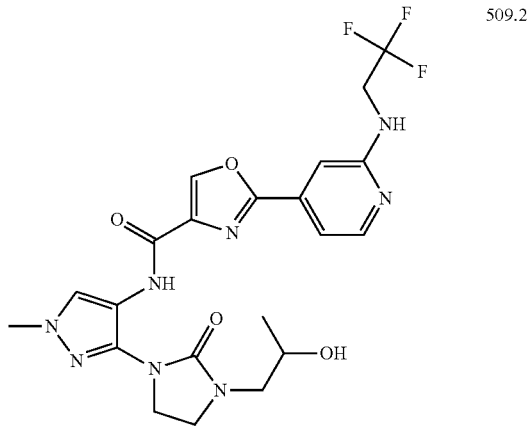 | 509.2 |
| 165 | N-(3-(3,3-dimethyl-2-oxopyrrolidin-1-yl)-1-methyl-1H-pyrazol-4-yl)-6-(4-formyl-1H-imidazol-1-yl)pyridine-2-carboxamide | 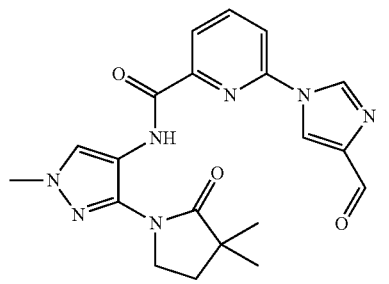 [SMILES: Cn1cc(NC(=O)c2cccc(-n3cnc(C=O)c3)n2)c(N2CCC(C)(C)C2=O)n1] | 408.1 |
| 166 | N-(3-(3,3-dimethyl-2-oxopyrrolidin-1-yl)-1-methyl-1H-pyrazol-4-yl)-2-(4-((methylamino)methyl)-1H-pyrazol-1-yl)-1,3-thiazole-4-carboxamide | 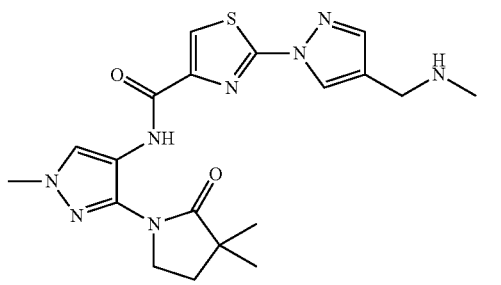 | 429.1 |
| 167 | N-(3-(3,3-dimethyl-2-oxopyrrolidin-1-yl)-1-methyl-1H-pyrazol-4-yl)-6-(2-oxoimidazolidin-1-yl)pyridine-2-carboxamide | 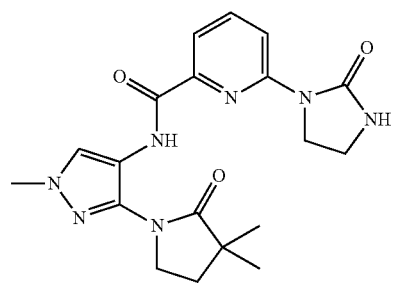 [SMILES: Cn1cc(NC(=O)c2cccc(N3CCNC3=O)n2)c(N2CCC(C)(C)C2=O)n1] | 398.2 |

TABLE 1-25-continued

| 168 | N-(3-(4-(acetamidomethyl)-3,3-dimethyl-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide | 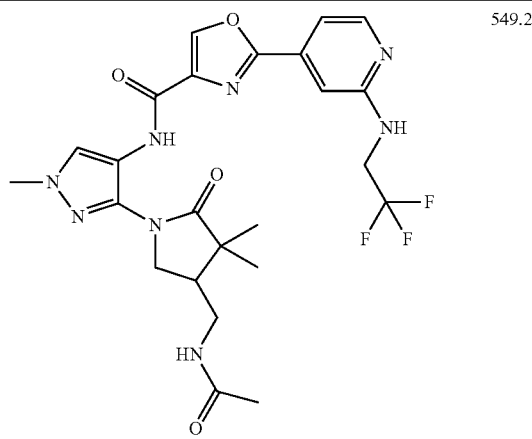 | 549.2 |
| --- | --- | --- | --- |
| 169 | N-(3-(4-(((cyclopropylcarbonyl)amino)methyl)-3,3-dimethyl-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide | 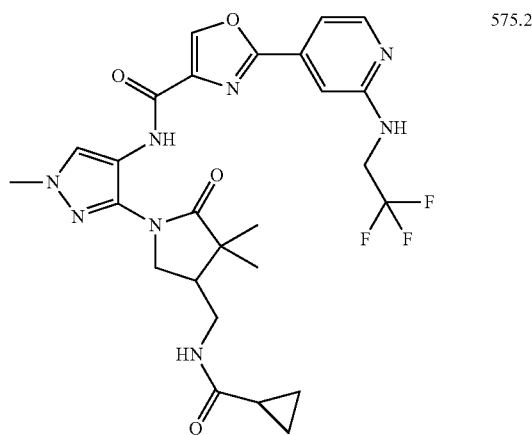 | 575.2 |
| 170 | N-(3-(3,3-dimethyl-2-oxopyrrolidin-1-yl)-1-methyl-1H-pyrazol-4-yl)-6-(4-(hydroxymethyl)-2-oxopyrrolidin-1-yl)pyridine-2-carboxamide | 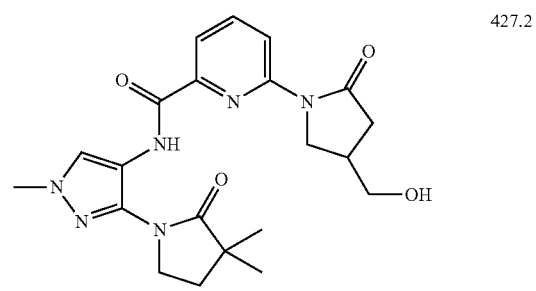 | 427.2 |

TABLE 1-26

| 171 | 6-(4-(aminomethyl)-1H-pyrazol-1-yl)-N-(1-methyl-3-(3-methyl-2-oxoimidazolidin-1-yl)-1H-pyrazol-4-yl)pyridine-2-carboxamide | 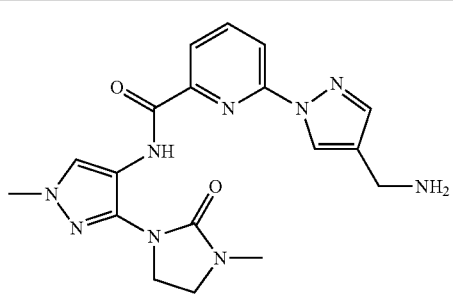 [SMILES: CN1CCN(c2nn(C)cc2NC(=O)c2cccc(-n3cc(CN)cn3)n2)C1=O] | 396.2 |
| --- | --- | --- | --- |

TABLE 1-26-continued

| 172 | N-(3-(3,3-dimethyl-2-oxopyrrolidin-1-yl)-1-methyl-1H-pyrazol-4-yl)-6-(2,4-dioxoimidazolidin-1-yl)pyridine-2-carboxamide | 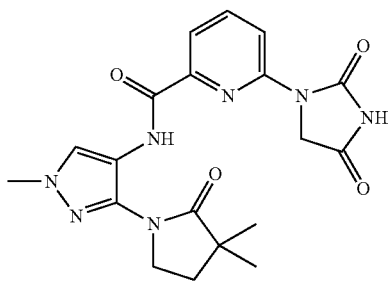 [SMILES: Cn1cc(NC(=O)c2cccc(N3CC(=O)NC3=O)n2)c(N2CCC(C)(C)C2=O)n1] | 412.2 |
| 173 | N-(3-(3,3-dimethyl-2-oxopyrrolidin-1-yl)-1-methyl-1H-pyrazol-4-yl)-6-((4S)-4-(hydroxymethyl)-2-oxoimidazolidin-1-yl)pyridine-2-carboxamide | 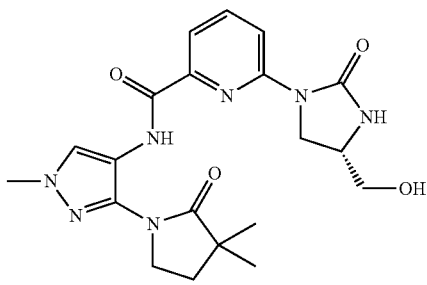 [SMILES: Cn1cc(NC(=O)c2cccc(N3C[C@@H](CO)NC3=O)n2)c(N2CCC(C)(C)C2=O)n1] | 428.2 |
| 174 | N-(3-((4S)-4-(hydroxymethyl)-2-oxoimidazolidin-1-yl)-1-methyl-1H-pyrazol-4-yl)-2-(2-((2,2,2-trifluoroethyl)amino)pyridin-4-yl)-1,3-oxazole-4-carboxamide | 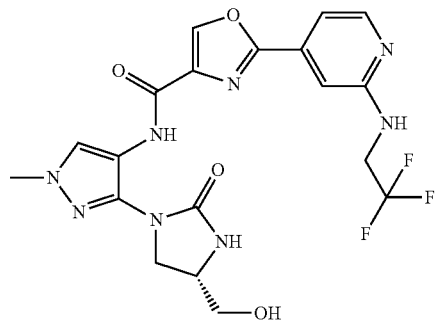 [SMILES: Cn1cc(NC(=O)c2coc(-c3ccnc(NCC(F)(F)F)c3)n2)c(N2C[C@@H](CO)NC2=O)n1] | 481.1 |
| 175 | 6-(4-(aminomethyl)-2-oxopyrrolidin-1-yl)-N-(3-(3,3-dimethyl-2-oxopyrrolidin-1-yl)-1-methyl-1H-pyrazol-4-yl)pyridine-2-carboxamide | 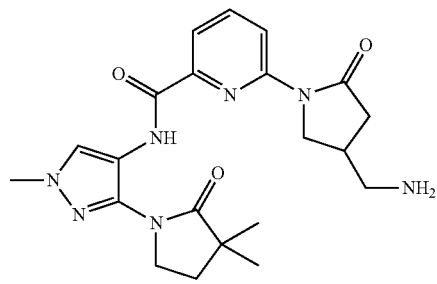 [SMILES: Cn1cc(NC(=O)c2cccc(N3CC(CN)CC3=O)n2)c(N2CCC(C)(C)C2=O)n1] | 426.1 |
| 176 | 6-(4-(aminomethyl)-1H-imidazol-1-yl)-N-(3-(3,3-dimethyl-2-oxopyrrolidin-1-yl)-1-methyl-1H-pyrazol-4-yl)pyridine-2-carboxamide | 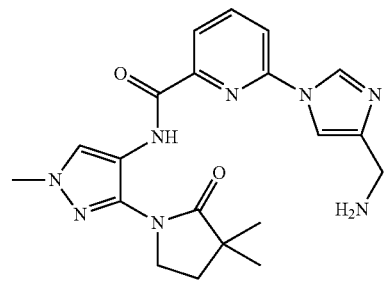 [SMILES: Cn1cc(NC(=O)c2cccc(-n3cnc(CN)c3)n2)c(N2CCC(C)(C)C2=O)n1] | 409.1 |

TABLE 1-26-continued

| 177 | 6-(4-(aminomethyl)-1H-pyrazol-1-yl)-N-(3-(3-(4-methoxybenzyl)-2-oxoimidazolidin-1-yl)-1-methyl-1H-pyrazol-4-yl)pyridine-2-carboxamide | 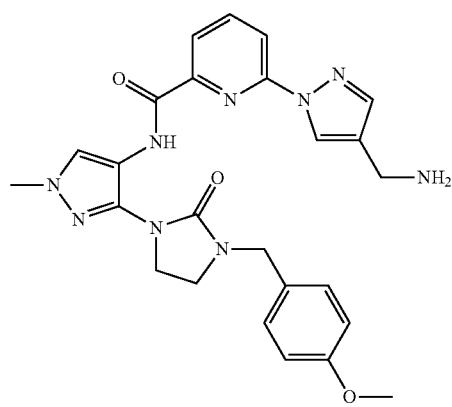 [SMILES: COc1ccc(CN2CCN(c3nn(C)cc3NC(=O)c3cccc(-n4cc(CN)cn4)n3)C2=O)cc1] | 502.2 |

TABLE 1-27

| 178 | N-(3-(3,3-dimethyl-2-oxopyrrolidin-1-yl)-1-methyl-1H-pyrazol-4-yl)-6-(1-methyl-1H-pyrazol-4-yl)pyridine-2-carboxamide | 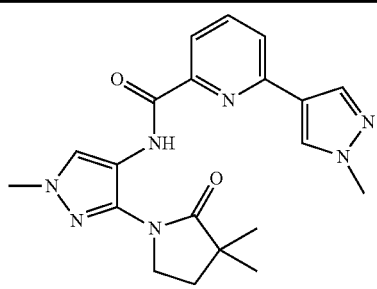 | 394.2 |
| 179 | N-(3-(3,3-dimethyl-2-oxopyrrolidin-1-yl)-1-methyl-1H-pyrazol-4-yl)-2-(5-((2,2,2-trifluoroethyl)amino)pyridin-3-yl)-1,3-oxazole-4-carboxamide | 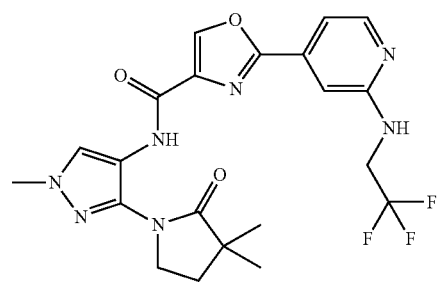 [SMILES: Cn1cc(NC(=O)c2coc(-c3ccnc(NCC(F)(F)F)c3)n2)c(N2CCC(C)(C)C2=O)n1] | 478.1 |
| 180 | N-(3-(3,3-dimethyl-2-oxopyrrolidin-1-yl)-1-methyl-1H-pyrazol-4-yl)-6-(5-(hydroxymethyl)-4,5-dihydro-1,2-oxazol-3-yl)pyridine-2-carboxamide | 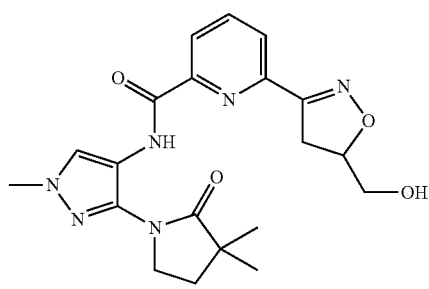 [SMILES: Cn1cc(NC(=O)c2cccc(C3=NOC(CO)C3)n2)c(N2CCC(C)(C)C2=O)n1] | 413.2 |
| 181 | N-(3-(3,3-dimethyl-2-oxopyrrolidin-1-yl)-1-methyl-1H-pyrazol-4-yl)-6-(3-hydroxy-2-oxopyrrolidin-1-yl)pyridine-2-carboxamide | 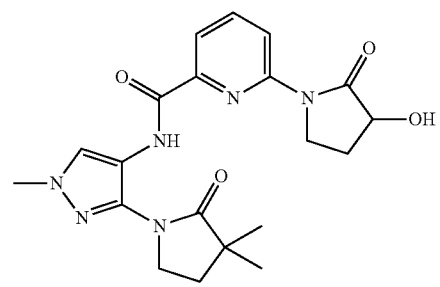 [SMILES: Cn1cc(NC(=O)c2cccc(N3CCC(O)C3=O)n2)c(N2CCC(C)(C)C2=O)n1] | 413.2 |

TABLE 1-27-continued

| 182 | 6-(4-(aminomethyl)-1H-pyrazol-1-yl)-N-(1-methyl-3-(2-oxoimidazolidin-1-yl)-1H-pyrazol-4-yl)pyridine-2-carboxamide | 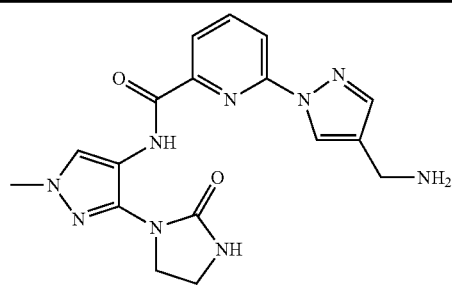 | | 382.1 |

| 183 | 6-(4-(aminomethyl)-1H-pyrazol-1-yl)-N-(3-(3-(2-hydroxyethyl)-2-oxoimidazolidin-1-yl)-1-methyl-1H-pyrazol-4-yl)pyridine-2-carboxamide | 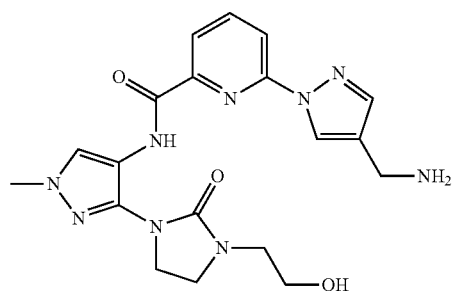 [SMILES: Cn1cc(NC(=O)c2cccc(-n3cc(CN)cn3)n2)c(N2CCN(CCO)C2=O)n1] | | 426.3 |

| 184 | 6-(5,6-dihydropyrrolo[3,4-c]pyrazol-2(4H)-yl)-N-(3-(3,3-dimethyl-2-oxopyrrolidin-1-yl)-1-methyl-1H-pyrazol-4-yl)pyridine-2-carboxamide | 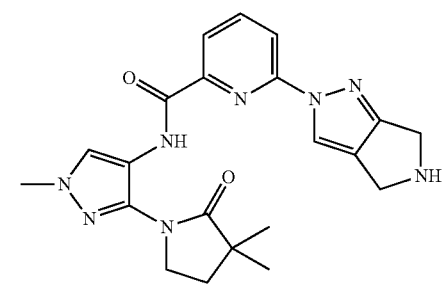 [SMILES: Cn1cc(NC(=O)c2cccc(-n3cc4c(n3)CNC4)n2)c(N2CCC(C)(C)C2=O)n1] | HCl | 421.1 |

TABLE 1-28

| 185 | 6-(1-cyclopropyl-1H-pyrazol-4-yl)-N-(3-(3,3-dimethyl-2-oxopyrrolidin-1-yl)-1-methyl-1H-pyrazol-4-yl)pyridine-2-carboxamide | 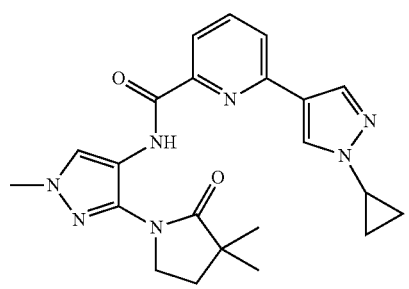 [SMILES: Cn1cc(NC(=O)c2cccc(-c3cnn(C4CC4)c3)n2)c(N2CCC(C)(C)C2=O)n1] | 420.2 |

| 186 | 6-(5-(aminomethyl)-4,5-dihydro-1,2-oxazol-3-yl)-N-(3-(3,3-dimethyl-2-oxopyrrolidin-1-yl)-1-methyl-1H-pyrazol-4-yl)pyridine-2-carboxamide | 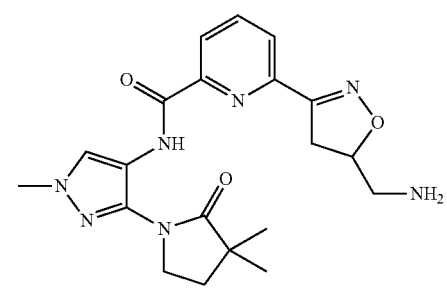 [SMILES: Cn1cc(NC(=O)c2cccc(C3=NOC(CN)C3)n2)c(N2CCC(C)(C)C2=O)n1] | 412.2 |

| | | | |
|---|---|---|---|
| 187 | N-(3-(3,3-dimethyl-2-oxopyrrolidin-1-yl)-1-methyl-1H-pyrazol-4-yl)-6-(5-(1,3-dioxolan-2-yl)-1,3-thiazol-2-yl)pyridine-2-carboxamide | 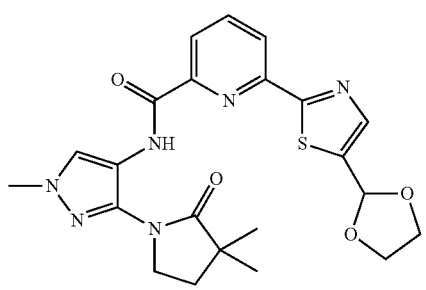 [SMILES: Cn1cc(NC(=O)c2cccc(-c3ncc(C4OCCO4)s3)n2)c(N2CCC(C)(C)C2=O)n1] | 469.2 |
| 188 | N-(3-(3,3-dimethyl-2-oxopyrrolidin-1-yl)-1-methyl-1H-pyrazol-4-yl)-6-(5-(hydroxymethyl)-1,3-thiazol-2-yl)pyridine-2-carboxamide | 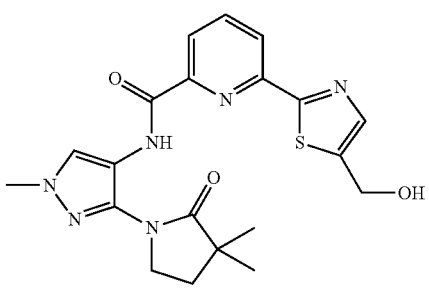 [SMILES: Cn1cc(NC(=O)c2cccc(-c3ncc(CO)s3)n2)c(N2CCC(C)(C)C2=O)n1] | 427.2 |
| 189 | N-(3-(3,3-dimethyl-2-oxopyrrolidin-1-yl)-1-methyl-1H-pyrazol-4-yl)-6-(1-(2,2,2-trifluoroethyl)-1H-pyrazol-4-yl)pyridine-2-carboxamide | 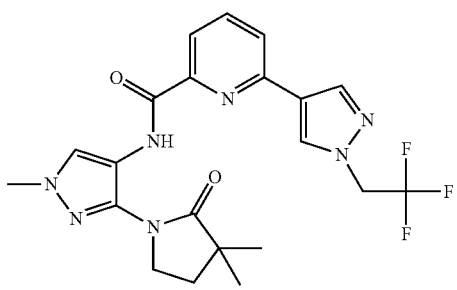 [SMILES: Cn1cc(NC(=O)c2cccc(-c3cnn(CC(F)(F)F)c3)n2)c(N2CCC(C)(C)C2=O)n1] | 462.2 |
| 190 | N-(3-(3,3-dimethyl-2-oxopyrrolidin-1-yl)-1-methyl-1H-pyrazol-4-yl)-6-(1H-pyrazol-4-yl)pyridine-2-carboxamide | 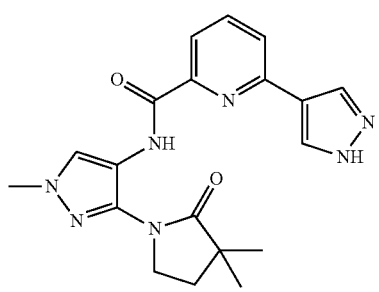 [SMILES: Cn1cc(NC(=O)c2cccc(-c3cn[nH]c3)n2)c(N2CCC(C)(C)C2=O)n1] | HCl 380.2 |
| 191 | N-(3-(3,3-dimethyl-2-oxopyrrolidin-1-yl)-1-methyl-1H-pyrazol-4-yl)-6-(1-methyl-1H-imidazol-4-yl)pyridine-2-carboxamide | 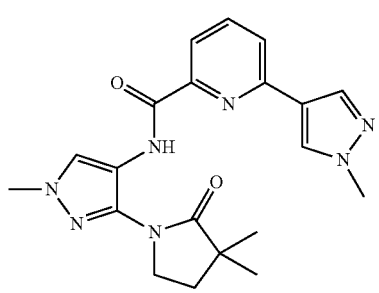 [SMILES: Cn1cc(-c2cccc(C(=O)Nc3cn(C)nc3N3CCC(C)(C)C3=O)n2)cn1] | 394.2 |

TABLE 1-29

| 192 | 6-(5-(azidomethyl)-1,3-thiazol-2-yl)-N-(3-(3,3-dimethyl-2-oxopyrrolidin-1-yl)-1-methyl-1H-pyrazol-4-yl)pyridine-2-carboxamide | 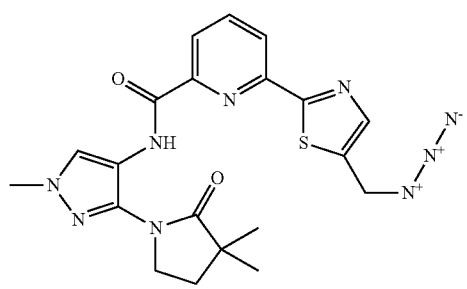 [SMILES: Cn1cc(NC(=O)c2cccc(-c3ncc(C[NH2+][NH2+][NH-])s3)n2)c(N2CCC(C)(C)C2=O)n1] | 452.1 |
|---|---|---|---|
| 193 | 6-(5-(aminomethyl)-1,3-thiazol-2-yl)-N-(3-(3,3-dimethyl-2-oxopyrrolidin-1-yl)-1-methyl-1H-pyrazol-4-yl)pyridine-2-carboxamide | 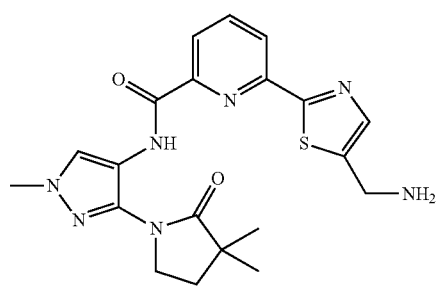 [SMILES: Cn1cc(NC(=O)c2cccc(-c3ncc(CN)s3)n2)c(N2CCC(C)(C)C2=O)n1] | 426.1 |
| 194 | N-(3-(4-(aminomethyl)-3,3-dimethyl-2-oxopyrrolidin-1-yl)-1-methyl-1H-pyrazol-4-yl)-2-(2-((2,2,2-trifluoroethyl)amino)pyridin-4-yl)-1,3-oxazole-4-carboxamide | 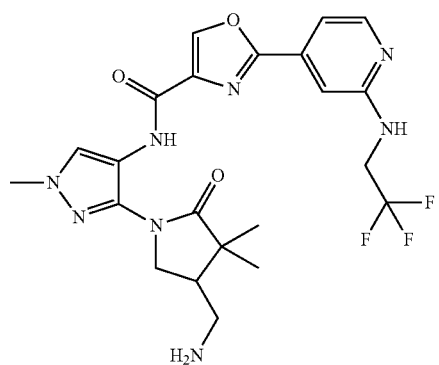 [SMILES: Cn1cc(NC(=O)c2coc(-c3ccnc(NCC(F)(F)F)c3)n2)c(N2CC(CN)C(C)(C)C2=O)n1] | 507.1 |
| 195 | 6-(4-(difluoromethyl)-1H-pyrazol-1-yl)-N-(3-(3,3-dimethyl-2-oxopyrrolidin-1-yl)-1-methyl-1H-pyrazol-4-yl)pyridine-2-carboxamide | 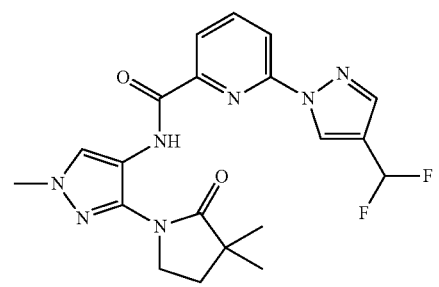 [SMILES: Cn1cc(NC(=O)c2cccc(-n3cc(C(F)F)cn3)n2)c(N2CCC(C)(C)C2=O)n1] | 430.1 |
| 196 | 6-(4-amino-1H-pyrazol-1-yl)-N-(3-(3,3-dimethyl-2-oxopyrrolidin-1-yl)-1-methyl-1H-pyrazol-4-yl)pyridine-2-carboxamide | 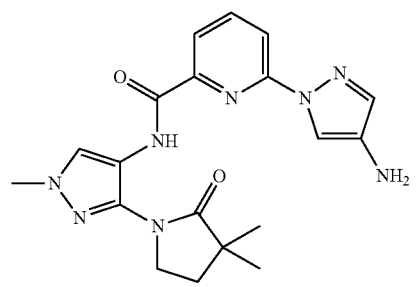 [SMILES: Cn1cc(NC(=O)c2cccc(-n3cc(N)cn3)n2)c(N2CCC(C)(C)C2=O)n1] | 395.2 |

TABLE 1-29-continued

| 197 | 6-((4S)-4-carbamoyl-2-oxoimidazolidin-1-yl)-N-(3-(3,3-dimethyl-2-oxopyrrolidin-1-yl)-1-methyl-1H-pyrazol-4-yl)pyridine-2-carboxamide | 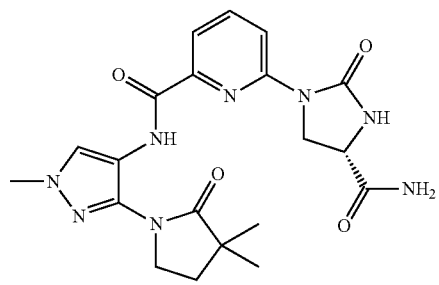 [SMILES: Cn1cc(NC(=O)c2cccc(N3C[C@@H](C(N)=O)NC3=O)n2)c(N2CCC(C)(C)C2=O)n1] | | 441.2 |
| --- | --- | --- | --- | --- |
| 198 | N-(3-(3,3-dimethyl-2-oxopyrrolidin-1-yl)-1-methyl-1H-pyrazol-4-yl)-2-(3-(2-hydroxyethyl)pyridin-4-yl)-1,3-oxazole-4-carboxamide | 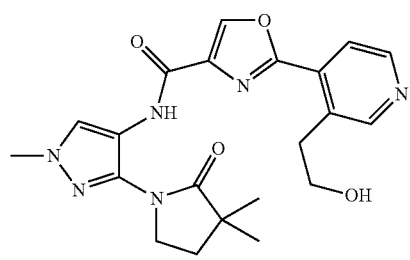 [SMILES: Cn1cc(NC(=O)c2coc(-c3ccncc3CCO)n2)c(N2CCC(C)(C)C2=O)n1] | | 425.1 |

TABLE 1-30

| 199 | 6-((4R)-4-(aminomethyl)-2-oxoimidazolidin-1-yl)-N-(3-(3,3-dimethyl-2-oxopyrrolidin-1-yl)-1-methyl-1H-pyrazol-4-yl)pyridine-2-carboxamide | 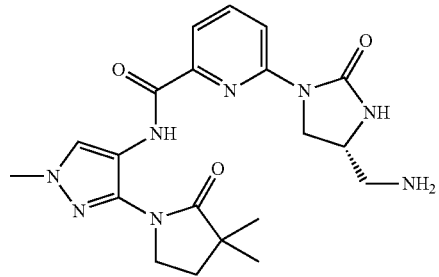 | | 427.2 |
| --- | --- | --- | --- | --- |
| 200 | 6-(4-(1-aminoethyl)-1H-pyrazol-1-yl)-N-(3-(3,3-dimethyl-2-oxopyrrolidin-1-yl)-1-methyl-1H-pyrazol-4-yl)pyridine-2-carboxamide | 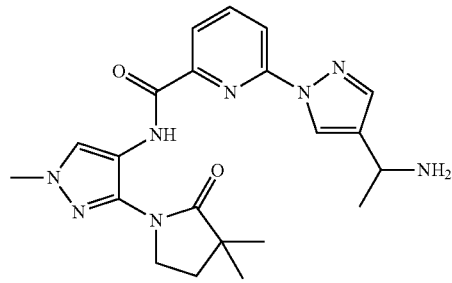 [SMILES: CC(N)c1cnn(-c2cccc(C(=O)Nc3cn(C)nc3N3CCC(C)(C)C3=O)n2)c1] | CF3COOH | 423.1 |
| 201 | 6-(4-(1-aminoethyl)-1H-pyrazol-1-yl)-N-(1-methyl-3-(3-methyl-2-ozoimidazo1idin-1-yl)-1H-pyrazol-4-yl)pyridine-2-carboxamide | 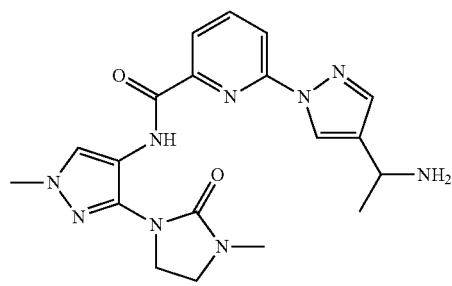 [SMILES: CC(N)c1cnn(-c2cccc(C(=O)Nc3cn(C)nc3N3CCN(C)C3=O)n2)c1] | HCl | 410.1 |

TABLE 1-30-continued

| 202 | N-(3-(3-allyl-2-oxoimidazolidin-1-yl)-1-methyl-1H-pyrazol-4-yl)-6-(4-formyl-1H-pyrazol-1-yl)pyridine-2-carboxamide | 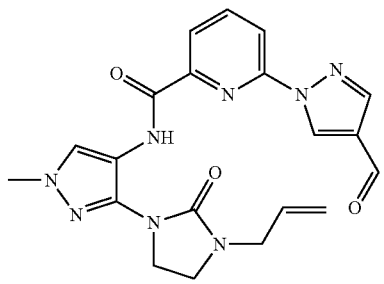 [SMILES: C=CCN1CCN(c2nn(C)cc2NC(=O)c2cccc(-n3cc(C=O)cn3)n2)C1=O] | 421.2 |
| 203 | N-(3-(3,3-dimethyl-2-oxopyrrolidin-1-yl)-1-methyl-1H-pyrazol-4-yl)-6-(3-oxopiperazin-1-yl)pyridine-2-carboxamide | 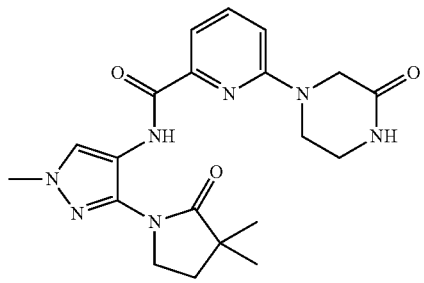 [SMILES: Cn1cc(NC(=O)c2cccc(N3CCNC(=O)C3)n2)c(N2CCC(C)(C)C2=O)n1] | 412.2 |
| 204 | 6-((4R)-4-((dimethylamino)methyl)-2-oxoimidazolidin-1-yl)-N-(3-(3,3-dimethyl-2-oxopyrrolidin-1-yl)-1-methyl-1H-pyrazol-4-yl)pyridine-2-carboxamide | 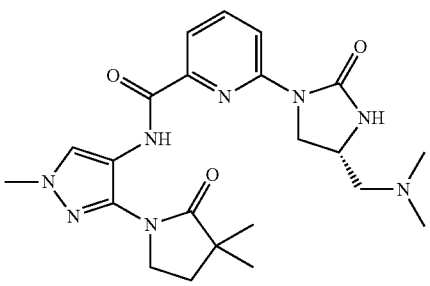 | 455.2 |
| 205 | 6-(7-benzyl-2-oxo-1,3,7-triazaspiro[4.4]non-3-yl)-N-(3-(3,3-dimethyl-2-oxopyrrolidin-1-yl)-1-methyl-1H-pyrazol-4-yl)pyridine-2-carboxamide | 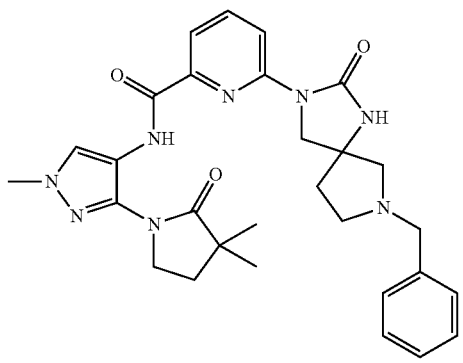 [SMILES: Cn1cc(NC(=O)c2cccc(N3CC4(CCN(Cc5ccccc5)C4)NC3=O)n2)c(N2CCC(C)(C)C2=O)n1] | 543.3 |

TABLE 1-31

| 206 | N-(3-(3,3-dimethyl-2-oxopyrrolidin-1-yl)-1-methyl-1H-pyrazol-4-yl)-6-(2-oxo-1,3,7-triazaspiro[4.4]non-3-yl)pyridine-2-carboxamide | 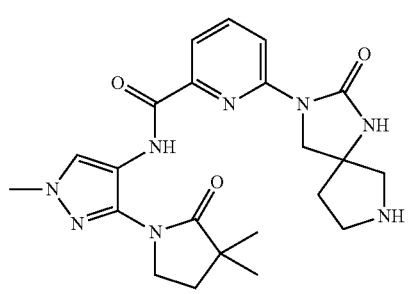 [SMILES: Cn1cc(NC(=O)c2cccc(N3CC4(CCNC4)NC3=O)n2)c(N2CCC(C)(C)C2=O)n1] | 453.2 |

TABLE 1-31-continued

| | | | |
|---|---|---|---|
| 207 | 6-(4-(aminomethyl)-2-thioxoimidazolidin-1-yl)-N-(3-(3,3-dimethyl-2-oxopyrrolidin-1-yl)-1-methyl-1H-pyrazol-4-yl)pyridine-2-carboxamide | 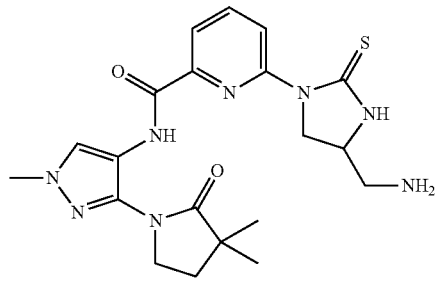 | 443.2 |
| 208 | 3-((4R)-4-(aminomethyl)-2-oxoimidazolidin-1-yl)-N-(3-(3,3-dimethyl-2-oxopyrrolidin-1-yl)-1-methyl-1H-pyrazol-4-yl)benzamide | 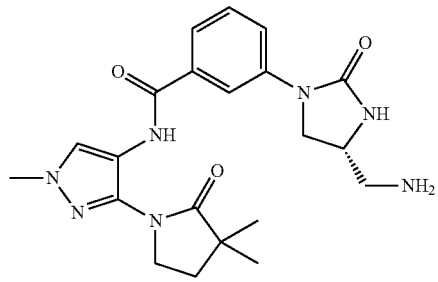 [SMILES: Cn1cc(NC(=O)c2cccc(N3C[C@@H](CN)NC3=O)c2)c(N2CCC(C)(C)C2=O)n1] | 426.1 |
| 209 | 6-((4R)-4-(cyanomethyl)-2-oxoimidazolidin-1-yl)-N-(3-(3,3-dimethyl-2-oxopyrrolidin-1-yl)-1-methyl-1H-pyrazol-4-yl)pyridine-2-carboxamide | 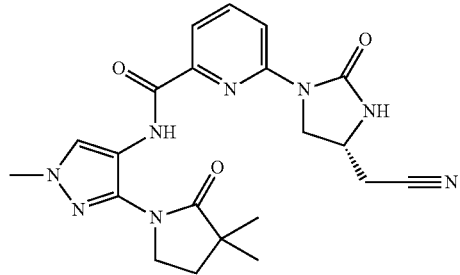 [SMILES: Cn1cc(NC(=O)c2cccc(N3C[C@@H](CC#N)NC3=O)n2)c(N2CCC(C)(C)C2=O)n1] | 437.1 |
| 210 | N-(3-(3,3-dimethyl-2-oxopyrrolidin-1-yl)-1-methyl-1H-pyrazol-4-yl)-3-(2-oxo-1,3,7-triazaspiro[4.4]non-3-yl)benzamide | 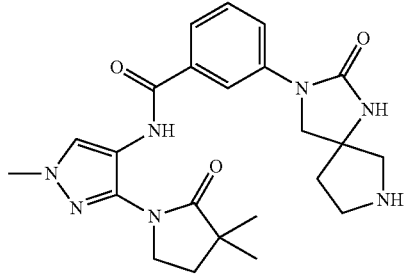 [SMILES: Cn1cc(NC(=O)c2cccc(N3CC4(CCNC4)NC3=O)c2)c(N2CCC(C)(C)C2=O)n1] | 452.1 |
| 211 | 6-(4-(aminomethyl)-2-thioxoimidazolidin-1-yl)-N-(3-(3-(2-hydroxyethyl)-2-oxoimidazolidin-1-yl)-1-methyl-1H-pyrazol-4-yl)pyridine-2-carboxamide | 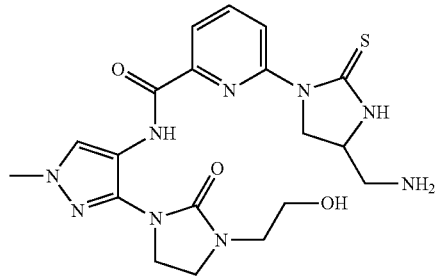 [SMILES: Cn1cc(NC(=O)c2cccc(N3CC(CN)NC3=S)n2)c(N2CCN(CCO)C2=O)n1] | 460.1 |

TABLE 1-31-continued

| 212 | 3-((4R)-4-(aminomethyl)-2-oxoimidazolidin-1-yl)-N-(3-(3,3-dimethyl-2-oxopyrrolidin-1-yl)-1-methyl-1H-pyrazol-4-yl)-5-fluorobenzamide | 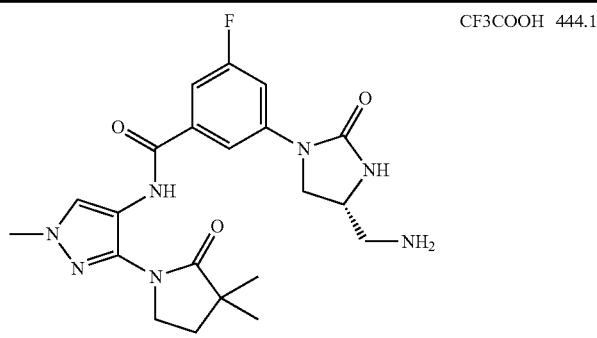 | CF3COOH | 444.1 |

TABLE 1-32

| 213 | N-(3-(3,3-dimethyl-2-oxopyrrolidin-1-yl)-1-methyl-1H-pyrazol-4-yl)-6-(7-methyl-2-oxo-1,3,7-triazaspiro[4.4]non-3-yl)pyridine-2-carboxamide | 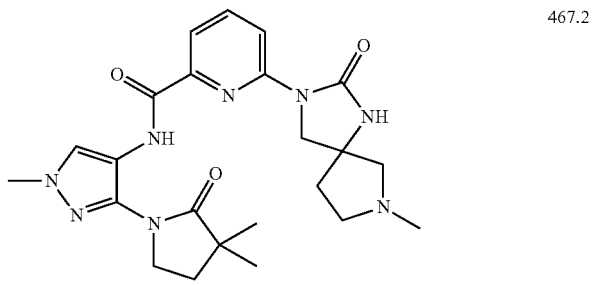 | | 467.2 |
| 214 | 6-((4R)-4-(2-aminoethyl)-2-oxoimidazolidin-1-yl)-N-(3-(3,3-dimethyl-2-oxopyrrolidin-1-yl)-1-methyl-1H-pyrazol-4-yl)pyridine-2-carboxamide | 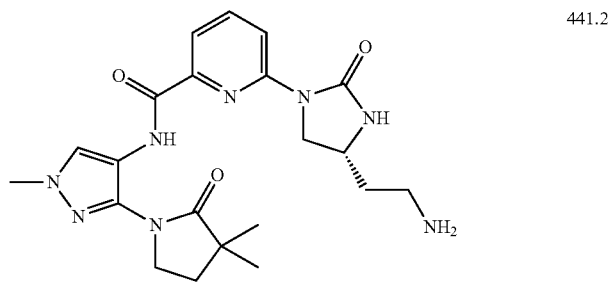 | | 441.2 |
| 215 | N-(1-methyl-3-(3-methyl-2-oxoimidazolidin-1-yl)-1H-pyrazol-4-yl)-6-(2-oxo-1,3,7-triazaspiro[4.4]non-3-yl)pyridine-2-carboxamide | 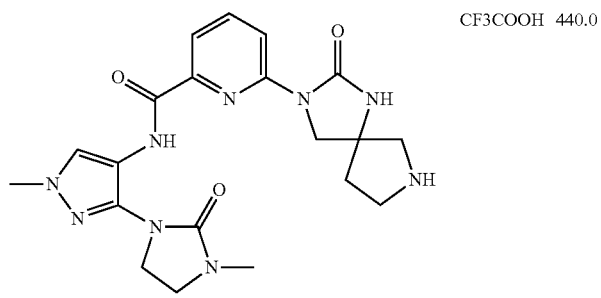 | CF3COOH | 440.0 |
| 216 | N-(3-(3,3-dimethyl-2-oxopyrroidin-1-yl)-1-methyl-1H-pyrazol-4-yl)-6-(2-oxo-7-thia-1,3-diazaspiro[4.4]non-3-yl)pyridine-2-carboxamide | 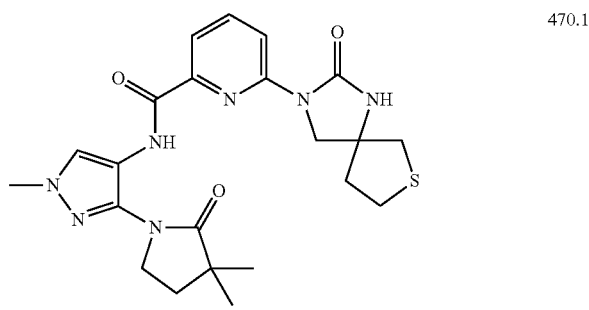 | | 470.1 |

| | | |
|---|---|---|
| 217 | N-(3-(3,3-dimethyl-2-oxopyrrolidin-1-yl)-1-methyl-1H-pyrazol-4-yl)-6-(7,7-dioxido-2-oxo-7-thia-1,3-diazaspiro[4.4]non-3-yl)pyridine-2-carboxamide | 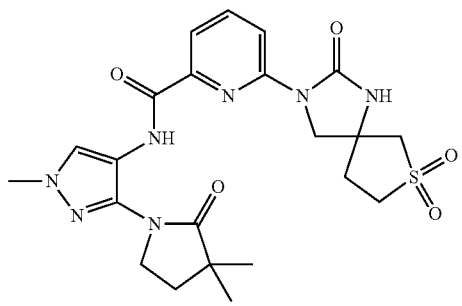 [SMILES: Cn1cc(NC(=O)c2cccc(N3CC4(CCS(=O)(=O)C4)NC3=O)n2)c(N2CCC(C)(C)C2=O)n1] 502.1 |

Experimental Example 1

IRAK-4 Enzyme Inhibition Test

IRAK-4 enzyme inhibitory activities of test compounds were measured by LANCE method (PerkinElmer). First, a test compound diluted with assay buffer (50 mM HEPES (pH7.5), 10 mM $MgCl_2$, 1 mM EGTA, 2 mM DTT, 0.01% Tween 20, 0.01% BSA) was added to 384-well plate at 2 μL each. Then, IRAK-4 (Carna Biosciences, Inc.) and a fluorescence-labeled peptide substrate (ULight-ACC peptide, PerkinElmer) solution diluted with assay buffer at 240 ng/mL and 37.5 nM, respectively were added at 2 μL each. Then, enzyme reaction was started by adding 2 μL each of ATP solution prepared with assay buffer at 1.5 mM. After the reaction at room temperature for 1 hr, Detection Buffer (PerkinElmer) prepared to be 20 mM EDTA, 1 nM europium-labeled anti-phospho ACC antibody (PerkinElmer) was added at 6 μL each. After standing at room temperature for 1 hr, fluorescence intensity (excitation wavelength 340 nm, fluorescence wavelength 665 nm, delay time 100 microseconds) was measured by a plate reader, Envision (PerkinElmer). The inhibitory activity of each compound was calculated as relative value where fluorescence intensity of a well without enzyme is considered as 100% inhibition.

IRAK-4 enzyme inhibitory rates at 1 μM of the concentration of the compounds are shown in the following Table 2.

TABLE 2

| Test compound | IRAK4 enzyme inhibitory rate (%) at 1 μM |
|---|---|
| Example 1 | 98 |
| Example 2 | 98 |
| Example 3 | 100 |
| Example 13 | 98 |
| Example 16 | 98 |
| Example 17 | 77 |
| Example 36 | 36 |
| Example 40 | 56 |

TABLE 2-continued

| Test compound | IRAK4 enzyme inhibitory rate (%) at 1 μM |
|---|---|
| Example 46 | 30 |
| Example 48 | 99 |
| Example 55 | 99 |
| Example 57 | 100 |
| Example 58 | 99 |
| Example 59 | 100 |
| Example 60 | 99 |
| Example 61 | 100 |
| Example 62 | 100 |
| Example 77 | 99 |
| Example 101 | 99 |
| Example 110 | 98 |
| Example 128 | 102 |
| Example 164 | 98 |
| Example 199 | 99 |
| Example 206 | 100 |
| Example 215 | 100 |

Experimental Example 2

R848 Tolerance Test in Rat

6-Week-old male LEW/CrlCrlj (Lewis) rats (Japane Charles River Laboratories) were used as 8 rats/group. R848 (Enzo Life Sciences) was dissolved in dimethyl sulfoxide (500 mM), and the concentration of solution was adjusted to 300 μM with saline, and 1.0 mL thereof was intraperitoneally administered in the rat. The compound was orally administered 1 hr before R848 administration. 0.5% Methyl cellulose (5 mL/kg) was orally administered as a control. The blood was collected from the abdominal aorta 1 hr after R848 administration. The blood was left overnight at 4° C., and the serum was collected by centrifugation. The amount of the tumor necrosis factor (TNFα) production in the serum was measured by Human TNF-alpha Quantikine ELISA Kit (R&D Systems). Shirley-Williams test was used for a dose-dependent manner, and $p \leq 0.05$ was evaluated as a significance level. The results are shown in Table 3.

TABLE 3

| | | Example 57 (mg/kg) | | | |
|---|---|---|---|---|---|
| | Control | 0.3 | 1 | 3 | 10 |
| TNFα production amount (pg/mL) | 1090 ± 137 | 1349 ± 181 | 736 ± 76.2 | 306 ± 45.9* | 236 ± 26.8* |

TABLE 3-continued

| | Control | Example 58 (mg/kg) | | | |
|---|---|---|---|---|---|
| | | 0.27 | 0.91 | 2.73 | 9.09 |
| TNFα production amount (pg/mL) | 945 ± 106 | 1070 ± 160 | 804 ± 116 | 628 ± 31.1 | 326 ± 41.1* |

Data (mean ± S.E.)
*p ≤ 0.05 vs. Control (Shirley-Williams test)

Experimental Example 3

NC1-Induced Nephritis in Rat

8-Week-old female WKY rats (Japan Charles River Laboratories) were used as 7 rats/group. Bovine NC1 (The non-collagenous domain of α3 chain of type IV collagen, Chondrex, inc) was dissolved in phosphate buffer to adjust the concentration to 0.3 mg/mL. The equal amount of complete Freund's adjuvant (H37 Ra, Diffco) was added thereto to give an emulsion. The emulsion (0.2 mL) was inoculated intracutaneously into the rat tail head (the 0 day). The compound was orally administered for 5 weeks (the 0 to 35th day, twice a day). 0.5% Methyl cellulose (5 mL/kg) was orally administered as a control. The urine was collected for 4 hr on the −1st day (Pre value) and the 35th day. The collected urine was centrifuged at 400 G, for 5 min at 4° C., the supernatant was kept at −80° C., and the amounts of creatinine and protein were measured. The body weight was measured on the 0th day and the 35th day. A comparison between the groups was analyzed by Dunnett test, and p≤0.05 was evaluated as a significance level. The results are shown in Table 4 and Table 5.

TABLE 4

| | Proteinuria (mg/mg Cre 4 hr) | |
|---|---|---|
| Group | Pre (−1st day) | 35th day |
| Non-Treated | 0.25 ± 0.04 | 3.90 ± 0.42 |
| Control | 0.23 ± 0.03 | 31.7 ± 4.26 |
| Example 57 (3 mg/kg) | 0.32 ± 0.05 | 18.1 ± 2.43 * |

Data (mean ± S.E.)
* p ≤ 0.05 vs. Control (Dunnett test)

TABLE 5

| Group | Body weight difference from the 0th day on the 35th day (g) |
|---|---|
| Non-Treated | +54.1 ± 2.9 |
| Control | +48.9 ± 1.9 |
| Example 57 (3 mg/kg) | +63.7 ± 2.8 * |

Data (mean ± S.E.)
* p ≤ 0.05 vs. Control (Dunnett test)

Formulation Example 1

Production of Capsule

| 1) compound of Example 1 | 30 mg |
|---|---|
| 2) fine powder cellulose | 10 mg |
| 3) lactose | 19 mg |
| 4) magnesium stearate | 1 mg |
| Total | 60 mg |

1), 2), 3) and 4) are mixed and filled in a gelatin capsule.

Formulation Example 2

Production of Tablet

| 1) compound of Example 1 | 30 g |
|---|---|
| 2) lactose | 50 g |
| 3) cornstarch | 15 g |
| 4) calcium carboxymethylcellulose | 44 g |
| 5) magnesium stearate | 1 g |
| 1000 tablets total | 140 g |

The total amount of 1), 2) and 3) and 4) (30 g) is kneaded with water, vacuum dried, and sieved. The sieved powder is mixed with 4) (14 g) and 5) (1 g), and the mixture is punched by a tableting machine, whereby 1000 tablets containing 30 mg of the compound of Example 1 per tablet are obtained.

Formulation Example 3

Production of Ointment

| 1) compound of Example 1 | 0.5 g |
|---|---|
| 2) liquid paraffin | 1 g |
| 3) white vaseline | 98.5 g |
| Total | 60 mg |

1) and 2) are mixed well in a mortar, and 3) is added gradually thereto with kneading to make the total weight 100 g. The obtained kneaded product is filled into tubes in parts to give an ointment.

INDUSTRIAL APPLICABILITY

The compound of the present invention has a superior IRAK-4 inhibitory action, which is useful as an agent for the prophylaxis or treatment of inflammatory disease, autoimmune disease, osteoarticular degenerative disease, neoplastic disease and the like.

This application is based on patent applications No. 2013-232571 filed on Nov. 8, 2013 and No. 2014-128562 filed on Jun. 23, 2014 in Japan, the contents of which are encompassed in full herein.

The invention claimed is:
1. A compound represented by the formula (I):

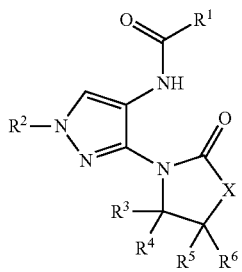

wherein
R$^1$ is an aromatic heterocyclic group or a C$_{6-14}$ aryl group, each of which is optionally substituted by 1 to 3 substituents selected from
(1) a halogen atom,
(2) a C$_{1-6}$ alkyl group optionally having substituent(s) selected from Substituent Group A,
(3) a C$_{6-14}$ aryl group optionally having substituent(s) selected from Substituent Group A,
(4) a heterocyclic group optionally having substituent(s) selected from Substituent Group A and a thioxo group (the substituent is optionally further substituted by substituent(s) selected from Substituent Group A, an azido group and a mono- or di-C$_{1-6}$ alkylamino group (the alkyl is substituted by substituent(s) selected from a C$_{3-10}$ cycloalkyl group and a halogen atom)),
(5) a C$_{3-10}$ cycloalkylsulfonyl group,
(6) a C$_{1-6}$ alkyl-carbonyl group,
(7) an aromatic heterocyclylsulfonyl group, and
(8) a halogenated sulfanyl group;
R$^2$ is
(1) a C$_{1-6}$ alkyl group optionally having substituent(s) selected from Substituent Group A, and a non-aromatic heterocyclic group having oxo group(s),
(2) a C$_{3-10}$ cycloalkyl group optionally having substituent(s) selected from Substituent Group A, or
(3) a non-aromatic heterocyclic group optionally having substituent(s) selected from Substituent Group A;
R$^3$ and R$^4$ are independently a hydrogen atom or a C$_{1-6}$ alkyl group optionally having substituent(s) selected from Substituent Group A;
R$^5$ and R$^6$ are independently
(1) a hydrogen atom,
(2) a hydroxy group,
(3) a C$_{1-6}$ alkyl group optionally having substituent(s) selected from (1) Substituent Group A, and (2) an amino group mono- or di-substituted by substituent(s) selected from (a) a C$_{1-6}$ alkyl group, (b) a C$_{3-10}$ cycloalkyl group optionally substituted by 1 to 3 halogen atoms, (c) a non-aromatic heterocyclic group, (d) a C$_{1-6}$ alkylsulfonyl group, and (e) a C$_{3-10}$ cycloalkyl-carbonyl group,
(4) a C$_{1-6}$ alkoxy group optionally having substituent(s) selected from Substituent Group A,
(5) an amino group optionally mono- or di-substituted by substituent(s) selected from
(i) a C$_{1-6}$ alkyl group optionally having substituent(s) selected from Substituent Group A,
(ii) a C$_{1-6}$ alkyl-carbonyl group optionally having substituent(s) selected from Substituent Group A, and
(iii) a C$_{1-6}$ alkylsulfonyl group optionally having substituent(s) selected from Substituent Group A,
(6) a non-aromatic heterocyclic group optionally having substituent(s) selected from Substituent Group A,
(7) a carboxy group, or
(8) a carbamoyl group optionally mono- or di-substituted by C$_{1-6}$ alkyl group(s), or
R$^5$ and R$^6$ in combination optionally form
(1) a non-aromatic heterocycle optionally having substituent(s) selected from Substituent Group A, or
(2) a C$_{3-10}$ cycloalkane optionally having substituent(s) selected from Substituent Group A;
X is CR$^7$R$^8$, NR$^9$, O or S;
R$^7$ and R$^8$ are independently
(1) a hydrogen atom,
(2) a cyano group,
(3) a C$_{1-6}$ alkyl group optionally having substituent(s) selected from Substituent Group A, or
(4) a hydroxy group, or
R$^7$ and R$^8$ in combination optionally form
(1) a C$_{3-10}$ cycloalkane optionally having substituent(s) selected from Substituent Group A, or
(2) a non-aromatic heterocycle optionally having substituent(s) selected from Substituent Group A and a C$_{7-16}$ aralkyl group; and
R$^9$ is
(1) a hydrogen atom,
(2) a C$_{1-6}$ alkyl group optionally having substituent(s) selected from Substituent Group A,
(3) a C$_{2-6}$ alkenyl group optionally having substituent(s) selected from Substituent Group A, or
(4) a C$_{7-16}$ aralkyl group optionally having substituent(s) selected from Substituent Group A, or a salt thereof;
wherein Substituent Group A consists of
(1) a halogen atom,
(2) a nitro group,
(3) a cyano group,
(4) an oxo group,
(5) a hydroxy group,
(6) an optionally halogenated C$_{1-6}$ alkoxy group,
(7) a C$_{6-14}$ aryloxy group,
(8) a C$_{7-16}$ aralkyloxy group,
(9) a 5- to 14-membered aromatic heterocyclyloxy group,
(10) a 3- to 14-membered non-aromatic heterocyclyloxy group,
(11) a C$_{1-4}$ alkyl-carbonyloxy group,
(12) a C$_{6-14}$ aryl-carbonyloxy group,
(13) a C$_{3-6}$ alkoxy-carbonyloxy group,
(14) a mono- or di-C$_{1-6}$ alkyl-carbamoyloxy group,
(15) a C$_{6-14}$ aryl-carbamoyloxy group,
(16) a 5- to 14-membered aromatic heterocyclylcarbonyloxy group,
(17) a 3- to 14-membered non-aromatic heterocyclylcarbonyloxy group,
(18) an optionally halogenated C$_{1-6}$ alkylsulfonyloxy group,
(19) a C$_{6-14}$ arylsulfonyloxy group optionally substituted by a C$_{1-6}$ alkyl group,
(20) an optionally halogenated C$_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated C$_{1-6}$ alkyl-carbonyl group,
(26) a C$_{6-14}$ aryl-carbonyl group,

(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(30) a $C_{6-14}$ aryloxy-carbonyl group,
(31) a $C_{7-16}$ aralkyloxy-carbonyl group,
(32) a carbamoyl group,
(33) a thiocarbamoyl group,
(34) a mono- or di-$C_{1-6}$ alkyl-carbamoyl group,
(35) a $C_{6-14}$ aryl-carbamoyl group,
(36) a 5- to 14-membered aromatic heterocyclylcarbamoyl group,
(37) a 3- to 14-membered non-aromatic heterocyclylcarbamoyl group,
(38) an optionally halogenated $C_{1-6}$ alkylsulfonyl group,
(39) a $C_{6-14}$ arylsulfonyl group,
(40) a 5- to 14-membered aromatic heterocyclylsulfonyl group,
(41) an optionally halogenated $C_{1-6}$ alkylsulfinyl group,
(42) a $C_{6-14}$ arylsulfinyl group,
(43) a 5- to 14-membered aromatic heterocyclylsulfinyl group,
(44) an amino group,
(45) a mono- or di-$C_{1-6}$ alkylamino group,
(46) a mono- or di-$C_{6-14}$ arylamino group,
(47) a 5- to 14-membered aromatic heterocyclylamino group,
(48) a $C_{7-16}$ aralkylamino group,
(49) a formylamino group,
(50) a $C_{1-6}$ alkyl-carbonylamino group,
(51) a ($C_{1-6}$ alkyl)($C_{1-6}$ alkyl-carbonyl)amino group,
(52) a $C_{6-14}$ aryl-carbonylamino group,
(53) a $C_{1-6}$ alkoxy-carbonylamino group,
(54) a $C_{7-16}$ aralkyloxy-carbonylamino group,
(55) a $C_{1-6}$ alkylsulfonylamino group,
(56) a $C_{6-14}$ arylsulfonylamino group optionally substituted by a $C_{1-6}$ alkyl group,
(57) an optionally halogenated $C_{1-6}$ alkyl group,
(58) a $C_{2-6}$ alkenyl group,
(59) a $C_{2-6}$ alkenyl group,
(60) a $C_{3-10}$ cycloalkyl group,
(61) a $C_{3-10}$ cycloalkenyl group and
(62) a $C_{6-14}$ aryl group.

2. The compound or salt of claim 1, wherein
X is CR7R8 or NR9; and
R3 and R4 are both hydrogen atoms.

3. N-(3-(3-(2-Hydroxyethyl)-2-oxoimidazolidin-1-yl)-1-methyl-1H-pyrazol-4-yl)-2-(2-((2,2,2-trifluoroethyl)amino)pyridin-4-yl)-1,3-oxazole-4-carboxamide or a salt thereof.

4. N-(1-Methyl-3-(2-oxoimidazolidin-1-yl)-1H-pyrazol-4-yl)-2-(2-((2,2,2-trifluoroethyl)amino)pyridin-4-yl)-1,3-oxazole-4-carboxamide or a salt thereof.

5. N-(1-Methyl-3-((3 S)-3-methyl-2-oxopyrrolidin-1-yl)-1H-pyrazol-4-yl)-2-(2-((2,2,2-trifluoroethyl)amino)pyridin-4-yl)-1,3-oxazole-4-carboxamide or a salt thereof.

6. A medicament comprising the compound or salt of claim 1.

7. The medicament of claim 6, which is an interleukin 1 receptor-associated kinase 4 inhibitor.

8. The medicament of claim 6, which is an agent for the treatment of autoimmune disease and/or inflammatory disease.

9. The medicament of claim 8, wherein the medicament is an agent for the treatment of multiple sclerosis, systemic lupus erythematosus, gout or hay fever.

10. A method of inhibiting interleukin 1 receptor-associated kinase 4 in a mammal, which comprises administering an effective amount of the compound or salt of claim 1 to the mammal.

11. A method for the treatment of autoimmune disease and/or inflammatory disease in a mammal, which comprises administering an effective amount of the compound or salt of claim 1 to the mammal.

12. The method of claim 11, wherein the method is for the treatment of multiple sclerosis, systemic lupus erythematosus, gout or hay fever.

13. A compound represented by the formula (I):

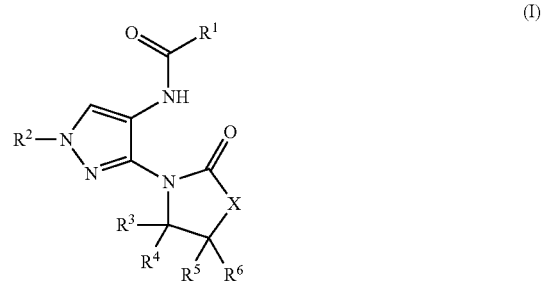

wherein
R$^1$ is an aromatic heterocyclic group or a $C_{6-14}$ aryl group, each of which is optionally substituted by 1 to 3 substituents selected from
(1) a halogen atom,
(2) a $C_{1-6}$ alkyl group optionally substituted by 1 to 3 substituents selected from
(i) a halogen atom, and
(ii) a hydroxy group,
(3) a $C_{6-14}$ aryl group optionally substituted by 1 to 3 halogen atoms,
(4) an aromatic heterocyclic group optionally substituted by 1 to 3 substituents selected from
(i) an amino group optionally mono- or di-substituted by $C_{1-6}$ alkyl group(s) optionally substituted by 1 to 3 substituents selected from
(a) a halogen atom, and
(b) a $C_{3-10}$ cycloalkyl group,
(ii) a halogen atom,
(iii) a $C_{1-6}$ alkoxy group,
(iv) a cyano group,
(v) a $C_{1-6}$ alkyl group optionally substituted by 1 to 3 substituents selected from
(a) an azido group,
(b) an amino group optionally mono- or di-substituted by $C_{1-6}$ alkyl group(s) optionally substituted by 1 to 3 substituents selected from a halogen atom and a $C_{3-10}$ cycloalkyl group,
(c) a hydroxy group, and
(d) a halogen atom,
(vi) a formyl group,
(vii) a carboxy group,
(viii) a carbamoyl group,
(ix) a $C_3$-$C_{10}$ cycloalkyl group, and
(x) a non-aromatic heterocyclic group,
(5) a non-aromatic heterocyclic group optionally substituted by 1 to 3 substituents selected from
(i) a $C_{1-6}$ alkyl group optionally substituted by 1 to 3 substituents selected from
(a) a hydroxy group,
(b) an amino group optionally mono- or di-substituted by $C_{1-6}$ alkyl group(s), (c) a cyano group, and
(d) a $C_{6-14}$ aryl group,
(ii) an oxo group,
(iii) a hydroxy group,
(iv) a carbamoyl group, and
(v) a thioxo group,
(6) a $C_{3-10}$ cycloalkylsulfonyl group,
(7) a $C_{1-6}$ alkyl-carbonyl group,
(8) an aromatic heterocyclylsulfonyl group, and
(9) a halogenated thio group;
$R^2$ is
(1) a $C_{1-6}$ alkyl group optionally substituted by 1 to 3 substituents selected from
(i) a $C_{1-6}$ alkoxy-carbonyl group,
(ii) a $C_{1-6}$ alkylsulfonyl group,
(iii) a carbamoyl group,
(iv) a cyano group,
(v) a non-aromatic heterocyclic group optionally substituted by 1 to 3 oxo groups, and
(vi) a halogen atom,
(2) a $C_{3-10}$ cycloalkyl group optionally substituted by 1 to 3 hydroxy groups, or
(3) a non-aromatic heterocyclic group;
$R^3$ and $R^4$ are independently
(1) a hydrogen atom, or
(2) a $C_{1-6}$ alkyl group optionally substituted by 1 to 3 substituents selected from an amino group optionally mono- or di-substituted by $C_{1-6}$ alkyl group(s);
$R^5$ and $R^6$ are independently
(1) a hydrogen atom,
(2) a hydroxy group,
(3) a $C_{1-6}$ alkyl group optionally substituted by 1 to 3 substituents selected from
(i) a hydroxy group,
(ii) an amino group optionally mono- or di-substituted by substituent(s) selected from
(a) a $C_{1-6}$ alkyl group optionally substituted by 1 to 3 halogen atoms,
(b) a $C_{3-10}$ cycloalkyl group optionally substituted by 1 to 3 halogen atoms,
(c) a non-aromatic heterocyclic group,
(d) a $C_{1-6}$ alkylsulfonyl group,
(e) a $C_{1-6}$ alkyl-carbonyl group, and
(f) a $C_{3-10}$ cycloalkyl-carbonyl group,
(iii) a halogen atom,
(iv) a $C_{1-6}$ alkylsulfanyl group,
(v) a $C_{1-6}$ alkylsulfinyl group, and
(vi) a $C_{1-6}$ alkylsulfonyl group,
(4) a $C_{1-6}$ alkoxy group,
(5) an amino group optionally mono- or di-substituted by substituent(s) selected from
(i) a $C_{1-6}$ alkyl group,
(ii) a $C_{1-6}$ alkyl-carbonyl group, and
(iii) a $C_{1-6}$ alkylsulfonyl group,
(6) a non-aromatic heterocyclic group,
(7) a carboxy group, or
(8) a carbamoyl group optionally mono- or di-substituted by $C_{1-6}$ alkyl group(s), or
$R^5$ and $R^6$ in combination optionally form
(1) a non-aromatic heterocycle, or
(2) a $C_{3-10}$ cycloalkane;
X is $CR^7R^8$, $NR^9$, O or S;
$R^7$ and $R^8$ are independently
(1) a hydrogen atom,
(2) a cyano group,
(3) a $C_{1-6}$ alkyl group optionally substituted by 1 to 3 hydroxy groups, or
(4) a hydroxy group, or
$R^7$ and $R^8$ in combination optionally form
(1) a $C_{3-10}$ cycloalkane optionally substituted by 1 to 3 substituents selected from
(i) an oxo group, and
(ii) a hydroxy group, or
(2) a non-aromatic heterocycle optionally substituted by 1 to 3 $C_{7-16}$ aralkyl groups; and
$R^9$ is
(1) a hydrogen atom,
(2) a $C_{1-6}$ alkyl group optionally substituted by 1 to 3 substituents selected from
(i) a hydroxy group,
(ii) a $C_{1-6}$ alkoxy group optionally substituted by 1 to 3 $C_{6-14}$ aryl groups, and
(iii) an amino group optionally mono- or di-substituted by $C_{1-6}$ alkyl group(s),
(3) a $C_{2-6}$ alkenyl group, or
(4) a $C_{7-16}$ aralkyl group optionally substituted by 1 to 3 $C_{1-6}$ alkoxy groups,
or a salt thereof.

* * * * *

UNITED STATES PATENT AND TRADEMARK OFFICE
CERTIFICATE OF CORRECTION

PATENT NO. : 9,321,757 B2
APPLICATION NO. : 14/533326
DATED : April 26, 2016
INVENTOR(S) : Masato Yoshida et al.

It is certified that error appears in the above-identified patent and that said Letters Patent is hereby corrected as shown below:

In the claims,

Col. 212, claim 1, line 49, "(13) a $C_{3-6}$ alkoxy-carbonyloxy group," should be --"(13) a $C_{1-6}$ alkoxy-carbonyloxy group,--.

Col. 213, claim 1, line 42, "(59) a $C_{2-6}$ alkenyl group," should be --(59) a $C_{2-6}$ alkynyl group,--.

Signed and Sealed this
Ninth Day of August, 2016

Michelle K. Lee
*Director of the United States Patent and Trademark Office*